US012325708B2

(12) United States Patent
Anand et al.

(10) Patent No.: US 12,325,708 B2
(45) Date of Patent: Jun. 10, 2025

(54) ADENOSINE 2 RECEPTOR ANTAGONISTS

(71) Applicant: Nektar Therapeutics, San Francisco, CA (US)

(72) Inventors: Neel K. Anand, San Mateo, CA (US); Natalia Aurrecoechea, Oakland, CA (US); Anthony James Brockway, Oakland, CA (US); Haiying Cai, Cupertino, CA (US); Lin Cheng, Sunnyvale, CA (US); Bo-Liang Deng, San Ramon, CA (US); Donogh John Roger O'Mahony, San Mateo, CA (US); Zhongxu Ren, Foster City, CA (US); Wen Zhang, Palo Alto, CA (US)

(73) Assignee: Nektar Therapeutics, San Francisco, CA (US)

( * ) Notice: Subject to any disclaimer, the term of this patent is extended or adjusted under 35 U.S.C. 154(b) by 738 days.

(21) Appl. No.: 17/608,582

(22) PCT Filed: May 1, 2020

(86) PCT No.: PCT/US2020/031185
§ 371 (c)(1),
(2) Date: Nov. 3, 2021

(87) PCT Pub. No.: WO2020/227156
PCT Pub. Date: Nov. 12, 2020

(65) Prior Publication Data
US 2022/0235056 A1 Jul. 28, 2022

Related U.S. Application Data

(60) Provisional application No. 62/863,377, filed on Jun. 19, 2019, provisional application No. 62/843,194, filed on May 3, 2019.

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01); *C07B 2200/05* (2013.01)

(58) Field of Classification Search
CPC .. C07D 487/04; C07D 519/00; C07B 2200/05
See application file for complete search history.

(56) References Cited

U.S. PATENT DOCUMENTS

2002/0099061 A1 7/2002 Neustadt et al.
2005/0239795 A1 10/2005 Neustadt et al.

FOREIGN PATENT DOCUMENTS

| WO | WO 03/048163 A1 | 6/2003 |
|---|---|---|
| WO | WO 2012/135084 A1 | 10/2012 |
| WO | WO 2014/114578 A1 | 7/2014 |
| WO | WO 2016/209787 A1 | 12/2016 |

OTHER PUBLICATIONS

Neustadt, 2009, Bioorganic & Medicinal Chemistry Letters, vol. 19, 967-971. (Year: 2009).*
Beavis et al., "Blockade of $A_{2A}$ receptors potently suppresses the metastasis of CD73+tumors", PNAS, vol. 110, No. 36, pp. 14711-14716, (Sep. 3, 2013).
Berge et al., "Pharmaceutical Salts", Journal of Pharmaceutical Sciences, vol. 66, No. 1, pp. 1-19, (Jan. 1977).
Blay et al., "The Extracellular Fluid of Solid Carcinomas Immunosuppressive Concentrations of Adenosine", Cancer Research, vol. 57, pp. 2602-2605, (Jul. 1, 1997).
Borodovsky et al., "Abstract 3751: Inhibition of $A_{2A}R$ by AZD4635 induces anti-tumor immunity alone and in combination with anti-PD-L1 in preclinical models", Cancer Research, vol. 78, 13 Supplement, 3751, (2018).
Nair et al., "A simple practice guide for dose conversion between animals and human", J. Basic Clin. Pharm., vol. 7, pp. 27-31, (2016).
Neustadt et al., "Potent and selective adenosine $A_{2A}$ receptor antagonists: 1,2,4-Triazolo[1,5-c]pyrimidines", Bioorganic & Medicinal Chemistry Letters, vol. 19, pp. 967-971, (2009).
Stocchi et al., "Randomized trial of preladenant, given as monotherapy, in patients with early Parkinson disease", Neurology, vol. 88, pp. 2198-2206, (2017).
Yang et al., "Characterization of the potency, selectivity, and pharmacokinetic profile for six adenosine $A_{2A}$ receptor antagonists", Naunyn-Schmiedeberg's Arch Pharmacol, vol. 375, pp. 133-144, (2007).
PCT International Search Report and Written Opinion corresponding to PCT Application No. PCT/US2020/031185 date of mailing Sep. 4, 2020.
PCT International Preliminary Report on Patentability corresponding to PCT Application No. PCT/US2020/031185 date of mailing Nov. 18, 2021.
Enzon Pharmaceuticals, Macromolecular Engineering Technologies, 16 pages, (2004).
NEKTAR™—Transforming Therapeutics, Nektar Molecule Engineering: Polyethylene Glycol and Derivatives for Advanced PEGylation, 24 pages, Catalog—2003, (Jul. 2003).
NEKTAR™—Transforming Therapeutics, Nektar Advanced PEGylation: Polyethylene Glycol and Derivatives for Advanced PEGylation, 27 pages, Catalog—2004, (Jul. 2004).
NEKTAR™—Transforming Therapeutics, Nektar Advanced PEGylation: Polyethylene Glycol and Derivatives for Advanced PEGylation, 33 pages, (Catalog 2005-2006).

(Continued)

Primary Examiner — D Margaret Seaman
(74) Attorney, Agent, or Firm — Jacqueline F. Mahoney

(57) ABSTRACT

The instant disclosure provides novel adenosine receptor antagonist compounds, compositions, methods of making and methods of using. In a further aspect, a method of treating a subject in need thereof, comprising administering a therapeutically effective amount of any one or more of the compounds described herein. In some embodiments, the subject has cancer and the method is a method of treating cancer.

17 Claims, 5 Drawing Sheets

(56) References Cited

OTHER PUBLICATIONS

NOF Corporation, PEG Derivatives, Phospholipid and Drug Delivery Materials for Pharmaceuticals, 46 pages, Catalogue 2003-1$^{st}$, (Jan. 2003).

NOF Corporation, PEG Derivatives, Phospholipid and Drug Delivery Materials for Pharmaceuticals, 27 pages, Catalogue 2003-2$^{nd}$, (Mar. 2004).

NOF Corporation, PEG Derivatives, Phospholipids and Drug Delivery Materials for Pharmaceutical Products and Formulations, 60 pages, Catalogue Ver. 8, (Apr. 2006).

Polypure Products, PEG amines; PEG acids and amino acids; PEG thiols and disulfides; Biotins, 5 pages, (Apr. 2004).

Polypure Products, PEG amines; PEG acids and amino acids; PEG thiols and disulfides; Biotins, 5 pages, (Apr. 2005).

Quanta Biodesign, Labeling, Derivatization and Crosslinking Reagents for Biological and Related Materials with dPEG™, 38 pages, (Mar. 12, 2004).

Quanta Biodesign, Labeling, Modification and Crosslinking Reagents incorporating our unique monodispersed dPEG™ Technology, 31 pages, (Nov. 5, 2004).

Quanta Biodesign, Ltd., Leading innovator, producer and provider of monodisperse discrete PEG™ (dPEG™) derivatives, (Product Catalog), 26 pages, (Updated: Jul. 18, 2005).

Quanta Biodesign, Ltd., Leading innovator, producer and provider of monodisperse discrete PEG™ (dPEG™) derivatives, (Product Catalog), 26 pages, (Updated: Nov. 17, 2005).

Shearwater Polymers, Inc., Polyethylene Glycol Derivatives, 50 pages, Catalog—(Mar. 1995).

Shearwater Polymers, Inc., Polyethylene Glycol Derivatives, 55 pages, Catalog 1997-1998, (Jul. 1997).

Shearwater Polymers, Inc., Polyethylene Glycol and Derivatives: Functionalized Biocompatible Polymers for Research and Pharmaceuticals, 50 pages, Catalog—(Jan. 2000).

Shearwater Corporation, Polyethylene Glycol and Derivatives for Biomedical Applications, 20 pages, Catalog—(Jul. 2001).

* cited by examiner

ADENOSINE 2 RECEPTOR ANTAGONISTS

CROSS REFERENCE TO RELATED APPLICATIONS

This application is a 35 U.S.C. § 371 application of International Application No. PCT/US2020/031185 filed May 1, 2020, designating the United States, which claims the benefit of priority under 35 U.S.C. § 119 (e) to U.S. Provisional Patent Application No. 62/843,194, filed May 3, 2019 and U.S. Provisional Patent Application No. 62/863,377, filed Jun. 19, 2019, the disclosures of which are each incorporated herein by reference.

FIELD

The instant disclosure is directed to (among other things) therapeutic compounds and compositions comprising an adenosine $A_{2A}$ receptor ($A_{2A}R$) selective antagonist, and related methods of use, for example, to provide therapeutic use in treating cancer.

BACKGROUND

Adenosine is a purine nucleoside that has been recognized as a key metabolic pathway with the ability to modulate the immune response as well as inflammatory processes (Blay, *Cancer Res.*, 57:2602-2605 (1997)).

Adenosine is an immunosuppressive metabolite that has been found within the tumor microenvironment (Leone et al., *J. Immunother. Cancer*, 6:57 (2018)). Adenosine levels found in the tumor extracellular fluid of mouse colon carcinoma and lung models were sufficient to cause immunosuppression of T-killer cell function (Blay). The ability of adenosine to modulate tumor growth results from interaction with the adenosine receptors (Fishman et al., Handbook of Experimental Pharmacology, C. N. Wilson and S. J. Mustafa (eds.), Berlin, 2009). The adenosine receptor is a member of the G protein-coupled receptor family and includes four sub-types: $A_1$, $A_{2A}$, $A_{2B}$ and $A_3$.

In addition to the high levels of adenosine in the tumor microenvironment allowing for cancer immune evasion, the adenosine receptors (AR) have also been found to be upregulated in various tumor cells (Fishman). The $A_{2A}$ adenosine receptor ($A_{2A}R$) is expressed on T cells and natural killer T (NKT) cells, monocytes, macrophages, dendritic cells (DC), and natural killer (NK) cells. Activation of the $A_{2A}R$ has been found to inhibit the immune response to tumors via suppression of T regulatory cell function and via inhibition of natural killer cell cytotoxicity and tumor-specific CD4+/CD8+ activity (Fishman). Previous in vivo studies have shown that CD73 inhibits antitumor immunity through activation of adenosine receptors (e.g. $A_{2A}R$) in a breast cancer model (Beavis et. al., PNAS USA, 110(36): 14711-14716 (2013)). Activation of the $A_{2B}$ adenosine ($A_{2B}R$) receptor has also been found to inhibit ERK1/2 phosphorylation and MAP kinase activity, which are involved in tumor cell growth signals (Fishman).

A number of adenosine $A_{2A}$ receptor ($A_{2A}R$) selective antagonists such as preladenant (Merck) have been explored as therapeutics for treatment of Parkinson's Disease. Based on the immunomodulatory effect of $A_{2A}R$ activation, it has also been suggested that inhibition of $A_{2A}R$ activation may be useful in cancer therapy (Fishman). Blockage of the $A_{2A}R$ was found to result in enhanced NK cell activity in vitro and in vivo and reduced metastasis in a perforin-dependent manner (Beavis). AZD4635 (AstraZeneca), a selective $A_{2A}R$ antagonist, is currently being studied in a Phase I clinical trial as a single agent and in combination with durvalumab (an anti-PD-L1 antibody) in patients with solid malignancies. Data from the trial has shown that blockade of $A_{2A}R$ signaling can reduce tumor burden and enhance antitumor immunity (AACR Annual Meeting 2018, Abstract 3751). However, a clinical trial evaluating the safety and preliminary efficacy of preladenant alone and in combination with pembrolizumab in patients with advanced solid tumors was terminated based on failure of the data to support study endpoints (clinicaltrials.gov).

There remains a need for improved anticancer immunotherapies. The present disclosure addresses these and other needs by providing, in particular, improved $A_{2A}R$ selective antagonist compounds that are highly selective for the $A_{2A}$ receptor, are selective for the $A_{2A}$ receptor over the $A_{2B}$ receptor, have relatively low clearance, have good oral bioavailability, and/or exhibit reduced penetration of the blood-brain barrier such as evidenced by a low brain/plasma ratio after administration.

SUMMARY

In a first aspect, improved $A_{2A}R$-selective antagonist compounds are provided herein. In some embodiments, the $A_{2A}R$-selective antagonist compounds have the formula:

Formula I

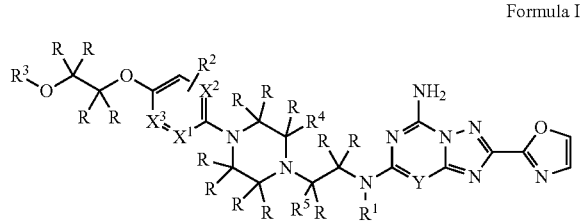

wherein R, in each instance, is independently selected from H and D;
$R^1$ is selected from —CH$_3$ and —CD$_3$;
$R^2$ is selected from the group consisting of H, F, Cl, —CF$_3$, —OCH$_3$, and —OCD$_3$;
$R^3$ is selected from hydrogen, —CH$_3$, —CD$_3$, and —CF$_3$;
$R^4$ and $R^5$ are each selected from H, D, or combine with the intervening atoms to form a 5-membered ring;
$X^1$, $X^2$ and $X^3$ are independently selected from —N— and —CH—;
Y is selected from —CH— and —N—.

In further embodiments, the $A_{2A}R$-selective antagonist compounds have the formula:

Formula Ia

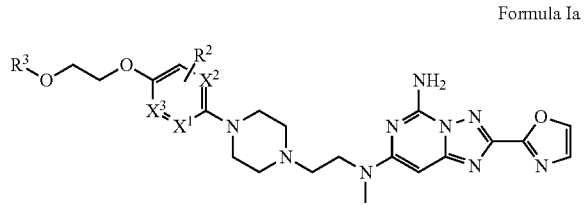

wherein:
$X^1$, $X^2$ and $X^3$ are independently selected from —N— and —CH—;
$R^2$ is selected from the group consisting of H, F, Cl, —CF$_3$, —OCH$_3$, and —OCD$_3$; and
$R^3$ is selected from —CH$_3$, —CD$_3$, and —CF$_3$.

In additional embodiments, the $A_{2A}R$-selective antagonist compounds have the formula:

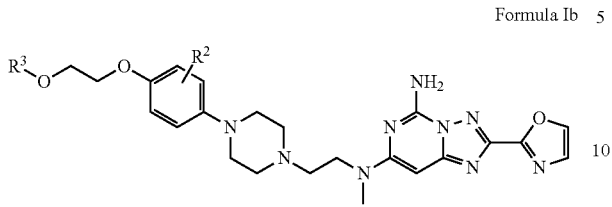

Formula Ib wherein:

$R^2$ is selected from the group consisting of F, Cl, —CF$_3$, —OCH$_3$, and —OCD$_3$; and $R^3$ is selected from —CH$_3$, —CD$_3$, and —CF$_3$.

In yet additional embodiments, the $A_{2A}R$-selective antagonist compounds have the formula:

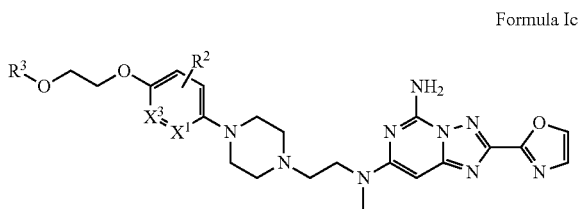

Formula Ic wherein:

one of $X^1$ or $X^2$ is —N— and the other of $X^1$ or $X^2$ is —CH—;

$R^2$ is selected from the group consisting of F, Cl, and —CF$_3$; and $R^3$ is selected from —CH$_3$, —CD$_3$, and —CF$_3$.

In further embodiments, the $A_{2A}R$-selective antagonist compounds have the formula:

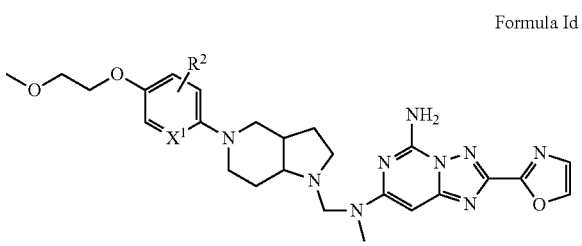

Formula Id wherein:

$X^1$ is selected from —N— and —CH—;

$R^2$ is selected from the group consisting of H, F, Cl, —CF$_3$, —OCH$_3$, and —OCD$_3$.

In yet additional embodiments, the $A_{2A}R$-selective antagonist compounds have the formula:

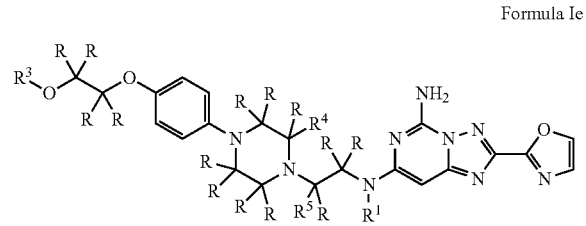

Formula Ie wherein:

R, in each instance, is independently selected from H and D;

$R^1$ is selected from —CH$_3$ and —CD$_3$;

$R^3$ is selected from —CH$_3$ and —CD$_3$; and $R^4$ and $R^5$ are each selected from H and D.

In some embodiments, the compound is a pharmaceutically acceptable salt.

In another aspect, compositions comprising a compound as described herein and at least one pharmaceutically acceptable excipient.

In a further aspect, a method of treating method of treating a subject in need thereof, comprising administering a therapeutically effective amount of any one or more of the compounds described herein. In some embodiments, the subject has cancer and the method is a method of treating cancer.

Additional embodiments of the present compounds, compositions, methods, and the like will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims.

DETAILED DESCRIPTION

Figure 1:
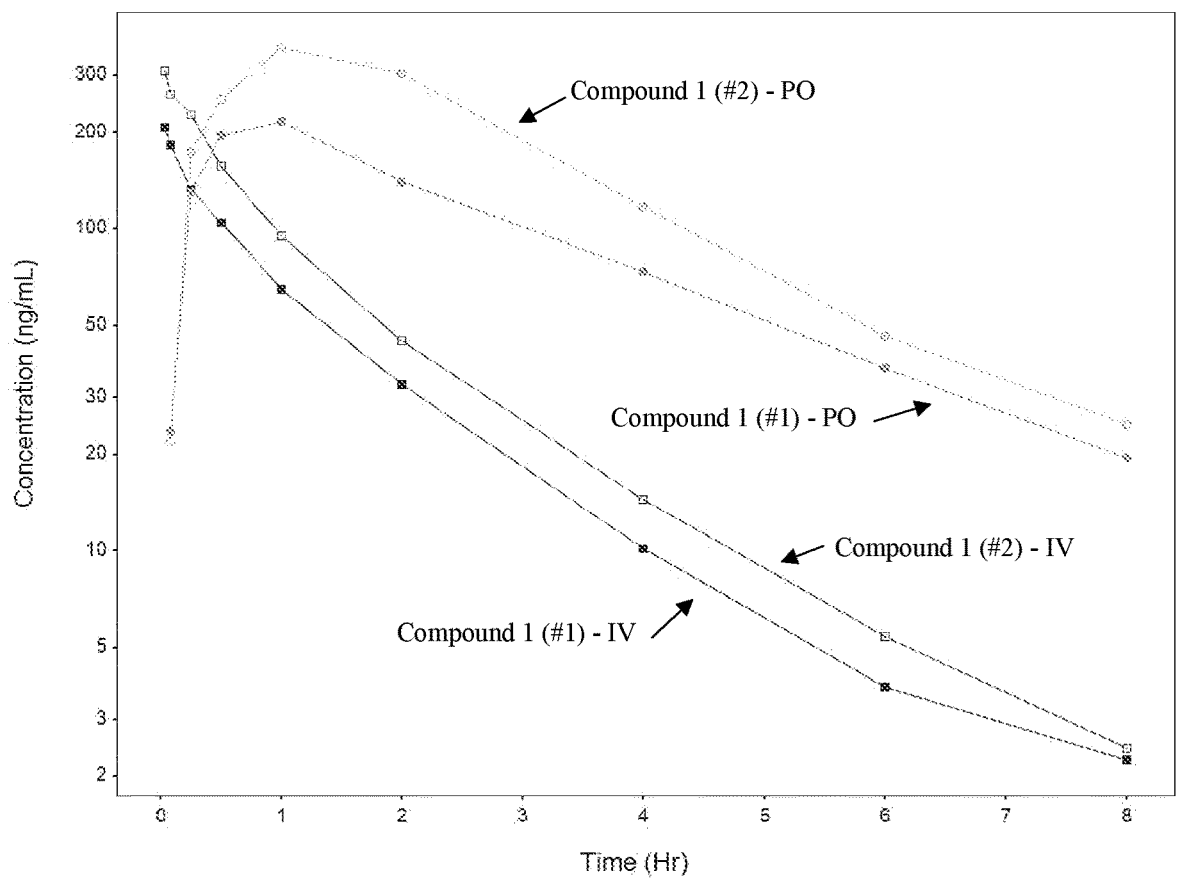
FIG. 1 is a plot of the plasma concentration (ng/mL) of $N^7$-(2-(4-(4-(2-methoxyethoxy)phenyl)piperazin-1-yl)ethyl)-$N^7$-methyl-2-(oxazol-2-yl)-[1,2,4]triazolo[1,5-c]pyrimidine-5,7-diamine (Compound 1) over time (Hr) following administration to mice of 0.5 mg/kg of Compound 1 intravenously (■ and □) or 2.5 mg/kg of Compound 1 orally via gavage (● and ○), as described in Example 28.

Before describing one or more aspects or embodiments of the present disclosure in detail, it should be noted that the presented disclosure is not intended to be limited to the particular synthetic techniques as such may vary as would be understood by one having ordinary skill in the art to which this disclosure applies.

In describing and claiming certain features of this disclosure, the following terminology will be used in accordance with the definitions described below unless indicated otherwise.

As used in this specification, the singular forms "a," "an," and "the" include plural referents unless the context clearly dictates otherwise.

As used herein, "adenosine A$_{2A}$ receptor selective antagonist", "A$_{2A}$R antagonist", or "A$_{2A}$R antagonist" are used interchangeably and refer to a receptor ligand that blocks or dampens a biological response of the A$_{2A}$R receptor. An "A$_{2A}$R selective antagonist" as used herein refers to an antagonist that selectively binds to the A$_{2A}$ receptor with greater affinity than any one or all of the A$_1$, A$_{2B}$ or A$_3$ receptors.

The phrases "pharmaceutically effective amount" and "pharmacologically effective amount" and "therapeutically effective amount" and "physiologically effective amount" are used interchangeably herein and refer to the amount of an A$_{2A}$R antagonist as described herein that is needed to provide a desired level of the substance in the bloodstream or in a target tissue to produce a desired biological or medicinal response. In particular, the amount of the A$_{2A}$R antagonist as described herein that is needed to provide effect in (i) blocking A$_{2A}$R signaling; (ii) significantly inhibiting or reducing A$_{2A}$R signaling; (iii) enhancing the maturation and generation of NK cells and/or enhance the cytotoxicity of NK cells; (iv) enhancing the generation of tumor-specific effector memory cells; (v) supporting CD8 T-cell survival and memory formation; and/or (vi) decrease or block the upregulation of Treg cells. The precise amount will depend upon numerous factors, such as for example, the particular condition being treated, the intended patient population, individual patient considerations, the components and physical characteristics of the therapeutic composition and particular combination to be administered, and the like, and may be readily determined by one skilled in the art.

The term "patient," or "subject" as used herein refers to a living organism suffering from or prone to a condition that can be prevented or treated by administration of a compound or composition as provided herein. Subjects include, but are not limited to, mammals (e.g., murines, simians, equines, bovines, porcines, canines, felines, and the like), and preferably are human.

A "physiologically cleavable" or "hydrolyzable" or "degradable" bond is a relatively labile bond that reacts with water (i.e., is hydrolyzed) under physiological conditions. The tendency of a bond to hydrolyze in water may depend not only on the general type of linkage connecting two atoms within a given molecule but also on the substituents attached to these atoms. Appropriate hydrolytically unstable or weak linkages may include but are not limited to carboxylate ester, phosphate ester, anhydrides, acetals, ketals, acyloxyalkyl ether, imines, orthoesters, peptides, oligonucleotides, thioesters, and carbonates.

A covalent "releasable" linkage, for example, in the context of a polyethylene glycol that may be covalently attached to an active moiety, is one that releases or detaches a polyethylene glycol polymer from the active moiety under physiological conditions, e.g., by any suitable mechanism, at a rate that is clinically useful and includes, for example and without limitation, hydrolyzable bonds and enzymatically degradable linkages.

An "enzymatically degradable linkage" means a linkage that is subject to degradation by one or more enzymes.

A "stable" linkage or bond refers to a chemical bond that is substantially stable in water, that is to say, does not undergo hydrolysis under physiological conditions to any appreciable extent over an extended period of time. Examples of hydrolytically stable linkages generally include but are not limited to the following: carbon-carbon bonds (e.g., in aliphatic chains), ethers, amides, amines, and the like. Generally, a stable linkage is one that exhibits a rate of hydrolysis of less than about 1-2% per day under physiological conditions. Hydrolysis rates of representative chemical bonds can be found in most standard chemistry textbooks.

As used herein in reference to treatment of a subject having cancer, the terms "treatment," "treat," and "treating" are meant to include the full spectrum of intervention for the cancer from which the subject is suffering, such as administration of the combination to alleviate, slow, stop, or reverse one or more symptoms of the cancer or to delay the progression of the cancer even if the cancer is not actually eliminated. Treatment can include, for example, a decrease in the severity of a symptom, the number of symptoms, or frequency of relapse, e.g., the inhibition of tumor growth, the arrest of tumor growth, or the regression of already existing tumors.

A "functional group" is a group that may be used, under normal conditions of organic synthesis, to form a covalent linkage between the structure to which it is attached and another structure, which typically bears a further functional group. The functional group generally includes multiple bond(s) and/or heteroatom(s). Preferred functional groups for use in the polymers of the invention are described below.

The term "reactive" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

A "protecting group" is a moiety that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, i-butyl, t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl; substituted phenyl; and the like. For substitutions on a phenyl ring, the substituents may be in any orientation (i.e., ortho, meta, or para).

As used herein, "alkenyl" refers to a branched or unbranched hydrocarbon group of 1 to 15 atoms in length, containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon group of 2 to 15 atoms in length, containing at least one triple bond, ethynyl, n-propynyl, isopropynyl, n-butynyl, isobutynyl, octynyl, decynyl, and so forth.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom that is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Substantially" or "essentially" means nearly totally or completely, for instance, 95% or greater of a given quantity.

Similarly, "about" or "approximately" as used herein means within plus or minus 5% of a given quantity.

"Optional" or "optionally" means that the subsequently described circumstance may but need not necessarily occur, so that the description includes instances where the circumstance occurs and instances where it does not.

Overview

The instant disclosure is directed to, among other things, providing compounds, compositions, and methods relating to the treatment of cancer, comprising $A_{2A}R$-selective antagonists. Such compounds, compositions, and methods will ideally possess several advantageous and unpredictable features, such as, for example, at least one if not more of the following: (i) effective in blocking $A_{2A}R$ signaling; (ii) being highly selective for the $A_{2A}$ receptor; (iii) selectivity for the $A_{2A}$ receptor over the $A_{2B}$ receptor; (iv) enhancing the generation of tumor-specific effector memory cells; (v) supporting CD8 T-cell survival and memory formation; (vi) decreasing or blocking the upregulation of Treg cells; (vii) exhibiting reduced crossing or penetration of the blood-brain barrier to provide reduced CNS exposure to the $A_{2A}R$-selective antagonists; and (viii) exhibiting improved pharmacokinetic properties including improved solubility and/or reduced clearance. Surprisingly, the presently described compounds possess a unique combination of advantageous properties, to be described in greater detail below.

Adenosine $A_{2A}$ receptor ($A_{2A}R$) antagonists such as preladenant (Merck) have undergone advanced clinical testing as potential therapies for treating Parkinson's disease. However, $A_{2A}R$ antagonists previously studied exhibited significant drawbacks including poor pharmacokinetic (PK) properties exemplified by low aqueous solubility (WO 2016/209787) and high clearance in preclinical species (Yang et al., Arch Pharmacol. 375(2):133-133 (2007)).

Upon profiling scaffolds of multiple $A_{2A}R$ antagonists, compounds related to preladenant or ZM241385 were identified as a starting point for modification to improve at least PK properties such as improved solubility and reduced clearance, and/or to improve $A_{2A}R$ selectivity as compared to the known compounds.

Therapeutic Compounds, Compositions, and Methods of Use

In a first aspect, compounds having effect as $A_{2A}R$ selective antagonists are described herein.

Preladenant (Merck), a selective antagonist of the adenosine $A_{2A}$ receptor was researched as a potential treatment of Parkinson's disease. The structure of preladenant is:

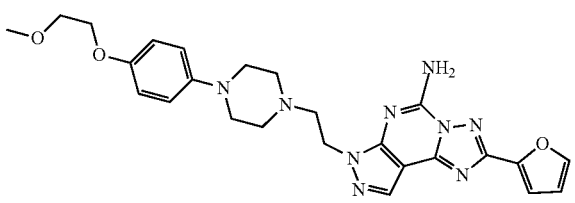

However, clinical trials provided no evidence for the efficacy of preladenant as a monotherapy (Stocchi et al., Neurology, 88(23):2198-2206 (2017)). Further, ZM241385, having the structure

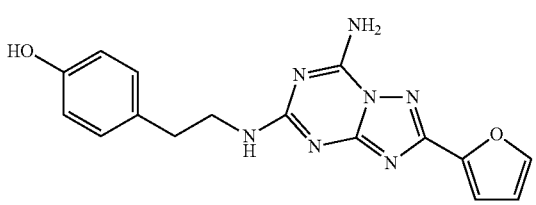 [SMILES: Nc1nc(NCCc2ccc(O)cc2)nc2nc(-c3ccco3)nn12]

was developed as a dual $A_{2A}R/A_{2A}R$ receptor antagonist. However, ZM241385 exhibited poor PK properties in very low aqueous solubility as well as significant phase 2 metabolism via glucuronidation of phenol.

It was surprisingly found that compounds as described herein that are structurally similar to preladenant or ZM241385 with modification of the tetrahydrofuran to an oxazole provide/retain efficacy as an $A_{2A}R$ selective antagonist as well as exhibit improved pharmacokinetic (PK) properties such as solubility and reduced clearance as compared to previous compounds.

Generally, compounds disclosed in accordance with the present disclosure have the formula:

Formula I

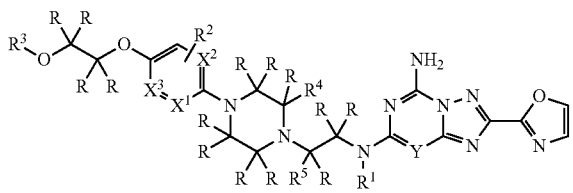

wherein R, in each instance, is independently selected from hydrogen and deuterium;
$R^1$ is selected from —CH$_3$ or —CD$_3$;
$R^2$ is selected from the group consisting of hydrogen, halo, alkyl, substituted alkyl, alkoxy, and substituted alkoxy;
$R^3$ is an alkyl or substituted alkyl;
$R^4$ and $R^5$ are each independently selected from hydrogen or deuterium, or taken together combine to form a fused optionally substituted heterocycle; $X^1$, $X^2$ and $X^3$ are e.g. independently selected from —N— and —CH—; and Y is selected from —CH— and —N—.

In one or more embodiments, $R^2$ is selected from the group consisting of H, F, Cl, —CF$_3$, —OCH$_3$, and —OCD$_3$.
In some embodiments, $R^3$ is selected from —CH$_3$, —CD$_3$, and —CF$_3$. In additional embodiments, $R^3$ is selected from —CH$_3$, —CD$_3$, and —CF$_3$. In further embodiments, $R^4$ and $R^5$ are each selected from H, D, or combine with any intervening atoms to form a 5-membered ring.

In further embodiments, $R^4$ and $R^5$ taken together combine to form a pyrrolidine. In still further embodiments, $R^4$ and $R^5$ taken together combine to form a pyrrolidine, and together with the adjoining heterocycle form a fused heterocyclic ring. In one particular embodiment, the fused heterocyclic ring is formed by the pyrrolidine formed by $R^4$ and $R^5$ and the adjacent pyrazine.

In additional embodiments, described herein are compounds having effect as $A_{2A}R$-selective having the formula:

Formula Ia

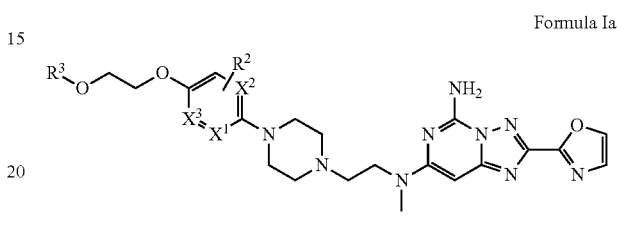

wherein:
$X^1$, $X^2$ and $X^3$ are e.g. independently selected from N and —CH—;
$R^2$ is selected from the group consisting of H, F, Cl, —CF$_3$, —OCH$_3$, and —OCD$_3$; and
$R^3$ is selected from —CH$_3$, —CD$_3$, and —CF$_3$.

In further embodiments, described herein are compounds having effect as $A_{2A}R$-selective activity having the formula:

Formula Ib wherein:
$R^2$ is selected from the group consisting of F, Cl, —CF$_3$, —OCH$_3$, and —OCD$_3$; and
$R^3$ is selected from —CH$_3$, —CD$_3$, and —CF$_3$.

In even further embodiments, described herein are compounds having effect as $A_{2A}R$-selective having the formula:

Formula Ic wherein:
one of $X^1$ or $X^2$ is N and the other of $X^1$ or $X^2$ is —CH—;
$R^2$ is selected from the group consisting of F, Cl, and —CF$_3$; and
$R^3$ is selected from —CH$_3$, —CD$_3$, and —CF$_3$.

In additional embodiments, described herein are compounds having effect as $A_{2A}R$-selective activity having the formula:

Formula Id

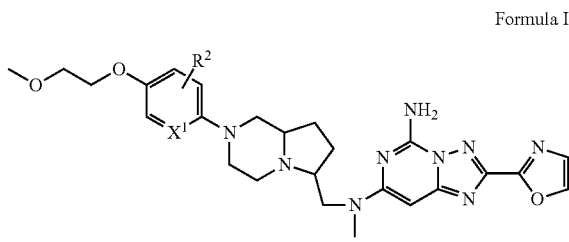

wherein:

X¹ is selected from N and —CH—; and

R² is selected from the group consisting of H, F, Cl, —CF₃, —OCH₃, and —OCD₃.

In further embodiments, described herein are compounds having effect as $A_{2A}R$-selective activity having the formula:

Formula Ie

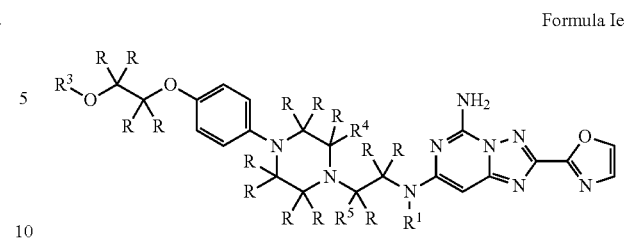

wherein:

R, in each instance, is independently selected from H and D;

R¹ is selected from —CH₃ and —CD₃;

R³ is selected from —CH₃ and —CD₃; and

R⁴ and R⁵ are each selected from H and D.

In certain embodiments, the compounds of Formula I are selected from compounds 1-24 as shown in Table 1.

TABLE 1

Exemplary compounds

| Compound No. | Chemical Structure |
| --- | --- |
| 1 | 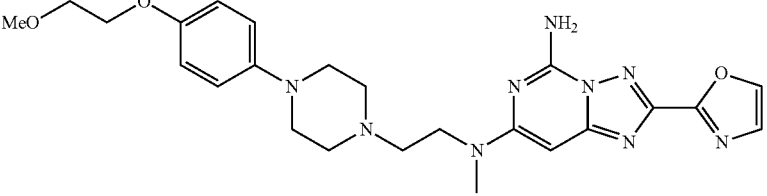 |
| 2 | 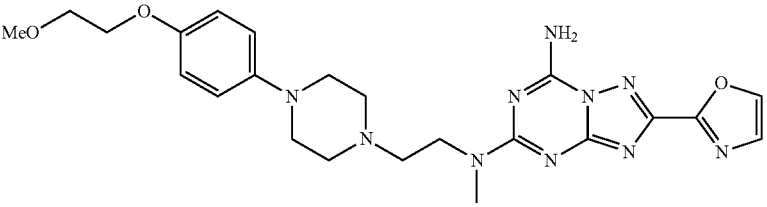 [SMILES: COCCOc1ccc(N2CCN(CCN(C)c3nc(N)n4nc(-c5ncco5)nc4n3)CC2)cc1] |
| 3 | 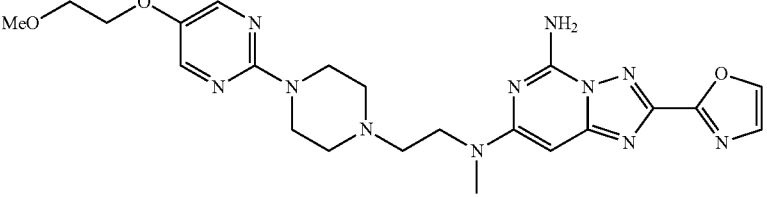 |
| 4 | 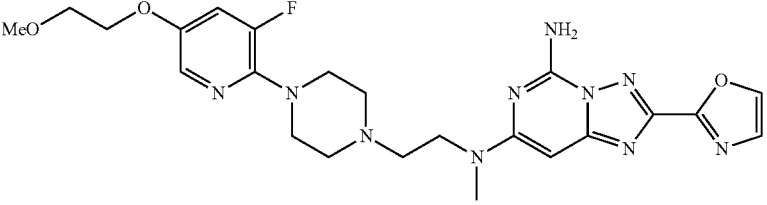 |

TABLE 1-continued
Exemplary compounds
| Compound No. | Chemical Structure |
|---|---|
| 5 | 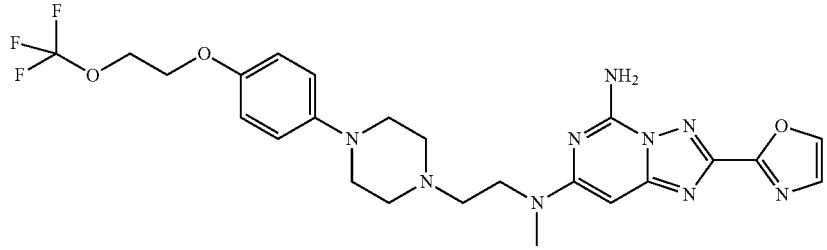 [SMILES: CN(CCN1CCN(c2ccc(OCCOC(F)(F)F)cc2)CC1)c1cc2nc(-c3ncco3)nn2c(N)n1] |
| 6 | 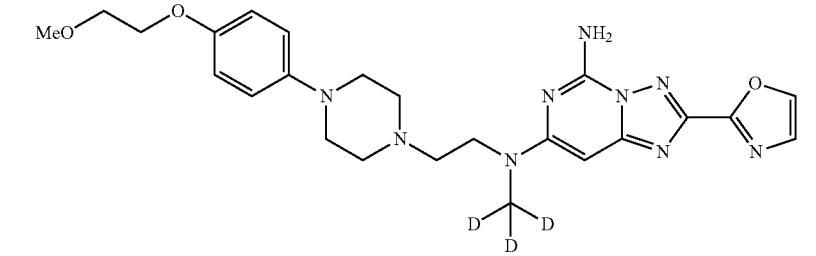 [SMILES: [2H]C([2H])([2H])N(CCN1CCN(c2ccc(OCCOC)cc2)CC1)c1cc2nc(-c3ncco3)nn2c(N)n1] |
| 7 | 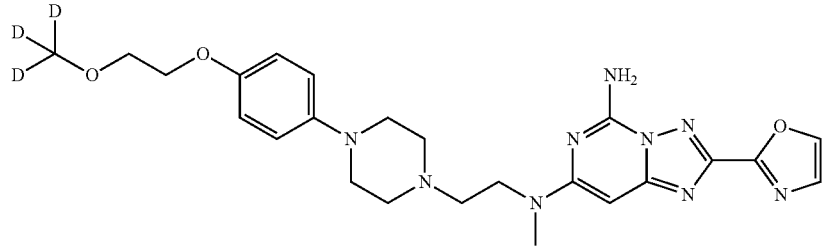 [SMILES: [2H]C([2H])([2H])OCCOc1ccc(N2CCN(CCN(C)c3cc4nc(-c5ncco5)nn4c(N)n3)CC2)cc1] |
| 8 | 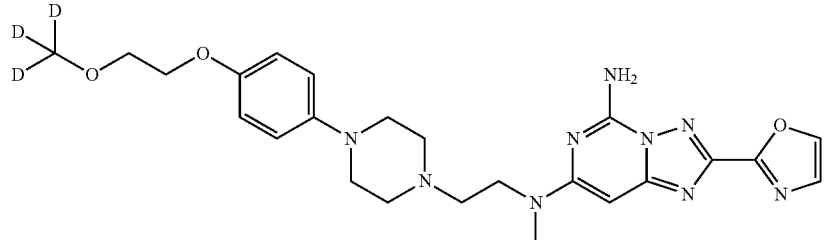 |
| 9 | 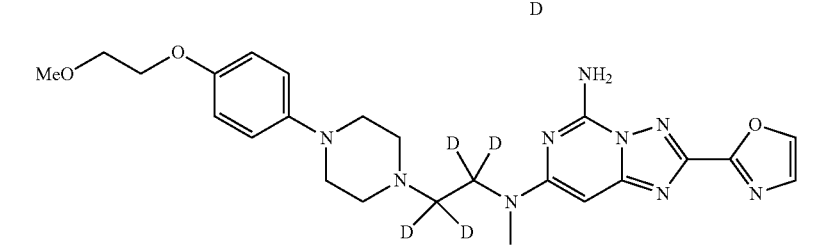 |
| 10 | 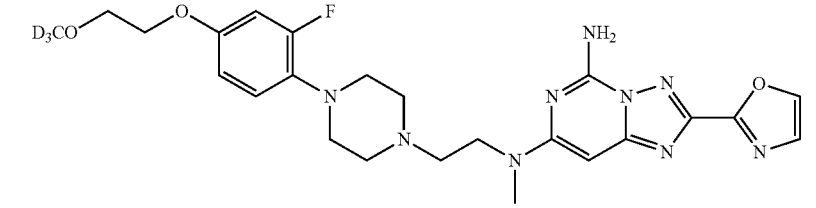 |

TABLE 1-continued

Exemplary compounds

| Compound No. | Chemical Structure |
| --- | --- |
| 11 | 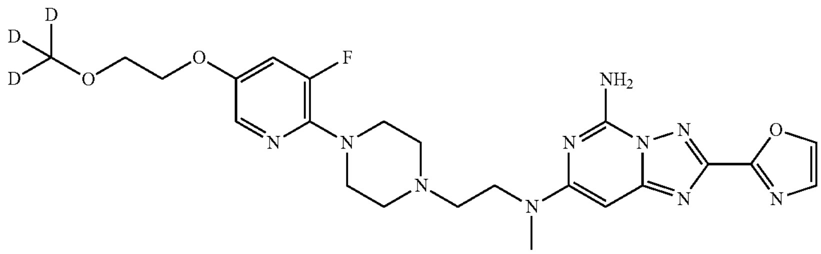 [SMILES: [2H]C([2H])([2H])OCCOc1cnc(N2CCN(CCN(C)c3cc4nc(-c5ncco5)nn4c(N)n3)CC2)c(F)c1] |
| 12 | 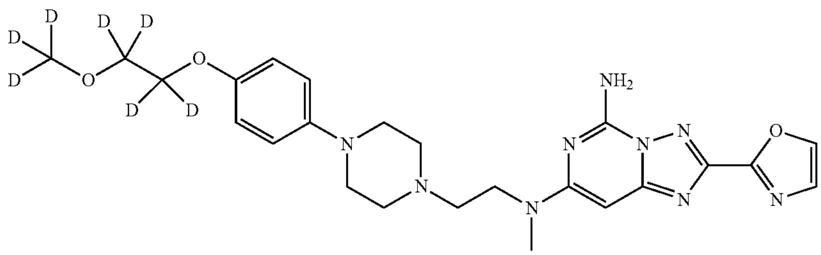 [SMILES: [2H]C([2H])([2H])OC([2H])([2H])C([2H])([2H])Oc1ccc(N2CCN(CCN(C)c3cc4nc(-c5ncco5)nn4c(N)n3)CC2)cc1] |
| 13 | 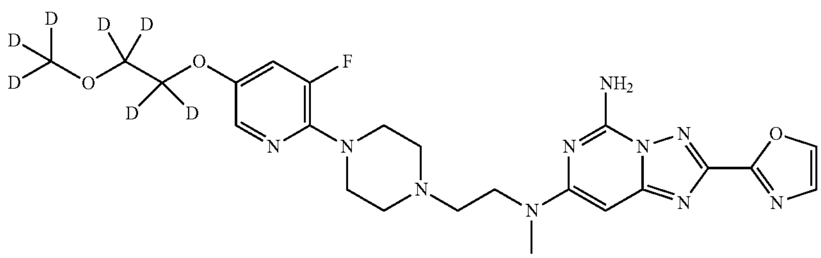 [SMILES: [2H]C([2H])([2H])OC([2H])([2H])C([2H])([2H])Oc1cnc(N2CCN(CCN(C)c3cc4nc(-c5ncco5)nn4c(N)n3)CC2)c(F)c1] |
| 14 | 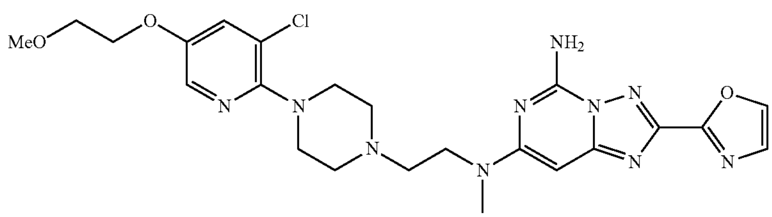 [SMILES: COCCOc1cnc(N2CCN(CCN(C)c3cc4nc(-c5ncco5)nn4c(N)n3)CC2)c(Cl)c1] |
| 15 | 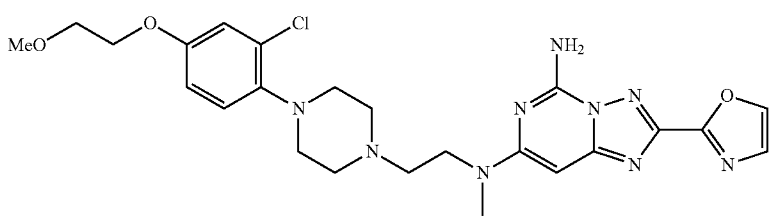 |
| 16 | 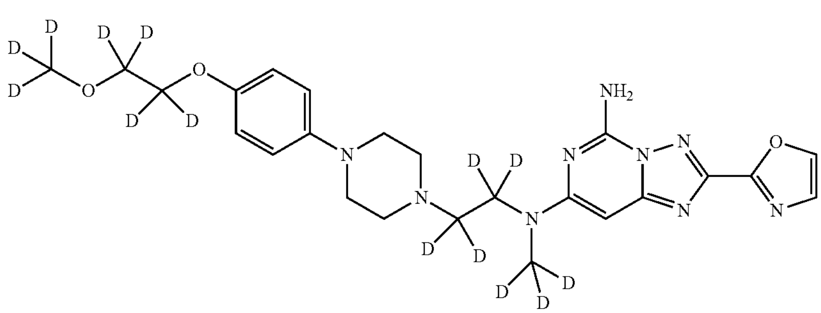 [SMILES: [2H]C([2H])([2H])OC([2H])([2H])C([2H])([2H])Oc1ccc(N2CCN(C([2H])([2H])C([2H])([2H])N(c3cc4nc(-c5ncco5)nn4c(N)n3)C([2H])([2H])[2H])CC2)cc1] |

TABLE 1-continued
Exemplary compounds
| Compound No. | Chemical Structure |
|---|---|
| 17 | 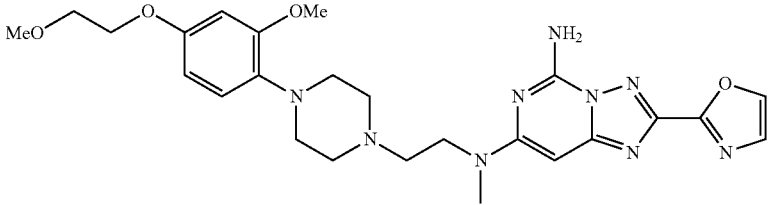 [SMILES: COCCOc1ccc(N2CCN(CCN(C)c3cc4nc(-c5ncco5)nn4c(N)n3)CC2)c(OC)c1] |
| 18 | 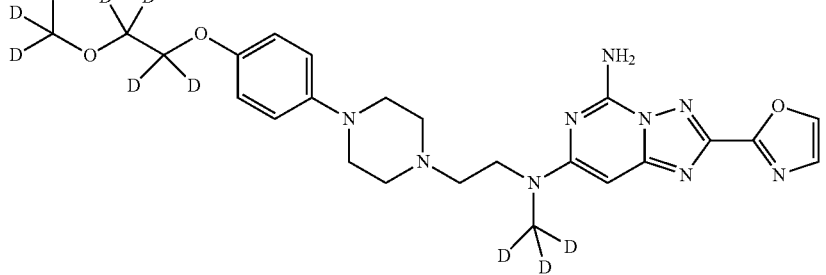 |
| 19 | 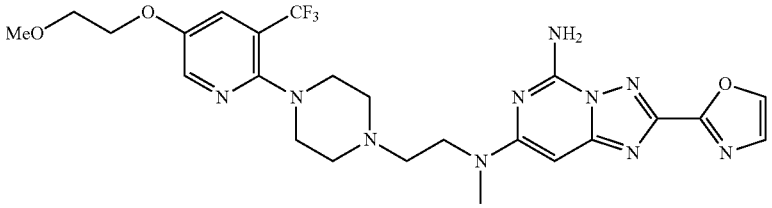 |
| 20 | 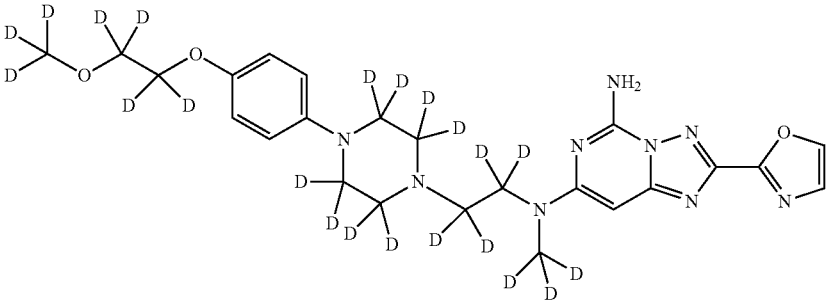 [SMILES: [2H]C([2H])([2H])OC([2H])([2H])C([2H])([2H])Oc1ccc(N2C([2H])([2H])C([2H])([2H])N(C([2H])([2H])C([2H])([2H])N(c3cc4nc(-c5ncco5)nn4c(N)n3)C([2H])([2H])[2H])C([2H])([2H])C2([2H])[2H])cc1] |
| 21 | 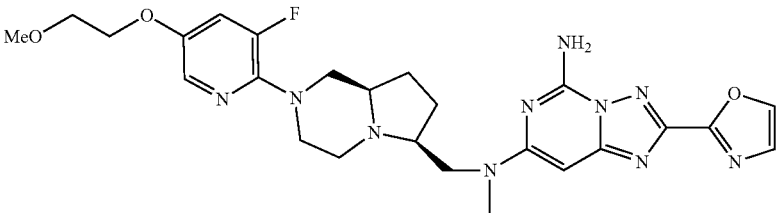 [SMILES: COCCOc1cnc(N2CCN3[C@H](CC[C@H]3CN(C)c3cc4nc(-c5ncco5)nn4c(N)n3)C2)c(F)c1] |
| 22 | 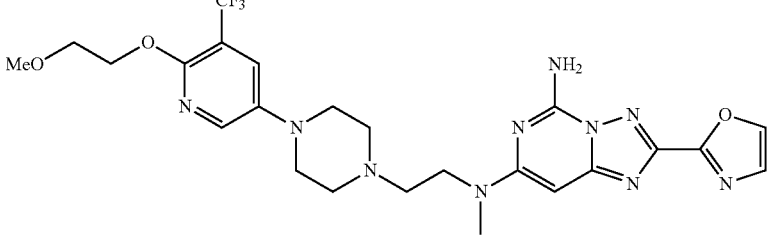 |

TABLE 1-continued

Exemplary compounds

| Compound No. | Chemical Structure |
|---|---|
| 23 | 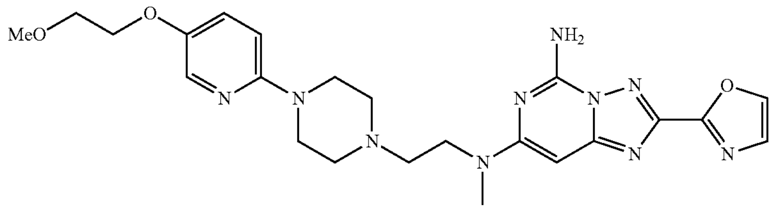 [SMILES: COCCOc1ccc(N2CCN(CCN(C)c3cc4nc(-c5ncco5)nn4c(N)n3)CC2)nc1] |
| 24 | 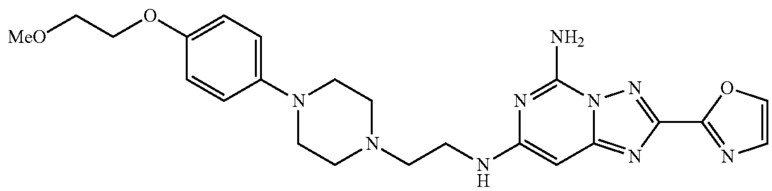 [SMILES: COCCOc1ccc(N2CCN(CCNc3cc4nc(-c5ncco5)nn4c(N)n3)CC2)cc1] |
| 25 | 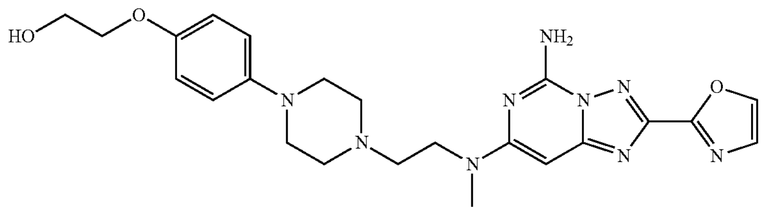 [SMILES: CN(CCN1CCN(c2ccc(OCCO)cc2)CC1)c1cc2nc(-c3ncco3)nn2c(N)n1] |

The compounds described herein, if chiral, may be in a racemic mixture, or an optically active form, for example, a single optically active enantiomer, or any combination or ratio of enantiomers (i.e., scalemic mixture). In addition, the compound may possess one or more geometric isomers. With respect to geometric isomers, a composition can comprise a single geometric isomer or a mixture of two or more geometric isomers.

The compounds described herein can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Every compound as described herein is meant to expressly include its pharmaceutically acceptable salt. Typically, such salts are formed by reaction with a pharmaceutically-acceptable acid or an acid equivalent. The term "pharmaceutically-acceptable salt" in this respect, will generally refer to the relatively non-toxic, inorganic and organic acid addition salts. These salts can be prepared in situ in the administration vehicle or the dosage form manufacturing process, or by separately reacting an $A_{2A}R$ antagonist as described herein with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, oxylate, mesylate, glucoheptonate, lactobionate, and laurylsulphonate salts and the like. (See, for example, Berge et al. (1977) "*Pharmaceutical Salts*", *J. Pharm. Sci.* 66:1-19). Thus, salts as described may be derived from inorganic acids such as hydrochloride, hydrobromic, sulfuric, sulfamic, phosphoric, nitric, and the like; or prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. The salts may be in some cases hydrates or solvates. The term "solvate" refers to a complex formed by the combining of a compound described herein and a solvent. The term "hydrate" refers to the complex formed by the combining of a compound described herein and water.

The compounds as described herein may be prepared using techniques known to one of skill in the art. In some embodiments, the compounds described herein may be prepared in accordance with the approaches described in the examples section. Example 1 provides two exemplary methods of preparing compounds as described herein. Further examples of preparing specific compounds are provided in Examples 2-26.

The compounds described herein have been discovered to possess certain notable and advantageous features. As shown in Example 27, the compounds described herein have been found to exhibit a substantial and unexpected improvement in plasma pharmacokinetic parameters. Oral bioavailability (F %) for Compounds 1, 4, and 19 was greater than 50% with oral bioavailability of Compounds 1, 4, and 19 being greater than 75%.

Compound 1 showed a substantial improved exposure and bioavailability when compared with the known furan analog 2-(furan-2-yl)-$N^7$-(2-(4-(4-(2-methoxyethoxy)phenyl)piperazin-1-yl)ethyl)-$N^7$-methyl-[1,2,4]triazolo[1,5-c]pyrimidine-5,7-diamine (reference compound) having the structure:

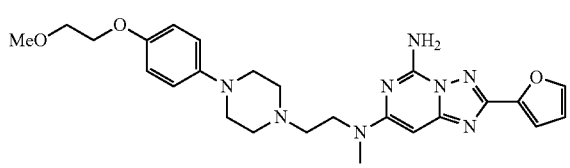 [SMILES: COCCOc1ccc(N2CCN(CCN(C)c3cc4nc(-c5ccco5)nn4c(N)n3)CC2)cc1]

(compound 16h in B. R. Neustadt et al, Bioorganic & Medicinal Chemistry Letters 19 (2009) 967-971), as well as a diminished brain penetration. The metabolically labile furan moiety was replaced by several heterocycles, yielding compounds with comparable potency and physicochemical properties but with no further improvement over the PK profile of the furan. Although the substitution of the furan by an oxazole as with the compounds described herein might be expected to diminish the brain penetration, the overall improvement in the metabolic parameters could not be anticipated.

As seen in Table 2, exemplary compounds described herein exhibit improved metabolic parameters as compared to a reference furan compound:

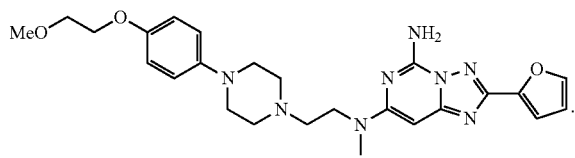 [SMILES: COCCOc1ccc(N2CCN(CCN(C)c3cc4nc(-c5ccco5)nn4c(N)n3)CC2)cc1]

TABLE 2

Plasma Pharmacokinetic Parameters of Certain Compounds

| Compound | Moiety | AUC (ng * hr/mL) | CL (mL/min/kg) | % F | B/P (1 h) |
|---|---|---|---|---|---|
| 1 | phenyl | 969[1] | 31[1] | 71[1] | 0.06[1] |
| 4 | F-pyridine | 898 | 34 | 78 | 0.04 |
| 14 | Cl-pyridine | 1477 | 17 | 56 | 0.025 |
| 19 | CF$_3$-pyridine | 4977[1] | 7 | 83[1] | 0.01 |
| Reference | | 408 | 34 | 34 | 0.17 |

[1]Represents the average of experiments

A similar unexpected result was obtained when the phenyl ring present on Compound 1 was replaced with a halogen substituted pyridine. The halogen was previously introduced on the phenyl ring with the aim of blocking a possible metabolic soft-spot, with similar results observed as for Compound 1 in terms of exposure, clearance and bioavailability (Compound 10 and Compound 15). The substituted pyridine ring was designed to modulate the lipophilicity and polar surface area, as well as to address metabolic soft-spot concerns. Clearance and bioavailability parameters remain similar between substituted phenyl and pyridine (Compound 4 and Compound 14) analogs, which span a range in cLogP of 2.7-3.2. It was therefore surprising the significant improvement in exposure and clearance observed for the more lipophilic Compound 19. Paradoxically, the brain-to-plasma ratio (B/P) was also greatly reduced even with a cLogP higher than Compound 4 and comparable polar surface area. A compound is commonly deemed to be a brain penetrant if the brain-to-blood/plasma concentration ratio (B/P) is greater than 0.04 using methods as known in the art (Schaffer, Annual Reports in Medicinal Chemistry, 45:55-70, 2010).

These results clearly demonstrate the difficulty in predicting the improved metabolic profile of the compounds described herein, as exemplified by Compound 19, by means of traditional medicinal chemistry efforts to modulate physicochemical properties and remove metabolic soft spots.

Figure 6:
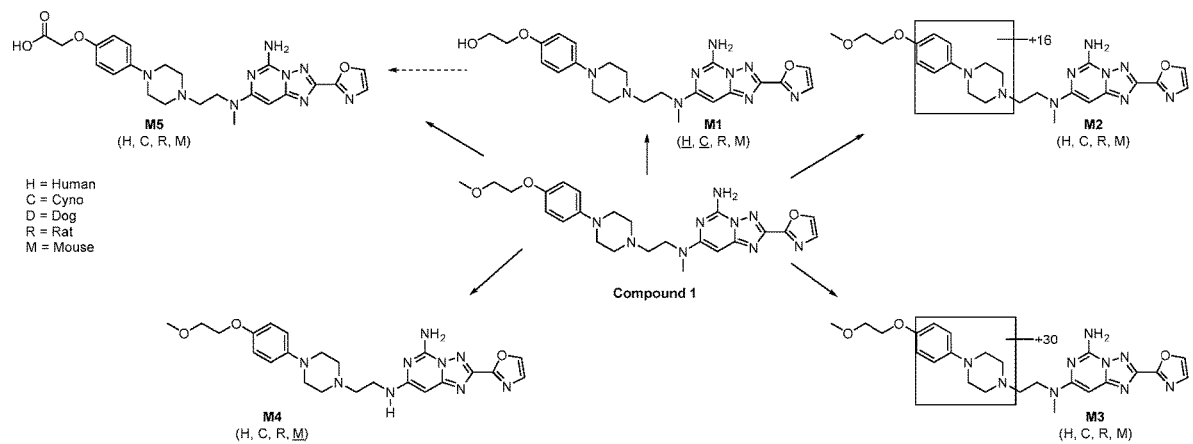
FIG. 6 is an illustration of the predominant metabolites (M1, M2, M3, M4 and M5) of compound 1 as observed after incubation of compound 1 with human, cynomolgus (cyno), dog, rat or mouse hepatocytes and liver microsomes for 1-2 hours.

In some embodiments, a metabolite of any one of the compounds as described herein is contemplated. Determination of metabolites of the presently described compounds may be made by any method as known in the art. In one exemplary embodiment, the metabolites of a compound may be determined by incubating a compound with liver microsomes or hepatocytes for 1-2 hours. The resulting metabolite identity and/or profile may be analyzed by a suitable method including but not limited to liquid chromatography (LC), mass spectrometry (MS), UV chromatography, etc. In some embodiments, the analysis may be performed by liquid chromatography-tandem mass spectrometry (LC/MS/MS). As shown in FIG. 6, the predominant metabolites (M1, M2, M3, M4, and M5) were determined for Compound 1. The underline indicates the predominant species for the particular metabolite. Briefly, compound 1 was incubated with human, cynomolgus monkey (cyno), dog, rat or mouse hepatocytes and liver microsomes for 1-2 hours. The resulting metabolites were identified and the metabolite profile was determined by a combination of one or more of the above referenced methods. The boxes indicate expected oxidation areas for M2 and M3. Synthesis of the metabolite identified as M1 is presented in Example 26 (Compound 25). Synthesis of the metabolite identified as M4 is presented in Example 25 (Compound 24).

In a second aspect, a composition comprising at least one of the compounds described herein is described herein. In further embodiments, one or more of the compounds described herein may be included in compositions comprising the compounds and one or more pharmaceutically acceptable excipients and/or carriers. In some embodiments, the compound itself will be in a solid form (e.g., a precipitate), which can be combined with a suitable pharmaceutical excipient that can be in either solid or liquid form.

The amount of the compound in the composition will vary depending on a number of factors, but will optimally be a therapeutically effective dose when the composition is stored in a unit dose container. A therapeutically effective dose can be determined experimentally by repeated administration of increasing amounts of the compound in order to determine which amount produces a clinically desired endpoint.

Exemplary excipients include, without limitation, those selected from the group consisting of carbohydrates, inorganic salts, antimicrobial agents, antioxidants, surfactants, buffers, acids, bases, and combinations thereof as known in the art.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient will be present in the composition in an amount of about 1% to about 99% by weight, in certain embodiments from about 5%-98% by weight, in certain embodiments from about 15-95% by weight of the excipient, and in certain embodiments concentrations less than 30% by weight.

These foregoing pharmaceutical excipients along with other excipients and general teachings regarding pharmaceutical compositions are described in "Remington: The Science & Practice of Pharmacy", 19$^{th}$ ed., Williams & Williams, (1995), the "Physician's Desk Reference", 52$^{nd}$ ed., Medical Economics, Montvale, NJ (1998), and Kibbe, A. H., Handbook of Pharmaceutical Excipients, 3$^{rd}$ Edition, American Pharmaceutical Association, Washington, D.C., 2000.

The pharmaceutical compositions can take any number of forms and the invention is not limited in this regard. In certain embodiments, preparations are in a form suitable for oral administration such as a tablet, caplet, capsule, gel cap, troche, dispersion, suspension, solution, elixir, syrup, lozenge, transdermal patch, spray, suppository, and powder. Oral dosage forms are preferred for those compounds that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts. In preferred embodiments, the compounds or compositions are formulated for oral administration.

Tablets and caplets, for example, can be manufactured using standard tablet processing procedures and equipment. Direct compression and granulation techniques are preferred when preparing tablets or caplets containing the compounds described herein. In addition to the compound, the tablets and caplets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum®. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also suitable oral dosage forms, in which case the compound-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, each typically being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The compound can also be administered through the skin using conventional transdermal patch or other transdermal delivery system as known in the art.

The composition can also be formulated into a suppository for rectal administration as known in the art.

In a third aspect, methods of treating a subject having cancer is provided herein. In accord with method described herein, the compounds are administered to a patient in a therapeutically effective amount. Further disclosed herein are methods of treatment comprising administering a compound provided herein to a patient suffering from a condition that is responsive to treatment with the compound. The method comprises administering, orally as an example, a therapeutically effective amount of the compound (in certain embodiments provided as part of a pharmaceutical preparation or composition). Other modes of administration as known in the art are also contemplated, including, but not limited to, pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

The method of administering may be used to treat any condition that can be remedied or prevented by administration of an $A_{2A}R$-selective antagonist.

In some embodiments, the administering is effective to stimulate NK activation and proliferation. In some additional embodiments, the administering is effective to support CD8 T-cell survival and memory formation. In some further embodiments, the administering is effective to result in a decrease in the number of tumor cells. In some related embodiments, the administering results in a 3-fold or greater reduction, or more preferably a 5-fold or greater reduction, or more preferably a 7-fold or greater reduction, in the number of tumor cells in the subject when compared to the number of tumor cells prior to the administration. In some further embodiments, the administering is effective to induce proliferation of NK cells (i.e., to increase the number of NK cells) and to activate their tumor cell killing capability, e.g., in bone marrow tissue.

For example, an improvement in the cancer or a cancer-related disease may be characterized as a complete or partial response. "Complete response" refers to an absence of clinically detectable disease with normalization of any previously abnormal radiographic studies, bone marrow, and cerebrospinal fluid (CSF) or abnormal monoclonal protein measurements. "Partial response" refers to at least about a 10%, 20%, 30%, 40%, 50%, 60%, 70%, 80%, or 90% decrease in all measurable tumor burden (i.e., the number of malignant cells present in the subject, or the measured bulk of tumor masses or the quantity of abnormal monoclonal protein) in the absence of new lesions. The term "treatment" contemplates both a complete and a partial response.

Generally, a therapeutically effective amount of the compound will range from about 1-500 mg, inclusive. In some embodiments, a therapeutically effective amount of the compound will range from about 1-200 mg, about 1-150 mg, about 1-100 mg, about 1-75 mg, about 1-50 mg, about 1-25 mg, about 1-10 mg, about 1-5 mg, about 5-500 mg, about 5-200 mg, about 5-150 mg, about 5-100 mg, about 5-75 mg, about 5-50 mg, about 5-25 mg, about 5-10 mg, about 10-500 mg, about 10-200 mg, about 10-150 mg, about 10-100 mg, about 10-75 mg, about 10-50 mg, about 10-25 mg, about 25-500 mg, about 25-200 mg, about 25-150 mg, about 25-100 mg, about 25-75 mg, about 25-50 mg, about 50-500 mg, about 50-200 mg, about 50-150 mg, about 50-100 mg, about 50-75 mg, about 75-500 mg, about 75-200 mg, about 75-150 mg, about 75-100 mg, about 100-500 mg, about 100-200 mg, about 100-150 mg, about 150-500 mg, about 150-200 mg, or about 200-500 mg. In some particular embodiments, a therapeutically effective amount may be selected from 1 mg, 5 mg, 10 mg, 15 mg, 20 mg, 25 mg, 50 mg, 75 mg, 100 mg, 125 mg, 150 mg, 200 mg, 250 mg, or 500 mg. A given dose can be periodically administered up until, for example, the clinician determines an appropriate endpoint (e.g., cure, regression, partial regression, and so forth) is achieved.

The actual dose of the compound to be administered will vary depending upon the age, weight, and general condition of the subject as well as the severity of the condition being treated, the judgment of the health care professional, and compound being administered. Therapeutically effective amounts are known to those skilled in the art and/or are described in the pertinent reference texts and literature.

With reference to the doses referenced in the examples herein, one of ordinary skill in the art could convert the animal doses (e.g. mouse) to a corresponding dose in humans using conversions as known in the art (e.g. Nair et al., J. Basic and Clin. Pharmacy (2016) 7:27-31).

With regard to the frequency of administering, the compounds can be administered in a variety of dosing schedules depending on the judgment of the clinician, needs of the patient, and so forth. The specific dosing schedule will be known by those of ordinary skill in the art or can be determined experimentally using routine methods. For example, a clinician can decide to administer the compounds relatively infrequently and progressively shorten the period between dosings as tolerated by the patient. Exemplary dosing schedules include, without limitation, administration once per day, every other day, every three days, every four days, every five days, every six days or once per week.

The treatment described herein can continue for as long as the clinician overseeing the patient's care deems the treatment method is effective. Non-limiting parameters that indicate the treatment method is effective include the following: tumor shrinkage (in terms of weight and/or volume); a decrease in the number of individual tumor colonies; tumor elimination; and progression-free survival.

Exemplary conditions for treatment are cancers, such as, for example, a sarcoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, colon cancer, colorectal cancer, prostate cancer, squamous cell cancer, basal cell cancer, head and neck cancer, adenocarcinoma, sweat gland cancer, sebaceous gland cancer, papillary cancer, papillary adenocarcinomas, cystadenocarcinoma, medullary cancer, bronchogenic cancer, renal cell cancer, hepatoma, bile duct cancer, choriocarcinoma, seminoma, embryonal cancer, Wilms' tumor, cervical cancer, testicular cancer, lung cancer, small cell lung cancer, non-small cell lung cancer, bladder cancer, epithelial cancer, glioma, astrocytoma, medulloblastoma, craniopharyngioma, ependymoma, pinealoma, hemangioblastoma, acoustic neuroma, oligodendroglioma, meningioma, melanoma (including, for example, uveal melanoma, mucosal melanoma, and leptomeningeal melanoma), neuroblastoma, retinoblastoma, and leukemias.

In one particular method, the compounds or compositions are used to treat a hematological malignancy such as a leukemia or lymphoma. In yet another method, the compounds or compositions are used to treat a solid cancer. In some embodiments, the solid cancer is, without limitation, selected from colon cancer, colorectal cancer, pancreatic cancer, breast cancer, ovarian cancer, prostate cancer, head and neck cancer, renal cell cancer, cervical cancer, and non-small cell lung cancer.

In a fourth aspect, a kit is provided herein. In embodiments, the kit comprises a therapeutic amount of an $A_{2A}R$-selective antagonist as described herein, further below accompanied by instructions for use, wherein the $A_{2A}R$-selective antagonist is contained in one or more individual unit dosage forms. The kit is useful, for example, for treating a subject with cancer.

The above exemplary compounds are meant to encompass, where applicable, analogues, derivatives, isomers, polymorphs, and pharmaceutically acceptable salt forms thereof.

All articles, books, patents, patent publications and other publications referenced herein are hereby incorporated by reference in their entireties.

It is to be understood that while the invention has been described in conjunction with certain and specific embodiments, the foregoing description as well as the examples that follow are intended to illustrate and not limit the scope of the invention. Other aspects, advantages and modifications within the scope of the invention will be apparent to those skilled in the art to which the invention pertains.

EXAMPLES

It is to be understood that while the present disclosure describes certain preferred and specific embodiments, the foregoing description as well as the examples that follow are intended to illustrate and not limit the scope of the invention. Other aspects, advantages and modifications within the scope of the invention will be apparent to those skilled in the pertinent art.

Unless otherwise indicated, all chemical reagents referred to in the appended examples are commercially available and/or can be synthesized in accordance with methods described in the literature unless otherwise indicated.

Abbreviations

AUC—Area under the plasma concentration vs time curve
CAC—Carotid artery cannula
$C_{max}$—Maximum plasma concentration
CL—Total body clearance
IV—Intravenous
JVC—Jugular vein cannula
MRT—Mean Residence Time
PEO—Polyethylene oxide 1105
PK—Pharmacokinetic(s)

Example 1

Synthesis of Adenosine $A_{2A}$ Receptor Selective Antagonists

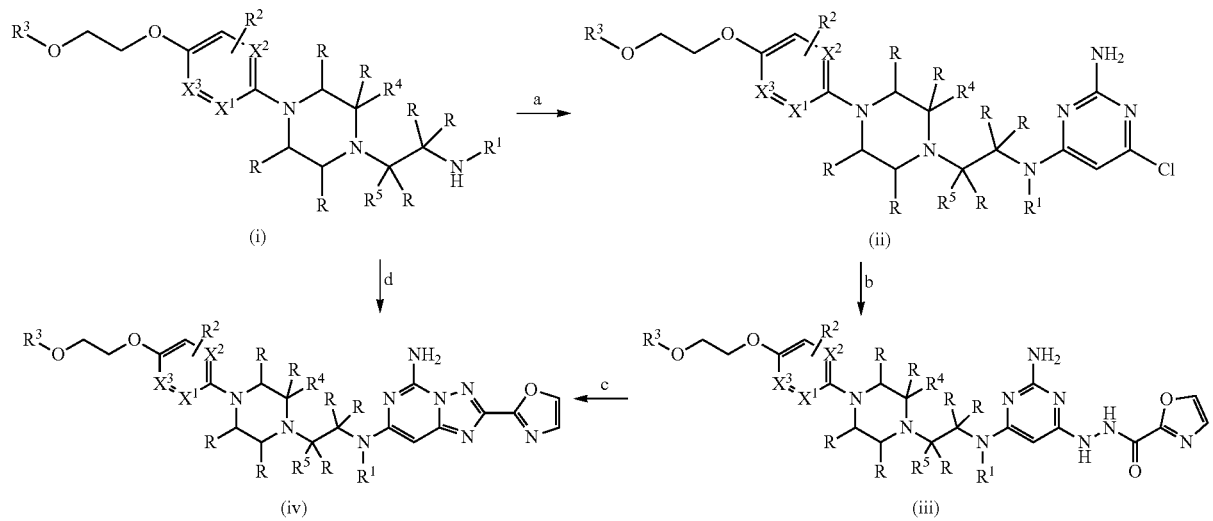

Reagents and Conditions: a) 4,6-dichloropyrimidin-2-amine, ACN, 50-80° C.; b) oxazole-2-carbohydrazide, HCl, EtOH, 100-150° C., µW; c) N,O-bis(trimethylsilyl)acetamide, 100-150° C.; d) 7-chloro-2-(1,3-oxazol-2-yl)[1,2,4]triazolo[1,5-c]pyrimidin-5-amine, CsF, DMSO, 100-150° C.

Method A:

A suspension of compound (i), 4,6-dichloropyrimidin-2-amine (0.9-1.2 equiv.) and triethylamine (2-4 equiv.) in a solvent such as acetonitrile is heated at 50-80° C. for 1-18 hours (h). The solvent is removed under reduced pressure and the residue is dissolved in a solvent such as dichloromethane and washed with a suitable buffer such as a phosphate buffer (pH=6-6.5). The organic layer is dried over anhydrous magnesium sulfate, is filtered and the solvent is removed under reduced pressure to afford compound (ii) that may be used without further purification.

A suspension of compound (ii) and oxazole-2-carbohydrazide (0.9-1.2 equiv.) in ethanol and concentrated hydrochloric acid (3-6 equiv.) is heated (e.g. in a microwave oven) at 100-150° C. for 10-60 minutes, and then again for additional 10-60 minutes, if needed. The solvent is removed under reduced pressure, and the residue is purified such as by reverse phase chromatography (5-100% water/acetonitrile in 10 mM ammonium hydroxide/water) to yield compound (iii).

A suspension of compound (iii) in N,O-bis(trimethylsilyl)acetamide (3-6 equiv.) is heated at 100-150° C. for 2-8 hours. The crude product is cooled at 0° C. and treated with water and 1 N hydrochloric acid (5-10 equiv.). The resulting two layers are separated, and the aqueous phase is directly purified by such as by reverse phase chromatography (5-100% water/acetonitrile in 10 mM ammonium hydroxide/water) to afford compound (iv).

Method B:

To a stirred solution of compound (i) in dimethyl sulfoxide is added 7-chloro-2-(1,3-oxazol-2-yl)[1,2,4]triazolo[1,5-c]pyrimidin-5-amine (1-2 equiv.), followed by cesium fluoride (2-5 equiv.). The solution is then heated (e.g. in a microwave oven) at 100-150° C. for 3-6 hours. The crude reaction is directly purified such as by using reverse phase chromatography (30 g C18, 5-95% Acetonitrile/water) to afford a white solid. The solid is further purified such as using normal phase flash chromatography (1-30% methanol in dichloromethane) to give compound (iv).

Example 2

Synthesis of $N^7$-(2-{4-[4-(2-methoxyethoxy)phenyl]piperazin-1-yl}ethyl)-$N^7$-methyl-2-(1,3-oxazol-2-yl)[1,2,4]triazolo[1,5-c]pyrimidine-5,7-diamine (Compound 1), Hydrochloride Salt Compound 1

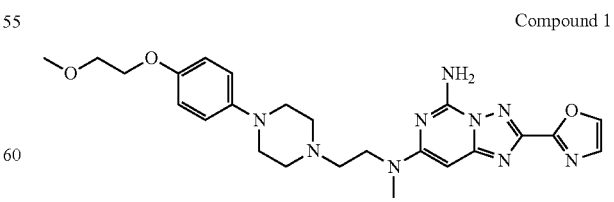

$N^7$-(2-{4-[4-(2-Methoxyethoxy)phenyl]piperazin-1-yl}ethyl)-$N^7$-methyl-2-(1,3-oxazol-2-yl)[1,2,4]triazolo[1,5-c]pyrimidine-5,7-diamine was synthesized according to the following reaction scheme.

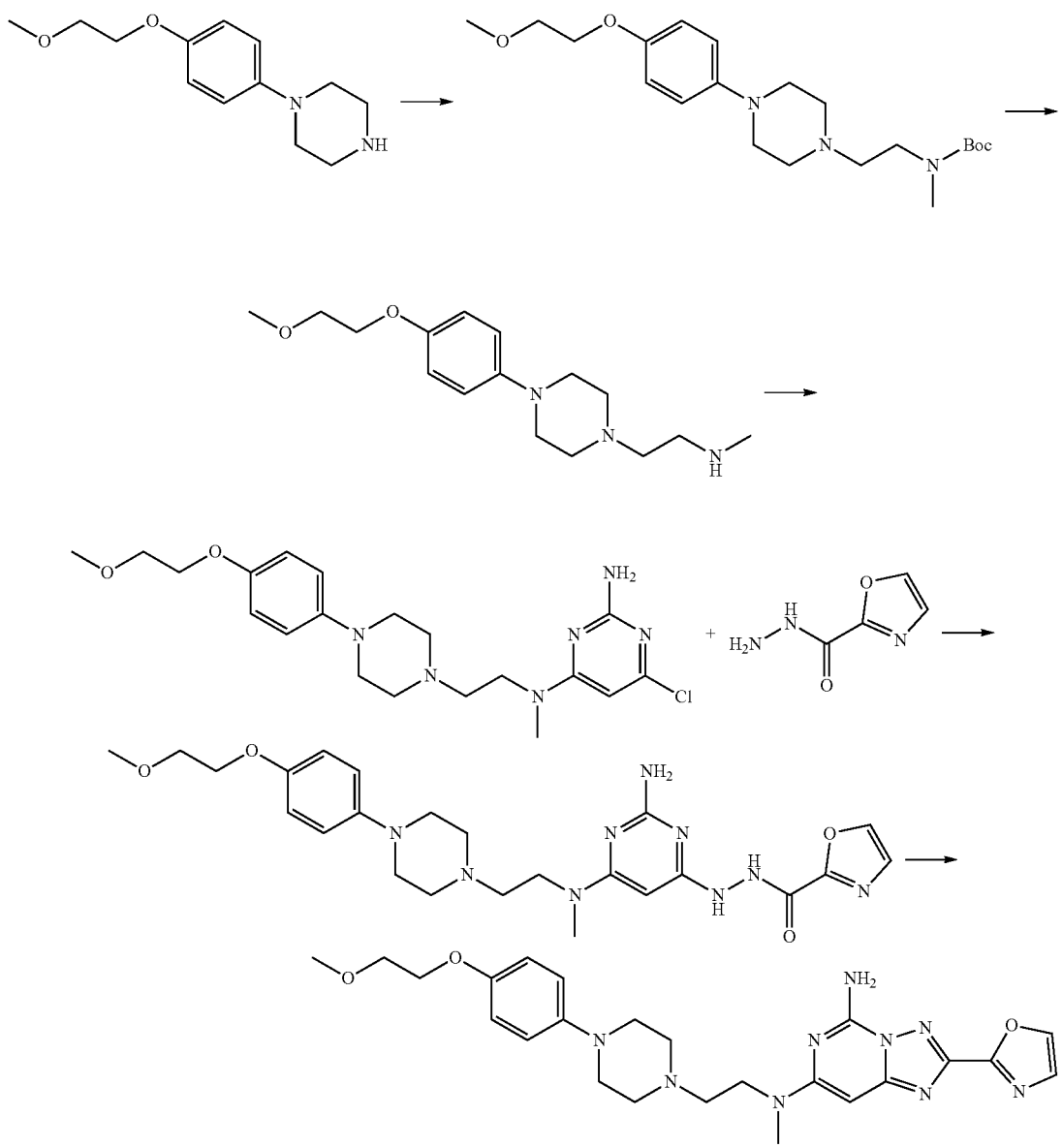

Step 1: Preparation of tert-butyl (2-{4-[4-(2-methoxyethoxy)phenyl]piperazin-1-yl}ethyl)methylcarbamate

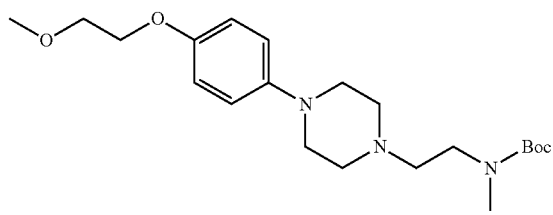 [SMILES: COCCOc1ccc(N2CCN(CCN(C)C(=O)OC(C)(C)C)CC2)cc1]

Acetic acid (0.18 mL) and tert-butyl methyl(2-oxoethyl)carbamate (0.40 mL, 2.40 mmol) were added to a suspension of 1-[4-(2-methoxyethoxy)phenyl]piperazine (0.51 g, 2.18 mmol) in methanol (7 mL). The resulting solution was treated with sodium triacetoxyborohydride (0.69 g, 3.68 mmol) and stirred at room temperature (rt) for 30 minutes. Water was added and the solvent was removed under reduced pressure. The residue was dissolved in dichloromethane (100 mL) and washed with 1 M sodium carbonate (50 mL). The organic layer was dried over anhydrous magnesium sulfate, was filtered and the solvent was removed under reduced pressure. The residue was first purified by reverse phase chromatography (5-100% water/acetonitrile in 10 mM ammonium hydroxide/water) and then by flash chromatography (3-10% methanol in dichloromethane) to afford tert-butyl (2-{4-[4-(2-methoxyethoxy)phenyl]piperazin-1-yl}ethyl)methylcarbamate (364 mg, 45% yield). $^1$H NMR (500 MHz, Chloroform-d) δ 6.89 (m, 4H), 4.09 (dd, J=5.5, 4.0 Hz, 2H), 3.75 (dd, J=5.5, 4.0 Hz, 2H), 3.46 (s, 3H), 3.42 (m, 2H), 3.11 (t, J=4.8 Hz, 4H), 2.91 (s, 3H), 2.68 (bs, 4H), 2.56 (bs, 2H), 1.48 (s, 9H). MS (EI) for $C_{21}H_{35}N_3O_4$: 394 (MH$^+$).

Step 2: Preparation of 2-{4-[4-(2-methoxyethoxy)phenyl]piperazin-1-yl}-N-methylethanamine

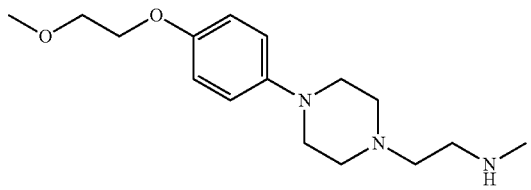

tert-Butyl (2-{4-[4-(2-methoxyethoxy)phenyl]piperazin-1-yl}ethyl)methylcarbamate (1.52 g, 3.86 mmol) was treated with 4 M hydrochloric acid in dioxane (6 mL) and the immediate suspension was stirred at rt for 3 hours. The solvent was removed under reduced pressure and the residue was suspended in dichloromethane (100 mL) and washed with 1 M sodium carbonate (25 mL). The organic layer was dried over anhydrous magnesium sulfate and concentrated to yield 2-{4-[4-(2-methoxyethoxy)phenyl]piperazin-1-yl}-N-methylethanamine (1.04 g, 91% yield) as an off white solid that was used without further purification. $^1$H NMR (500 MHz, Chloroform-d) δ 6.89 (m, 4H), 4.09 (m, 2H), 3.75 (m, 2H), 3.47 (s, 3H), 3.12 (m, 4H), 2.77 (t, J=6.1 Hz, 2H), 2.65 (m, 4H), 2.60 (dd, J=6.4, 5.8 Hz, 2H), 2.52 (s, 3H). MS (EI) for $C_{16}H_{27}N_3O_2$: 294 (MH$^+$).

Step 3: Preparation of 6-chloro-N$^4$-(2-{4-[4-(2-methoxyethoxy)phenyl]piperazin-1-yl}ethyl)-N$^4$-methylpyrimidine-2,4-diamine

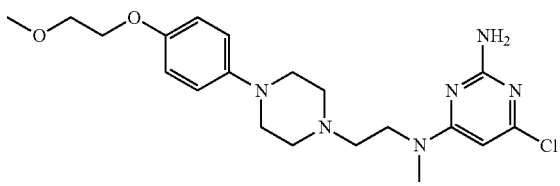 [SMILES: COCCOc1ccc(N2CCN(CCN(C)c3cc(Cl)nc(N)n3)CC2)cc1]

A suspension of 2-{4-[4-(2-methoxyethoxy)phenyl]piperazin-1-yl}-N-methylethanamine (198 mg, 0.67 mmol), 4,6-dichloropyrimidin-2-amine (105 mg, 0.64 mmol) and triethylamine (0.28 mL, 2.05 mmol) in acetonitrile (3 mL) was heated at 60° C. for 2 hours. The solvent was removed under reduced pressure and the residue was dissolved in dichloromethane (100 mL) and washed with phosphate buffer (pH=6-6.5). The organic layer was dried over anhydrous magnesium sulfate, was filtered and the solvent was removed under reduced pressure to afford 6-chloro-N$^4$-(2-{4-[4-(2-methoxyethoxy)phenyl]piperazin-1-yl}ethyl)-N$^4$-methylpyrimidine-2,4-diamine (222 mg, 82% yield) as an off white solid that was used without further purification. MS (EI) for $C_{20}H_{29}ClN_6O_2$: 421 (MH$^+$).

Step 4: Preparation of N-{2-amino-6-[(2-{4-[4-(2-methoxyethoxy)phenyl]piperazin-1-yl}ethyl)(methyl)amino]pyrimidin-4-yl}-1,3-oxazole-2-carbohydrazide

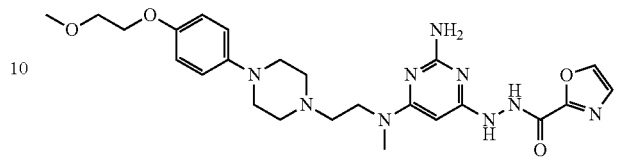

A suspension of 6-chloro-N$^4$-(2-{4-[4-(2-methoxyethoxy)phenyl]piperazin-1-yl}ethyl)-N$^4$-methylpyrimidine-2,4-diamine (154 mg, 0.36 mmol) and oxazole-2-carbohydrazide (46.5 mg, 0.36 mmol) in ethanol (1 mL) and concentrated hydrochloric acid (0.1 mL) was heated in a microwave oven at 120° C. for 20 minutes, and then again for other additional 20 minutes. The solvent was removed and the residue was purified by reverse phase chromatography (5-100% water/acetonitrile in 10 mM ammonium hydroxide/water) to yield N-{2-amino-6-[(2-{4-[4-(2-methoxyethoxy)phenyl]piperazin-1-yl}ethyl)(methyl)amino]pyrimidin-4-yl}-1,3-oxazole-2-carbohydrazide (72 mg, 39% yield) as a pinkish solid. MS (EI) for $C_{24}H_{33}N_9O_4$: 512 (MH$^+$).

Step 5: Preparation of N$^7$-(2-{4-[4-(2-methoxyethoxy)phenyl]piperazin-1-yl}ethyl)-N$^7$-methyl-2-(1,3-oxazol-2-yl)[1,2,4]triazolo[1,5-c]pyrimidine-5,7-diamine

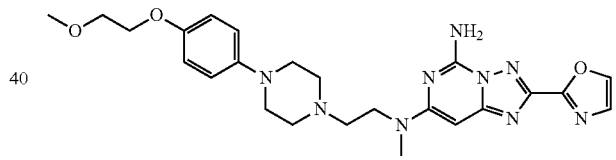

A suspension of N-{2-amino-6-[(2-{4-[4-(2-methoxyethoxy)phenyl]piperazin-1-yl}ethyl)(methyl)amino]pyrimidin-4-yl}-1,3-oxazole-2-carbohydrazide (72 mg, 0.14 mmol) in N,O-bis(trimethylsilyl)acetamide (1.5 mL) was heated at 120° C. for 5 hours. The crude was cooled at 0° C. and treated with water (0.5 mL) and 1 N hydrochloric acid (1 mL). The resulting two layers were separated and the aqueous phase was directly purified by reverse phase chromatography (5-100% water/acetonitrile in 10 mM ammonium hydroxide/water) to afford N$^7$-(2-{4-[4-(2-methoxyethoxy)phenyl]piperazin-1-yl}ethyl)-N$^7$-methyl-2-(1,3-oxazol-2-yl)[1,2,4]triazolo[1,5-c]pyrimidine-5,7-diamine (1) (52 mg, 73% yield) as a white solid. $^1$H NMR (500 MHz, Chloroform-d) δ 7.85 (d, J=0.8 Hz, 1H), 7.38 (d, J=0.8 Hz, 1H), 6.89 (m, 4H), 5.95 (s, 1H), 5.84 (bs, 2H), 4.09 (ddd, J=4.7, 3.9, 1.0 Hz, 2H), 3.80-3.72 (m, 4H), 3.47 (s, 3H), 3.13 (t, J=4.9 Hz, 4H), 3.09 (s, 3H), 2.72 (t, J=4.8 Hz, 4H), 2.65 (t, J=7.2 Hz, 2H). MS (EI) for $C_{24}H_{31}N_9O_3$: 494 (MH$^+$).

The compound was dissolved in acetonitrile (1 mL) and water (1 mL) and treated with 1N hydrochloric acid (400 µL). Solvents were removed in the lyophilizer to generate the hydrochloride salt of the tittle compound as a yellow solid.

Example 3

Preparation of N[5]-(2-{4-[4-(2-methoxyethoxy)phenyl]piperazin-1-yl}ethyl)-N[5]-methyl-2-(1,3-oxazol-2-yl)[1,2,4]triazolo[1,5-a][1,3,5]triazine-5,7-diamine (Compound 2), Hydrochloride Salt Compound 2

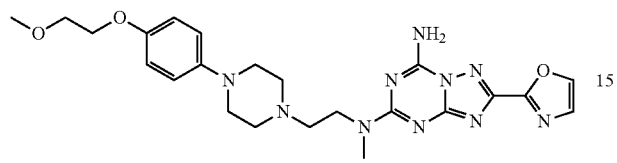

N[5]-(2-{4-[4-(2-Methoxyethoxy)phenyl]piperazin-1-yl}ethyl)-N[5]-methyl-2-(1,3-oxazol-2-yl)[1,2,4]triazolo[1,5-a][1,3,5]triazine-5,7-diamine was synthesized according to the following reaction scheme.

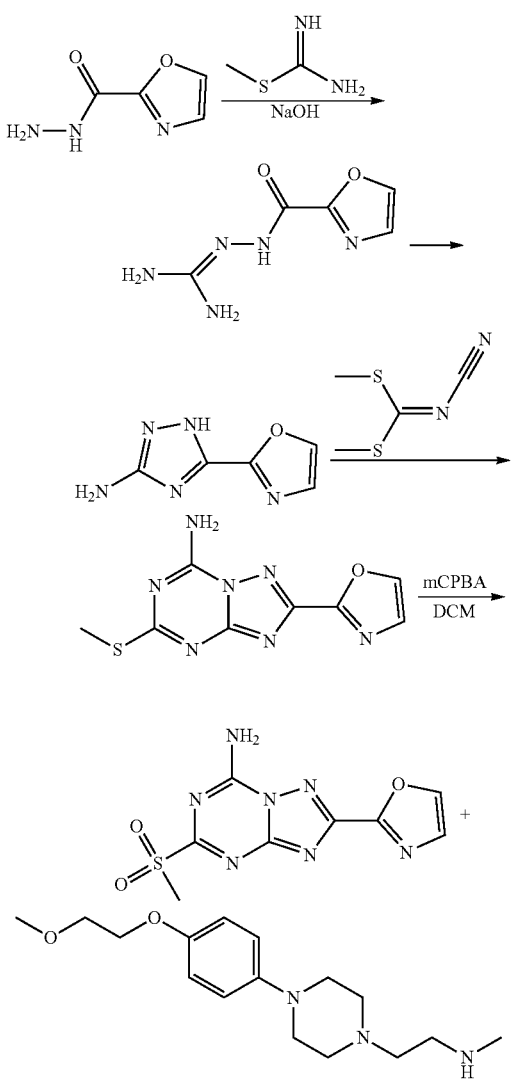

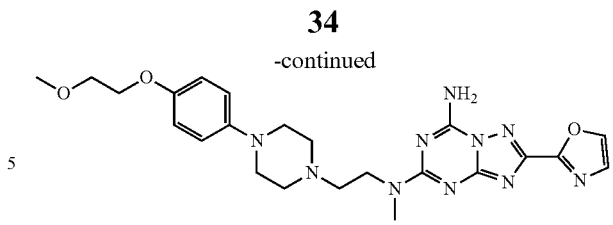

Step 1: Preparation of N''-(1,3-oxazol-2-ylcarbonyl)carbonohydrazonic Diamide

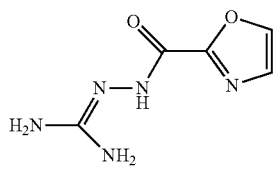

Oxazole-2-carbohydrazide (3.66 g, 28.8 mmol) and methyl carbamimidothioate hemisulfate (12.9 g, 144 mmol) were added to a solution of sodium hydroxide (381 mg, 9.52 mmol) in water (15 mL). The mixture was stirred at rt for 2 days and the resulting precipitate was filtered, washed with water and diethyl ether and dried under vacuum to afford N''-(1,3-oxazol-2-ylcarbonyl)carbonohydrazonic diamide as an off white solid (3.7 g, 76% yield) that was used without further purification. $^1$H NMR (500 MHz, Dimethylsulfoxide-d$_6$) δ 10.65 (s, 1H), 7.99 (d, J=0.8 Hz, 1H), 7.19 (d, J=0.8 Hz, 1H), 6.91 (bs, 4H). MS (EI) for $C_5H_7N_5O_2$: 170 (MH$^+$).

Step 2: Preparation of 5-(1,3-oxazol-2-yl)-1H-1,2,4-triazol-3-amine

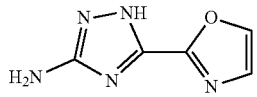

N''-(1,3-Oxazol-2-ylcarbonyl)carbonohydrazonic diamide (600 mg, 3.54 mmol) was suspended in water (10 mL) and was heated in a microwave oven at 140° C. for 1 hour. Acetonitrile (10 mL) was added to the reaction mixture and the solvents were removed in the lyophilizer to yield 5-(1,3-oxazol-2-yl)-1H-1,2,4-triazol-3-amine as a white solid (525 mg, 98% yield) that was used without further purification. $^1$H NMR (500 MHz, Dimethylsulfoxide-d$_6$) S 8.15 (s, 1H), 7.33 (s, 1H), 6.26 (bs, 2H). MS (EI) for $C_5H_5N_5O$: 152 (MH$^+$).

Step 3: Preparation of 5-(methylthio)-2-(1,3-oxazol-2-yl)[1,2,4]triazolo[1,5-a][1,3,5]triazin-7-amine

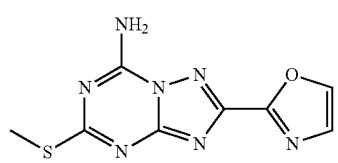 [SMILES: CSc1nc(N)n2nc(-c3ncco3)nc2n1]

5-(Oxazol-2-yl)-1H-1,2,4-triazol-3-amine (3.7 g, 24.53 mmol) and dimethyl cyanocarbonimidodithioate (3.5 g, 24.53 mmol) were suspended in N-methyl-2-pyrrolidone (16 mL) and heated in a microwave oven at 190° C. for 5 hours. The reaction mixture was poured into water (120 mL) and the resulting solid was filtered, washed with diethyl ether and dried to afford 5-(methylthio)-2-(1,3-oxazol-2-yl)[1,2,4]triazolo[1,5-a][1,3,5]triazin-7-amine as a beige solid (4.29 g, 70.2% yield). $^1$H NMR (500 MHz, Chloroform-d) δ 9.98 (bs, 1H), 9.71 (bs, 1H), 8.47 (d, J=0.8 Hz, 1H), 7.60 (d, J=0.8 Hz, 1H), 3.39 (s, 3H). MS (EI) for $C_8H_7N_7OS$: 250 (MH$^+$).

Step 4: Preparation of 5-(methylsulfonyl)-2-(1,3-oxazol-2-yl)[1,2,4]triazolo[1,5-a][1,3,5]triazin-7-amine

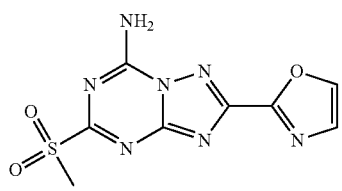 [SMILES: CS(=O)(=O)c1nc(N)n2nc(-c3ncco3)nc2n1]

5-(Methylthio)-2-(1,3-oxazol-2-yl)[1,2,4]triazolo[1,5-a][1,3,5]triazin-7-amine (1.95 g, 7.82 mmol) and 3-chlorobenzoperoxoic acid (7.01 g, 40.63 mmol) were suspended in dichloromethane (150 mL) and stirred at rt for 48 hours. The solvent was removed and the residue was suspended in ethanol (200 mL). The solid was filtered, washed with dichloromethane and diethyl ether, and the filtrate was concentrated and purified by flash chromatography (0-100% ethyl acetate in dichloromethane) to afford 5-(methylsulfonyl)-2-(1,3-oxazol-2-yl)[1,2,4]triazolo[1,5-a][1,3,5]triazin-7-amine (1.72 g combined from solid and chromatography, 78.3% yield) as a light yellow solid. $^1$H NMR (500 MHz, Dimethylsulfoxide-d$_6$) δ 9.98 (bs, 1H), 9.71 (bs, 1H), 8.46 (d, J=0.8 Hz, 1H), 7.60 (d, J=0.8 Hz, 1H), 3.33 (s, 3H). MS (EI) for $C_8H_7N_7O_3S$: 282 (MH$^+$).

Step 5: Preparation of N$^5$-(2-{4-[4-(2-methoxyethoxy)phenyl]piperazin-1-yl}ethyl)-N$^5$-methyl-2-(1,3-oxazol-2-yl)[1,2,4]triazolo[1,5-a][1,3,5]triazine-5,7-diamine

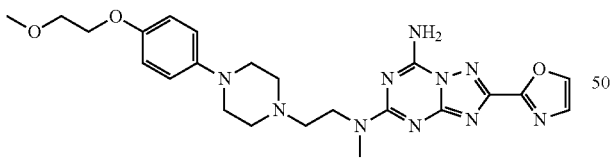

5-(Methylsulfonyl)-2-(1,3-oxazol-2-yl)[1,2,4]triazolo[1,5-a][1,3,5]triazin-7-amine (52.5 mg, 0.18 mmol) and triethylamine (48 μL, 0.34 mmol) were added over a solution of 2-{4-[4-(2-methoxyethoxy)phenyl]piperazin-1-yl}-N-methylethanamine (50 mg, 0.17 mmol) in dichloromethane (1 mL) and the resulting suspension was stirred at rt for 3 hours. The mixture was diluted with dichloromethane (50 mL) and washed with phosphate buffer pH=6-6.5 (20 mL). The organic layer was dried over anhydrous magnesium sulfate, was filtered and the solvent was removed under reduced pressure. The residue was purified by reverse phase chromatography (5-100% water/acetonitrile in 10 mM ammonium hydroxide/water) to afford N$^5$-(2-{4-[4-(2-methoxyethoxy)phenyl]piperazin-1-yl}ethyl)-N$^5$-methyl-2-(1,3-oxazol-2-yl)[1,2,4]triazolo[1,5-a][1,3,5]triazine-5,7-diamine (2) (29 mg, 34.5% yield) as a white solid. $^1$H NMR (500 MHz, Methanol-d$_4$) δ 8.16 (s, 1H), 7.47 (s, 1H), 6.95 (d, J=8.6 Hz, 2H), 6.87 (d, J=8.6 Hz, 2H), 4.06 (t, J=4.6 Hz, 2H), 3.90 (t, J=6.9 Hz, 2H), 3.72 (t, J=4.6 Hz, 2H), 3.43 (s, 3H), 3.26 (d, J=13.1 Hz, 3H), 3.10 (m, 4H), 2.75 (m, 6H). MS (EI) for $C_{23}H_{30}N_{10}O_3$: 495 (MH$^+$).

The compound was dissolved in acetonitrile and water and treated with 1N hydrochloric acid. Solvents were removed in the lyophilizer to generate the hydrochloride salt of the tittle compound as a white solid.

Example 4

Synthesis of N$^7$-methyl-2-(1,3-oxazol-2-yl)-N$^7$-[2-(4-{4-[2-(trifluoromethoxy)ethoxy]phenyl}piperazin-1-yl)ethyl][1,2,4]triazolo[1,5-c]pyrimidine-5,7-diamine (Compound 5), Hydrochloride Salt Compound 5

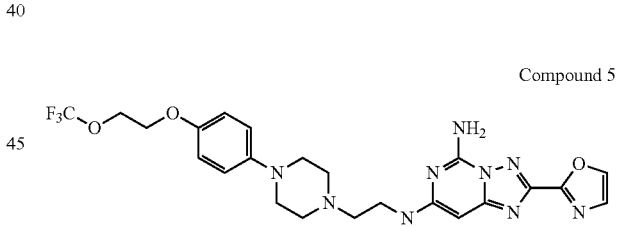

N$^7$-Methyl-2-(1,3-oxazol-2-yl)-N$^7$-[2-(4-{4-[2-(trifluoromethoxy)ethoxy]phenyl}piperazin-1-yl)ethyl][1,2,4]triazolo[1,5-c]pyrimidine-5,7-diamine was synthesized according to the following reaction scheme.

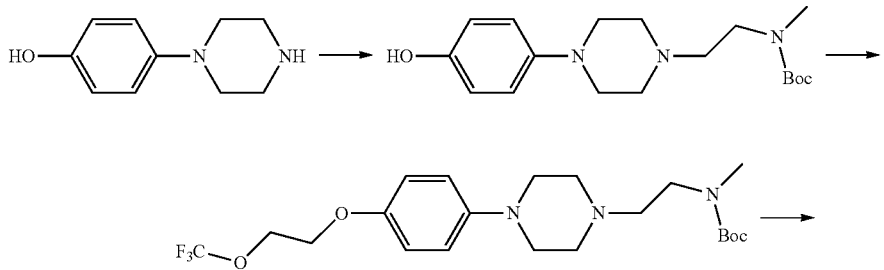

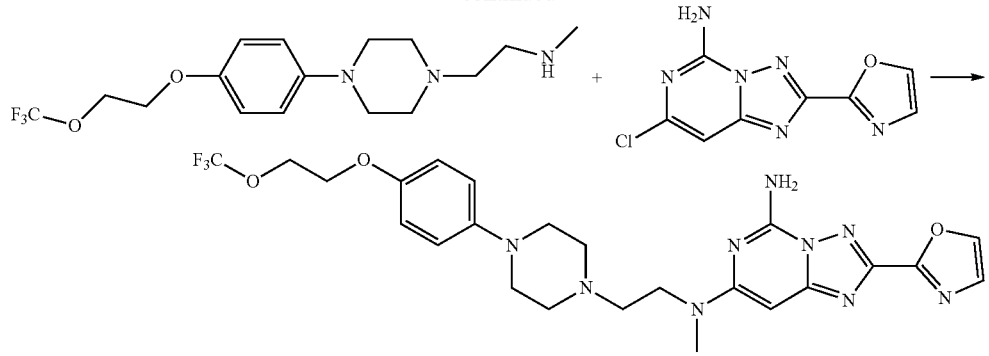

Step 1: Preparation of tert-butyl {2-[4-(4-hydroxyphenyl)piperazin-1-yl]ethyl}methylcarbamate

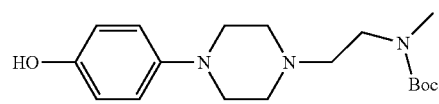

tert-Butyl methyl(2-oxoethyl)carbamate (5.35 g, 30.9 mmol) was added to a suspension of 4-(piperazin-1-yl)phenol (5.0 g, 28.1 mmol) in 1,2-dichloroethane (30 mL). The resulting solution was treated with sodium triacetoxyborohydride (11.89 g, 56.1 mmol) and stirred at rt for 22 hours. Water was added and the solvent was removed under reduced pressure. The residue was dissolved in dichloromethane (400 mL) and washed with 1 N sodium carbonate (200 mL). The organic layer was dried over anhydrous sodium sulfate, was filtered and the solvent was removed under reduced pressure to afford tert-butyl {2-[4-(4-hydroxyphenyl)piperazin-1-yl]ethyl}methylcarbamate that was used without further purification (9.41 g, 99% yield). MS (EI) for $C_{18}H_{29}N_3O_3$: 336 (MH$^+$).

Step 2: Preparation of tert-butyl methyl[2-(4-{4-[2-(trifluoromethoxy)ethoxy]phenyl}piperazin-1-yl)ethyl]carbamate To a dimethylformamide solution of tert-butyl {2-[4-(4-hydroxyphenyl)piperazin-1-yl]ethyl}methylcarbamate (400 mg, 1.19 mmol) and 1-bromo-2-(trifluoromethoxy)ethane (503 mg, 2.61 mmol) was added sodium hydride in 60% mineral oil (143 mg, 3.73 mmol). The mixture was stirred at rt for 22 hours. Water was added and the mixture was then partitioned between hexane and 1 N sodium hydroxide solution. The organic layer was washed with 1 N sodium hydroxide solution three times, dried over anhydrous sodium sulfate and evaporated to give a white solid. The white solid was purified by flash chromatography (30-90% ethyl acetate in hexane) to afford tert-butyl methyl[2-(4-{4-[2-(trifluoromethoxy)ethoxy]phenyl}piperazin-1-yl)ethyl]carbamate (131 mg, 24% yield). MS (EI) for $C_{21}H_{32}F_3N_3O_4$: 448 (MH$^+$).

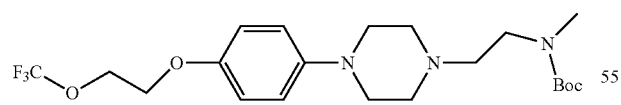

Step 3: Preparation of N-methyl-2-(4-{4-[2-(trifluoromethoxy)ethoxy]phenyl}piperazin-1-yl)ethanamine

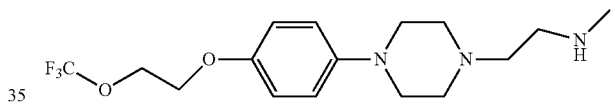

tert-Butyl methyl[2-(4-{4-[2-(trifluoromethoxy)ethoxy]phenyl}piperazin-1-yl)ethyl]carbamate (102 mg, 0.228 mmol) was treated with 4 N hydrochloric acid in dioxane (1 mL) and the immediate suspension was stirred at room temperature for 5 hours. The solvent was removed under reduced pressure and the residue was dissolved in methanol (5 mL). AG+8 basic resin was added into the solution until pH 8-9. The resin was filtered off and the organic solvent was evaporated to give N-methyl-2-(4-{4-[2-(trifluoromethoxy)ethoxy]phenyl}piperazin-1-yl)ethanamine as an off white solid that was used without further purification. MS (EI) for $C_{16}H_{24}F_3N_3O_2$: 348 (MH$^+$).

Step 4: Preparation of N$^7$-methyl-2-(1,3-oxazol-2-yl)-N$^7$-[2-(4-{4-[2-(trifluoromethoxy)ethoxy]phenyl}piperazin-1-yl)ethyl][1,2,4]triazolo[1,5-c]pyrimidine-5,7-diamine

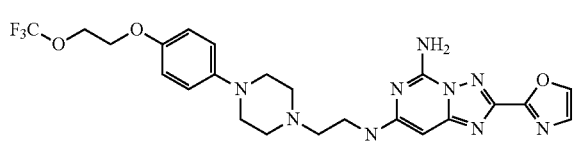

To a stirred solution of N-methyl-2-(4-{4-[2-(trifluoromethoxy)ethoxy]phenyl}piperazin-1-yl)ethanamine (79 mg, 0.23 mmol) in 2.0 mL of dimethyl sulfoxide was added 7-chloro-2-(oxazol-2-yl)-[1,2,4]triazolo[1,5-c]pyrimidin-5-amine (81 mg, 0.34 mmol), followed by cesium fluoride (104 mg, 0.78 mmol). The solution was then heated to 120° C. for 4 hours. The crude reaction was directly purified using reverse phase chromatography (30 g C18, 5-95% Acetonitrile/water) to afford a white solid. The solid was further purified using normal phase flash chromatography (1-20% methanol in ethyl acetate) to give $N^7$-methyl-2-(1,3-oxazol-2-yl)-$N^7$-[2-(4-{4-[2-(trifluoromethoxy)ethoxy]phenyl}piperazin-1-yl)ethyl][1,2,4]triazolo[1,5-c]pyrimidine-5,7-diamine (5) as a white solid. $^1$H NMR (500 MHz, Methanol-$d_4$) δ 8.30 (s, 1H), 7.58 (s, 1H), 7.06 (d, J=9.0 Hz, 2H), 6.93 (d, J=9.0 Hz, 2H), 4.32 (dd, J=4.0 Hz, 2.0 Hz, 2H), 4.20-4.17 (m, 4H), 3.97 (bs, 2H), 3.70 (bs, 2H), 3.55 (bs, 2H), 3.44 (m, 4H), 3.21 (s, 3H). MS (EI) for $C_{24}H_{28}F_3N_9O_3$: 548 (MH$^+$).

The compound was dissolved in acetonitrile (1 mL) and treated with 1N hydrochloric acid in diethyl ether (300 μL). Solvents were removed under pressure and the residue was dried in vacuo to generate the hydrochloride salt of the title compound as a white solid (18.9 mg, 13% yield).

Example 5

Synthesis of $N^7$-(2-{4-[2-chloro-4-(2-methoxyethoxy)phenyl]piperazin-1-yl}ethyl)-$N^7$-methyl-2-(1,3-oxazol-2-yl)[1,2,4]triazolo[1,5-c]pyrimidine-5,7-diamine (Compound 15), Hydrochloride Salt

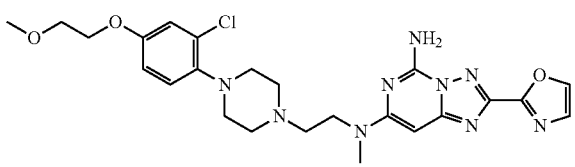

Compound 15

$N^7$-(2-{4-[2-Chloro-4-(2-methoxyethoxy)phenyl]piperazin-1-yl}ethyl)-$N^7$-methyl-2-(1,3-oxazol-2-yl)[1,2,4]triazolo[1,5-c]pyrimidine-5,7-diamine was synthesized according to the following reaction scheme.

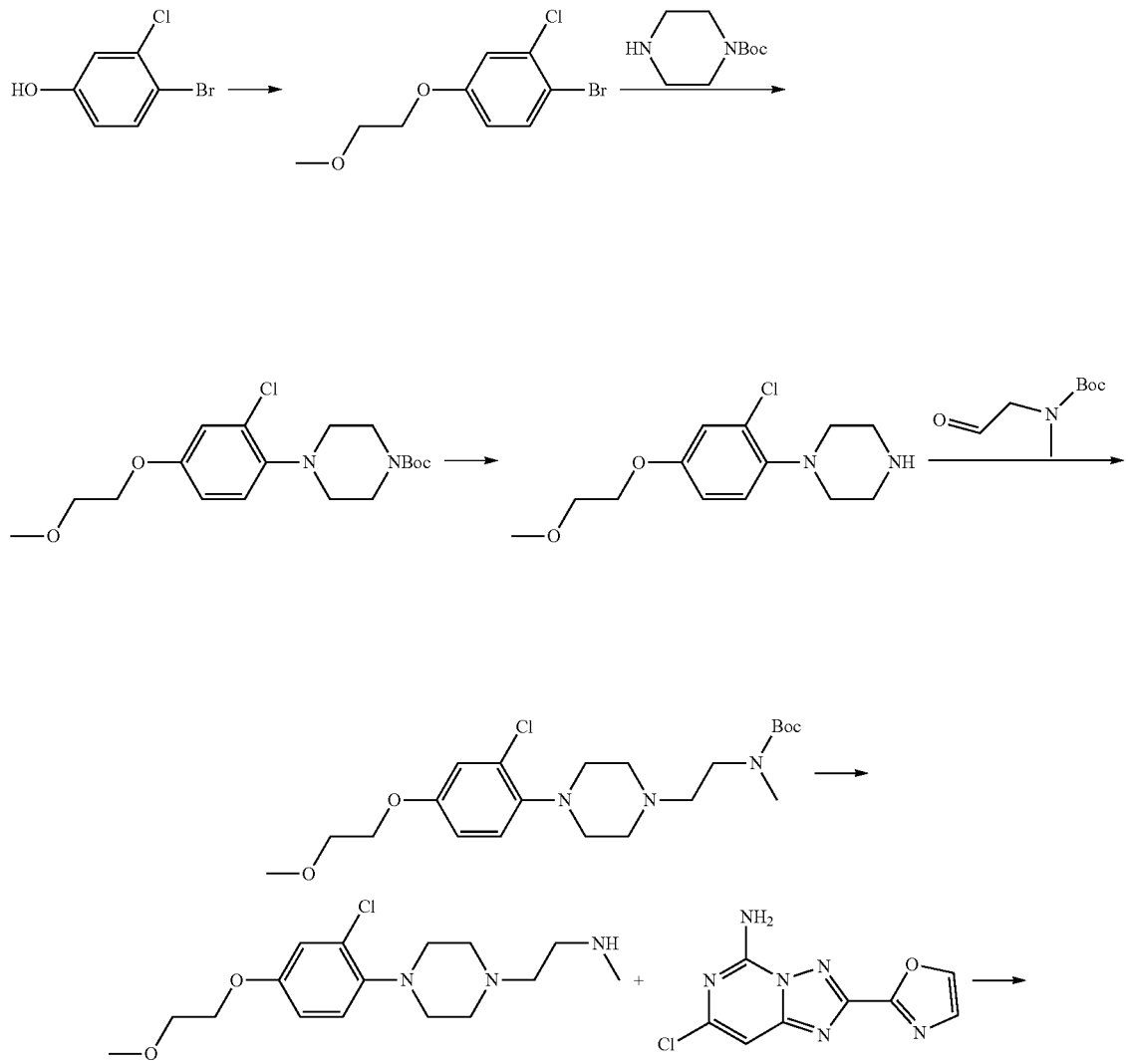

-continued

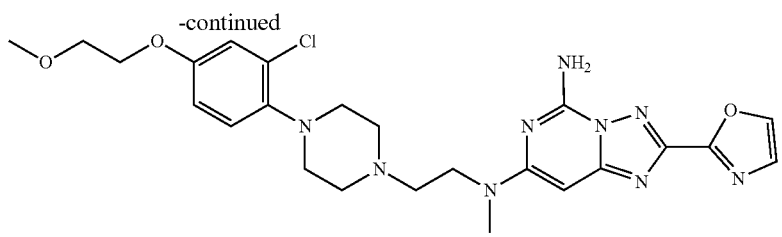

Step 1: Preparation of 1-bromo-2-chloro-4-(2-methoxyethoxy)benzene

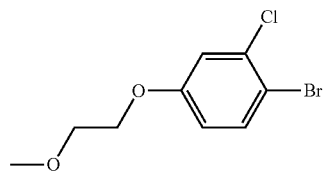

A 20 mL screw capped vial was charged with 4-bromo-3-chloro-phenol (500 mg, 2.41 mmol), 1-bromo-2-methoxyethane (502 mg, 3.62 mmol), dry dimethylformamide (3 mL) and potassium carbonate (1.34 g, 9.69 mmol). 60% sodium hydride in mineral oil (480 mg, 12.1 mmol) was slowly added. The mixture was stirred at room temperature for 18 hours. The mixture was partitioned between ethyl acetate (100 mL) and 0.1N sodium hydroxide solution (100 mL). The organic layer was washed with 0.1 N sodium hydroxide solution (2×100 mL), was dried over sodium sulfate, was filtered and was concentrated in vacuo to afford 1-bromo-2-chloro-4-(2-methoxyethoxy)benzene (462 mg, 72% yield) as an orange oil. $^1$H NMR (500 MHz, Chloroform-d): δ 7.47 (d, J=8.5 Hz, 1H), 7.04 (d, J=2.5 Hz, 1H), 6.73 (dd, J=3.0 Hz, 1H), 4.09 (dd, J=3.0 Hz, 2H), 3.74 (dd, J=3.0, 2H), 3.45 (s, 3H).

Step 2: Preparation of tert-Butyl 4-[2-chloro-4-(2-methoxyethoxy)phenyl]piperazine-1-carboxylate

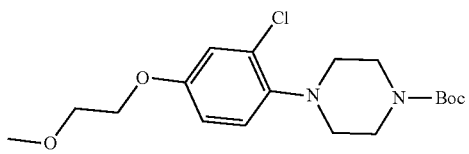 [SMILES: COCCOc1ccc(N2CCN(C(=O)OC(C)(C)C)CC2)c(Cl)c1]

The toluene solution of 1-bromo-2-chloro-4-(2-methoxyethoxy)benzene (660 mg, 2.49 mmol) and tert-butyl piperazine-1-carboxylate (462 mg, 2.49 mmol) was azetroped and purged with nitrogen three times. tris(Dibenzylideneacetone)dipalladium(0):BINAP:sodium tert-butoxide (411 mg, 1.24 mmol) was added. The reaction mixture was heated at 100° C. for 4 hours. After cooled to room temperature all solvents were evaporated. The residue was purified by flash chromatography (10-95% ethyl acetate in hexane) to afford tert-butyl 4-[2-chloro-4-(2-methoxyethoxy)phenyl]piperazine-1-carboxylate (440 mg, 47% yield). MS (EI) for $C_{18}H_{27}ClN_2O_4$: 371 (MH$^+$).

Step 3: Preparation of 1-[2-chloro-4-(2-methoxyethoxy)phenyl]piperazine

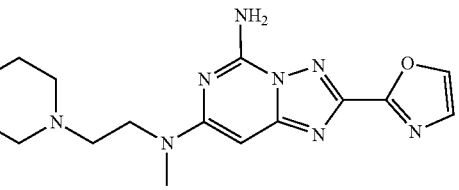

tert-Butyl 4-[2-chloro-4-(2-methoxyethoxy)phenyl]piperazine-1-carboxylate (440 mg, 1.19 mmol) was treated with 4 N hydrochloric acid in dioxane (2 mL) and the immediate suspension was stirred at room temperature for 6 hours. The solvent was removed under reduced pressure and the residue was dissolved in methanol (5 mL). AG+8 basic resin was added into the solution until pH 8-9. The resin was filtered off and the organic solvent was evaporated to give 1-[2-chloro-4-(2-methoxyethoxy)phenyl]piperazine as an off white solid that was used without further purification (321 mg, 100% yield). MS (EI) for $C_{13}H_{19}ClN_2O_2$: 271 (MH$^+$).

Step 4: Preparation of tert-butyl (2-{4-[2-chloro-4-(2-methoxyethoxy)phenyl]piperazin-1-yl}ethyl)methylcarbamate

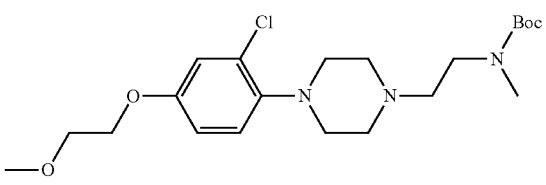 [SMILES: COCCOc1ccc(N2CCN(CCN(C)C(=O)OC(C)(C)C)CC2)c(Cl)c1]

tert-Butyl methyl(2-oxoethyl)carbamate (267 mg, 1.54 mmol) was added to a suspension of 1-[2-chloro-4-(2-methoxyethoxy)phenyl]piperazine (321 mg, 1.19 mmol) in 1,2-dichloroethane (5 mL). The resulting solution was treated with sodium triacetoxyborohydride (502 mg, 2.37 mmol) and stirred at rt for 4 hours. Water was added and the solvent was removed under reduced pressure. The residue was dissolved in dichloromethane (100 mL) and washed with 1 N sodium carbonate (100 mL). The organic layer was dried over anhydrous sodium sulfate, was filtered and the solvent was removed under reduced pressure to afford tert-butyl (2-{4-[2-chloro-4-(2-methoxyethoxy)phenyl]piperazin-1-yl}ethyl)methylcarbamate that was used without further purification. MS (EI) for $C_{21}H_{34}ClN_3O_4$: 428 (MH$^+$).

Step 5: Preparation of 2-{4-[2-chloro-4-(2-methoxyethoxy)phenyl]piperazin-1-yl}-N-methyl-ethanamine

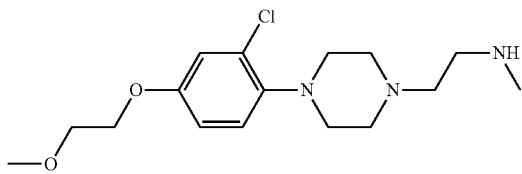

tert-Butyl methyl[2-(4-{4-[2-(trifluoromethoxy)ethoxy]phenyl}piperazin-1-yl)ethyl]carbamate (300 mg, 0.70 mmol) was treated with 4 N hydrochloric acid in dioxane (2 mL) and the immediate suspension was stirred at room temperature for 1.5 hours. The solvent was removed under reduced pressure and the residue was dissolved in methanol (5 mL). AG+8 basic resin was added into the solution until pH 8-9. The resin was filtered off and the organic solvent was evaporated to give 2-{4-[2-chloro-4-(2-methoxyethoxy)phenyl]piperazin-1-yl}-N-methylethanamine as an off white solid that was used without further purification. MS (EI) for $C_{16}H_{26}ClN_3O_2$: 328 (MH$^+$).

Step 6: Preparation of $N^7$-(2-{4-[2-chloro-4-(2-methoxyethoxy)phenyl]piperazin-1-yl}ethyl)-$N^7$-methyl-2-(1,3-oxazol-2-yl)[1,2,4]triazolo[1,5-c]pyrimidine-5,7-diamine

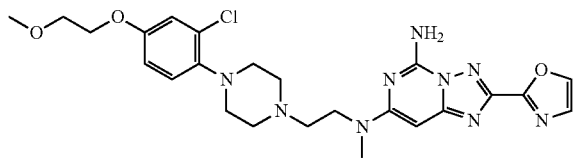 [SMILES: COCCOc1ccc(N2CCN(CCN(C)c3cc4nc(-c5ncco5)nn4c(N)n3)CC2)c(Cl)c1]

To a stirred solution of 2-{4-[2-chloro-4-(2-methoxyethoxy)phenyl]piperazin-1-yl}-N-methylethanamine (229 mg, 0.70 mmol) in 5 mL of dimethyl sulfoxide was added 7-chloro-2-(oxazol-2-yl)-[1,2,4]triazolo[1,5-c]pyrimidin-5-amine (248 mg, 1.05 mmol), followed by cesium fluoride (316 mg, 2.10 mmol). The solution was heated in a microwave oven at 100° C. for 5 hours. The mixture was partitioned between ethyl acetate (100 mL) and 1 N sodium carbonate solution (100 mL). The organic layer was washed with 1 N sodium carbonate solution (2×100 mL), dried (Na$_2$SO$_4$), filtered and concentrated to give a white solid. The solid was purified by normal phase flash chromatography (1-30% methanol in dichloromethane) to give $N^7$-(2-{4-[2-chloro-4-(2-methoxyethoxy)phenyl]piperazin-1-yl}ethyl)-$N^7$-methyl-2-(1,3-oxazol-2-yl)[1,2,4]triazolo[1,5-c]pyrimidine-5,7-diamine (15) as a white solid. $^1$H NMR (500 MHz, chloroform-d) δ 7.86 (s, 1H), 7.38 (s, 1H), 7.00 (d, 2H), 6.83 (d, 1H), 5.96 (s, 1H), 5.81 (bs, 2H), 4.09 (dd, 2H), 3.75 (m, 4H), 3.47 (s, 3H) 3.10 (s, 3H), 3.03 (bs, 4H), 2.75 (bs, 4H), 2.68 (t, 2H). MS (EI) for $C_{24}H_{30}ClN_9O_3$: 528 (MH$^+$).

The compound was dissolved in acetonitrile (1 mL) and treated with 1 N hydrochloric acid in diethyl ether (500 μL). Solvents were removed under pressure and the residue was dried in vacuo to generate the hydrochloride salt of the tittle compound as a white solid (115 mg, 27% yield).

Example 6

Synthesis of $N^7$-(2-{4-[2-methoxy-4-(2-methoxyethoxy)phenyl]piperazin-1-yl}ethyl)-$N^7$-methyl-2-(1,3-oxazol-2-yl)[1,2,4]triazolo[1,5-c]pyrimidine-5,7-diamine (Compound 17), Hydrochloride Salt

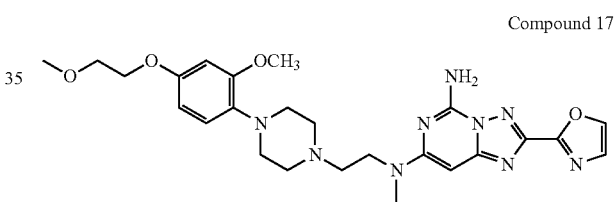

Compound 17

$N^7$-(2-{4-[2-Methoxy-4-(2-methoxyethoxy)phenyl]piperazin-1-yl}ethyl)-$N^7$-methyl-2-(1,3-oxazol-2-yl)[1,2,4]triazolo[1,5-c]pyrimidine-5,7-diamine was synthesized according to the following reaction scheme.

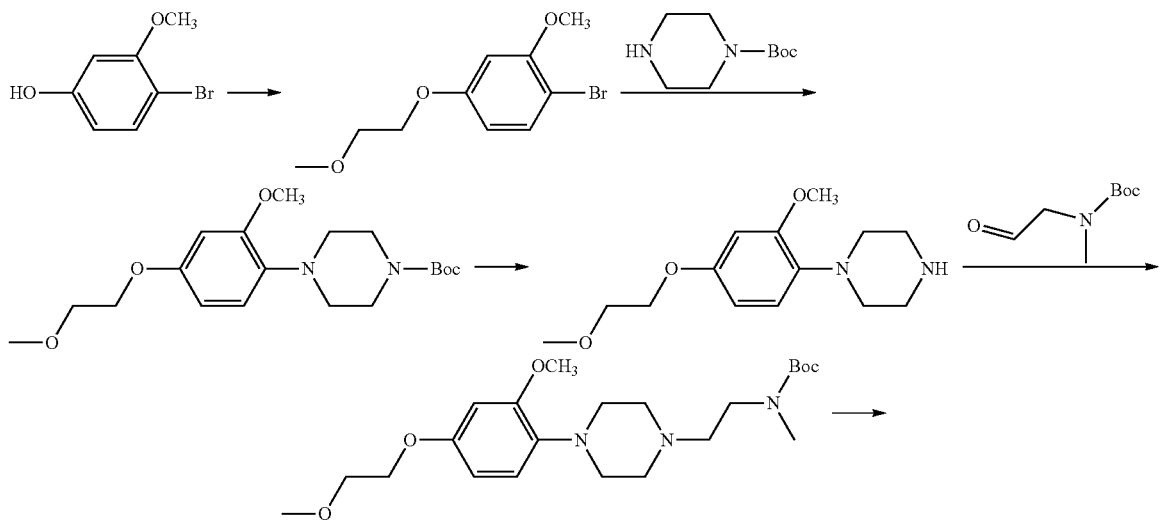

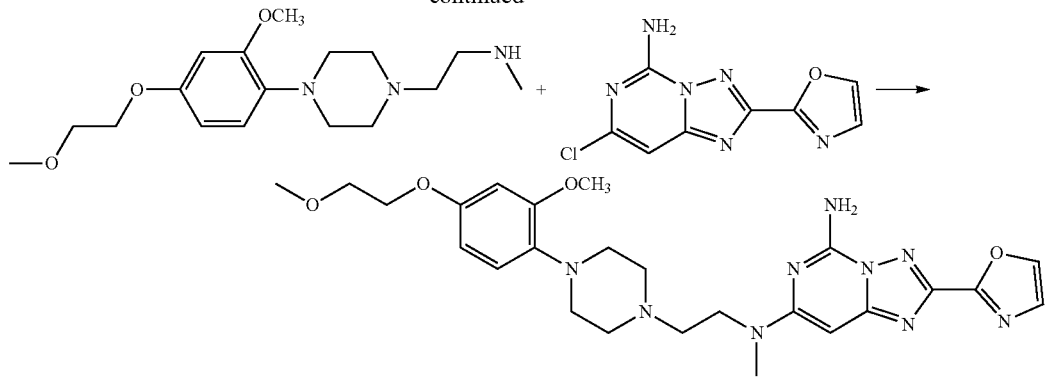

Step 1: Preparation of 1-bromo-2-methoxy-4-(2-methoxyethoxy)benzene

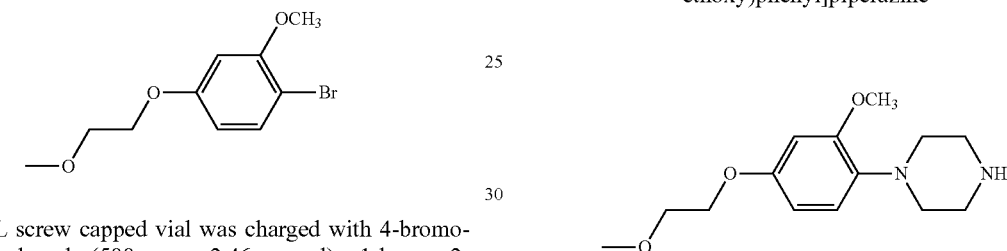

A 20 mL screw capped vial was charged with 4-bromo-3-methoxy-phenol (500 mg, 2.46 mmol), 1-bromo-2-methoxy-ethane (513 mg, 3.69 mmol) and dry dimethylformamide (3 mL). 60% sodium hydride in mineral oil (492 mg, 12.3 mmol) was slowly added. The mixture was stirred at room temperature for 18 hours. The mixture was partitioned between ethyl acetate (100 mL) and 0.1 N sodium hydroxide solution (100 mL). The organic layer was washed with 0.1 N sodium hydroxide solution (2×100 mL), dried ($Na_2SO_4$), filtered and concentrated in vacuo to afford 1-bromo-2-methoxy-4-(2-methoxyethoxy)benzene as a colorless oil (640 mg, 99% yield). MS (EI) for $C_{10}H_{13}BrO_3$: 261 (MH+).

Step 2: Preparation of tert-butyl 4-[2-methoxy-4-(2-methoxyethoxy)phenyl]piperazine-1-carboxylate

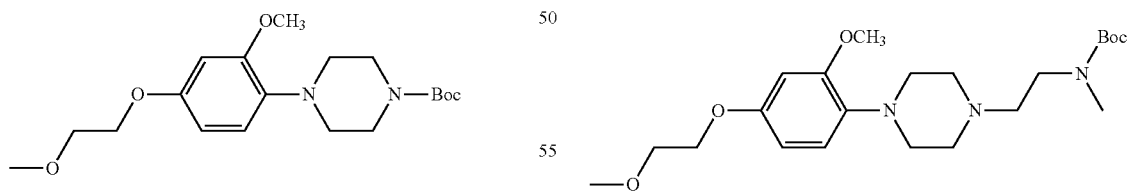

The toluene solution of 1-bromo-2-methoxy-4-(2-methoxyethoxy)benzene (640 mg, 2.45 mmol) and tert-butyl piperazine-1-carboxylate (456 mg, 2.45 mmol) was azetroped and purged with $N_2$ three times. tris(Dibenzylideneacetone)dipalladium(0):BINAP:sodium tert-butoxide (405 mg, 1.23 mmol) was added. The reaction mixture was heated at 100° C. for 8 hours. After cooled to room temperature all solvents were evaporated. The residue was purified by flash chromatography (5-50% ethyl acetate in hexane) to afford tert-butyl 4-[2-methoxy-4-(2-methoxyethoxy)phenyl]piperazine-1-carboxylate as a yellow oil (280 mg, 31% yield). MS (EI) for $C_{19}H_{30}N_2O_5$: 367 (MH+).

Step 3: Preparation of 1-[2-methoxy-4-(2-methoxyethoxy)phenyl]piperazine tert-Butyl 4-[2-methoxy-4-(2-methoxyethoxy)phenyl]piperazine-1-carboxylate (280 mg, 0.76 mmol) was treated with 4 N hydrochloric acid in dioxane (2 mL) and the immediate suspension was stirred at room temperature for 5 hours. The solvent was removed under reduced pressure to give 1-[2-methoxy-4-(2-methoxyethoxy)phenyl]piperazine as a brown solid that was used without further purification (203 mg, 100% yield). MS (EI) for $C_{14}H_{22}N_2O_3$: 267 (MH+).

Step 4: Preparation of tert-butyl (2-{4-[2-methoxy-4-(2-methoxyethoxy)phenyl]piperazin-1-yl}ethyl)methylcarbamate tert-Butyl methyl(2-oxoethyl)carbamate (145 mg, 0.84 mmol) was added to a suspension of 1-[2-chloro-4-(2-methoxyethoxy)phenyl]piperazine (203 mg, 0.76 mmol) in 1,2-dichloroethane (5 mL). The resulting solution was treated with sodium triacetoxyborohydride (482 mg, 2.29 mmol) and stirred at room temperature for 16 hours. Water was added and the solvent was removed under reduced pressure to afford tert-butyl (2-{4-[2-methoxy-4-(2-methoxyethoxy)phenyl]piperazin-1-yl}ethyl)methylcarbamate (322 mg, 99% yield) that was used without further purification. MS (EI) for $C_{22}H_{37}N_3O_5$: 424 (MH+).

Step 5: Preparation of 2-{4-[2-methoxy-4-(2-methoxyethoxy)phenyl]piperazin-1-yl}-N-methyl-ethanamine

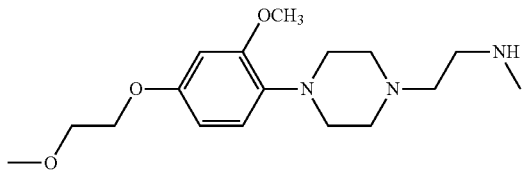

tert-Butyl (2-{4-[2-methoxy-4-(2-methoxyethoxy)phenyl]piperazin-1-yl}ethyl)methylcarbamate (322 mg, 0.76 mmol) was treated with 4 N hydrochloric acid in dioxane (2 mL) and the immediate suspension was stirred at room temperature for 1.5 hours. The solvent was removed under reduced pressure and the residue was dissolved in methanol (5 mL). AG+8 basic resin was added into the solution until pH 8-9. The resin was removed by filtration and the organic solvent was evaporated to give 2-{4-[2-methoxy-4-(2-methoxyethoxy)phenyl]piperazin-1-yl}-N-methyl-ethanamine that was used without further purification. MS (EI) for $C_{17}H_{29}N_3O_3$: 324 (MH+).

Step 6: Preparation of $N^7$-(2-{4-[2-methoxy-4-(2-methoxyethoxy)phenyl]piperazin-1-yl}ethyl)-$N^7$-methyl-2-(1,3-oxazol-2-yl)[1,2,4]triazolo[1,5-c]pyrimidine-5,7-diamine

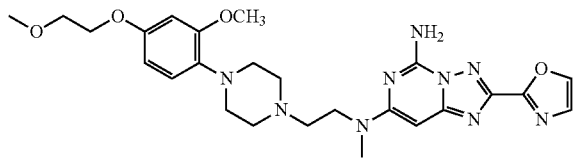 [SMILES: COCCOc1ccc(N2CCN(CCN(C)c3cc4nc(-c5ncco5)nn4c(N)n3)CC2)c(OC)c1]

To a stirred solution of 2-{4-[2-methoxy-4-(2-methoxyethoxy)phenyl]piperazin-1-yl}-N-methylethanamine (123 mg, 0.38 mmol) in 1 mL of dimethyl sulfoxide was added 7-chloro-2-(oxazol-2-yl)-[1,2,4]triazolo[1,5-c]pyrimidin-5-amine (99 mg, 0.41 mmol), followed by cesium fluoride (172 mg, 1.14 mmol). The solution was heated in a microwave at 140° C. for 5 hours. The mixture was partitioned between ethyl acetate (100 mL) and 1 N sodium carbonate solution (100 mL). The organic layer was washed with 1 N sodium carbonate solution (2×100 mL), dried (Na₂SO₄), filtered and concentrated to give a white solid. The solid was purified by normal phase flash chromatography (5-50% methanol in ethyl acetate) to give $N^7$-(2-{4-[2-methoxy-4-(2-methoxyethoxy)phenyl]piperazin-1-yl}ethyl)-$N^7$-methyl-2-(1,3-oxazol-2-yl)[1,2,4]triazolo[1,5-c]pyrimidine-5,7-diamine (17) as a white solid. $^1$H NMR (500 MHz, Chloroform-d) δ 7.83 (s, 1H), 7.36 (s, 1H), 6.84 (d, 1H), 6.55 (d, 1H), 6.42 (d, 1H), 5.94 (s, 1H), 5.86 (bs, 2H), 4.08 (dd, 2H), 3.83 (s, 3H), 3.75 (m, 4H), 3.45 (s, 3H), 3.07 (s, 3H), 3.03 (bs, 4H), 2.73 (bs, 4H), 2.64 (t, 2H). MS (EI) for $C_{25}H_{33}N_9O_4$: 524 (MH+).

The compound was dissolved in acetonitrile (1 mL) and treated with 1N hydrochloric acid in ether (300 μL). Solvents were removed under pressure and the residue was dried in vacuo to generate the hydrochloride salt of the tittle compound as a white solid (11 mg, 5% yield).

Example 7

Synthesis of $N^7$-(2-{4-[3-chloro-5-(2-methoxyethoxy)pyridin-2-yl]piperazin-1-yl}ethyl)-$N^7$-methyl-2-(1,3-oxazol-2-yl)[1,2,4]triazolo[1,5-c]pyrimidine-5,7-diamine (Compound 14), Hydrochloride Salt

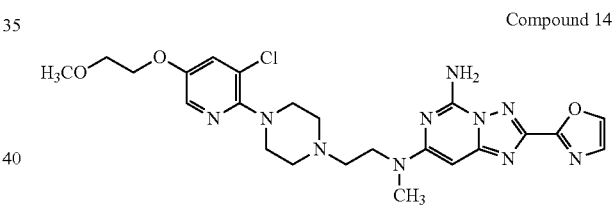

Compound 14

$N^7$-(2-{4-[3-Chloro-5-(2-methoxyethoxy)pyridin-2-yl]piperazin-1-yl}ethyl)-$N^7$-methyl-2-(1,3-oxazol-2-yl)[1,2,4]triazolo[1,5-c]pyrimidine-5,7-diamine was synthesized according to the following reaction scheme.

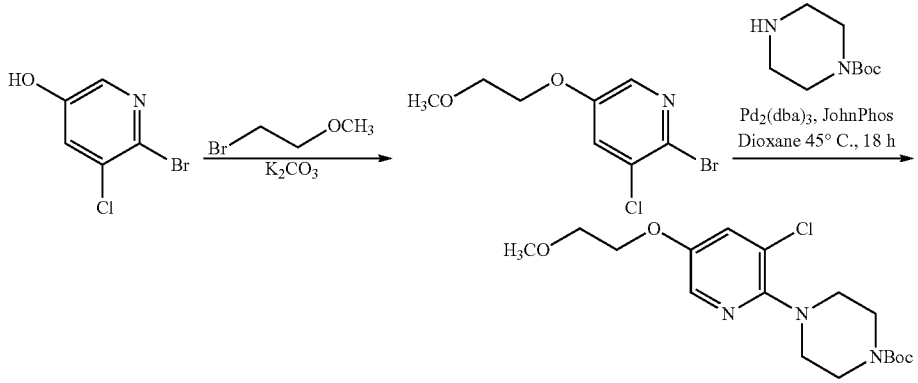

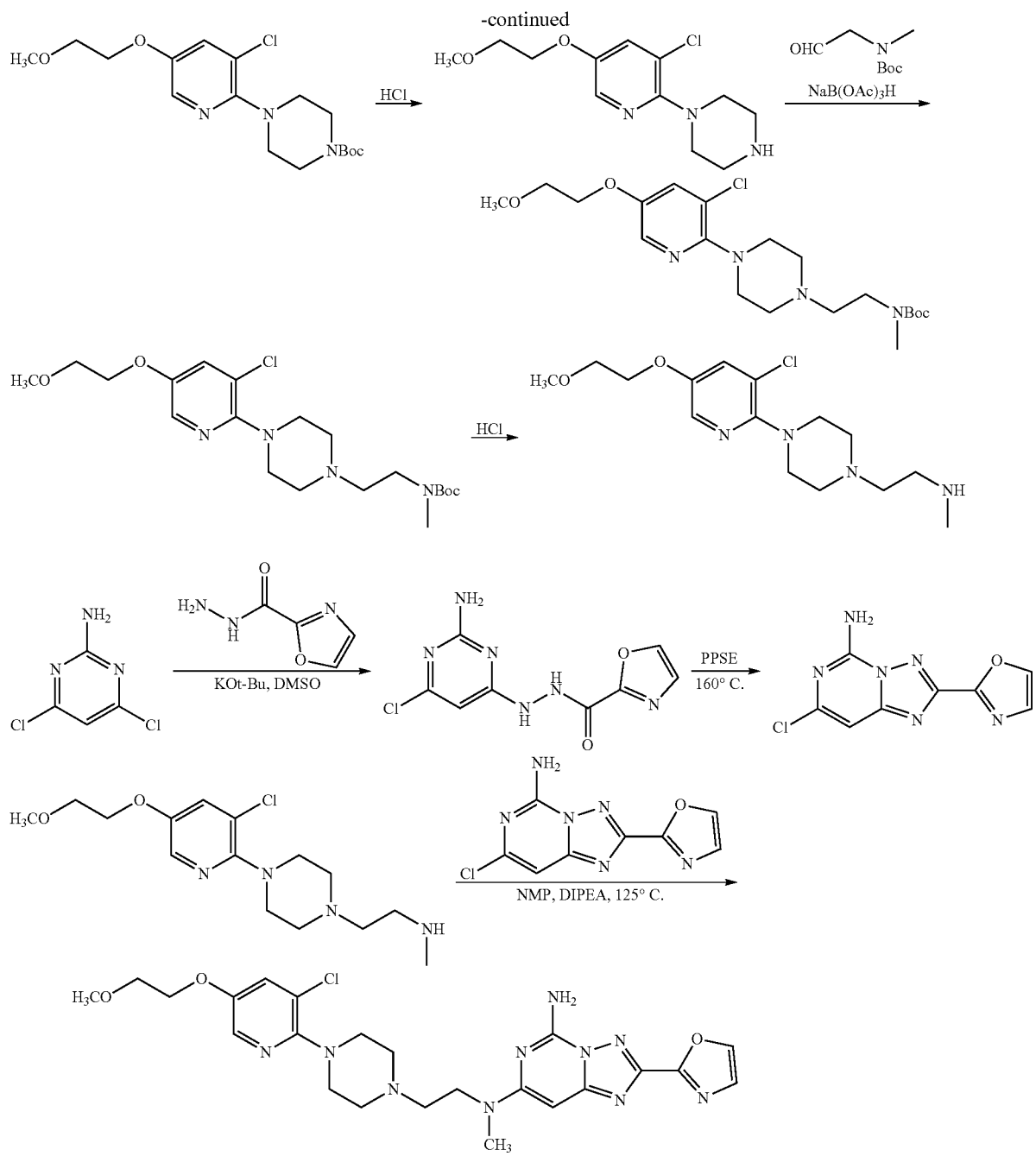

Step 1: Preparation of 2-bromo-3-chloro-5-(2-methoxyethoxy)pyridine

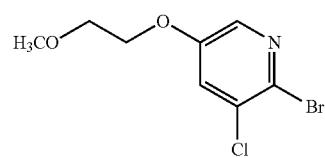 [SMILES: COCCOc1cnc(Br)c(Cl)c1]

A 20 mL vial was charged with 6-bromo-5-chloropyridin-3-ol (1.01 g, 4.85 mmol), dry N,N-dimethylformamide (9 mL), and potassium carbonate (1.34 g, 9.69 mmol). The mixture was stirred at room temperature for 10 min before neat 1-bromo-2-methoxy-ethane (0.59 mL, 6.30 mmol) was added in one portion. The mixture was stirred at room temperature for 18 hours. The mixture was then partitioned between ethyl acetate (100 mL) and water (50 mL). The aqueous layer was extracted with ethyl acetate (3×50 mL), and the combined organic layers were washed with brine (2×50 mL), dried (sodium sulfate), filtered and concentrated in vacuo to afford 2-bromo-3-chloro-5-(2-methoxyethoxy) pyridine (1.29 g, 99% yield) as an orange oil which was carried forward to the next step without further purification. MS (EI) for $C_8H_9BrClNO_2$: 267 (MH$^+$).

Step 2: Preparation of tert-butyl 4-[3-chloro-5-(2-methoxyethoxy)pyridin-2-yl]piperazine-1-carboxylate

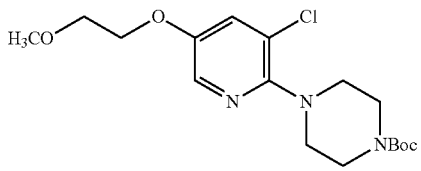

A 100 mL flask was charged with tert-butyl piperazine-1-carboxylate (0.48 g, 2.57 mmol), (1E,4E)-1,5-diphenylpenta-1,4-dien-3-one; palladium (0.22 g, 0.25 mmol), di-tert-butyl-(2-phenylphenyl)phosphane (0.29 g, 0.98 mmol) and sodium tert-butoxide (0.94 g, 9.80 mmol). The flask was purged with nitrogen and dry degassed dioxane (30 mL) was added. A solution of 2-bromo-3-chloro-5-(2-methoxyethoxy)pyridine (0.65 g, 2.45 mmol) in dry degassed dioxane (10 mL) was added, and the mixture stirred at room temperature for 10 min, then heated at 45° C. for 18 hours. The reaction was quenched with 10 mL of saturated ammonium chloride and then concentrated to remove most of the dioxane. The mixture was then diluted with ethyl acetate (50 mL) and water (10 mL). The mixture was filtered through Celite®, diluted with brine (100 mL), and the organic layer washed with 1 M sodium phosphate monobasic (2×25 mL), dried (sodium sulfate), filtered and concentrated in vacuo to afford crude tert-butyl 4-[3-chloro-5-(2-methoxyethoxy)pyridin-2-yl]piperazine-1-carboxylate as a brown-orange oil, which was carried forward to the next step without further purification. MS (EI) for $C_{17}H_{26}ClN_3O_4$: 372 (MH$^+$).

Step 3: Preparation of 1-[3-chloro-5-(2-methoxyethoxy)pyridin-2-yl]piperazine

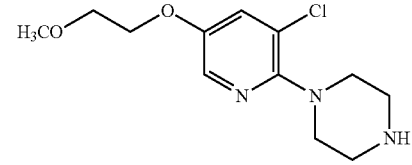 [SMILES: COCCOc1cnc(N2CCNCC2)c(Cl)c1]

A 4 M solution of hydrochloric acid in dioxane (6.05 mL, 24.2 mmol) was added slowly to a solution of tert-butyl 4-[3-chloro-5-(2-methoxyethoxy)pyridin-2-yl]piperazine-1-carboxylate in 1,4-dioxane (6 mL). The reaction was stirred at room temperature for 1.5 hours before being concentrated in vacuo. The residual solid was dissolved in ethyl acetate (50 mL) and was then extracted with 1 M sodium phosphate monobasic (2×50 mL), cleanly extracting the desired piperazine. The aqueous layers were combined, basified to pH>12 with 4 M sodium hydroxide, and extracted with dichloromethane (100 mL, 50 mL). The dichloromethane layers were combined, dried (sodium sulfate), filtered and concentrated in vacuo to afford 1-[3-chloro-5-(2-methoxyethoxy)pyridin-2-yl]piperazine (0.57 g, 88% yield over 2 steps) as a yellow oil. MS (EI) for $C_{12}H_{18}ClN_3O_2$: 272 (MH$^+$).

Step 4: Preparation of tert-butyl (2-{4-[3-chloro-5-(2-methoxyethoxy)pyridin-2-yl]piperazin-1-yl}ethyl)methylcarbamate

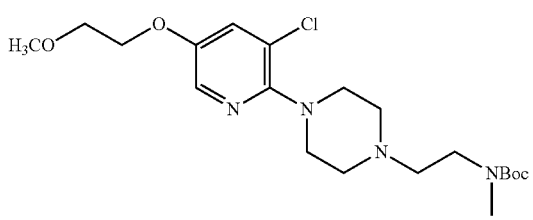 [SMILES: COCCOc1cnc(N2CCN(CCN(C)C(=O)OC(C)(C)C)CC2)c(Cl)c1]

Neat tert-butyl N-methyl-N-(2-oxoethyl)carbamate (0.43 mL, 2.55 mmol) was added to a stirred solution of 1-[3-chloro-5-(2-methoxyethoxy)pyridin-2-yl]piperazine (0.58 g, 2.12 mmol) in dichloroethane (10 mL). Sodium triacetoxyborohydride (0.42 g, 1.99 mmol) was then added in one portion and the mixture stirred at room temperature for 30 minutes. 1 M sodium carbonate was added (10 mL) and the mixture was extracted with dichloromethane (3×50 mL), dried (sodium sulfate), filtered and concentrated to a yellow oil. Chromatography on silica gel (1-10% methanol/dichloromethane) afforded tert-butyl (2-{4-[3-chloro-5-(2-methoxyethoxy)pyridin-2-yl]piperazin-1-yl}ethyl)methylcarbamate as a clear oil (0.56 g, 56% yield). MS (EI) for $C_{20}H_{33}ClN_4O_4$: 429 (MH$^+$).

Step 5: Preparation of 2-{4-[3-chloro-5-(2-methoxyethoxy)pyridin-2-yl]piperazin-1-yl}-N-methylethanamine

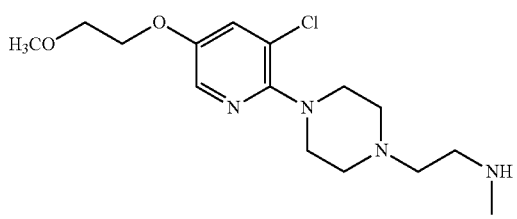

tert-Butyl (2-{4-[3-chloro-5-(2-methoxyethoxy)pyridin-2-yl]piperazin-1-yl}ethyl)methylcarbamate (0.56 g, 1.31 mmol) was dissolved in 4 mL of dioxane before 4 mL of 4 M hydrochloric acid in dioxane was added. The mixture was stirred at room temperature for 1 hour. The mixture was concentrated in vacuo before being dissolved in 5 mL of methanol and basified to pH~ 9 using AG-1-X8 basic resin. The solution was filtered and concentrated in vacuo to afford 2-{4-[3-chloro-5-(2-methoxyethoxy)pyridin-2-yl]piperazin-1-yl}-N-methylethanamine as a yellow oil (0.41 g, 95% yield). MS (EI) for $C_{15}H_{25}ClN_4O_2$: 329 (MH$^+$).

Step 6: Preparation of N-(2-amino-6-chloropyrimidin-4-yl)-1,3-oxazole-2-carbohydrazide

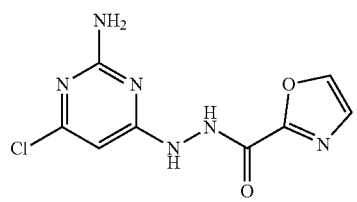 [SMILES: Nc1nc(Cl)cc(NNC(=O)c2ncco2)n1]

4,6-Dichloropyrimidin-2-amine (20.0 g, 122 mmol) and oxazole-2-carbohydrazide (17.1 g, 134 mmol) were dissolved in dimethyl sulfoxide (150 mL) followed by the addition of potassium tert-butoxide (28.7 g, 256 mmol) in three roughly equal portions over 20-30 minutes. The reaction was then stirred at room temperature for 15 hours. The solution was cooled to 5-10° C. before 10 mL of saturated ammonium chloride and 50 mL of water were added. The resulting gelatinous reaction slurry was stirred for 30 min, filtered and slurried again with 200 mL of acetonitrile. The solution was then filtered and the solid washed with methyl tert-butyl ether to give N-(2-amino-6-chloropyrimidin-4-yl)-1,3-oxazole-2-carbohydrazide as an off-white solid (31.0 g, 86% yield). MS (EI) for $C_8H_7ClN_6O_2$: 255 (MH$^+$).

Step 7: Preparation of 7-chloro-2-(1,3-oxazol-2-yl)[1,2,4]triazolo[1,5-c]pyrimidin-5-amine

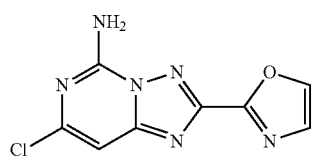 [SMILES: Nc1nc(Cl)cc2nc(-c3ncco3)nn12]

N-(2-Amino-6-chloropyrimidin-4-yl)-1,3-oxazole-2-carbohydrazide (40.0 g, 150 mmol) was charged in a 1 L round-bottom flask equipped with a mechanical stirrer. To this flask was added 100 ml of trimethylsilyl polyphosphate under nitrogen atmosphere. The solution was then heated to 160° C. for 9 hours. 2000 mL of water was added, and the mixture was stirred for 2 hours. The undissolved crude product was washed with 2.5 L of acetone:methanol (1:1) and filtered to give 7-chloro-2-(1,3-oxazol-2-yl)[1,2,4]triazolo[1,5-c]pyrimidin-5-amine as a yellow solid (16 g, 43% yield). MS (EI) for $C_8H_5N_6O$: 237 (MH$^+$).

Step 8: Preparation of $N^7$-(2-{4-[3-chloro-5-(2-methoxyethoxy)pyridin-2-yl]piperazin-1-yl}ethyl)-$N^7$-methyl-2-(1,3-oxazol-2-yl)[1,2,4]triazolo[1,5-c]pyrimidine-5,7-diamine

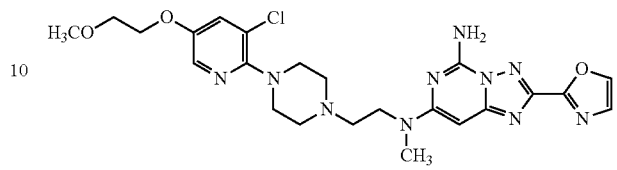

To a stirred solution of 2-{4-[3-chloro-5-(2-methoxyethoxy)pyridin-2-yl]piperazin-1-yl}-N-methylethanamine (175 mg, 0.53 mmol) in 1.0 mL of N-methyl-2-pyrrolidone was added 7-chloro-2-(1,3-oxazol-2-yl)[1,2,4]triazolo[1,5-c]pyrimidin-5-amine (105 mg, 0.44 mmol), followed by N,N-diisopropylethylamine (0.15 mL, 0.74 mmol). The solution was then heated to 125° C. for 18 hours. The crude reaction was directly purified using reverse phase Isolera™ (30 g C18, 5-100% acetonitrile/ammonium hydroxide in water) to afford a white solid. The solid was further purified using normal phase flash chromatography (4-20% methanol/ethyl acetate) to give $N^7$-(2-{4-[3-chloro-5-(2-methoxyethoxy)pyridin-2-yl]piperazin-1-yl}ethyl)-$N^7$-methyl-2-(1,3-oxazol-2-yl)[1,2,4]triazolo[1,5-c]pyrimidine-5,7-diamine (14) as a white solid (68.0 mg, 29% yield). $^1$H NMR (500 MHz, Chloroform-d) δ 7.93 (d, J=2.7 Hz, 1H), 7.84 (d, J=0.7 Hz, 1H), 7.36 (d, J=0.7 Hz, 1H), 7.30 (d, J=2.7 Hz, 1H), 6.13 (s, 2H), 5.92 (s, 1H), 4.10 (m, 2H), 3.77-3.71 (m, 4H), 3.44 (s, 3H), 3.27 (s, 4H), 3.07 (s, 3H), 2.74-2.66 (m, 4H), 2.63 (m, 2H). MS (EI) for $C_{23}H_{29}ClN_{10}O_3$: 529 (M+H)$^+$.

The compound was dissolved in acetonitrile and water and treated with 1N hydrochloric acid. Solvents were removed in the lyophilizer to generate the hydrochloride salt of the title compound as a solid.

Example 8

Synthesis of $N^7$-methyl-$N^7$-{2-[4-(4-{2-[($^2$H$_3$)methyloxy]ethoxy}phenyl)piperazin-1-yl]ethyl}-2-(1,3-oxazol-2-yl)[1,2,4]triazolo[1,5-c]pyrimidine-5,7-diamine (Compound 7), Hydrochloride Salt Compound 7

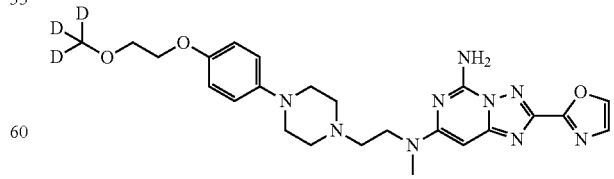

$N^7$-Methyl-$N^7$-{2-[4-(4-{2-[($^2$H$_3$)methyloxy]ethoxy}phenyl)piperazin-1-yl]ethyl}-2-(1,3-oxazol-2-yl)[1,2,4]triazolo[1,5-c]pyrimidine-5,7-diamine was synthesized according to the following reaction scheme.

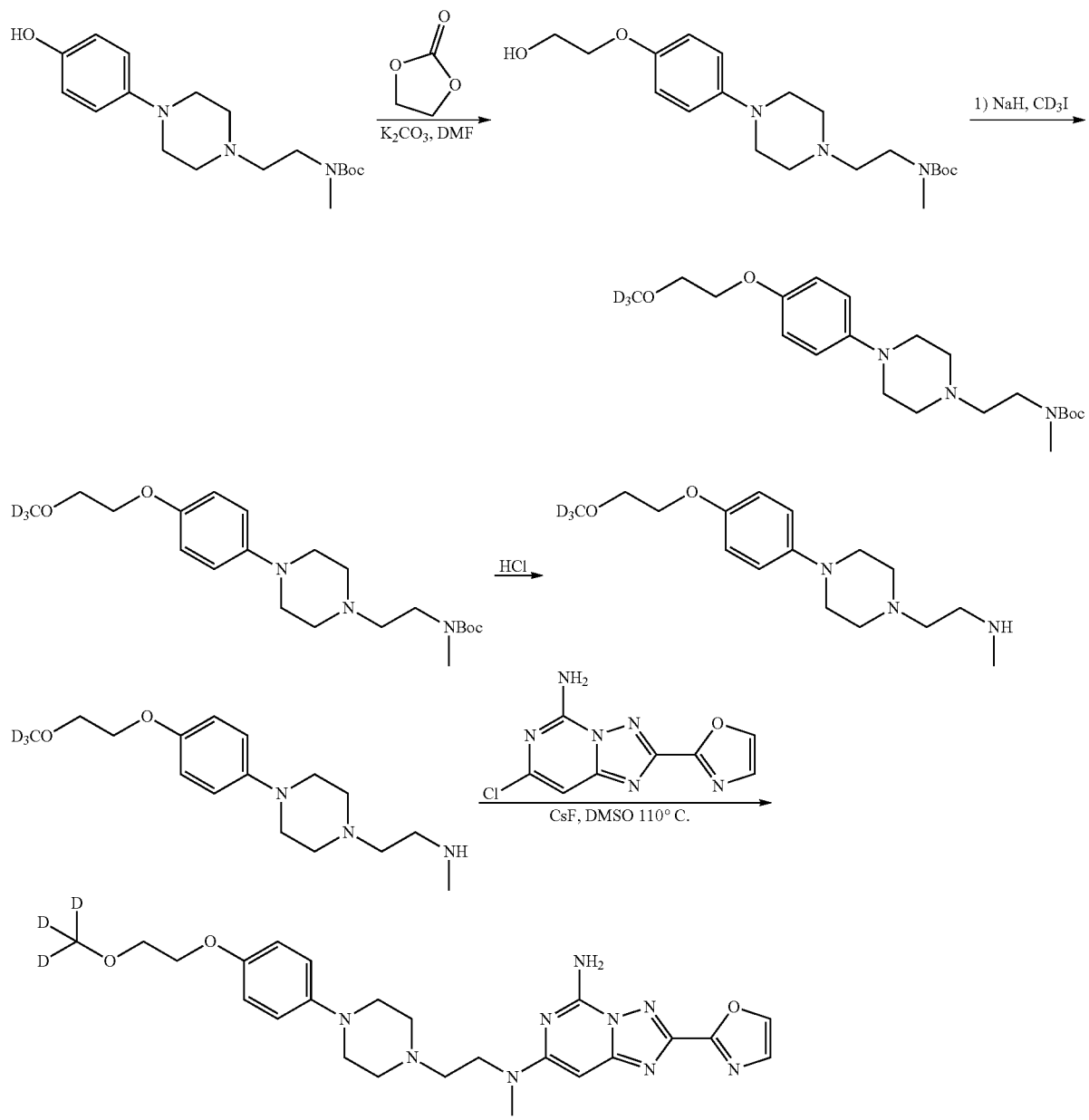

Step 1: Preparation of tert-butyl (2-{4-[4-(2-hydroxyethoxy)phenyl]piperazin-1-yl}ethyl)methylcarbamate

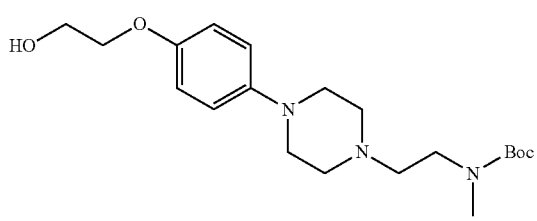 [SMILES: CN(CCN1CCN(c2ccc(OCCO)cc2)CC1)C(=O)OC(C)(C)C]

To a stirred solution of tert-butyl (2-(4-(4-hydroxyphenyl)piperazin-1-yl)ethyl)(methyl)carbamate (Step 1, Compound 5) (1.9 g, 5.66 mmol) in 11 mL of N,N-dimethylformamide was added potassium carbonate (1.57 g, 11.3 mmol). Ethylene carbonate (2.0 g, 22.7 mmol) was added and the mixture was heated to 80° C. for 18 hours. The reaction was diluted with 100 mL of ethyl acetate and washed with 1 M sodium hydroxide (3×50 mL) followed by 100 mL of brine. The organic layer was dried and concentrated to give a yellow oil. The oil was purified by flash chromatography (4-10% methanol/dichloromethane) to afford tert-butyl (2-{4-[4-(2-hydroxyethoxy)phenyl]piperazin-1-yl}ethyl)methylcarbamate (0.66 g, 30% yield) as a clear oil. $^1$H NMR (500 MHz, Chloroform-d) δ 6.93-6.82 (m, 4H), 4.04 (t, J=4.5 Hz, 2H), 3.93 (t, J=4.5 Hz, 2H), 3.39 (m, 2H), 3.14-3.05 (br, 4H), 2.94-2.86 (br, 3H), 2.70-2.63 (br, 4H), 2.59-2.51 (br, 2H), 2.10 (br s, 1H), 1.47 (s, 9H). MS (EI) for $C_{20}H_{34}N_3O_4$: 380 (MH$^+$).

Step 2: Preparation of tert-butyl methyl{2-[4-(4-{2-[($^2$H$_3$)methyloxy]ethoxy}phenyl)piperazin-1-yl]ethyl}carbamate

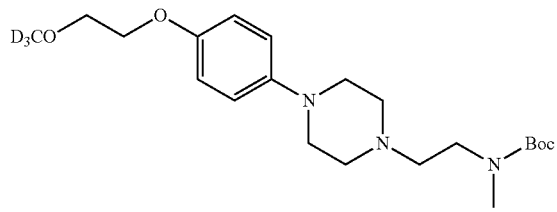

Sodium hydride (0.21 g, 5.16 mmol) was suspended in N,N-dimethylformamide (2 mL) and cooled to 0° C. A solution of tert-butyl (2-{4-[4-(2-hydroxyethoxy)phenyl]piperazin-1-yl}ethyl)methylcarbamate (0.65 g, 1.72 mmol) in N,N-dimethylformamide (3 mL) was added dropwise and the solution was stirred at 0° C. for 10 min and then at room temperature for 20 min. The solution was then cooled to 0° C. before iodomethane-d$_3$ (0.16 mL, 2.58 mmol) was added dropwise via syringe. The solution was then allowed to stir at room temperature for 45 min. The reaction was quenched with saturated ammonium chloride (10 mL) and extracted with 3×50 mL of ethyl acetate. The combined organic layers were washed with 2×100 mL of brine, dried and concentrated in vacuo. The reaction was purified by flash chromatography (1-10% methanol/dichloromethane) to give tert-butyl methyl{2-[4-(4-{2-[($^2$H$_3$)methyloxy]ethoxy}phenyl)piperazin-1-yl]ethyl}carbamate as a yellow oil (0.17 g, 25% yield). $^1$H NMR (500 MHz, Chloroform-d) δ 6.88-6.76 (m, 4H), 4.00 (t, J=4.7 Hz, 2H), 3.68 (t, J=4.7 Hz, 2H), 3.33 (m, 2H), 3.05 (br, 4H), 2.84 (m, 3H), 2.62 (br, 4H), 2.49 (m, 2H), 1.43 (s, 9H). MS (EI) for C$_{21}$H$_{33}$D$_3$N$_3$O$_4$: 397 (MH$^+$).

Step 3: Preparation of N-methyl-2-[4-(4-{2-[($^2$H$_3$)methyloxy]ethoxy}phenyl)piperazin-1-yl]ethanamine

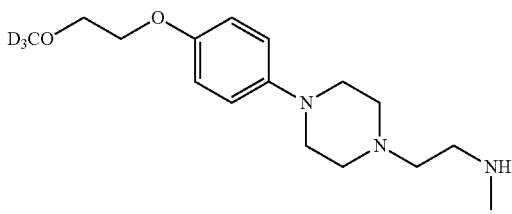

tert-Butyl methyl{2-[4-(4-{2-[($^2$H$_3$)methyloxy]ethoxy}phenyl)piperazin-1-yl]ethyl}carbamate (0.17 g, 0.41 mmol) was dissolved in 1 mL of dioxane before 1.0 mL of 4 M hydrochloric acid in dioxane was added. The mixture was stirred at room temperature for 3 hours. The mixture was concentrated in vacuo before being dissolved in 5 mL of methanol and basified to pH~ 9 using basic resin. The solution was filtered and concentrated in vacuo to give N-methyl-2-[4-(4-{2-[($^2$H$_3$)methyloxy]ethoxy}phenyl)piperazin-1-yl]ethanamine as an off-white solid (0.12 g, 96% yield). MS (EI) for C$_{16}$H$_{25}$D$_3$N$_3$O$_2$: 297 (MH$^+$).

Step 4: Preparation of N$^7$-methyl-N-{2-[4-(4-{2-[($^2$H$_3$)methyloxy]ethoxy}phenyl)piperazin-1-yl]ethyl}-2-(1,3-oxazol-2-yl)[1,2,4]triazolo[1,5-c]pyrimidine-5,7-diamine

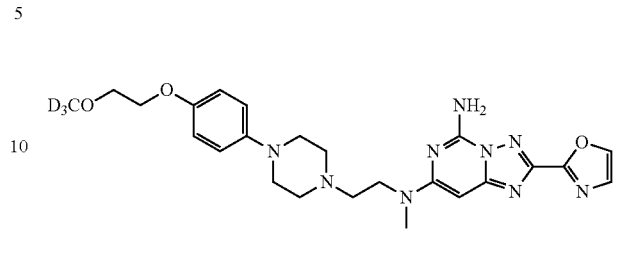

To a stirred solution of N-methyl-2-[4-(4-{2-[($^2$H$_3$)methyloxy]ethoxy}phenyl)piperazin-1-yl]ethanamine (120 mg, 0.41 mmol) in 2.0 mL of dimethyl sulfoxide was added 7-chloro-2-(1,3-oxazol-2-yl)[1,2,4]triazolo[1,5-c]pyrimidin-5-amine (compound 14, step 7) (80.0 mg, 0.337 mmol), followed by cesium fluoride (143 mg, 0.95 mmol). The solution was then heated to 110° C. for 18 hours. The crude reaction was directly purified using reverse phase Isolera™ (30 g C18, 5-100% acetonitrile/ammonium hydroxide in water) to afford a white solid. The solid was further purified using normal phase flash chromatography (4-20% methanol/ethyl acetate) to give N$^7$-methyl-N$^7$-{2-[4-(4-{2-[($^2$H$_3$)methyloxy]ethoxy}phenyl)piperazin-1-yl]ethyl}-2-(1,3-oxazol-2-yl)[1,2,4]triazolo[1,5-c]pyrimidine-5,7-diamine (7) as a white solid (40.0 mg, 24% yield). $^1$H NMR (500 MHz, Chloroform-d) δ 7.86 (d, J=1.0 Hz, 1H), 7.38 (d, J=1.0 Hz, 1H), 6.98-6.80 (m, 4H), 5.96 (s, 1H), 5.76 (br s, 2H), 4.13-4.04 (m, 2H), 3.82-3.72 (m, 4H), 3.25-3.07 (m, 7H), 2.74 (m, 6H). MS (EI) for C$_{24}$H$_{29}$D$_3$N$_9$O$_3$: 497 (MH$^+$).

The compound was dissolved in acetonitrile and water and treated with 1N hydrochloric acid. Solvents were removed in the lyophilizer to generate the hydrochloride salt of the title compound as a solid.

Example 9

Synthesis of N$^7$-(2-{4-[4-(2-methoxyethoxy)phenyl]piperazin-1-yl}ethyl)-N$^7$-($^2$H$_3$)methyl-2-(1,3-oxazol-2-yl)[1,2,4]triazolo[1,5-c]pyrimidine-5,7-diamine (Compound 6), Hydrochloride Salt Compound 6

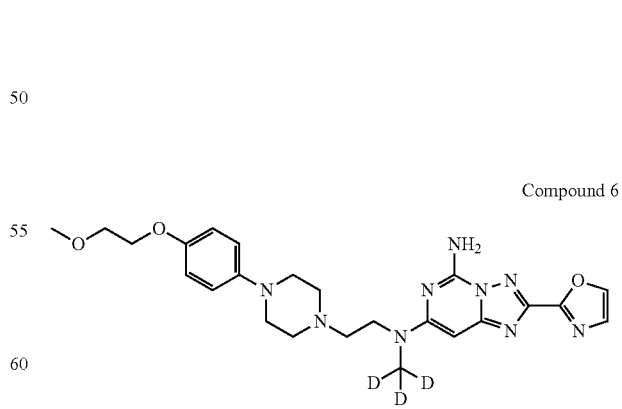

N$^7$-(2-{4-[4-(2-Methoxyethoxy)phenyl]piperazin-1-yl}ethyl)-N$^7$-($^2$H$_3$)methyl-2-(1,3-oxazol-2-yl)[1,2,4]triazolo[1,5-c]pyrimidine-5,7-diamine was synthesized according to the following reaction scheme.

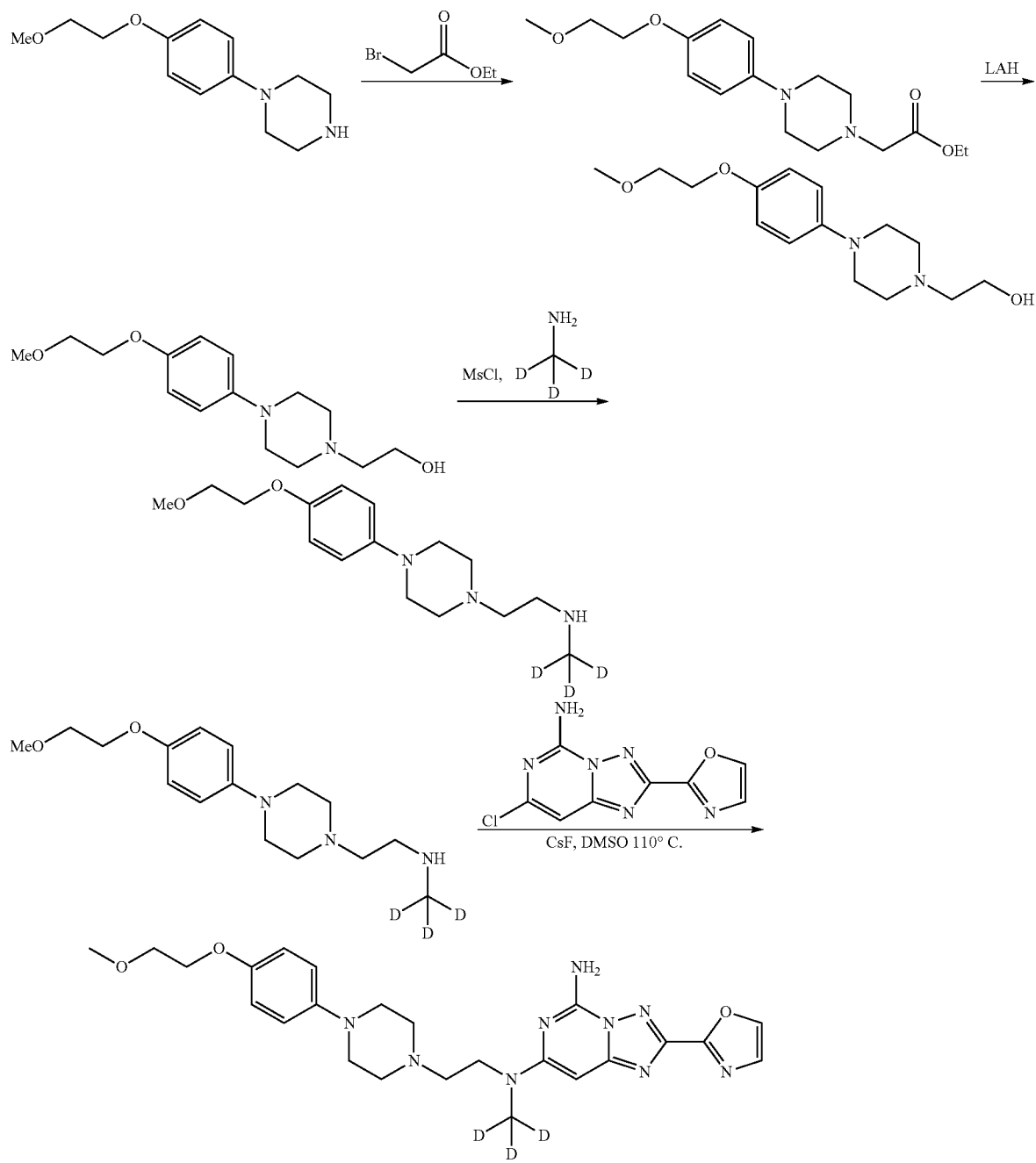

Step 1: Preparation of ethyl {4-[4-(2-methoxy-ethoxy)phenyl]piperazin-1-yl}acetate

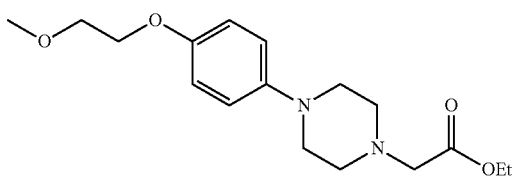 [SMILES: CCOC(=O)CN1CCN(c2ccc(OCCOC)cc2)CC1]

1-[4-(2-Methoxyethoxy)phenyl]piperazine dihydrochloride (5.02 g, 16.2 mmol) was suspended in acetonitrile (40 ml), followed by the addition of triethylamine (8.86 ml, 65 mmol) and ethyl bromoacetate (2.1 ml, 18.9 mmol). The reaction was stirred at room temperature for 18 h before being filtered and concentrated. The residue was redissolved in ethyl acetate (150 mL) and the solution was washed with brine (50 mL) and water (50 mL). The organic phase was dried over sodium sulfate and concentrated to afford ethyl {4-[4-(2-methoxyethoxy)phenyl]piperazin-1-yl}acetate as a white solid (5.10 g, 97% yield). MS (EI) for $C_{17}H_{26}N_2O_4$: 323 (MH)+.

Step 2: Preparation of 2-{4-[4-(2-methoxyethoxy)phenyl]piperazin-1-yl}ethanol

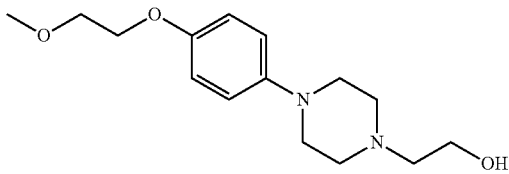 [SMILES: COCCOc1ccc(N2CCN(CCO)CC2)cc1]

To a cooled (0° C.) solution of ethyl {4-[4-(2-methoxyethoxy)phenyl]piperazin-1-yl}acetate (5.18 g, 16.06 mmol) in 20 mL of tetrahydrofuran was slowly added a 2 M solution of lithium aluminum hydride in tetrahydrofuran (4.03 ml, 8.03 mmol). The reaction was stirred at room temperature for one hour before being quenched with water (5 mL). 150 mL of dichloromethane were added and the resulted solution was washed with sodium bicarbonate (50 mL) and brine (50 mL). The solution was dried over sodium sulfate, filtered and concentrated to give 2-{4-[4-(2-methoxyethoxy)phenyl]piperazin-1-yl}ethanol as a white solid (4.06 g, 90% yield). MS (EI) for $C_{15}H_{24}N_2O_3$: 281 (MH$^+$).

Step 3: Preparation of 2-{4-[4-(2-methoxyethoxy)phenyl]piperazin-1-yl}-N-($^2H_3$)methylethanamine

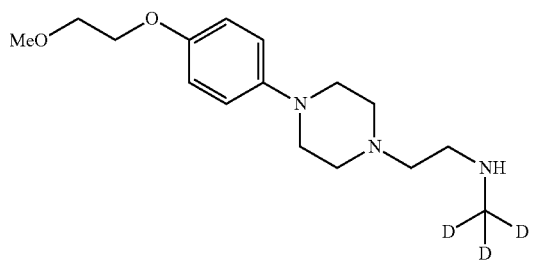 [SMILES: [2H]C([2H])([2H])NCCN1CCN(c2ccc(OCCOC)cc2)CC1]

To a stirred solution of 2-{4-[4-(2-methoxyethoxy)phenyl]piperazin-1-yl}ethanol (0.30 g, 1.07 mmol) in 3 mL of dichloromethane was added triethylamine (0.33 mL, 2.35 mmol). The mixture was cooled to 0° C. in an ice-bath before methanesulfonyl chloride (91 μL, 1.18 mmol) was added dropwise via syringe. After 15 minutes, the reaction was quenched with 5 mL brine and 25 mL dichloromethane, the layers were separated and the organic layer was dried and concentrated to give a yellow oil. The oil was dissolved in 5 mL of acetonitrile, transferred to a sealed tube to which was added d$_3$-methylamine-hydrochloric acid salt (0.30 mg, 4.28 mmol) followed by potassium carbonate (1.18 g, 8.56 mmol). The tube was then sealed and heated to 80° C. for 4 hours. The mixture was filtered and concentrated to give a yellow oil. The oil was purified using flash chromatography (1-10% methanol/ethyl acetate on a 28 g NH column) to give 2-{4-[4-(2-methoxyethoxy)phenyl]piperazin-1-yl}-N-($^2H_3$)methylethanamine as an off-white solid (37 mg, 12% yield. MS (EI) for $C_{16}H_{25}D_3N_3O_2$: 297 (MH$^+$).

Step 4: Preparation of N$^7$-(2-{4-[4-(2-methoxyethoxy)phenyl]piperazin-1-yl}ethyl)-N$^7$-($^2H_3$)methyl-2-(1,3-oxazol-2-yl)[1,2,4]triazolo[1,5-c]pyrimidine-5,7-diamine

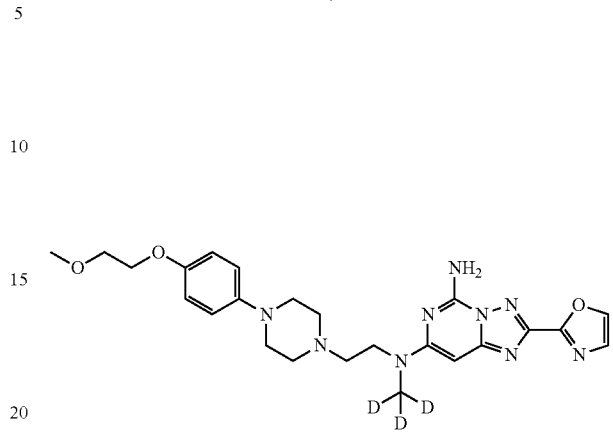

Using the approach described in Step 4 of Compound 7, 2-{4-[4-(2-methoxyethoxy)phenyl]piperazin-1-yl}-N-($^2H_3$)methylethanamine (55.0 mg, 0.19 mmol) yielded N$^7$-(2-{4-[4-(2-methoxyethoxy)phenyl]piperazin-1-yl}ethyl)-N$^7$-($^2H_3$)methyl-2-(1,3-oxazol-2-yl)[1,2,4]triazolo[1,5-c]pyrimidine-5,7-diamine (6) as a white solid (30.0 mg, 33% yield). $^1H$ NMR (500 MHz, Chloroform-d) δ 7.85 (s, 1H), 7.38 (s, 1H), 6.99-6.75 (m, 4H), 5.96 (s, 1H), 5.75 (br s, 2H), 4.12 (m, 2H), 3.88-3.70 (m, 4H), 3.47 (s, 3H), 3.14 (br s, 4H), 2.84-2.56 (m, 6H). MS (EI) for $C_{24}H_{29}D_3N_9O_3$: 497 (MH$^+$).

The compound was dissolved in acetonitrile and water and treated with 1N hydrochloric acid. Solvents were removed in the lyophilizer to generate the hydrochloride salt of the title compound as a solid.

Example 10

Synthesis of N$^7$-($^2H_3$)methyl-N$^7$-{2-[4-(4-{2-[($^2H_3$)methyloxy]ethoxy}phenyl)piperazin-1-yl]ethyl}-2-(1,3-oxazol-2-yl)[1,2,4]triazolo[1,5-c]pyrimidine-5,7-diamine (Compound 8), Hydrochloride Salt Compound 8

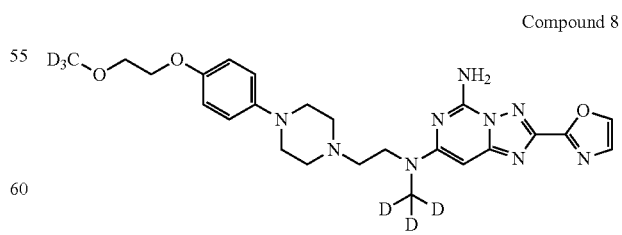

N$^7$-($^2H_3$)Methyl-N$^7$-{2-[4-(4-{2-[($^2H_3$)methyloxy]ethoxy}phenyl)piperazin-1-yl]ethyl}-2-(1,3-oxazol-2-yl)[1,2,4]triazolo[1,5-c]pyrimidine-5,7-diamine was synthesized according to the following reaction scheme:

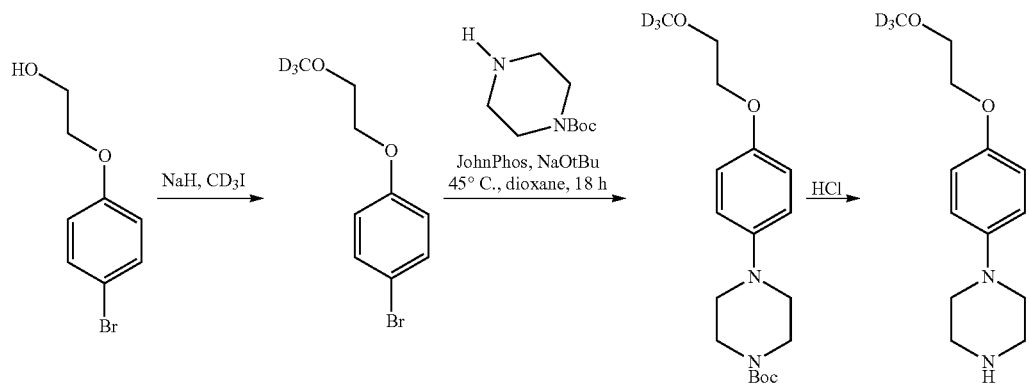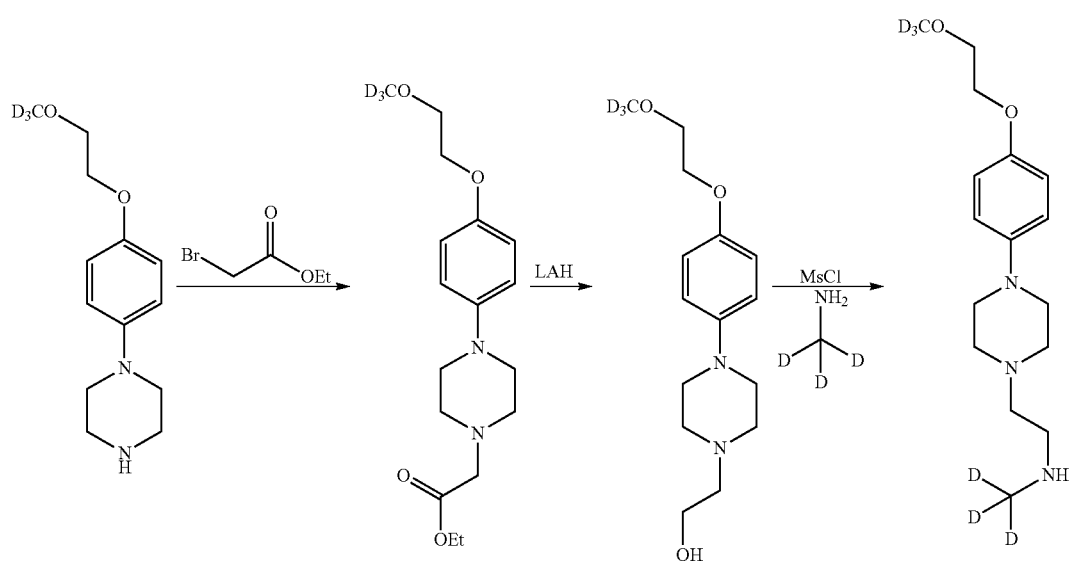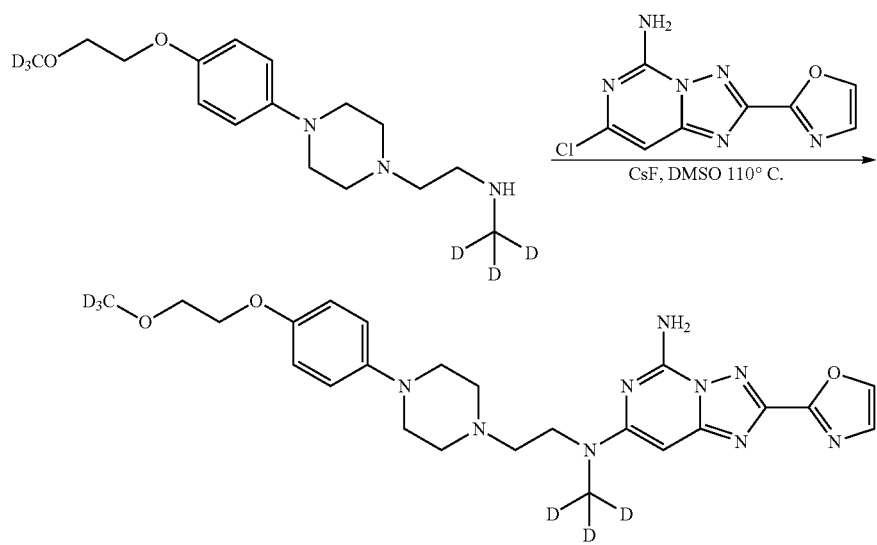

Step 1: Preparation of 1-bromo-4-{2-[($^2$H$_3$)methyloxy]ethoxy}benzene

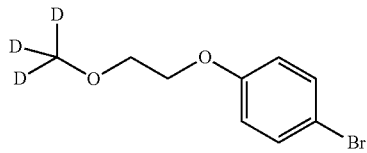 [SMILES: [2H]C([2H])([2H])OCCOc1ccc(Br)cc1]

To a cooled (0° C.) and stirred suspension of sodium hydride (1.49 g, 37.2 mmol) in tetrahydrofuran (50 mL) was added dropwise a solution of 2-(4-bromophenoxy)ethan-1-ol (5.38 g, 24.8 mmol) in tetrahydrofuran (25 mL). The solution was stirred at room temperature for 15 min before being cooled to 0° C. Iodomethane-d$_3$ (2.00 mL, 32.2 mmol) was then added dropwise via syringe. The solution was then stirred at room temperature overnight. The reaction was cooled to 0° C. and quenched with 5 mL of saturated ammonium chloride followed by the addition of 100 mL ethyl acetate and 50 mL of water. The aqueous layer was extracted with 2×50 mL ethyl acetate and the combined organic layers were washed with brine, dried and concentrated in vacuo to give 1-bromo-4-{2-[($^2$H$_3$)methyloxy]ethoxy}benzene as an orange oil (5.60 g, 96% yield). $^1$H NMR (500 MHz, Chloroform-d) δ 7.39 (d, J=9.0 Hz, 2H), 6.83 (d, J=9.0 Hz, 2H), 4.10 (t, J=4.5 Hz, 2H), 3.76 (t, J=4.5 Hz, 2H).

Step 2: Preparation of tert-butyl 4-(4-{2-[($^2$H$_3$)methyloxy]ethoxy}phenyl)piperazine-1-carboxylate

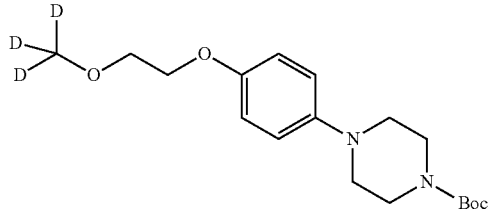 [SMILES: [2H]C([2H])([2H])OCCOc1ccc(N2CCN(C(=O)OC(C)(C)C)CC2)cc1]

Using the approach described in Step 2 of Compound 14, 1-bromo-4-{2-[($^2$H$_3$)methyloxy]ethoxy}benzene (2.75 g, 11.75 mmol) yielded tert-butyl 4-(4-{2-[($^2$H$_3$)methyloxy]ethoxy}phenyl)piperazine-1-carboxylate which was carried onto the next step with no additional purification. MS (EI) for C$_{18}$H$_{25}$D$_3$N$_2$O$_4$: 340 (MH$^+$).

Step 3: Preparation of 1-(4-{2-[($^2$H$_3$)methyloxy]ethoxy}phenyl)piperazine

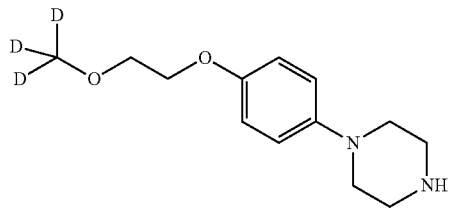 [SMILES: [2H]C([2H])([2H])OCCOc1ccc(N2CCNCC2)cc1]

Using the approach described in Step 3 of Compound 14, crude tert-butyl 4-(4-{2-[($^2$H$_3$)methyloxy]ethoxy}phenyl)piperazine-1-carboxylate yielded 1-(4-{2-[($^2$H$_3$)methyloxy]ethoxy}phenyl)piperazine as an off-white solid (0.64 g, 23% over two steps). MS (EI) for C$_{13}$H$_{17}$D$_3$N$_2$O$_2$: 240 (MH$^+$).

Step 4: Preparation of ethyl [4-(4-{2-[($^2$H$_3$)methyloxy]ethoxy}phenyl)piperazin-1-yl]acetate

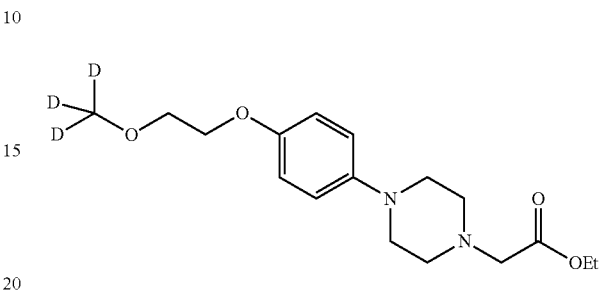

Using the method described in Step 1 of Compound 6, 1-(4-{2-[($^2$H$_3$)methyloxy]ethoxy}phenyl)piperazine (0.49 g, 2.04 mmol) afforded ethyl [4-(4-{2-[($^2$H$_3$)methyloxy]ethoxy}phenyl)piperazin-1-yl]acetate (0.67, 2.04 mmol) as an off-white solid. The solid was carried onto the next step with no further purification. MS (EI) for C$_{17}$H$_{23}$D$_3$N$_2$O$_4$: 326 (MH$^+$).

Step 5: Preparation of 2-[4-(4-{2-[($^2$H$_3$)Methyloxy]ethoxy}phenyl)piperazin-1-yl]ethanol

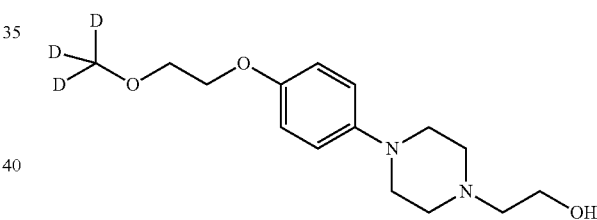

Using the method described in Step 2 of Compound 6, ethyl [4-(4-{2-[($^2$H$_3$)methyloxy]ethoxy}phenyl)piperazin-1-yl]acetate (0.67, 2.04 mmol) afforded 2-[4-(4-{2-[($^2$H$_3$)methyloxy]ethoxy}phenyl)piperazin-1-yl]ethanol as an off-white solid (0.34 g, 88% over 2 steps). MS (EI) for C$_{15}$H$_{21}$D$_3$N$_2$O$_2$: 284 (MH$^+$).

Step 6: Preparation of N-($^2$H$_3$)methyl-2-[4-(4-{2-[($^2$H$_3$)methyloxy]ethoxy}phenyl)piperazin-1-yl]ethanamine

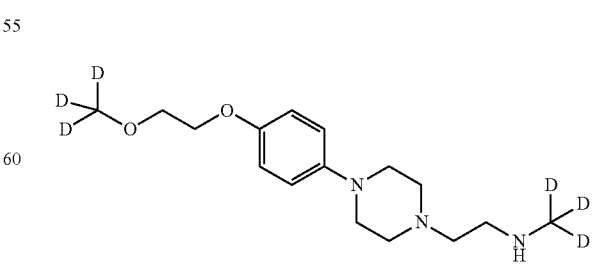

Using the approach described in Step 3 of Compound 6, 2-[4-(4-{2-[($^2$H$_3$)methyloxy]ethoxy}phenyl)piperazin-1-yl]

ethanol (0.34 g, 1.21 mmol) yielded 2 N-($^2$H$_3$)methyl-2-[4-(4-{2-[($^2$H$_3$)methyloxy]ethoxy}phenyl)piperazin-1-yl] ethanamine as an off-white solid (112 mg, 31% yield. MS (EI) for C$_{16}$H$_{21}$D$_6$N$_3$O$_2$: 300 (MH$^+$).

Step 7: Preparation of N$^7$-($^2$H$_3$)methyl-N$^7$-{2-[4-(4-{2-[($^2$H$_3$)methyloxy]ethoxy}phenyl)piperazin-1-yl]ethyl}-2-(1,3-oxazol-2-yl)[1,2,4]triazolo[1,5-c]pyrimidine-5,7-diamine

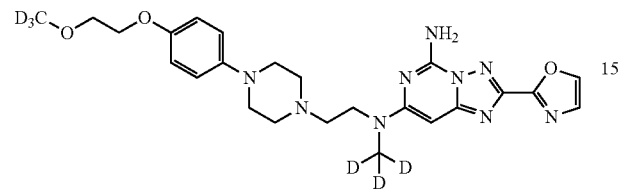

Using the approach described in Step 4 of Compound 7, N-($^2$H$_3$)methyl-2-[4-(4-{2-[($^2$H$_3$)methyloxy] ethoxy}phenyl)piperazin-1-yl]ethanamine (112 mg, 0.37 mmol yielded N$^7$-($^2$H$_3$)Methyl-N$^7$-{2-[4-(4-{2-[($^2$H$_3$)methyloxy]ethoxy}phenyl)piperazin-1-yl]ethyl}-2-(1,3-oxazol-2-yl)[1,2,4]triazolo[1,5-c]pyrimidine-5,7-diamine (8) as a white solid (40.0 mg, 24% yield). $^1$H NMR (500 MHz, Chloroform-d) δ 7.84 (d, J=0.9 Hz, 1H), 7.38 (d, J=0.9 Hz, 1H), 6.93-6.81 (m, 4H), 6.00-5.65 (m, 3H), 4.07 (m, 2H), 3.76-3.66 (m, 4H), 3.15-3.07 (m, 4H), 2.75-2.66 (m, 4H), 2.64 (t, J=7.2 Hz, 2H). MS (EI) for C$_{24}$H$_{25}$D$_6$N$_9$O$_3$: 500 (MH$^+$).

The compound was dissolved in acetonitrile and water and treated with 1N hydrochloric acid. Solvents were removed in the lyophilizer to generate the hydrochloride salt of the title compound as a solid.

Example 11

Synthesis of N$^7$-[2-{4-[4-(2-methoxyethoxy)phenyl]piperazin-1-yl}($^2$H$_4$)ethyl]-N$^7$-methyl-2-(1,3-oxazol-2-yl)[1,2,4]triazolo[1,5-c]pyrimidine-5,7-diamine (Compound 9), Hydrochloride Salt Compound 9

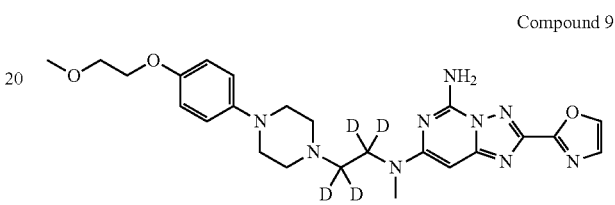

N$^7$-[2-{4-[4-(2-Methoxyethoxy)phenyl]piperazin-1-yl}($^2$H$_4$)ethyl]-N$^7$-methyl-2-(1,3-oxazol-2-yl)[1,2,4]triazolo[1,5-c]pyrimidine-5,7-diamine was synthesized according to the following reaction scheme.

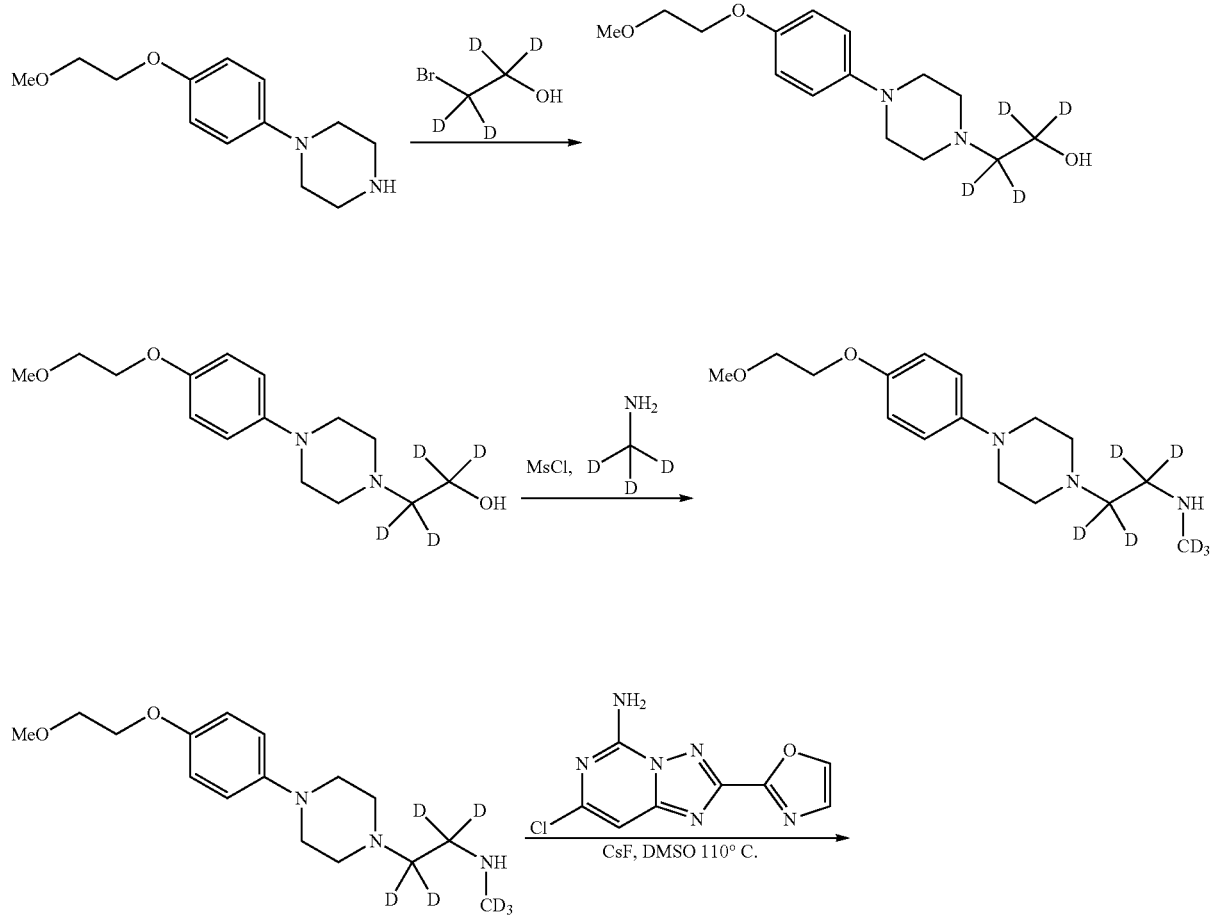

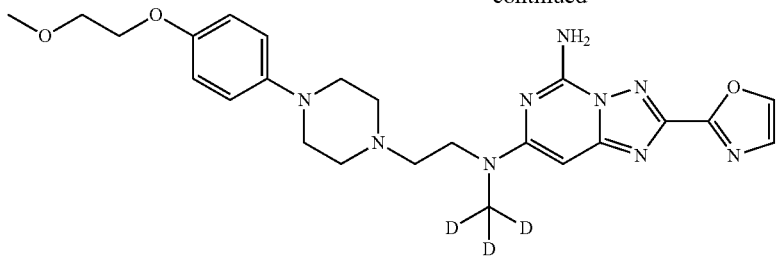

Step 1: Preparation of 2-{4-[4-(2-methoxyethoxy)phenyl]piperazin-1-yl}($^2$H$_4$)ethanol

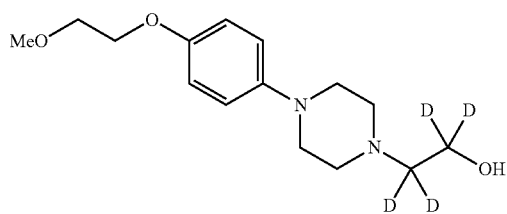 [SMILES: [2H]C([2H])(O)C([2H])([2H])N1CCN(c2ccc(OCCOC)cc2)CC1]

To a stirred suspension of 1-[4-(2-methoxyethoxy)phenyl]piperazine dihydrochloride (0.74 g, 2.39 mmol) in 12 mL of acetonitrile was added ethyldiisopropylamine (1.27 mL, 7.89 mmol) followed by 2-bromo-1,1,2,2-tetradeuterioethanol (0.34 g, 2.63 mmol) and 2 mL of N,N-dimethylformamide. The suspension was stirred at room temperature overnight followed by an additional 24 hours at 75° C. The reaction was cooled to room temperature and partitioned between ethyl acetate (100 mL) and brine (50 mL). The combined organic layers were dried and concentrated in vacuo to give 2-{4-[4-(2-methoxyethoxy)phenyl]piperazin-1-yl}($^2$H$_4$)ethanol as a white solid (0.60 g, 75% yield). MS (EI) for C$_{15}$H$_{20}$D$_4$N$_2$O$_3$: 285 (MH$^+$).

Step 2: Preparation of 2-{4-[4-(2-methoxyethoxy)phenyl]piperazin-1-yl}-N-methyl($^2$H$_4$)ethanamine

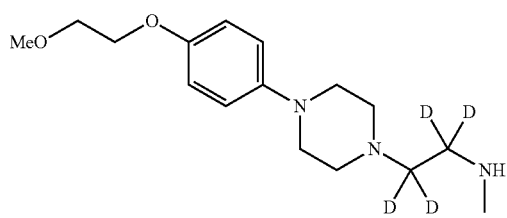 [SMILES: [2H]C([2H])(NC)C([2H])([2H])N1CCN(c2ccc(OCCOC)cc2)CC1]

To a stirred solution of 2-{4-[4-(2-methoxyethoxy)phenyl]piperazin-1-yl}($^2$H$_4$)ethanol (0.30 g, 1.05 mmol) in 3 mL of dichloromethane was added triethylamine (0.19 mL, 1.37 mmol). The mixture was cooled to 0° C. in an ice-bath before methanesulfonyl chloride (91 µL, 1.18 mmol) was added dropwise via syringe. After 15 minutes the reaction was quenched with 5 mL of brine and 25 mL of dichloromethane, the layers were separated and the organic layer was dried and concentrated to give a yellow oil. The oil was dissolved in 5 mL of ethanol, transferred to a sealed tube to which was added methylamine 30% in ethanol (9.63 mL, 21.1 mmol). The tube was sealed and heated to 80° C. for two hours. The mixture was filtered and concentrated to give 2-{4-[4-(2-methoxyethoxy)phenyl]piperazin-1-yl}-N-methyl($^2$H$_4$)ethanamine as an off white solid (0.29 g, 91% yield). MS (EI) for C$_{16}$H$_{23}$D$_4$N$_3$O$_2$: 298 (MH$^+$).

Step 3: Preparation of N$^7$-[2-{4-[4-(2-methoxyethoxy)phenyl]piperazin-1-yl}($^2$H$_4$)ethyl]-N$^7$-methyl-2-(1,3-oxazol-2-yl)[1,2,4]triazolo[1,5-c]pyrimidine-5,7-diamine

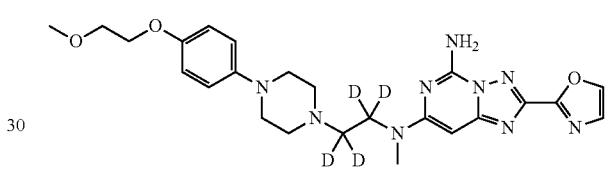

Using the approach described in Step 4 of Compound 7, 2-{4-[4-(2-methoxyethoxy)phenyl]piperazin-1-yl}-N-methyl($^2$H$_4$)ethanamine (151 mg, 0.51 mmol) yielded N$^7$-[2-{4-[4-(2-methoxyethoxy)phenyl]piperazin-1-yl}($^2$H$_4$)ethyl]-N$^7$-methyl-2-(1,3-oxazol-2-yl)[1,2,4]triazolo[1,5-c]pyrimidine-5,7-diamine (9) as a white solid (46 mg, 22% yield). $^1$H NMR (500 MHz, Chloroform-d) δ 7.82 (t, J=0.8 Hz, 1H), 7.37 (d, J=0.8 Hz, 1H), 6.88 (m, 4H), 6.08 (s, 2H), 5.94 (s, 1H), 4.11-3.95 (m, 2H), 3.83-3.66 (m, 2H), 3.45 (s, 3H), 3.17-3.09 (m, 4H), 3.07 (s, 3H), 2.77-2.66 (m, 4H). MS (EI) for C$_{24}$H$_{27}$D$_4$N$_9$O$_3$: 498 (MH$^+$).

The compound was dissolved in acetonitrile and water and treated with 1N hydrochloric acid. Solvent was removed in the lyophilizer to generate the hydrochloride salt of the title compound as a solid.

Example 12

Synthesis of N$^7$-(2-{4-[5-(2-methoxyethoxy)-3-(trifluoromethyl)pyridin-2-yl]piperazin-1-yl}ethyl)-N$^7$-methyl-2-(1,3-oxazol-2-yl)[1,2,4]triazolo[1,5-c]pyrimidine-5,7-diamine (Compound 19), Hydrochloride Salt Compound 19

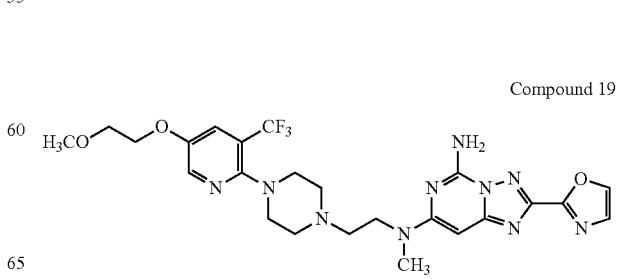

N[7]-(2-{4-[5-(2-Methoxyethoxy)-3-(trifluoromethyl)pyridin-2-yl]piperazin-1-yl}ethyl)-N[7]-methyl-2-(1,3-oxazol-2-yl)[1,2,4]triazolo[1,5-c]pyrimidine-5,7-diamine was synthesized according to the following reaction scheme.
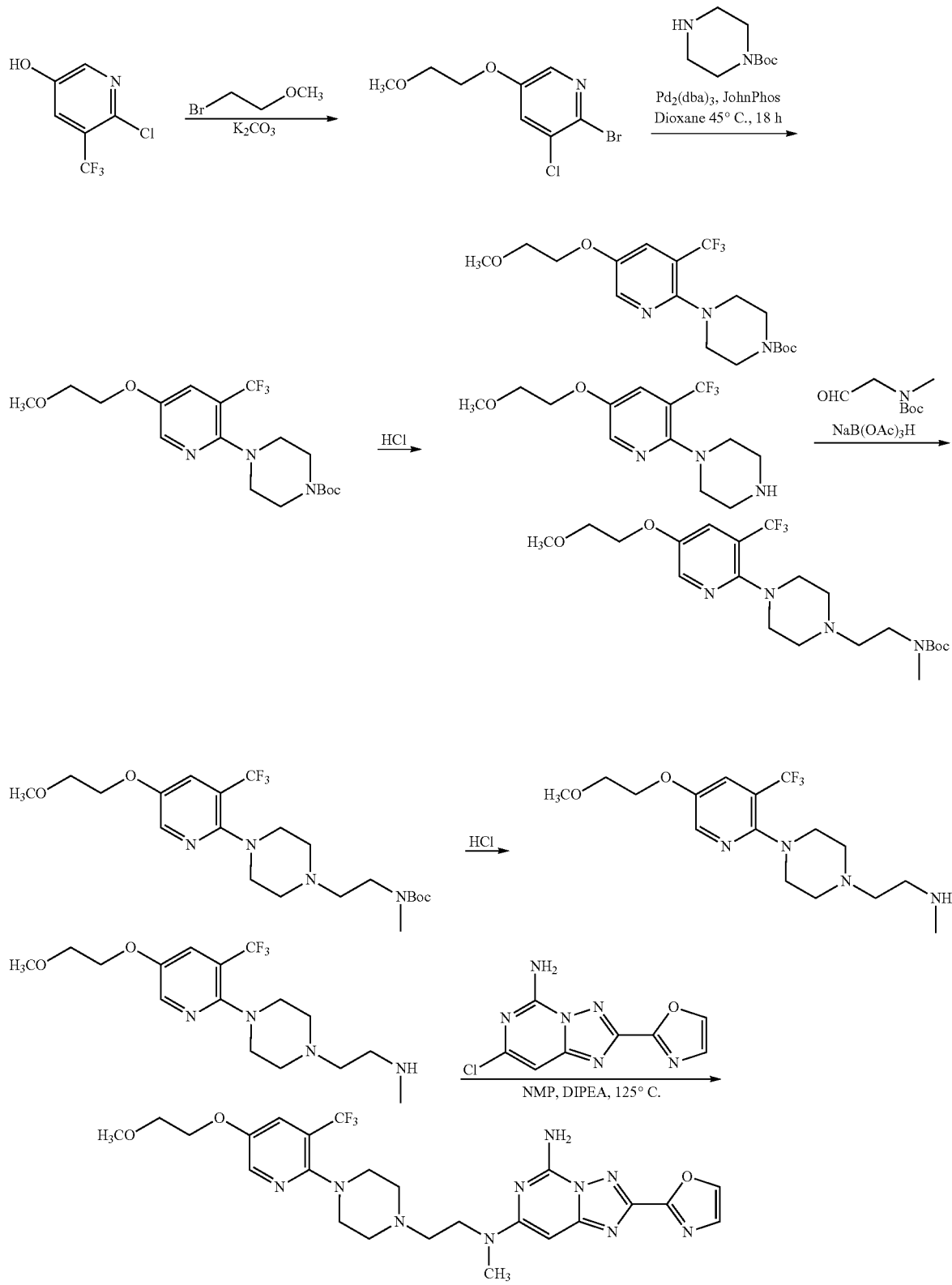

Step 1: Preparation of 2-chloro-5-(2-methoxyethoxy)-3-(trifluoromethyl)pyridine

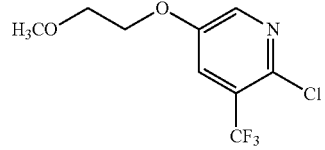 [SMILES: COCCOc1cnc(Cl)c(C(F)(F)F)c1]

Using the approach described in Step 1 of Compound 14, 6-chloro-5-(trifluoromethyl)pyridin-3-ol (0.97 g, 4.93 mmol) yielded 2-chloro-5-(2-methoxyethoxy)-3-(trifluoromethyl)pyridine (1.04 g, 4.07 mmol, 82% yield) as an orange oil. MS (EI) for $C_9H_9ClF_3NO_2$: 256 (MH$^+$).

Step 2: Preparation of tert-butyl 4-[5-(2-methoxyethoxy)-3-(trifluoromethyl)pyridin-2-yl]piperazine-1-carboxylate

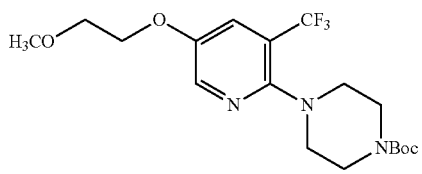

Using the approach described in Step 2 of Compound 14, 2-chloro-5-(2-methoxyethoxy)-3-(trifluoromethyl)pyridine (1.00 g, 3.91 mmol) yielded tert-butyl 4-[5-(2-methoxyethoxy)-3-(trifluoromethyl)pyridin-2-yl]piperazine-1-carboxylate as a brown-orange oil, which was carried forward to the next step without further purification. MS (EI) for $C_{18}H_{26}F_3N_3O_4$: 406 (MH$^+$).

Step 3: Preparation of 1-[5-(2-methoxyethoxy)-3-(trifluoromethyl)pyridin-2-yl]piperazine

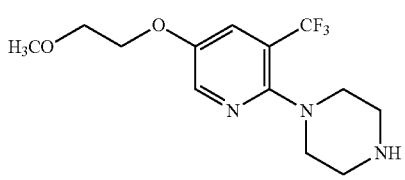

Using the approach described in Step 3 of Compound 14, the crude tert-butyl 4-[5-(2-methoxyethoxy)-3-(trifluoromethyl)pyridin-2-yl]piperazine-1-carboxylate yielded 1-[5-(2-methoxyethoxy)-3-(trifluoromethyl)pyridin-2-yl]piperazine (0.40 g, 33% over 2 steps) as a yellow oil. MS (EI) for $C_{13}H_{18}F_3N_3O_2$: 306 (MH$^+$).

Step 4: Preparation of tert-butyl (2-{4-[5-(2-methoxyethoxy)-3-(trifluoromethyl)pyridin-2-yl]piperazin-1-yl}ethyl)methylcarbamate

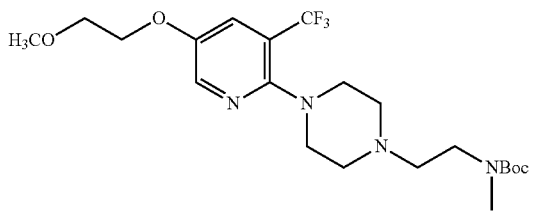

Using the approach described in Step 4 of Compound 14, 1-[5-(2-methoxyethoxy)-3-(trifluoromethyl)pyridin-2-yl]piperazine (0.41 g, 1.33 mmol) yielded tert-butyl (2-{4-[5-(2-methoxyethoxy)-3-(trifluoromethyl)pyridin-2-yl]piperazin-1-yl}ethyl)methylcarbamate as a clear oil (0.46 g, 75% yield). MS (EI) for $C_{21}H_{33}F_3N_4O_4$: 463 (MH$^+$).

Step 5: Preparation of 2-{4-[5-(2-methoxyethoxy)-3-(trifluoromethyl)pyridin-2-yl]piperazin-1-yl}-N-methylethanamine

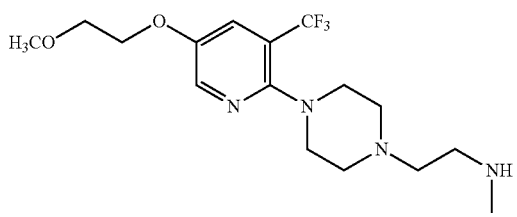 [SMILES: CNCCN1CCN(c2ncc(OCCOC)cc2C(F)(F)F)CC1]

Using the approach described in Step 5 of Compound 14, tert-butyl (2-{4-[5-(2-methoxyethoxy)-3-(trifluoromethyl)pyridin-2-yl]piperazin-1-yl}ethyl)methylcarbamate (0.41 g, 1.33 mmol) yielded 2-{4-[5-(2-methoxyethoxy)-3-(trifluoromethyl)pyridin-2-yl]piperazin-1-yl}-N-methylethanamine as a yellow oil (0.36 g, 100% yield). MS (EI) for $C_{16}H_{25}F_3N_4O_2$: 363 (MH$^+$).

Step 6: Preparation of $N^7$-(2-{4-[5-(2-methoxyethoxy)-3-(trifluoromethyl)pyridin-2-yl]piperazin-1-yl}ethyl)-$N^7$-methyl-2-(1,3-oxazol-2-yl)[1,2,4]triazolo[1,5-c]pyrimidine-5,7-diamine

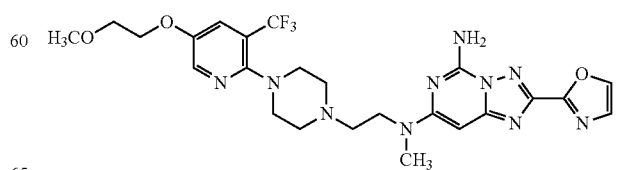

Using the approach described in Step 8 of Compound 14, 2-{4-[5-(2-methoxyethoxy)-3-(trifluoromethyl)pyridin-2-yl]piperazin-1-yl}-N-methylethanamine (155 mg, 0.42 mmol) yielded $N^7$-(2-{4-[5-(2-methoxyethoxy)-3-(trifluoromethyl)pyridin-2-yl]piperazin-1-yl}ethyl)-$N^7$-methyl-2-(1,3-oxazol-2-yl)[1,2,4]triazolo[1,5-c]pyrimidine-5,7-diamine (19) as a white solid (68.0 mg, 32% yield). $^1$H NMR (500 MHz, Chloroform-d) δ 8.24 (d, J=3.0 Hz, 1H), 7.86 (d, J=0.8 Hz, 1H), 7.51 (d, J=3.0 Hz, 1H), 7.38 (d, J=0.8 Hz, 1H), 5.95 (s, 1H), 5.78 (s, 2H), 4.19-4.11 (m, 2H), 3.82-3.74 (m, 4H), 3.47 (s, 3H), 3.18-3.13 (m, 4H), 3.10 (s, 3H), 2.74-2.57 (m, 6H). MS (EI) for $C_{24}H_{29}F_3N_{10}O_3$: 563 (MH$^+$).

The compound was dissolved in acetonitrile and water and treated with 1N hydrochloric acid. Solvent was removed in the lyophilizer to generate the hydrochloride salt of the title compound as a solid.

Example 13

Synthesis of $N^7$-{2-[4-(2-fluoro-4-{2-[($^2$H$_3$)methyloxy]ethoxy}phenyl)piperazin-1-yl]ethyl}-$N^7$-methyl-2-(1,3-oxazol-2-yl)[1,2,4]triazolo[1,5-c]pyrimidine-5,7-diamine (Compound 10), Hydrochloride Salt

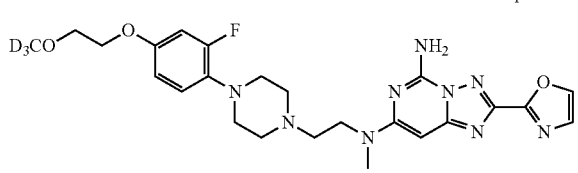

Compound 10

$N^7$-{2-[4-(2-Fluoro-4-{2-[($^2$H$_3$)methyloxy]ethoxy}phenyl)piperazin-1-yl]ethyl}-$N^7$-methyl-2-(1,3-oxazol-2-yl)[1,2,4]triazolo[1,5-c]pyrimidine-5,7-diamine was synthesized according to the following reaction scheme.

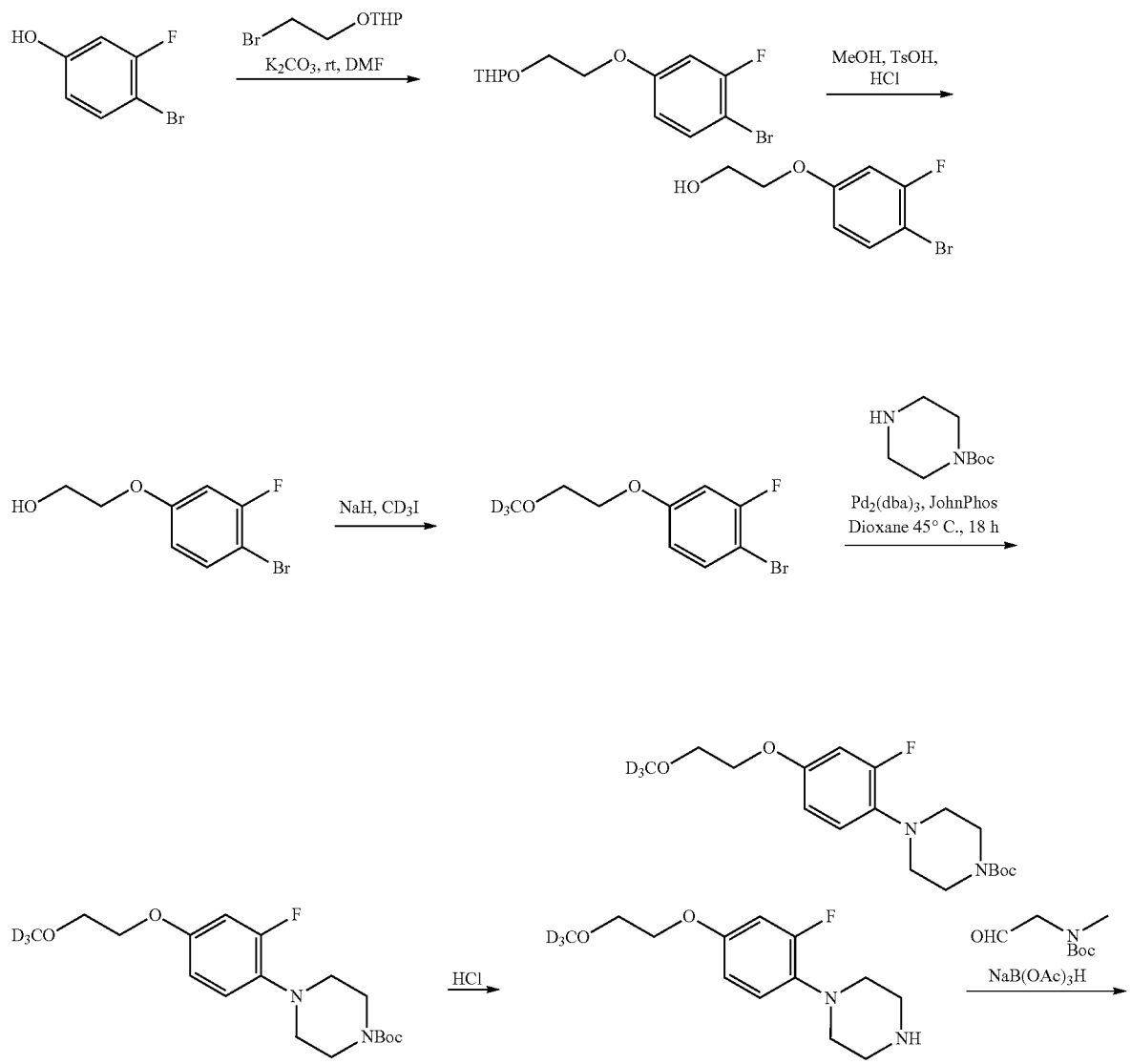

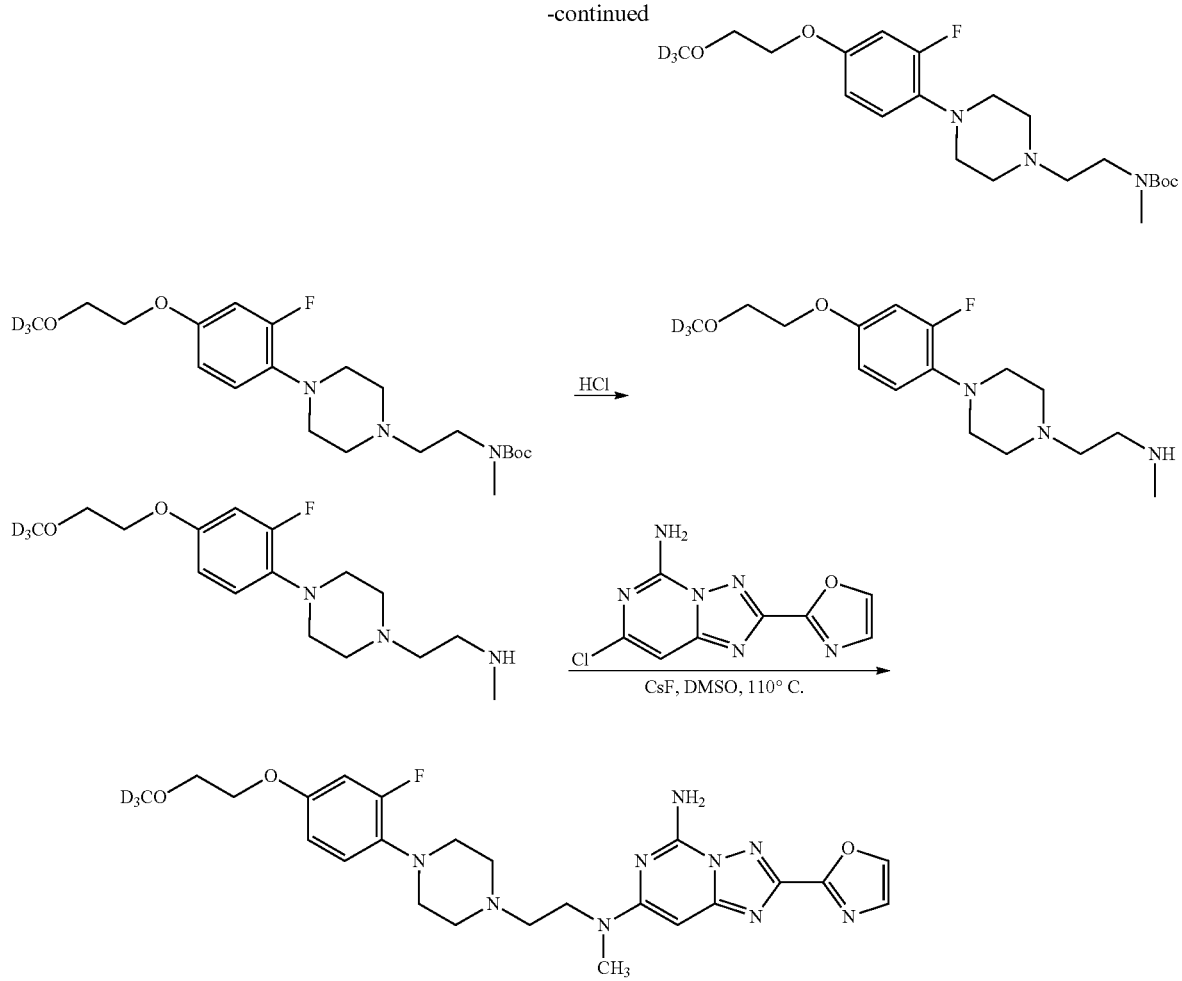

Step 1: Preparation of 2-[2-(4-bromo-3-fluorophenoxy)ethoxy]tetrahydro-2H-pyran

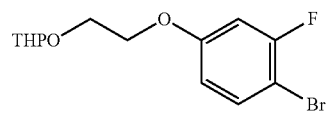

A 100 mL flask was charged with 4-bromo-3-fluorophenol (5.63 g, 29.4 mmol), anhydrous potassium carbonate (8.15 g, 59.0 mmol), dry N,N-dimethylformamide (26 mL) and stirred at room temperature. After 10 minutes, neat 2-(2-bromoethoxy)tetrahydro-2H-pyran (5.80 mL, 38.3 mmol) was added in one portion, and the orange brown mixture was stirred at room temperature for 3 days. The mixture was partitioned between ethyl acetate (200 mL) and water (100 mL). The aqueous layer was back-extracted with ethyl acetate (3×150 mL), and the combined organic layers were washed with brine (2×150 mL), dried (sodium sulfate), filtered and concentrated to afford crude 2-[2-(4-bromo-3-fluorophenoxy)ethoxy]tetrahydro-2H-pyran (9.00 g, 85% yield) as an orange/brown oil which was carried forward to the next step without further purification. MS (EI) for $C_{13}H_{16}BrFO_3$: 320 (MH+).

Step 2: Preparation of 2-(4-Bromo-3-fluorophenoxy)ethanol

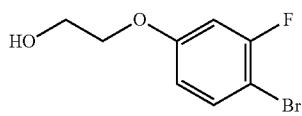

2-[2-(4-Bromo-3-fluorophenoxy)ethoxy]tetrahydro-2H-pyran (9.00 g, 28.2 mmol) was dissolved in a mixture of 20 mL of dioxane and 5 mL of methanol. To this solution was added para-toluene sulfonic acid (5.36 g, 28.2 mmol) followed by 4 M hydrochloric acid in dioxane (35.2 mL, 141 mmol). The solution was stirred at room temperature for 18 hours and the reaction was then concentrated in vacuo. The oily residue was partitioned between 100 mL ethyl acetate and 50 mL saturated sodium hydrogen carbonate. The aqueous was extracted with 3×50 mL of Ethyl acetate. The combined organic layers were combined and washed with 100 mL of brine, dried, and concentrated to give 2-(4-Bromo-3-fluorophenoxy)ethanol (5.68 g, 86% yield) as an orange oil. MS (EI) for $C_8H_8BrFO_2$: 236 (MH+).

Step 3: Preparation of 1-bromo-2-fluoro-4-{2-[($^2$H$_3$)methyloxy]ethoxy}benzene

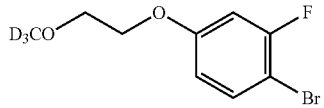

Using the approach described in Step 1 of Compound 8, 2-(4-bromo-3-fluorophenoxy)ethanol yielded 1-bromo-2-fluoro-4-{2-[($^2$H$_3$)methyloxy]ethoxy}benzene (5.27 g, 87% yield) as an orange oil. $^1$H NMR (500 MHz, Chloroform-d) δ 7.42 (m, 1H), 6.75 (m, 1H), 6.66 (m 1H), 4.10 (m, 2H), 3.76 (m, 2H).

Step 4: Preparation of tert-butyl 4-(2-fluoro-4-{2-[($^2$H$_3$)methyloxy]ethoxy}phenyl)piperazine-1-carboxylate

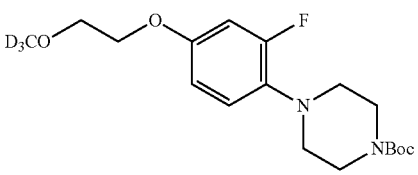

Using the approach described in Step 2 of Compound 14, 1-bromo-2-fluoro-4-{2-[($^2$H$_3$)methyloxy]ethoxy}benzene (0.65 g, 2.45 mmol) yielded tert-butyl 4-(2-fluoro-4-{2-[($^2$H$_3$)methyloxy]ethoxy}phenyl)piperazine-1-carboxylate as a brown-orange oil, which was carried forward to the next step without further purification. MS (EI) for $C_{18}H_{23}D_3FN_2O_4$: 358 (MH$^+$).

Step 5: Preparation of 1-(2-fluoro-4-{2-[($^2$H$_3$)methyloxy]ethoxy}phenyl)piperazine

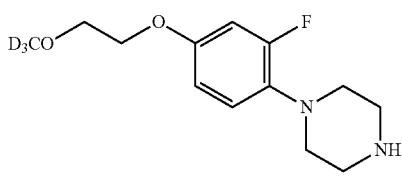

Using the approach described in Step 3 of Compound 14, crude tert-butyl 4-(2-fluoro-4-{2-[($^2$H$_3$)methyloxy]ethoxy}phenyl)piperazine-1-carboxylate yielded 1-(2-fluoro-4-{2-[($^2$H$_3$)methyloxy]ethoxy}phenyl)piperazine (4.32 g, 80% yield) as a yellow oil. MS (EI) for $C_{13}H_{16}D_3FN_2O_2$: 258 (MH$^+$).

Step 6: Preparation of tert-butyl {2-[4-(2-fluoro-4-{2-[($^2$H$_3$)methyloxy]ethoxy}phenyl)piperazin-1-yl]ethyl}methylcarbamate

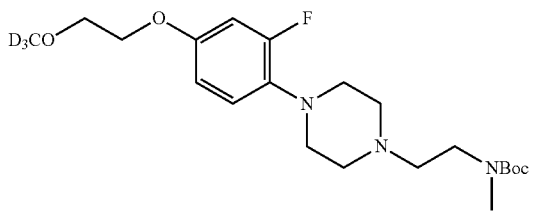

Using the approach described in Step 4 of Compound 14, 1-(2-fluoro-4-{2-[($^2$H$_3$)methyloxy]ethoxy}phenyl)piperazine (4.32 g, 16.8 mmol) yielded tert-butyl {2-[4-(2-fluoro-4-{2-[($^2$H$_3$)methyloxy]ethoxy}phenyl)piperazin-1-yl]ethyl}methylcarbamate as a yellow oil (6.40 g, 92% yield). MS (EI) for $C_{21}H_{31}D_3FN_3O_4$: 415 (MH$^+$).

Step 7: Preparation of 2-[4-(2-Fluoro-4-{2-[($^2$H$_3$)methyloxy]ethoxy}phenyl)piperazin-1-yl]-N-methylethanamine

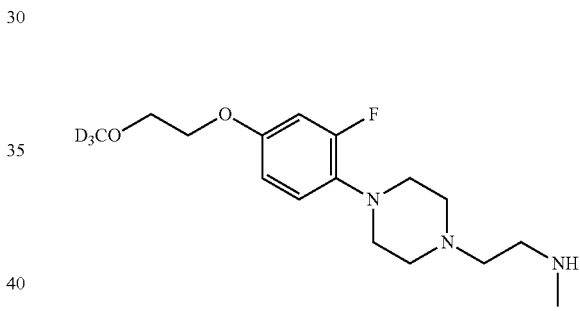

Using the approach described in Step 5 of Compound 14, tert-butyl {2-[4-(2-fluoro-4-{2-[($^2$H$_3$)methyloxy]ethoxy}phenyl)piperazin-1-yl]ethyl}methylcarbamate (6.40 g, 15.4 mmol yielded 2-[4-(2-fluoro-4-{2-[($^2$H$_3$)methyloxy]ethoxy}phenyl)piperazin-1-yl]-N-methylethanamine as an orange oil (4.50 g, 93% yield). MS (EI) for $C_{16}H_{31}D_3FN_3O_4$: 315 (MH$^+$).

Step 8: Preparation of $N^7$-{2-[4-(2-fluoro-4-{2-[($^2$H$_3$)methyloxy]ethoxy}phenyl)piperazin-1-yl]ethyl}-$N^7$-methyl-2-(1,3-oxazol-2-yl)[1,2,4]triazolo[1,5-c]pyrimidine-5,7-diamine

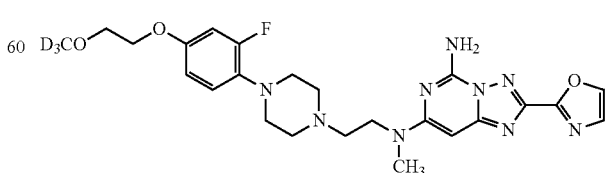

Using the approach described in Step 4 of Compound 7, 2-[4-(2-fluoro-4-{2-[($^2$H$_3$)methyloxy]ethoxy}phenyl)piperazin-1-yl]-N-methylethanamine (215 mg, 0.69 mmol) yielded N$^7$-{2-[4-(2-fluoro-4-{2-[($^2$H$_3$)methyloxy]ethoxy}phenyl)piperazin-1-yl]ethyl}-N$^7$-methyl-2-(1,3-oxazol-2-yl)[1,2,4]triazolo[1,5-c]pyrimidine-5,7-diamine (10) as a white solid (68.0 mg, 29% yield). $^1$H NMR (500 MHz, Chloroform-d) δ 7.83 (d, J=0.8 Hz, 1H), 7.37 (d, J=0.8 Hz, 1H), 6.88 (m, 1H), 6.69 (m, 1H), 6.64 (m, 1H), 6.07 (s, 2H), 5.94 (s, 1H), 4.05 (m, 2H), 3.80-3.70 (m, 4H), 3.07-3.03 (m, 7H), 2.72 (br s, 4H), 2.64 (m, 2H). MS (EI) for C$_{24}$H$_{27}$D$_3$FN$_9$O$_3$: 515 (MH$^+$).

The compound was dissolved in acetonitrile and water and treated with 1N hydrochloric acid. Solvents were removed in the lyophilizer to generate the hydrochloride salt of the title compound as a solid.

Example 14

Synthesis of N$^7$-(2-{4-[5-(2-methoxyethoxy)pyrimidin-2-yl]piperazin-1-yl}ethyl)-N$^7$-methyl-2-(1,3-oxazol-2-yl)[1,2,4]triazolo[1,5-c]pyrimidine-5,7-diamine (Compound 3), Hydrochloride Salt

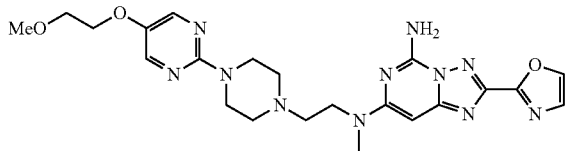

Compound 3

N$^7$-(2-{4-[5-(2-Methoxyethoxy)pyrimidin-2-yl]piperazin-1-yl}ethyl)-N$^7$-methyl-2-(1,3-oxazol-2-yl)[1,2,4]triazolo[1,5-c]pyrimidine-5,7-diamine was synthesized according to the following reaction scheme.

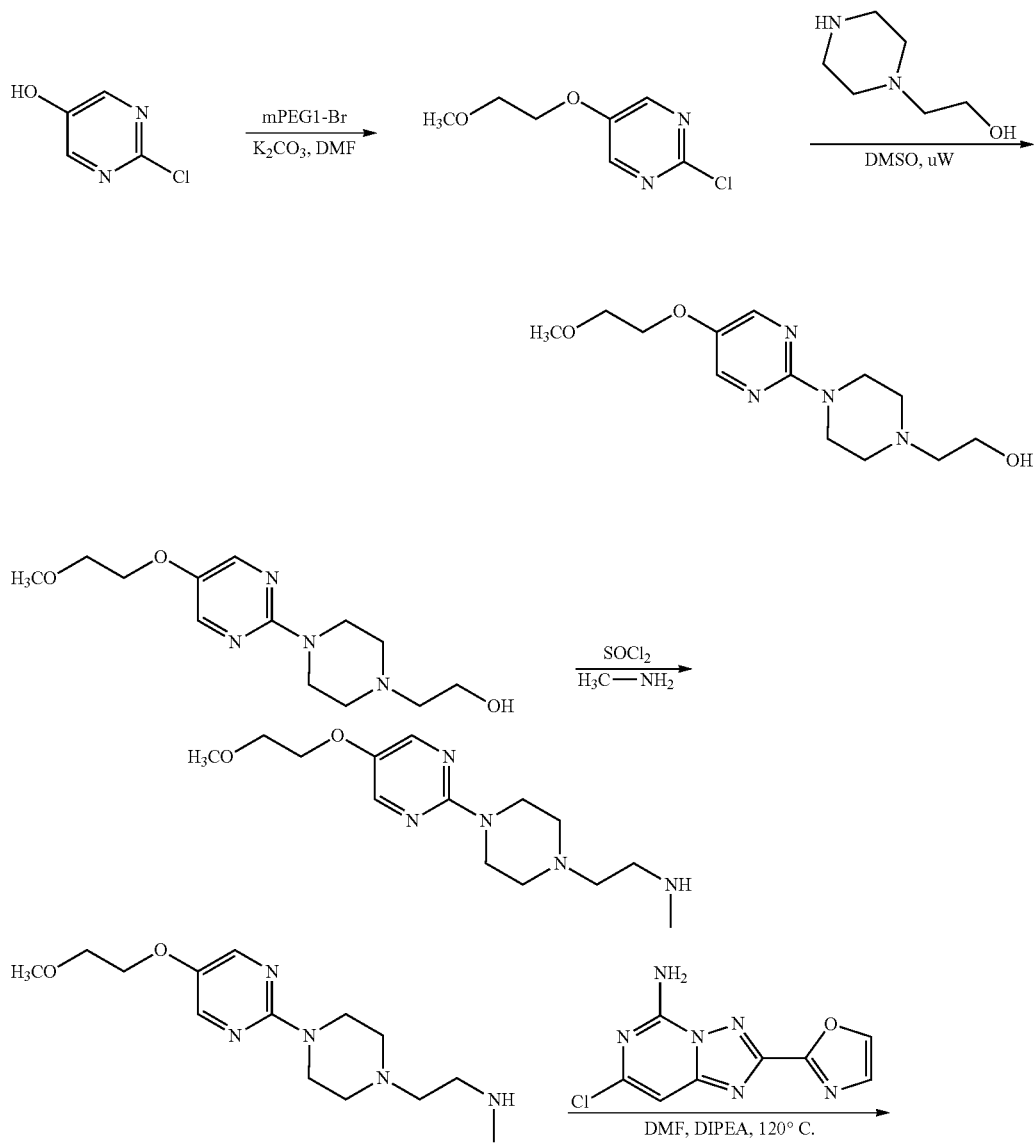

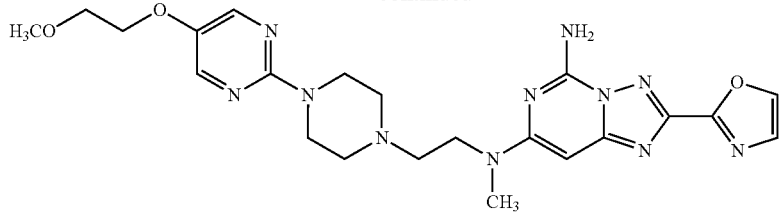

Step 1: Preparation of 2-chloro-5-(2-methoxyethoxy)pyrimidine

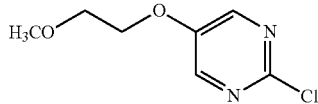 [SMILES: COCCOc1cnc(Cl)nc1]

Using the approach described in Step 1 of Compound 14, 2-chloropyrimidin-5-ol (2.06 g, 15.8 mmol) yielded 2-chloro-5-(2-methoxyethoxy)pyrimidine (2.56 g, 88% yield) as a tan solid. MS (EI) for $C_7H_9ClN_2O_2$: 189 (MH+).

Step 2: Preparation of 2-{4-[5-(2-methoxyethoxy)pyrimidin-2-yl]piperazin-1-yl}ethanol

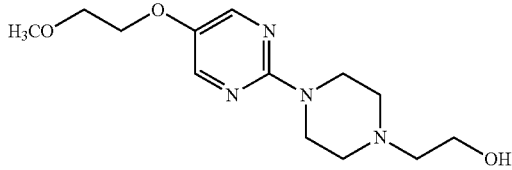 [SMILES: COCCOc1cnc(N2CCN(CCO)CC2)nc1]

To a solution of 2-chloro-5-(2-methoxyethoxy)pyrimidine (0.21 g, 1.09 mmol) in 2.5 mL of dimethyl sulfoxide was added 2-(piperazin-1-yl)ethanol (0.17 g, 1.30 mmol) followed by ethyldiisopropylamine (0.29 mL, 1.63 mmol). The vial was capped and heated to 120° C. under microwave heating for four hours. The reaction was directly purified using reverse phase Isolera™ (30 g C18, 5-100% acetonitrile/ammonium hydroxide in water) to afford 2-{4-[5-(2-methoxyethoxy)pyrimidin-2-yl]piperazin-1-yl}ethanol (0.24 g, 79% yield) as a tan solid. $^1$H NMR (500 MHz, Dimethylsulfoxide-$d_6$) δ 8.20 (s, 2H), 4.43 (t, J=5.4 Hz, 1H), 4.13-4.04 (m, 2H), 3.63-3.57 (m, 6H), 3.55-3.49 (m, 2H), 3.29 (s, 2H), 2.47-2.43 (m, 4H), 2.41 (t, J=6.2 Hz, 2H). MS (EI) for $C_{13}H_{22}N_4O_3$: 283 (M+H)+.

Step 3: Preparation of 2-{4-[5-(2-methoxyethoxy)pyrimidin-2-yl]piperazin-1-yl}-N-methylethanamine

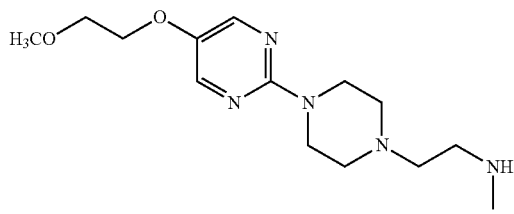 [SMILES: CNCCN1CCN(c2ncc(OCCOC)cn2)CC1]

To a stirred and cooled (0° C.) solution of 2-{4-[5-(2-methoxyethoxy)pyrimidin-2-yl]piperazin-1-yl}ethanol (0.24 g, 0.85 mmol) in a mixture of 2.8 mL of dichloromethane and 2.8 mL of acetonitrile was added thionyl chloride (186 µL, 2.55 mmol) dropwise via syringe. The solution was then allowed to warm to room temperature and was stirred for 18 hours. 10 mL of methanol was then added and the reaction was concentrated in vacuo. The residual solid was dissolved in 5 mL of ethanol and transferred to a sealed tube. To this solution was then added a 33% solution of methylamine in ethanol (1.05 mL, 8.50 mmol). The tube was sealed and heated to 80° C. for 4 hours before being cooled to room temperature. One gram of potassium carbonate was added, the solution was stirred for 30 min before being filtered and concentrated in vacuo to give 2-{4-[5-(2-methoxyethoxy)pyrimidin-2-yl]piperazin-1-yl}-N-methylethanamine (0.22 g, 88% yield) as an orange solid. MS (EI) for $C_{14}H_{25}N_5O_2$: 283 (MH+).

Step 4: Preparation of $N^7$-(2-{4-[5-(2-methoxyethoxy)pyrimidin-2-yl]piperazin-1-yl}ethyl)-$N^7$-methyl-2-(1,3-oxazol-2-yl)[1,2,4]triazolo[1,5-c]pyrimidine-5,7-diamine

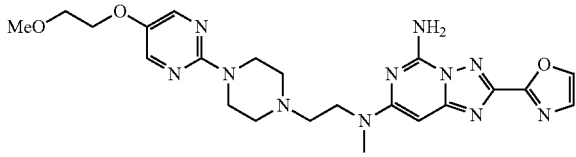 [SMILES: COCCOc1cnc(N2CCN(CCN(C)c3cc4nc(-c5ncco5)nn4c(N)n3)CC2)nc1]

Using the approach described in Step 8 of Compound 14, 2-{4-[5-(2-methoxyethoxy)pyrimidin-2-yl]piperazin-1-yl}-N-methylethanamine (105 mg, 0.33 mmol) yielded $N^7$-(2-{4-[5-(2-methoxyethoxy)pyrimidin-2-yl]piperazin-1-yl}ethyl)-$N^7$-methyl-2-(1,3-oxazol-2-yl)[1,2,4]triazolo[1,5-c]pyrimidine-5,7-diamine (3) as a white solid (12.0 mg, 9% yield). $^1$H NMR (500 MHz, Methanol-$d_4$) δ 8.23-8.03 (m, 3H), 7.46 (s, 1H), 5.90 (s, 1H), 4.18-4.08 (m, 2H), 3.88-3.83 (m, 2H), 3.76-3.70 (m, 6H), 3.42 (s, 3H), 3.10 (s, 3H), 2.75-2.66 (m, 6H). MS (EI) for $C_{22}H_{29}N_{11}O_3$: 496 (MH+).

The compound was dissolved in acetonitrile and water and treated with 1N hydrochloric acid. Solvents were removed in the lyophilizer to generate the hydrochloride salt of the title compound as a solid.

Example 15
Synthesis of N[7]-(2-{4-[6-(2-methoxyethoxy)-5-(trifluoromethyl)pyridin-3-yl]piperazin-1-yl}ethyl)-N[7]-methyl-2-(1,3-oxazol-2-yl)[1,2,4]triazolo[1,5-c]pyrimidine-5,7-diamine (Compound 22), Hydrochloride Salt
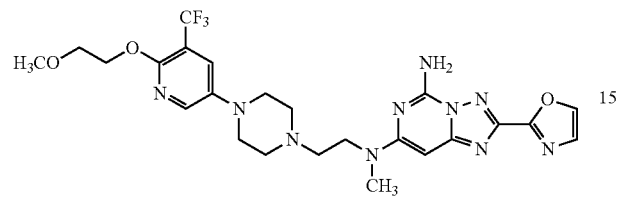
Compound 22
N[7]-(2-{4-[6-(2-Methoxyethoxy)-5-(trifluoromethyl)pyridin-3-yl]piperazin-1-yl}ethyl)-N[7]-methyl-2-(1,3-oxazol-2-yl)[1,2,4]triazolo[1,5-c]pyrimidine-5,7-diamine was synthesized according to the following reaction scheme.
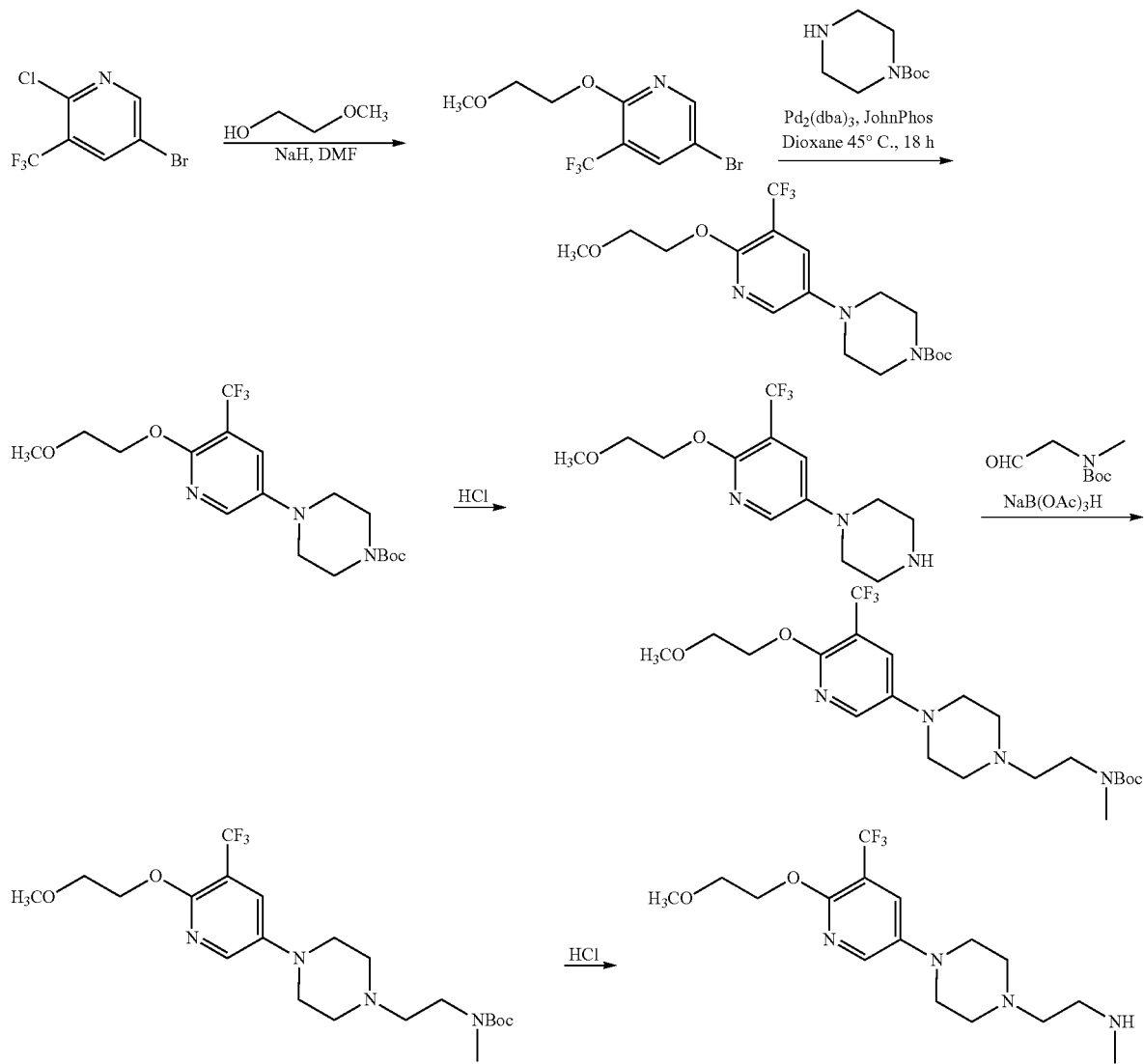

-continued

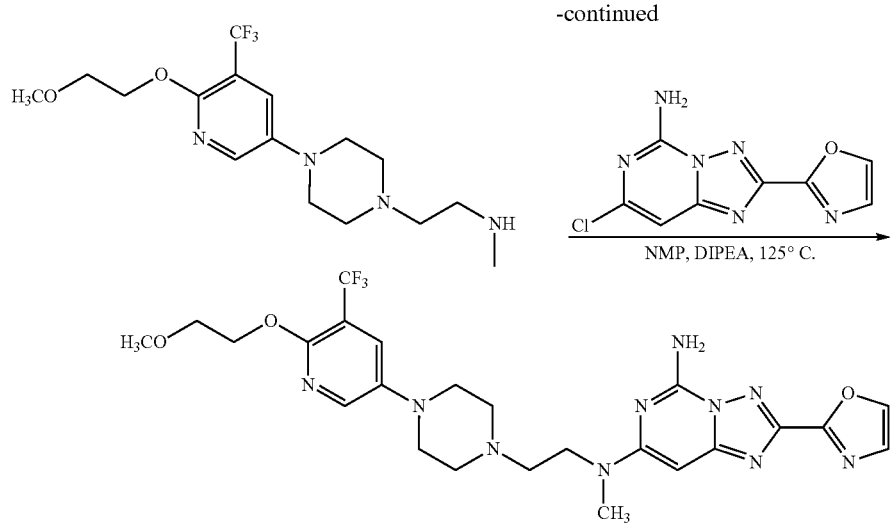

Step 1: Preparation of 5-bromo-2-(2-methoxy-ethoxy)-3-(trifluoromethyl)pyridine

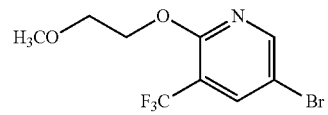

Sodium hydride (0.74 g, 18.5 mmol) was suspended in 10 mL of tetrahydrofuran and cooled to 0° C. before 2-methoxyethanol (0.71 g, 9.28 mmol) was added dropwise via syringe. The solution was stirred at room temperature for 15 min before being cooled to 0° C. A solution of 5-bromo-2-chloro-3-(trifluoromethyl)pyridine (2.02 g, 7.74 mmol) in 10 mL of tetrahydrofuran was added dropwise via syringe. The solution was stirred at room temperature for one hour before being quenched with 5 mL of saturated ammonium chloride. The mixture was partitioned between ethyl acetate (100 mL) and water (50 mL). The aqueous layer was back-extracted with ethyl acetate (3×50 mL) and the combined organic layers were washed with brine (2×50 mL), dried (sodium sulfate), filtered and concentrated to afford 5-bromo-2-(2-methoxyethoxy)-3-(trifluoromethyl)pyridine (2.09 g, 90% yield) as a white solid. $^1$H NMR (500 MHz, Chloroform-d) δ 8.36 (d, J=3.2 Hz, 1H), 7.97 (d, J=3.2 Hz, 1H), 4.63-4.52 (m, 2H), 3.81-3.74 (m, 2H), 3.45 (s, 3H).

Step 2: Preparation of tert-butyl 4-[6-(2-methoxy-ethoxy)-5-(trifluoromethyl)pyridin-3-yl]piperazine-1-carboxylate

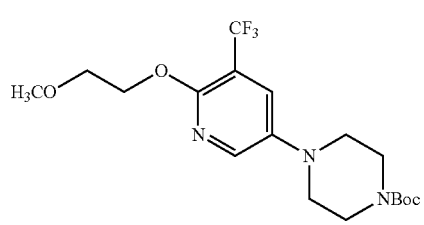 [SMILES: COCCOc1ncc(N2CCN(C(=O)OC(C)(C)C)CC2)cc1C(F)(F)F]

Using the approach described in Step 2 of Compound 14, 5-bromo-2-(2-methoxyethoxy)-3-(trifluoromethyl)pyridine (1.78 g, 3.91 mmol) yielded tert-butyl 4-[6-(2-methoxy-ethoxy)-5-(trifluoromethyl)pyridin-3-yl]piperazine-1-carboxylate as a brown-orange oil, which was carried forward to the next step without further purification. MS (EI) for $C_{18}H_{26}F_3N_3O_4$: 406 (MH$^+$).

Step 3: Preparation of 1-[6-(2-methoxyethoxy)-5-(trifluoromethyl)pyridin-3-yl]piperazine

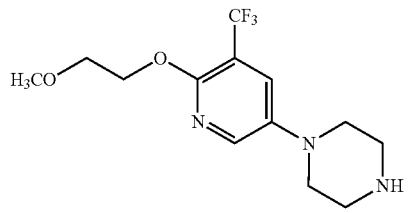 [SMILES: COCCOc1ncc(N2CCNCC2)cc1C(F)(F)F]

Using the approach described in Step 3 of Compound 14, crude tert-butyl 4-[6-(2-methoxyethoxy)-5-(trifluoromethyl)pyridin-3-yl]piperazine-1-carboxylate yielded 1-[6-(2-methoxyethoxy)-5-(trifluoromethyl)pyridin-3-yl]piperazine (0.75 g, 37% over 2 steps) as an orange oil. MS (EI) for $C_{13}H_{18}F_3N_3O_2$: 306 (MH$^+$).

Step 4: Preparation of tert-butyl (2-{4-[6-(2-methoxyethoxy)-5-(trifluoromethyl)pyridin-3-yl]piperazin-1-yl}ethyl)methylcarbamate

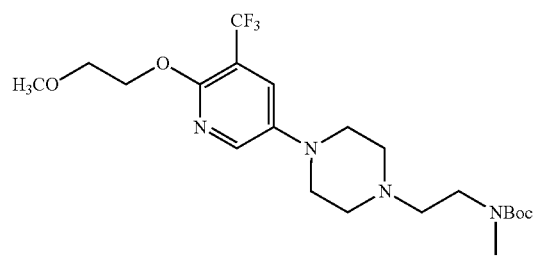 [SMILES: COCCOc1ncc(N2CCN(CCN(C)C(=O)OC(C)(C)C)CC2)cc1C(F)(F)F]

Using the approach described in Step 4 of Compound 14, 1-[6-(2-methoxyethoxy)-5-(trifluoromethyl)pyridin-3-yl]piperazine (0.75 g, 2.46 mmol) yielded tert-butyl (2-{4-[6-(2-methoxyethoxy)-5-(trifluoromethyl)pyridin-3-yl]piperazin-1-yl}ethyl)methylcarbamate as a clear oil (0.56 g, 49% yield). MS (EI) for $C_{21}H_{33}F_3N_4O_4$: 463 (MH$^+$).

Step 5: Preparation of 2-{4-[6-(2-methoxyethoxy)-5-(trifluoromethyl)pyridin-3-yl]piperazin-1-yl}-N-methylethanamine

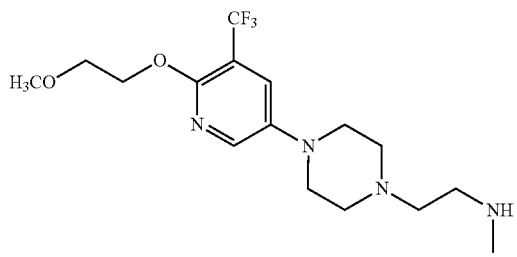 [SMILES: CNCCN1CCN(c2cnc(OCCOC)c(C(F)(F)F)c2)CC1]

Using the approach described in Step 5 of Compound 14, tert-butyl (2-{4-[6-(2-methoxyethoxy)-5-(trifluoromethyl)pyridin-3-yl]piperazin-1-yl}ethyl)methylcarbamate (0.56 g, 1.00 mmol) yielded 2-{4-[6-(2-methoxyethoxy)-5-(trifluoromethyl)pyridin-3-yl]piperazin-1-yl}-N-methylethanamine as a yellow oil (0.27 g, 62% yield). MS (EI) for $C_{16}H_{25}F_3N_4O_2$: 363 (MH$^+$).

Step 6: Preparation of N$^7$-(2-{4-[6-(2-methoxyethoxy)-5-(trifluoromethyl)pyridin-3-yl]piperazin-1-yl}ethyl)-N$^7$-methyl-2-(1,3-oxazol-2-yl)[1,2,4]triazolo[1,5-c]pyrimidine-5,7-diamine

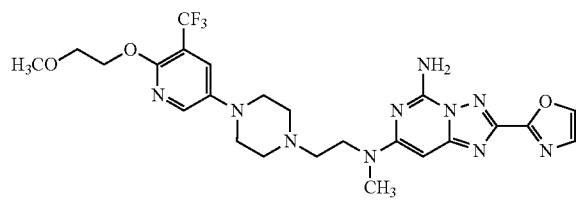 [SMILES: COCCOc1ncc(N2CCN(CCN(C)c3cc4nc(-c5ncco5)nn4c(N)n3)CC2)cc1C(F)(F)F]

Using the approach described in Step 8 of Compound 14, 2-{4-[6-(2-methoxyethoxy)-5-(trifluoromethyl)pyridin-3-yl]piperazin-1-yl}-N-methylethanamine (180 mg, 0.48 mmol) yielded N$^7$-(2-{4-[6-(2-methoxyethoxy)-5-(trifluoromethyl)pyridin-3-yl]piperazin-1-yl}ethyl)-N$^7$-methyl-2-(1,3-oxazol-2-yl)[1,2,4]triazolo[1,5-c]pyrimidine-5,7-diamine (22) as a white solid (55.0 mg, 20% yield). $^1$H NMR (500 MHz, Chloroform-d) δ 7.93 (d, J=2.9 Hz, 1H), 7.86 (d, J=0.8 Hz, 1H), 7.52 (d, J=2.9 Hz, 1H), 7.38 (d, J=0.8 Hz, 1H), 5.97 (s, 1H), 5.74 (s, 2H), 4.56-4.50 (m, 2H), 3.91-3.61 (m, 4H), 3.45 (s, 3H), 3.15 (s, 4H), 3.10 (s, 3H), 2.79-2.64 (m, 6H). MS (EI) for $C_{24}H_{29}F_3N_{10}O_3$: 563 (MH$^+$).

The compound was dissolved in acetonitrile and water and treated with 1N hydrochloric acid. Solvents were removed in the lyophilizer to generate the hydrochloride salt of the title compound as a solid.

Example 16

Synthesis of N$^7$-(2-{4-[5-(2-methoxyethoxy)pyridin-2-yl]piperazin-1-yl}ethyl)-N$^7$-methyl-2-(1,3-oxazol-2-yl)[1,2,4]triazolo[1,5-c]pyrimidine-5,7-diamine (Compound 23), Hydrochloride Salt

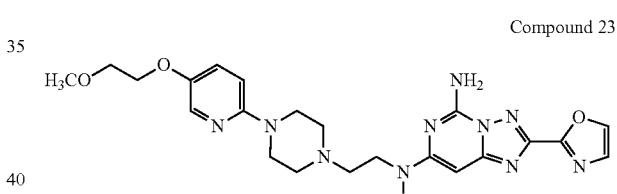

N$^7$-(2-{4-[5-(2-Methoxyethoxy)pyridin-2-yl]piperazin-1-yl}ethyl)-N$^7$-methyl-2-(1,3-oxazol-2-yl)[1,2,4]triazolo[1,5-c]pyrimidine-5,7-diamine was synthesized according to the following reaction scheme.

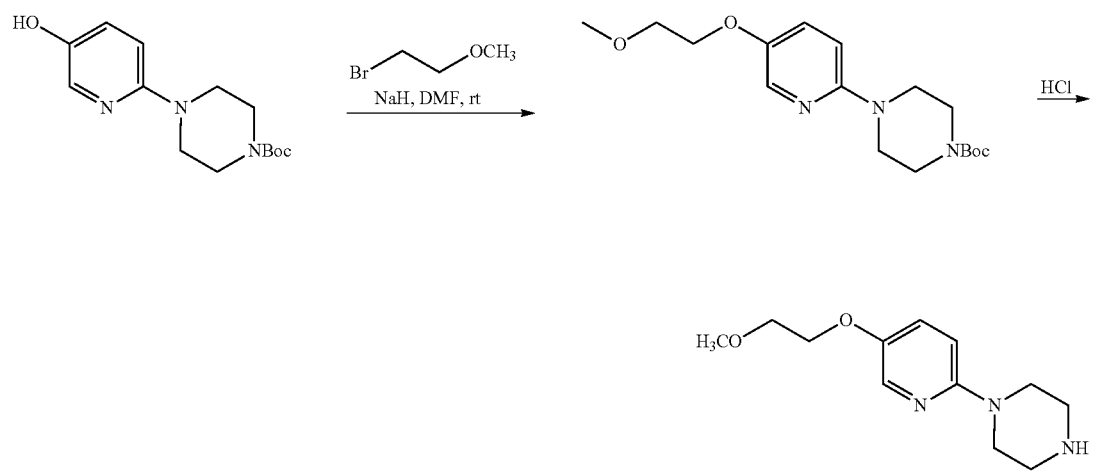

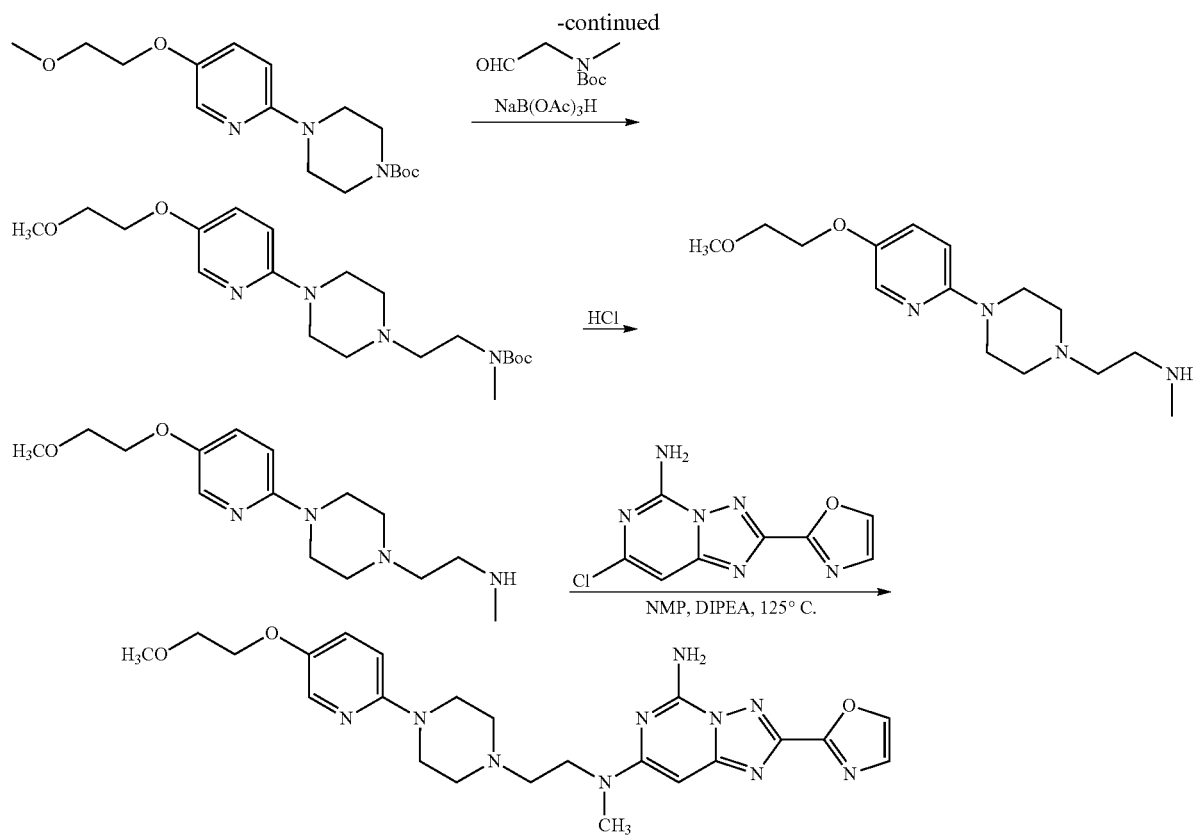

Step 1: Preparation of tert-butyl 4-[5-(2-methoxyethoxy)pyridin-2-yl]piperazine-1-carboxylate

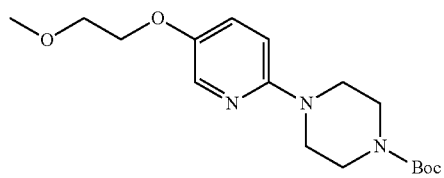 [SMILES: COCCOc1ccc(N2CCN(C(=O)OC(C)(C)C)CC2)nc1]

Sodium hydride (0.57 g, 14.3 mmol) was suspended in 6 mL of N,N-dimethylformamide and cooled to 0° C. before tert-butyl 4-(5-hydroxypyridin-2-yl)piperazine-1-carboxylate (2.00 g, 7.16 mmol) in 6 mL of N,N-dimethylformamide was added dropwise via syringe. The solution was then stirred at room temperature for 15 min before being cooled back to 0° C. 2-bromoethyl methyl ether (0.88 mL, 9.31 mmol) was then added dropwise via syringe. The solution was allowed to warm to room temperature and was stirred at room temperature for 18 hours before being quenched with 5 mL of saturated ammonium chloride. The mixture was partitioned between ethyl acetate (100 mL) and water (50 mL). The aqueous layer was back-extracted with ethyl acetate (3×50 mL), and the combined organic layers were washed with brine (2×50 mL), dried (sodium sulfate), filtered and concentrated to give tert-butyl 4-[5-(2-methoxyethoxy)pyridin-2-yl]piperazine-1-carboxylate as a yellow oil. The oil was taken to the next step with no further purification. MS (EI) for $C_{17}H_{27}N_3O_4$: 337 (MH$^+$).

Step 2: Preparation of 1-[5-(2-methoxyethoxy)pyridin-2-yl]piperazin

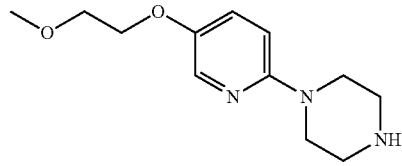 [SMILES: COCCOc1ccc(N2CCNCC2)nc1]

Using the approach described in Step 3 of Compound 14, crude tert-butyl 4-[5-(2-methoxyethoxy)pyridin-2-yl]piperazine-1-carboxylate yielded 1-[5-(2-methoxyethoxy)pyridin-2-yl]piperazin (0.97 g, 57% over 2 steps) as an yellow solid. MS (EI) for $C_{12}H_{19}N_3O_2$: 238 (MH$^+$).

Step 3: Preparation of tert-butyl (2-{4-[5-(2-methoxyethoxy)pyridin-2-yl]piperazin-1-yl}ethyl)methylcarbamate

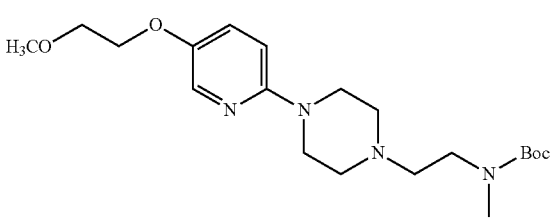 [SMILES: COCCOc1ccc(N2CCN(CCN(C)C(=O)OC(C)(C)C)CC2)nc1]

Using the approach described in Step 4 of Compound 14, 1-[5-(2-methoxyethoxy)pyridin-2-yl]piperazin (0.78 g, 3.29 mmol) yielded tert-butyl (2-{4-[5-(2-methoxyethoxy)pyridin-2-yl]piperazin-1-yl}ethyl)methylcarbamate as a yellow oil (1.05 g, 81% yield). MS (EI) for $C_{20}H_{34}N_4O_4$: 395 (MH$^+$).

Step 4: Preparation of 2-{4-[5-(2-methoxyethoxy)pyridin-2-yl]piperazin-1-yl}-N-methylethanamine

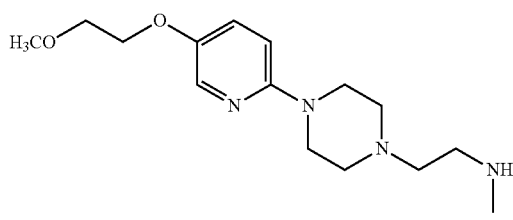 [SMILES: CNCCN1CCN(c2ccc(OCCOC)cn2)CC1]

Using the approach described in Step 5 of Compound 14, tert-butyl (2-{4-[5-(2-methoxyethoxy)pyridin-2-yl]piperazin-1-yl}ethyl)methylcarbamate (1.05 g, 2.66 mmol) yielded 2-{4-[5-(2-methoxyethoxy)pyridin-2-yl]piperazin-1-yl}-N-methylethanamine as a yellow solid (0.65 g, 83% yield). MS (EI) for $C_{15}H_{26}N_4O_2$: 295 (M+H)$^+$.

Step 5: Preparation of N$^7$-(2-{4-[5-(2-methoxyethoxy)pyridin-2-yl]piperazin-1-yl}ethyl)-N$^7$-methyl-2-(1,3-oxazol-2-yl)[1,2,4]triazolo[1,5-c]pyrimidine-5,7-diamine

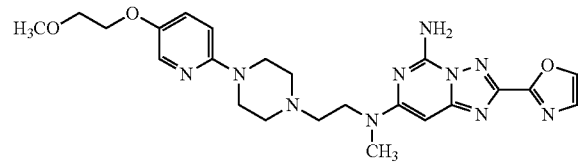 [SMILES: COCCOc1ccc(N2CCN(CCN(C)c3cc4nc(-c5ncco5)nn4c(N)n3)CC2)nc1]

Using the approach described in Step 8 of Compound 14, 2-{4-[5-(2-methoxyethoxy)pyridin-2-yl]piperazin-1-yl}-N-methylethanamine (150 mg, 0.51 mmol) yielded N$^7$-(2-{4-[5-(2-methoxyethoxy)pyridin-2-yl]piperazin-1-yl}ethyl)-N$^7$-methyl-2-(1,3-oxazol-2-yl)[1,2,4]triazolo[1,5-c]pyrimidine-5,7-diamine (23) (42.0 mg, 18% yield) as a white solid. $^1$H NMR (500 MHz, Dimethyl Sulfoxide-d$_6$) δ 8.34 (d, J=0.8 Hz, 1H), 7.87 (d, J=3.1 Hz, 1H), 7.71 (s, 2H), 7.49 (d, J=0.8 Hz, 1H), 7.26 (dd, J=9.3, 3.1 Hz, 1H), 6.79 (d, J=9.3 Hz, 1H), 5.85 (s, 1H), 4.07-4.02 (m, 2H), 3.74-3.69 (m, 2H), 3.63-3.59 (m, 2H), 3.32-3.29 (m, 7H), 3.03 (s, 3H), 2.58-2.54 (m, 6H). MS (EI) for $C_{23}H_{30}N_{10}O_3$: 495 (MH$^+$).

The compound was dissolved in acetonitrile and water and treated with 1N hydrochloric acid. Solvent was removed in the lyophilizer to generate the hydrochloride salt of the title compound as a solid.

Example 17

Synthesis of N$^7$-(2-{4-[3-fluoro-5-(2-methoxyethoxy)pyridin-2-yl]piperazin-1-yl}ethyl)-N$^7$-methyl-2-(1,3-oxazol-2-yl)[1,2,4]triazolo[1,5-c]pyrimidine-5,7-diamine (Compound 4), Hydrochloride Salt Compound 4

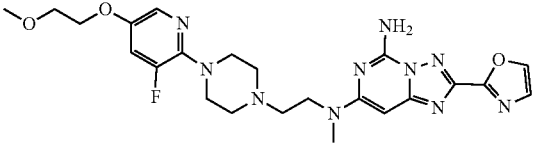

N$^7$-(2-{4-[3-Fluoro-5-(2-methoxyethoxy)pyridin-2-yl]piperazin-1-yl}ethyl)-N$^7$-methyl-2-(1,3-oxazol-2-yl)[1,2,4]triazolo[1,5-c]pyrimidine-5,7-diamine was synthesized according to the following reaction scheme.

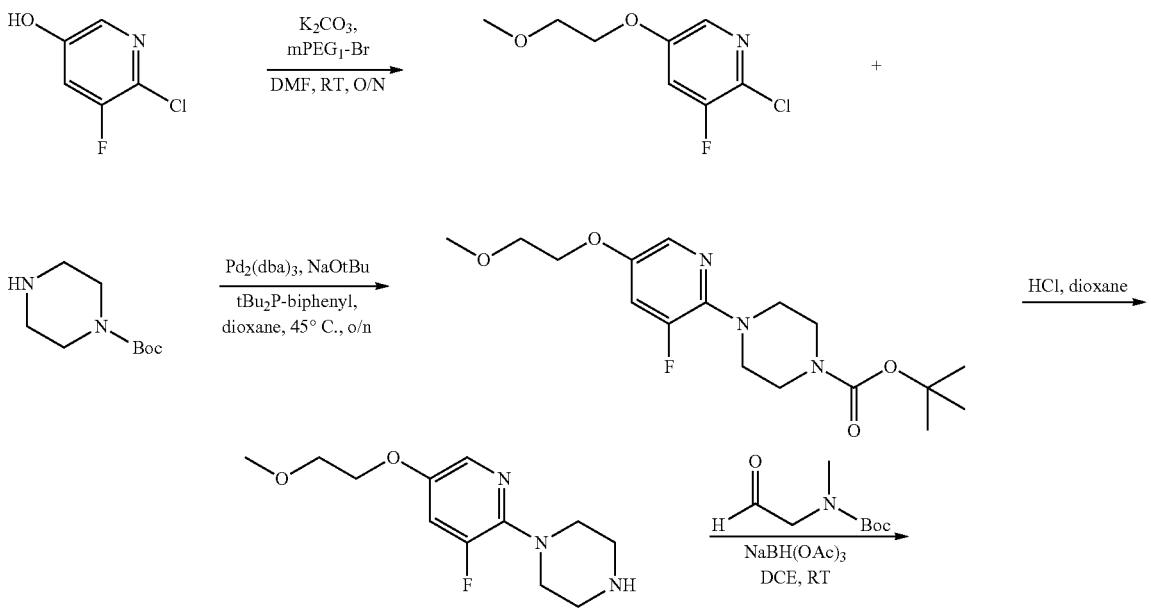

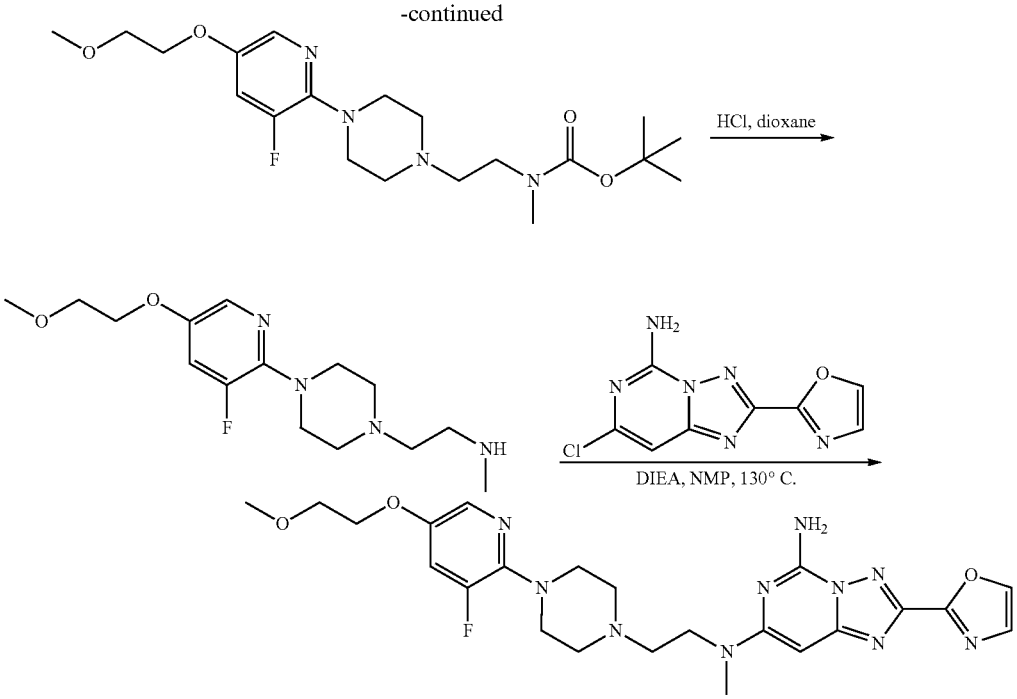

Step 1: Preparation of 2-chloro-3-fluoro-5-(2-methoxyethoxy)pyridine

Step 2: Preparation of tert-butyl 4-[3-fluoro-5-(2-methoxyethoxy)pyridin-2-yl]piperazine-1-carboxylate

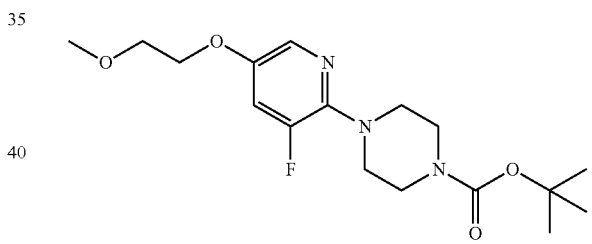

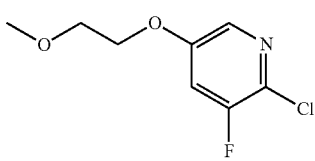

A 250 mL flask was charged with 6-chloro-5-fluoro-pyridin-3-ol (10.16 g, 68.9 mmol), anhydrous potassium carbonate (19.04 g, 137 mmol) and dry N,N-dimethylformamide (50 mL) and stirred at room temperature. After 10 minutes, neat 1-bromo-2-methoxy-ethane (8.4 mL, 90 mmol) was added in one portion, and the orange brown mixture stirred overnight at room temperature. The mixture was partitioned between ethyl acetate (350 mL) and brine (250 mL). The aqueous layer was back-extracted with ethyl acetate (150 mL), and the combined organic layers were washed with brine (4×100 mL), dried (sodium sulfate), filtered and concentrated to afford crude 2-chloro-3-fluoro-5-(2-methoxyethoxy)pyridine (11.4 g, 81% yield) as a brown oil, which was carried forward to the next step without further purification. MS (EI) for $C_8H_9ClFNO_2$: 206 (MH$^+$).

A 250 mL flask was charged with tert-butyl piperazine-1-carboxylate (13.42 g, 72.1 mmol), (1E,4E)-1,5-diphenyl-penta-1,4-dien-3-one; palladium (1.27 g, 1.39 mmol), di-tert-butyl-(2-phenylphenyl)phosphine (1.82 g, 6.1 mmol), sodium tert-butoxide (5.33 g, 55.4 mmol) and purged with nitrogen, and dry nitrogen sparged dioxane (30 mL) was added. A solution of 2-chloro-3-fluoro-5-(2-methoxyethoxy)pyridine (11.4 g, 55.44 mmol) in dry nitrogen sparged dioxane (70 mL) was added, and the mixture stirred at room temperature for 10 min, then placed in an oil bath heated at 45° C. for 17 hours. The reaction was quenched with saturated ammonium chloride (10 mL), concentrated to remove most of the dioxane, then diluted with ethyl acetate (250 mL) and water (150 mL). The mixture was filtered through Celite®, diluted with brine (100 mL), and the organic layer washed with 1 M sodium dihydrogen phosphate (2×75 mL), dried (sodium sulfate), filtered and concentrated to afford crude tert-butyl 4-[3-fluoro-5-(2-methoxyethoxy)pyridin-2-yl]piperazine-1-carboxylate (19.26 g) as a brown-orange oil, which was carried forward to the next step without further purification. MS (EI) for $C_{17}H_{26}FN_3O_4$: 356 (MH$^+$).

Step 3: Preparation of 1-[3-fluoro-5-(2-methoxyethoxy)pyridin-2-yl]piperazine

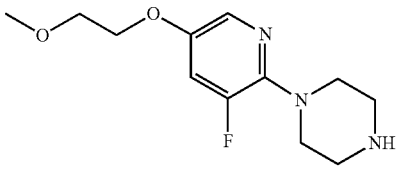 [SMILES: COCCOc1cnc(N2CCNCC2)c(F)c1]

4 M hydrogen chloride in dioxane (68 mL, 270 mmol) was added slowly over 2 minutes to a solution of tert-butyl 4-[3-fluoro-5-(2-methoxyethoxy)pyridin-2-yl]piperazine-1-carboxylate (19.26 g, 54 mmol) in 1,4-dioxane (50 mL). After 5 minutes, the mixture began to effervesce. After 6 days, the solution was decanted, and the precipitate partitioned between ethyl acetate (200 mL) and 2 M sodium carbonate (250 mL). The organic layer was extracted with 0.5 M disodium hydrogen phosphate (50 mL), and 1 M sodium dihydrogen phosphate (2×50 mL). The aqueous phases were combined and acidified to pH 5 with neat 85% phosphoric acid, then washed with ethyl acetate (200 mL), basified to pH>12 with 12 M sodium hydroxide and extracted with dichloromethane (100 mL, 50 mL). The dichloromethane layers were combined, dried (sodium sulfate), filtered and concentrated to afford 1-[3-fluoro-5-(2-methoxyethoxy)pyridin-2-yl]piperazine (10.26 g, 74% yield) as a pale brown oil, which partially solidified on standing. $^1$H NMR (500 MHz, Chloroform-d) δ 7.80 (d, J=2.5 Hz, 1H), 7.02 (dd, J=13.3, 2.5 Hz, 1H), 4.15-4.06 (m, 2H), 3.77-3.70 (m, 2H), 3.46 (d, J=0.9 Hz, 3H), 3.32-3.26 (m, 4H), 3.03 (dd, J=6.1, 3.9 Hz, 4H). MS (EI) for $C_{12}H_{18}FN_3O_2$: 256 (MH$^+$).

Step 4: Preparation of tert-butyl (2-{4-[3-fluoro-5-(2-methoxyethoxy)pyridin-2-yl]piperazin-1-yl}ethyl)methylcarbamate

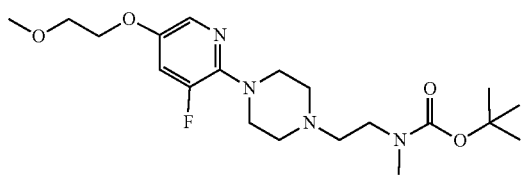 [SMILES: COCCOc1cnc(N2CCN(CCN(C)C(=O)OC(C)(C)C)CC2)c(F)c1]

Neat tert-butyl N-methyl-N-(2-oxoethyl)carbamate (3.8 mL, 22 mmol) was added to a stirred solution of 1-[3-fluoro-5-(2-methoxyethoxy)pyridin-2-yl]piperazine (5.18 g, 20.3 mmol) in 1,2-dichloroethane (100 mL). Sodium triacetoxyborohydride (8.6 g, 40.6 mmol) was then added in one portion, and the mixture stirred at room temperature. After 1.2 h, 2 M sodium carbonate was added (150 mL), the mixture was diluted with ethyl acetate (350 mL), washed with 0.7 M pH6 disodium hydrogen phosphate (2×50 mL), 1 M sodium bicarbonate (50 mL), dried (sodium sulfate), filtered and concentrated to a yellow oil. Chromatography on silica (ethyl acetate to 4% methanol/ethyl acetate) afforded tert-butyl (2-{4-[3-fluoro-5-(2-methoxyethoxy)pyridin-2-yl]piperazin-1-yl}ethyl)methylcarbamate (6.76 g, 81% yield) as a very pale yellow oil. $^1$H NMR (500 MHz, Chloroform-d) δ 7.80 (d, J=2.4 Hz, 1H), 7.01 (dd, J=13.3, 2.4 Hz, 1H), 4.15-4.09 (m, 2H), 3.75 (dd, J=5.4, 3.8 Hz, 2H), 3.46 (s, 3H), 3.44-3.28 (m, 6H), 2.91 (d, J=6.3 Hz, 3H), 2.65 (t, J=4.8 Hz, 4H), 2.55 (t, J=6.8 Hz, 2H), 1.48 (s, 9H). MS (EI) for $C_{20}H_{33}FN_4O_4$: 413 (MH$^+$).

Step 5: Preparation of 2-{4-[3-fluoro-5-(2-methoxyethoxy)pyridin-2-yl]piperazin-1-yl}-N-methylethanamine

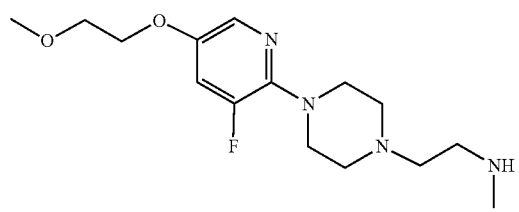 [SMILES: CNCCN1CCN(c2ncc(OCCOC)cc2F)CC1]

A solution of tert-butyl (2-{4-[3-fluoro-5-(2-methoxyethoxy)pyridin-2-yl]piperazin-1-yl}ethyl)methylcarbamate (6.76 g, 16.39 mmol) in 1,4-dioxane (20 mL) was treated with hydrogen chloride, 4 M in dioxane (20.48 mL, 81.94 mmol), and the mixture stirred at room temperature. Additional 4 M hydrogen chloride in dioxane (4 mL, 1 equiv) was added after 1 h, and the mixture stirred overnight. After 26 h, the suspension was concentrated to remove dioxane, and the residue partitioned between dichloromethane (150 mL) and 2 M sodium carbonate (150 mL). The aqueous layer was extracted with dichloromethane (2×50 mL), and the combined organic layers were dried (sodium sulfate), filtered and concentrated to afford 2-{4-[3-fluoro-5-(2-methoxyethoxy)pyridin-2-yl]piperazin-1-yl}-N-methylethanamine (5.23 g, quant.) as a pale brown/tan semi-solid. $^1$H NMR (500 MHz, Chloroform-d) δ 7.79 (d, J=2.5 Hz, 1H), 7.01 (dd, J=13.3, 2.5 Hz, 1H), 4.15-4.09 (m, 2H), 3.75 (dd, J=5.3, 3.9 Hz, 2H), 3.46 (d, J=0.9 Hz, 3H), 3.35 (t, J=4.9 Hz, 4H), 2.74 (t, J=6.1 Hz, 2H), 2.62 (t, J=4.9 Hz, 4H), 2.57 (t, J=6.1 Hz, 2H), 2.49 (d, J=0.9 Hz, 3H). MS (EI) for $C_{15}H_{25}FN_4O_2$: 313 (MH$^+$).

Step 6: Preparation of $N^7$-(2-{4-[3-fluoro-5-(2-methoxyethoxy)pyridin-2-yl]piperazin-1-yl}ethyl)-$N^7$-methyl-2-(1,3-oxazol-2-yl)[1,2,4]triazolo[1,5-c]pyrimidine-5,7-diamine

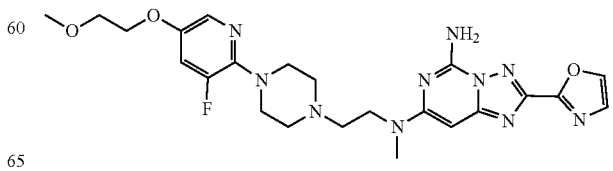

A 4 mL vial was charged with 2-{4-[3-fluoro-5-(2-methoxyethoxy)pyridin-2-yl]piperazin-1-yl}-N-methyl-ethanamine (86 mg, 0.28 mmol), 7-chloro-2-(1,3-oxazol-2-yl)[1,2,4]triazolo[1,5-c]pyrimidin-5-amine (50 mg, 0.21 mmol), N,N-diisopropylethylamine (0.074 mL, 0.42 mmol), dry N-methyl-2-pyrrolidinone (0.4 mL), and the mixture heated at 110° C. for 16 h, then at 130° C. for 6 hours. Purification by reverse-phase preparative HPLC (25-40% acetonitrile in 10 mM ammonium hydroxide/water on a 150×30 mm i.d., 10 um Gemini C18 column), then flash chromatography on silica (0-20% methanol/ethyl acetate) afforded $N^7$-(2-{4-[3-fluoro-5-(2-methoxyethoxy)pyridin-2-yl]piperazin-1-yl}ethyl)-$N^7$-methyl-2-(1,3-oxazol-2-yl)[1,2,4]triazolo[1,5-c]pyrimidine-5,7-diamine (4) (45 mg, 42% yield) as a light yellow-brown glass. $^1$H NMR (500 MHz, Chloroform-d) δ 7.84 (s, 1H), 7.79 (d, J=2.5 Hz, 1H), 7.37 (s, 1H), 7.01 (dd, J=13.2, 2.5 Hz, 1H), 6.03 (s, 2H), 5.94 (s, 1H), 4.14-4.08 (m, 2H), 3.79-3.71 (m, 4H), 3.45 (s, 3H), 3.37 (t, J=4.9 Hz, 4H), 3.07 (s, 3H), 2.70 (d, J=4.8 Hz, 4H), 2.64 (t, J=7.2 Hz, 2H). MS (EI) for $C_{23}H_{29}FN_{10}O_3$: 513 (MH$^+$).

The entire sample (45 mg, 88 μmol) was dissolved in acetonitrile (5 mL) and converted to the hydrochloride salt by treatment with 4 M hydrogen chloride in dioxane (110 μL, 0.44 mmol, 5 equiv), concentrated to dryness twice from acetonitrile. The residue was dissolved in water/acetonitrile (10:1, 2.6 mL), and the contents frozen (−78° C.) and lyophilized to afford the di-hydrochloride salt as a cream solid (52.4 mg).

Example 18

Synthesis of $N^7$—({(6S,8aR)-2-[3-fluoro-5-(2-methoxyethoxy)pyridin-2-yl]octahydropyrrolo[1,2-a]pyrazin-6-yl}methyl)-$N^7$-methyl-2-(1,3-oxazol-2-yl)[1,2,4]triazolo[1,5-c]pyrimidine-5,7-diamine (Compound 21), hydrochloride salt

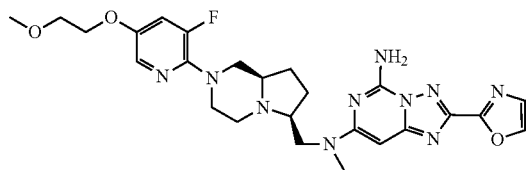

Compound 21

$N^7$—({(6S,8aR)-2-[3-Fluoro-5-(2-methoxyethoxy)pyridin-2-yl]octahydropyrrolo[1,2-a]pyrazin-6-yl}methyl)-$N^7$-methyl-2-(1,3-oxazol-2-yl)[1,2,4]triazolo[1,5-c]pyrimidine-5,7-diamine was synthesized according to the following reaction scheme.

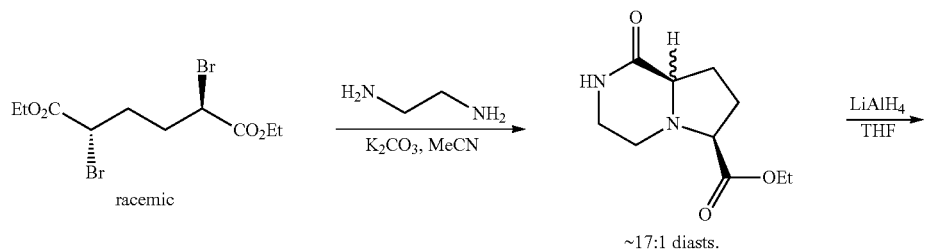

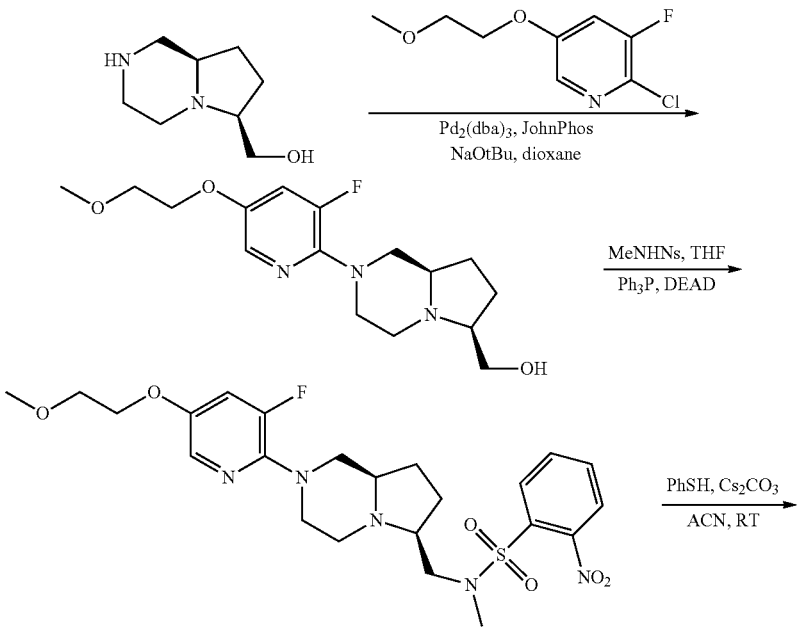

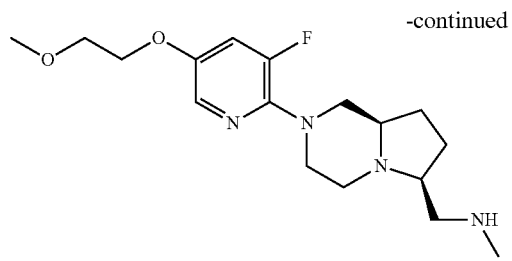 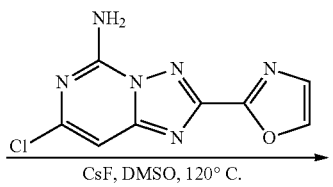

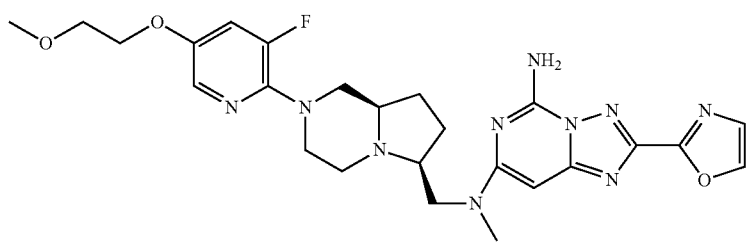

Step 1: Preparation of {(6S,8aR)-2-[3-fluoro-5-(2-methoxyethoxy)pyridin-2-yl]octahydropyrrolo[1,2-a]pyrazin-6-yl}methanol

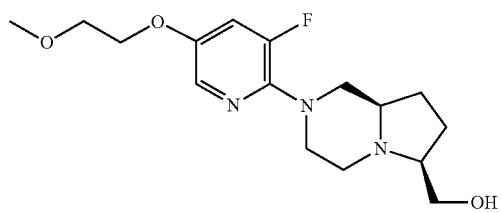 [SMILES: COCCOc1cnc(N2CCN3[C@H](CO)CC[C@@H]3C2)c(F)c1]

A 50 mL flask was charged with di-tert-butyl-(2-phenylphenyl)phosphine (64 mg, 0.21 mmol), tris(dibenzylidene)dipalladium (45 mg, 0.05 mmol), and sodium tert-butoxide (150 mg, 1.56 mmol), then purged with nitrogen. A solution of racemic 1,2,3,4,6,7,8,8a-octahydropyrrolo[1,2-a]pyrazin-6-ylmethanol (167 mg, 1.07 mmol; prepared in 2 steps from meso-diethyl-2,5-dibromoadipate and ethylene diamine, then reduction of the amido-ester with lithium aluminum hydride according to WO2014/114578 (Boehringer Ingelheim International GMBH), in dry 1,4-dioxane (6 mL) was added, followed by neat 2-chloro-3-fluoro-5-(2-methoxyethoxy)pyridine (200 mg, 0.97 mmol), and the resultant red-brown mixture was stirred at room temperature for 10 minutes, then heated at 45° C. for 17 hours. The reaction was quenched with saturated ammonium chloride (0.5 mL) and concentrated. The residue was diluted with ethyl acetate (40 mL), washed with 0.6 M pH 7 phosphate buffer (2×20 mL), then extracted with 1 M sodium dihydrogen phosphate (3×10 mL). The sodium dihydrogen phosphate aqueous extracts combined, basified to pH 10 with 2 sodium carbonate (20 mL), and back-extracted with dichloromethane (2×30 mL). The dichloromethane layers were combined, dried (sodium sulfate), filtered and concentrated to afford partially purified racemic {(6S,8aR)-2-[3-fluoro-5-(2-methoxyethoxy)pyridin-2-yl]octahydropyrrolo[1,2-a]pyrazin-6-yl}methanol (109 mg) as a pale orange-brown oil in sufficient purity for the next step. MS (EI) for $C_{16}H_{24}FN_3O_3$: 326 (MH$^+$).

Step 2: Preparation of N-({(6S,8aR)-2-[3-fluoro-5-(2-methoxyethoxy)pyridin-2-yl]octahydropyrrolo[1,2-a]pyrazin-6-yl}methyl)-N-methyl-2-nitrobenzenesulfonamide

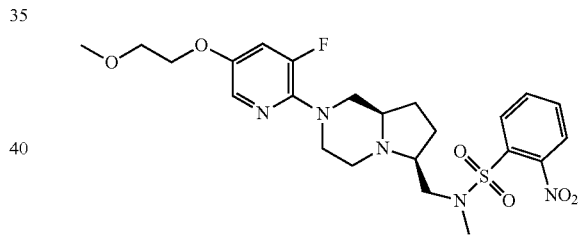

A 50 mL flask was charged with {(6S,8aR)-2-[3-fluoro-5-(2-methoxyethoxy)pyridin-2-yl]octahydropyrrolo[1,2-a]pyrazin-6-yl}methanol (107 mg, 0.36 mmol), triphenylphosphine (0.09 mL, 0.39 mmol), N-methyl-2-nitrobenzenesulfonamide (80 mg, 0.37 mmol) and purged with nitrogen. Dry tetrahydrofuran (5 mL) was added, and the stirred solution was cooled to 0° C., whereupon diethyl azodicarboxylate solution, 40% in toluene (0.14 mL, 0.37 mmol) was added dropwise over 15 min. After 10 min at 0° C., the reaction was warmed to room temperature, and stirred overnight. After 19 h, the mixture was concentrated in vacuo to an olive brown oil, and the residue chromatographed on silica (50-100% ethyl acetate/hexane, then to 3% methanol/ethyl acetate) to afford a partially purified single diastereomer N-({(6S,8aR)-2-[3-fluoro-5-(2-methoxyethoxy)pyridin-2-yl]octahydropyrrolo[1,2-a]pyrazin-6-yl}methyl)-N-methyl-2-nitrobenzenesulfonamide (183 mg) as a pale yellow solid, which was carried forward to the next step without further purification. MS (EI) for $C_{23}H_{30}FN_5O_6S$: 524 (MH$^+$).

Step 3: Preparation of 1-{(6S,8aR)-2-[3-fluoro-5-(2-methoxyethoxy)pyridin-2-yl]octahydropyrrolo[1,2-a]pyrazin-6-yl}-N-methylmethanamine

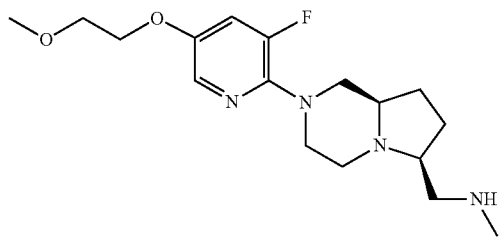

A 25 mL flask was charged with N-({(6S,8aR)-2-[3-fluoro-5-(2-methoxyethoxy)pyridin-2-yl]octahydropyrrolo[1,2-a]pyrazin-6-yl}methyl)-N-methyl-2-nitrobenzenesulfonamide (260 mg, 0.80 mmol), and cesium carbonate (183 mg), purged with nitrogen, whereupon dry acetonitrile (5 mL) and neat thiophenol (0.08 mL, 0.75 mmol) were added. After stirring for 65 h, the mixture was concentrated, and the residue partitioned between ethyl acetate (50 mL) and 0.5 M phosphoric acid (40 mL). The organic layer was extracted with 0.5 M phosphoric acid (10 mL), and the aqueous layers were combined, then basified to pH>12 with 4 M KOH (20 mL), and extracted with dichloromethane (3×25 mL). The combined dichloromethane layers were dried (sodium sulfate), filtered and concentrated to afford 1-{(6S,8aR)-2-[3-fluoro-5-(2-methoxyethoxy)pyridin-2-yl]octahydropyrrolo[1,2-a]pyrazin-6-yl}-N-methylmethanamine (61 mg, 17% over 3 steps) as a pale brown oil, which appeared to be a single diastereomer. $^1$H NMR (500 MHz, Chloroform-d) δ 7.82-7.77 (m, 1H), 7.01 (dd, J=13.3, 2.5 Hz, 1H), 4.15-4.09 (m, 2H), 3.89 (dt, J=11.6, 2.3 Hz, 1H), 3.85-3.78 (m, 1H), 3.80-3.72 (m, 2H), 3.47 (s, 3H), 3.11 (dt, J=10.7, 2.6 Hz, 1H), 3.03-2.93 (m, 1H), 2.80 (dd, J=11.5, 3.3 Hz, 1H), 2.70 (dd, J=11.7, 10.2 Hz, 1H), 2.63 (dd, J=11.5, 6.4 Hz, 1H), 2.49 (s, 3H), 2.49-2.45 (m, 1H), 2.39-2.26 (m, 2H), 1.99-1.84 (m, 1H), 1.80 (dddd, J=11.9, 9.1, 5.8, 2.7 Hz, 1H), 1.75-1.65 (m, 1H), 1.45 (qd, J=11.2, 7.6 Hz, 1H). MS (EI) for $C_{17}H_{27}FN_4O_2$: 339 (MH$^+$).

Step 4: Preparation of N$^7$—({(6S,8aR)-2-[3-fluoro-5-(2-methoxyethoxy)pyridin-2-yl]octahydropyrrolo[1,2-a]pyrazin-6-yl}methyl)-N$^7$-methyl-2-(1,3-oxazol-2-yl)[1,2,4]triazolo[1,5-c]pyrimidine-5,7-diamine

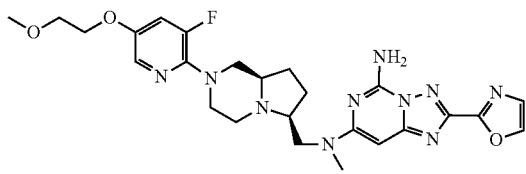 [SMILES: COCCOc1cnc(N2CCN3[C@H](CC[C@H]3CN(C)c3cc4nc(-c5ncco5)nn4c(N)n3)C2)c(F)c1]

Using the approach described in Step 4 of compound 7, coupling of 1-{(6S,8aR)-2-[3-fluoro-5-(2-methoxyethoxy)pyridin-2-yl]octahydropyrrolo[1,2-a]pyrazin-6-yl}-N-methylmethanamine (61 mg, 0.18 mmol) with 7-chloro-2-(1,3-oxazol-2-yl)[1,2,4]triazolo[1,5-c]pyrimidin-5-amine (86 mg, 0.36 mmol) in cesium fluoride (138 mg, 0.90 mmol) and dimethyl sulfoxide (0.4 mL) at 120° C. for 1 h 40 min afforded N$^7$—({(6S,8aR)-2-[3-fluoro-5-(2-methoxyethoxy)pyridin-2-yl]octahydropyrrolo[1,2-a]pyrazin-6-yl}methyl)-N$^7$-methyl-2-(1,3-oxazol-2-yl)[1,2,4]triazolo[1,5-c]pyrimidine-5,7-diamine (21) (41 mg, 41% yield) as a cream solid. $^1$H NMR (500 MHz, Chloroform-d) δ 7.88-7.84 (m, 1H), 7.80 (d, J=2.4 Hz, 1H), 7.40-7.36 (m, 1H), 7.02 (dd, J=13.3, 2.5 Hz, 1H), 5.98 (s, 1H), 5.72 (s, 2H), 4.15-4.09 (m, 2H), 3.97 (dd, J=14.2, 4.5 Hz, 1H), 3.90 (d, J=11.9 Hz, 1H), 3.83 (d, J=12.3 Hz, 1H), 3.78-3.72 (m, 2H), 3.50 (dd, J=14.5, 6.9 Hz, 1H), 3.47 (s, 3H), 3.20 (dd, J=10.2, 2.1 Hz, 1H), 3.12 (s, 3H), 3.01 (td, J=12.0, 3.0 Hz, 1H), 2.78-2.66 (m, 2H), 2.43 (td, J=11.1, 2.9 Hz, 1H), 2.39-2.30 (m, 1H), 1.93 (dq, J=12.5, 8.6 Hz, 1H), 1.85-1.76 (m, OH), 1.67 (dd, J=12.6, 9.1 Hz, 1H), 1.55-1.43 (m, 1H). MS (EI) for $C_{25}H_{31}FN_{10}O_3$: 539 (MH$^+$).

The sample was treated with hydrochloric acid, the solution frozen and lyophilized to afford the HCl salt as a cream solid.

Example 19

Synthesis of N$^7$-{2-[4-(3-fluoro-5-{2-[($^2$H$_3$)methyloxy]ethoxy}pyridin-2-yl)piperazin-1-yl]ethyl}-N$^7$-methyl-2-(1,3-oxazol-2-yl)[1,2,4]triazolo[1,5-c]pyrimidine-5,7-diamine (Compound 11)

Compound 11

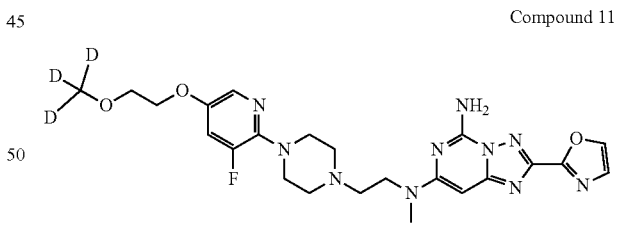

N$^7$-{2-[4-(3-Fluoro-5-{2-[($^2$H$_3$)methyloxy]ethoxy}pyridin-2-yl)piperazin-1-yl]ethyl}-N$^7$-methyl-2-(1,3-oxazol-2-yl)[1,2,4]triazolo[1,5-c]pyrimidine-5,7-diamine was synthesized according to the following reaction scheme.

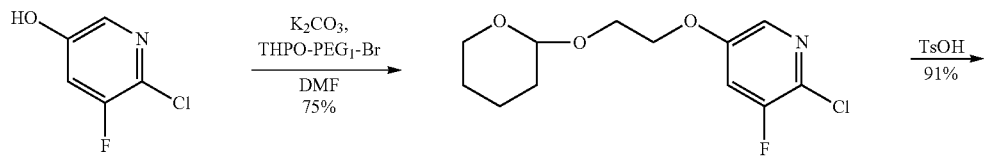

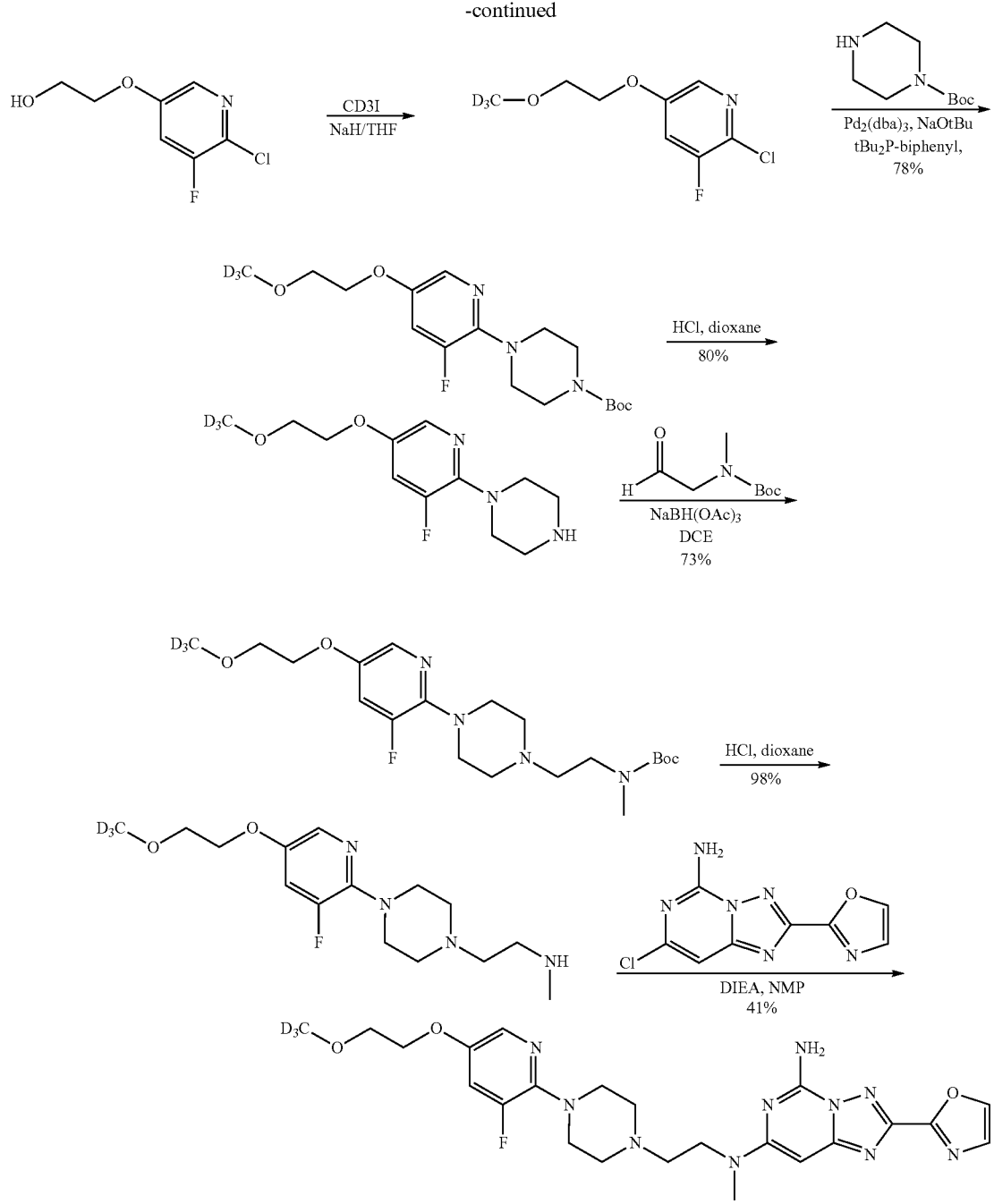

Step 1: Preparation of 2-chloro-3-fluoro-5-[2-(tetrahydro-2H-pyran-2-yloxy)ethoxy]pyridine

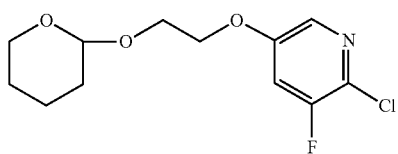 [SMILES: Fc1cc(OCCOC2CCCCO2)cnc1Cl]

A 100 mL flask was charged with 6-chloro-5-fluoropyridin-3-ol (2.00 g, 13.6 mmol), anhydrous potassium carbonate (3.75 g, 27.1 mmol), and dry dimethylformamide (10 mL). The mixture was stirred at room temperature for 10 minutes before 2-(2-bromoethoxy)tetrahydropyran (2.66 mL, 17.62 mmol) was added. The orange brown mixture was stirred over the weekend at room temperature. The mixture was partitioned between ethyl acetate (100 mL) and brine (100 mL). The aqueous layer was back-extracted with ethyl acetate (100 mL). The combined organic layers were washed with brine (4×50 mL), dried over sodium sulfate and concentrated to afford crude 2-chloro-3-fluoro-5-[2-(tetrahydro-2H-pyran-2-yloxy)ethoxy]pyridine (2.80 g, 10.16 mmol, 75% yield) as an oil which was carried forward to the next step without further purification. MS (EI) for $C_{12}H_{15}ClFNO_3$: 276 (MH$^+$).

Step 2: Preparation of 2-[(6-chloro-5-fluoropyridin-3-yl)oxy]ethanol

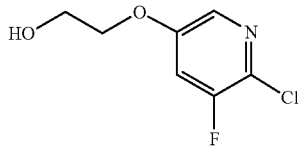 [SMILES: OCCOc1cnc(Cl)c(F)c1]

2-chloro-3-fluoro-5-[2-(tetrahydro-2H-pyran-2-yloxy)ethoxy]pyridine (2.50 g, 9.07 mmol) was dissolved in 15 mL of methanol and 4-methylbenzenesulfonic acid (3.45 g, 18.14 mmol) was added. The mixture was stirred for 60 min at room temperature. The solvent was removed and the residue was dissolved in 100 mL of ethyl acetate. The resultant solution was washed with sodium carbonate (10% yield) and saturated sodium chloride solution and dried over sodium sulfate. Evaporation of the solvent yielded 2-[(6-chloro-5-fluoropyridin-3-yl)oxy]ethanol as a yellow solid (1.58 g, 8.25 mmol, 91% yield). $^1$H NMR (500 MHz, Chloroform-d) δ 7.98 (s, 1H), 7.13 (dd, 1H), 4.15 (m, 2H), 4.03 (m, 2H), 2.10 (m, 1H). MS (EI) for $C_7H_7ClFNO_2$: 192 (MH$^+$).

Step 3: Preparation of 2-chloro-3-fluoro-5-{2-[($^2$H$_3$)methyloxy]ethoxy}pyridine

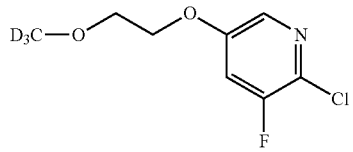 [SMILES: [2H]C([2H])([2H])OCCOc1cnc(Cl)c(F)c1]

2-[(6-chloro-5-fluoropyridin-3-yl)oxy]ethanol (0.50 g, 2.61 mmol) was dissolved in 5 mL of tetrahydrofuran and the solution was cooled in an ice bath for 10 min before sodium hydride (0.157 g, 3.91 mmol) was added under stirring. Finally, 1,1,1-trideuterio-2-iodo-ethane (0.21 mL, 3.13 mmol) was added. The mixture was stirred at room temperature overnight. 100 mL of dichloromethane was added and the mixture was washed with brine and water. The organic phase was dried over sodium sulfate, was filtered and the solvent was removed to obtain 2-chloro-3-fluoro-5-{2-[($^2$H$_3$)methyloxy]ethoxy}pyridine as a yellow oil (0.50 g, 2.38 mmol, 91.3% yield). MS (EI) for $C_8H_6D_3ClFNO_2$: 208 (MH$^+$).

Step 4: Preparation of tert-butyl 4-(3-fluoro-5-{2-[($^2$H$_3$)methyloxy]ethoxy}pyridin-2-yl)piperazine-1-carboxylate

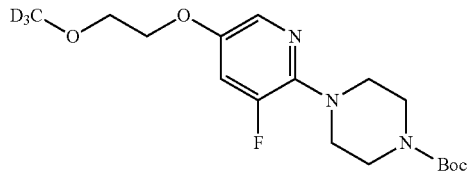 [SMILES: [2H]C([2H])([2H])OCCOc1cnc(N2CCN(C(=O)OC(C)(C)C)CC2)c(F)c1]

A 50 mL flask was charged with tert-butyl piperazine-1-carboxylate (0.7 g, 3.74 mmol), tris[(1E,4E)-1,5-diphenyl-penta-1,4-dien-3-one]dipalladium (0.07 g, 0.07 mmol), ditert-butyl-(2-phenylphenyl)phosphane (0.09 g, 0.32 mmol) and sodium tert-butoxide (0.28 g, 2.88 mmol). The mixture was purged with nitrogen and degassed anhydrous dioxane (3 mL) was added. A solution of 2-chloro-3-fluoro-5-{2-[($^2$H$_3$)methyloxy]ethoxy}pyridine (0.60 g, 2.88 mmol) in degassed anhydrous dioxane (2 mL) was added, and the mixture was stirred at room temperature for 10 min, then placed in an oil bath and heated at 45° C. for 24 hours. The reaction mixture was diluted with ethyl acetate (150 mL) and the resulted mixture was washed with brine and water. The organic phase was dried over sodium sulfate, filtered and concentrated to afford crude tert-butyl 4-(3-fluoro-5-{2-[($^2$H$_3$)methyloxy]ethoxy}pyridin-2-yl)piperazine-1-carboxylate (0.80 g, 2.23 mmol, 77.6% yield) as a brown-orange oil, which was carried forward to the next step without further purification. MS (EI) for $C_{17}H_{23}D_3FN_3O_4$: 359 (MH$^+$).

Step 5: Preparation of 1-(3-fluoro-5-{2-[($^2$H$_3$)methyloxy]ethoxy}pyridin-2-yl)piperazine

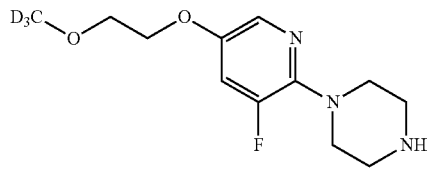 [SMILES: [2H]C([2H])([2H])OCCOc1cnc(N2CCNCC2)c(F)c1]

4 M hydrochloric acid in dioxane (5.58 mL, 22.32 mmol) was added into a solution of tert-butyl 4-(3-fluoro-5-{2-[($^2$H$_3$)methyloxy]ethoxy}pyridin-2-yl)piperazine-1-carboxylate (0.80 g, 2.23 mmol) in 1,4-dioxane (4 mL). The mixture was stirred for 2 hours. The solid was filtered out and the solution was concentrated. The residue from the solution was dissolved in 4 mL of water and extracted with 10 mL of ethyl acetate. The solid and the aqueous phase were combined and the resultant solution was adjusted to pH 10 by adding solid sodium carbonate, and then extracted with dichloromethane. The organic phase was dried over sodium sulfate, was filtered and the solvent was removed to yield 1-(3-fluoro-5-{2-[($^2$H$_3$)methyloxy]ethoxy}pyridin-2-yl)piperazine as yellow oil (0.42 g, 1.63 mmol, 72.8% yield). MS (EI) for $C_{12}H_{15}D_3FN_3O_2$: 259 (MH$^+$).

Step 6: Preparation of tert-butyl {2-[4-(3-fluoro-5-{2-[($^2$H$_3$)methyloxy]ethoxy}pyridin-2-yl)piperazin-1-yl]ethyl}methylcarbamate

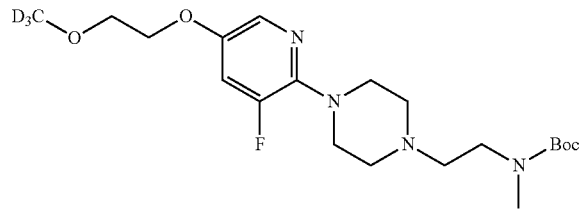 [SMILES: [2H]C([2H])([2H])OCCOc1cnc(N2CCN(CCN(C)C(=O)OC(C)(C)C)CC2)c(F)c1]

tert-Butyl N-methyl-N-(2-oxoethyl)carbamate (0.22 mL, 1.32 mmol) was added to a stirred solution of 1-(3-fluoro- 5-{2-[($^2$H$_3$)methyloxy]ethoxy}pyridin-2-yl)piperazine (0.42 g, 1.32 mmol) in 1,2-dichloroethane (3 mL). Sodium triacetoxyborohydride (0.56 g, 2.63 mmol) was then added in one portion, and the mixture was stirred at room temperature for 30 min. The reaction mixture was diluted with ethyl acetate (100 mL) and washed with brine and water. The organic phase was dried over sodium sulfate and then concentrated to a yellow oil. Chromatography on silica (Isolera™, ethyl acetate/methanol, 2-6%, 20 CV) afforded tert-butyl {2-[4-(3-fluoro-5-{2-[($^2$H$_3$)methyloxy]ethoxy}pyridin-2-yl)piperazin-1-yl]ethyl}methylcarbamate as a colorless oil (0.40 g, 0.96 mmol, 73.1% yield). $^1$H NMR (500 MHz, Chloroform-d) δ 7.80 (d, 1H), 7.02 (dd, 1H), 4.11 (m, 2H), 3.75 (m, 2H), 3.35 (m, 6H), 2.91 (m, 3H), 2.66 (m, 4H), 2.55 (m, 2H), 1.48 (s, 9H). MS (EI) for $C_{20}H_{30}D_3FN_4O_4$: 416 (MH$^+$).

Step 7: Preparation of 2-[4-(3-fluoro-5-{2-[($^2$H$_3$)methyloxy]ethoxy}pyridin-2-yl)piperazin-1-yl]-N-methylethanamine

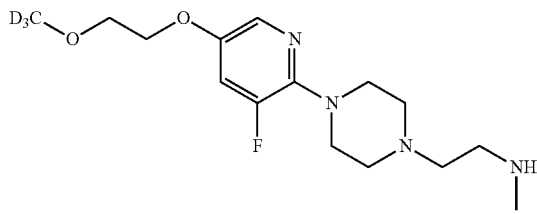 [SMILES: [2H]C([2H])([2H])OCCOc1cnc(N2CCN(CCNC)CC2)c(F)c1]

A solution of tert-butyl {2-[4-(3-fluoro-5-{2-[($^2$H$_3$)methyloxy]ethoxy}pyridin-2-yl)piperazin-1-yl]ethyl}methylcarbamate (0.34 g, 0.81 mmol) in 1,4-dioxane (1 mL) was treated with 4 M hydrochloric acid in dioxane (2.03 mL, 8.12 mmol), and the mixture was stirred at room temperature for 4 hours. The solvent was removed and the residue was dissolved in 10 mL of methanol and a prewashed AG 1-X8 resin was added. The mixture was shaken for 1 min and then the resin was filtered out. The filtrate was evaporated to provide 2-[4-(3-fluoro-5-{2-[($^2$H$_3$)methyloxy]ethoxy}pyridin-2-yl)piperazin-1-yl]-N-methylethanamine (0.23 g, 0.73 mmol, 90% yield). MS (EI) for $C_{15}H_{22}D_3FN_4O_2$: 316 (MH$^+$).

Step 8: Preparation of N$^7$-{2-[4-(3-fluoro-5-{2-[($^2$H$_3$)methyloxy]ethoxy}pyridin-2-yl)piperazin-1-yl]ethyl}-N$^7$-methyl-2-(1,3-oxazol-2-yl)[1,2,4]triazolo[1,5-c]pyrimidine-5,7-diamine

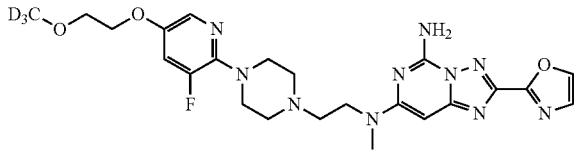 [SMILES: [2H]C([2H])([2H])OCCOc1cnc(N2CCN(CCN(C)c3cc4nc(-c5ncco5)nn4c(N)n3)CC2)c(F)c1]

A 4 mL vial was charged with 7-chloro-2-(1,3-oxazol-2-yl)[1,2,4]triazolo[1,5-c]pyrimidin-5-amine (0.10 g, 0.42 mmol) and 2-[4-(3-fluoro-5-{2-[($^2$H$_3$)methyloxy]ethoxy}pyridin-2-yl)piperazin-1-yl]-N-methylethanamine (0.17 g, 0.55 mmol). N,N-Diisopropylethylamine (0.15 mL, 0.85 mmol) in anhydrous N-methyl-2-pyrrolidinone (0.70 mL) was added into the reaction mixture. The resultant mixture was stirred in an oil bath at 120° C. for 30 hours. The reaction mixture was cooled down to room temperature and 100 mL of ethyl acetate was added. The solution was washed with sodium bicarbonate and water. The organic phase was dried over sodium sulfate, was filtered and the solvent was removed. The residue was purified twice by biotage (ethyl acetate/methanol, 6-15% yield) and (dichloromethane/methanol, 4-10% yield) to yield N$^7$-{2-[4-(3-fluoro-5-{2-[($^2$H$_3$)methyloxy]ethoxy}pyridin-2-yl)piperazin-1-yl]ethyl}-N$^7$-methyl-2-(1,3-oxazol-2-yl)[1,2,4]triazolo[1,5-c]pyrimidine-5,7-diamine (11) as a white solid (0.90 g, 0.17 mmol, 41.3% yield). $^1$H NMR (500 MHz, Chloroform-d) δ 7.80 (s, 1H), 7.74 (d, 1H), 7.33 (s, 1H), 6.97 (dd, 1H), 6.41 (d, 2H), 5.88 (s, 1H), 4.06 (m, 2H), 3.69 (m, 4H), 3.33 (m, 4H), 3.01 (s, 3H), 2.63 (m, 4H), 2.58 (m, 2H). MS (EI) for $C_{23}H_{26}D_3FN_{10}O_3$: 516 (MH$^+$).

The free base was dissolved in 1 mL of acetonitrile/1 N hydrochloric acid and lyophilized to afford the dihydrochloride salt as a cream solid.

Example 20

Synthesis of N$^7$-methyl-N$^7$-(2-{4-[4-({2-[($^2$H$_3$)methyloxy]($^2$H$_4$)ethyl}oxy)phenyl]piperazin-1-yl}ethyl)-2-(1,3-oxazol-2-yl)[1,2,4]triazolo[1,5-c]pyrimidine-5,7-diamine (Compound 12), Hydrochloride Salt Compound 12

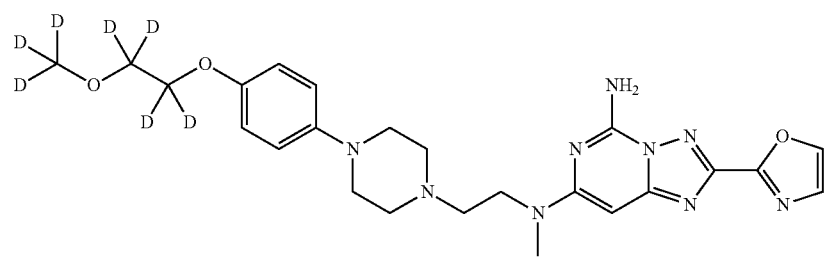

$N^7$-Methyl-$N^7$-(2-{4-[4-({2-[($^2H_3$)methyloxy]($^2H_4$)ethyl}oxy)phenyl]piperazin-1-yl}ethyl)-2-(1,3-oxazol-2-yl)[1,2,4]triazolo[1,5-c]pyrimidine-5,7-diamine was synthesized according to the following reaction scheme.

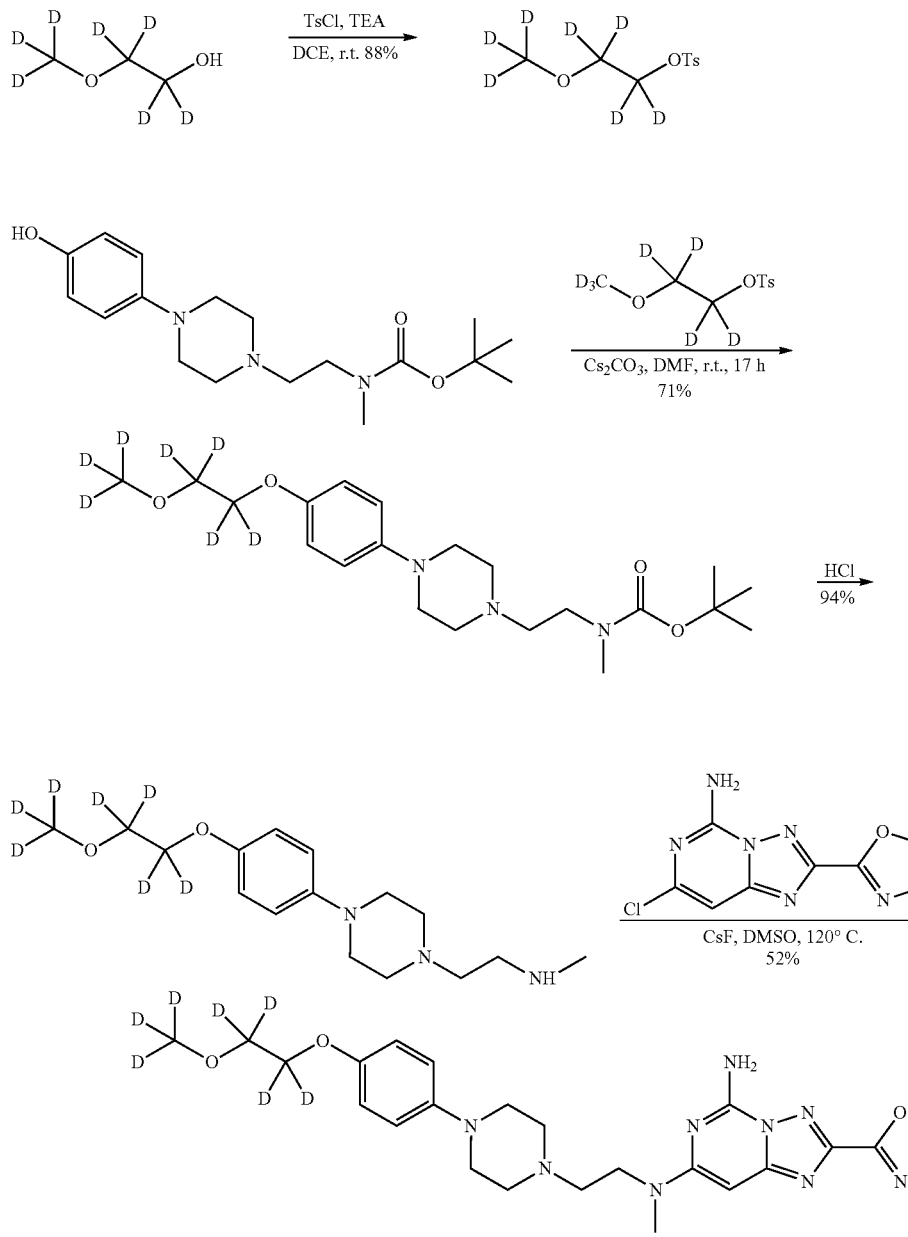

Step 1: Preparation of 2-[($^2H_3$)methyloxy]($^2H_4$)ethyl 4-methylbenzenesulfonate

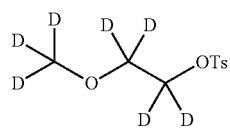

2-[($^2H_3$)Methyloxy]($^2H_4$)ethanol (1.94 g, 23.40 mmol) was dissolved in dichloroethane (100 mL) at room temperature, and then cooled to 0° C. p-Toluenesulfonyl chloride (4.36 g, 22.65 mmol) was added, followed by triethylamine (7.5 mL, 53.81 mmol). The resulting mixture was stirred at room temperature for 43.5 hours. The organic solution was diluted with dichloromethane, washed with 0.5 M hydrochloric acid (40 mL), saturated aqueous sodium bicarbonate solution and brine (twice), dried over anhydrous sodium sulfate and concentrated in vacuo. The residue was dried under high vacuum to afford 2-[($^2H_3$)methyloxy]($^2H_4$)ethyl 4-methylbenzenesulfonate (4.75 g, 88% yield). $^1$H NMR (500 MHz, Chloroform-d) δ 7.79-7.77 (m, 2H), 7.33-7.31 (m, 2H). MS (EI) for $C_{10}H_7D_7O_4S$: 255 (MNH$_4^+$).

Step 2: Preparation of tert-butyl methyl(2-{4-[4-({2-[($^2$H$_3$)methyloxy]($^2$H$_4$)ethyl}oxy)phenyl]piperazin-1-yl}ethyl)carbamate

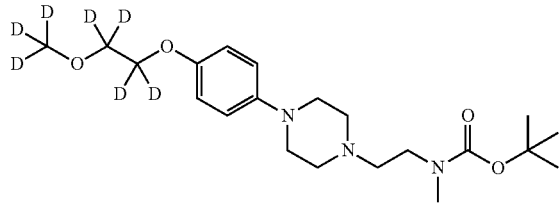 [SMILES: [2H]C([2H])([2H])OC([2H])([2H])C([2H])([2H])Oc1ccc(N2CCN(CCN(C)C(=O)OC(C)(C)C)CC2)cc1]

tert-butyl N-[2-[4-(4-hydroxyphenyl)piperazin-1-yl]ethyl]-N-methyl-carbamate (182.9 mg, 0.545 mmol) was dissolved in dimethylformamide (10 mL). Cesium carbonate (527.7 mg, 1.92 mmol) was added. Then 2-[($^2$H$_3$)methyloxy]($^2$H$_4$)ethyl 4-methylbenzenesulfonate (140.4 mg, 0.59 mmol) was added. The resulting mixture was stirred at room temperature for 17 hours. Water was added to quench the reaction and extracted with ethyl acetate. The organic solution was washed with brine, dried over anhydrous sodium sulfate and concentrated in vacuo. The residue was purified by silica gel column chromatography, eluting with 1-5% methanol/dichloromethane to afford tert-butyl methyl(2-{4-[4-({2-[($^2$H$_3$)methyloxy]($^2$H$_4$)ethyl}oxy)phenyl]piperazin-1-yl}ethyl)carbamate (155.3 mg, 71% yield). $^1$H NMR (500 MHz, Chloroform-d) δ 6.87-6.83 (m, 4H), 3.37-3.33 (m, 2H), 3.06 (m, 4H), 2.87-2.86 (m, 3H), 2.63 (m, 4H), 2.52 (m, 2H), 1.44 (s, 9H). MS (EI) for C$_{21}$H$_{28}$D$_7$N$_3$O$_4$: 401 (MH$^+$).

Step 3: Preparation of N-methyl-2-{4-[4-({2-[($^2$H$_3$)methyloxy]($^2$H$_4$)ethyl}oxy)phenyl]piperazin-1-yl}ethanamine

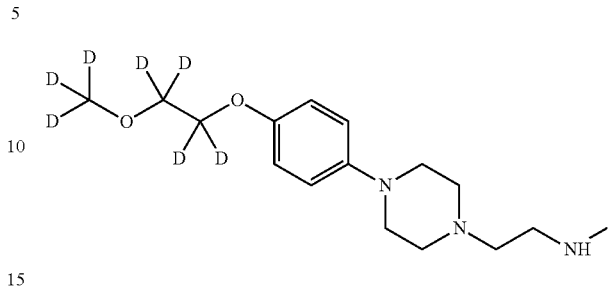

tert-Butyl methyl(2-{4-[4-({2-[($^2$H$_3$)methyloxy]($^2$H$_4$)ethyl}oxy)phenyl]piperazin-1-yl}ethyl)carbamate (155.3 mg, 0.38 mmol) was dissolved in dichloromethane (~10 mL), and then 4 N hydrochloric acid in dioxane (2 mL) was added. The resulting mixture was stirred at room temperature for 1 h and concentrated to remove the solvents. The residue was dissolved into methanol, stirred with AG®1-X8 resin (20-50 mesh, hydroxide form), filtrated and washed with methanol. The solution was collected and concentrated in vacuo to afford N-methyl-2-{4-[4-({2-[($^2$H$_3$)methyloxy]($^2$H$_4$)ethyl}oxy)phenyl]piperazin-1-yl}ethanamine (109.7 mg, 94% yield). $^1$H NMR (500 MHz, Chloroform-d) δ 6.87-6.83 (m, 4H), 3.07 (t, J=5.0 Hz, 4H), 2.69 (t, J=6.0 Hz, 2H), 2.59 (t, J=5.0 Hz, 4H), 2.53 (t, J=6.0 Hz, 2H), 2.44 (s, 3H). MS (EI) for C$_{16}$H$_{20}$D$_7$N$_3$O$_2$: 301 (MH$^+$).

Step 4: Preparation of N$^7$-methyl-N$^7$-(2-{4-[4-({2-[($^2$H$_3$)methyloxy]($^2$H$_4$)ethyl}oxy)phenyl]piperazin-1-yl}ethyl)-2-(1,3-oxazol-2-yl)[1,2,4]triazolo[1,5-c]pyrimidine-5,7-diamine

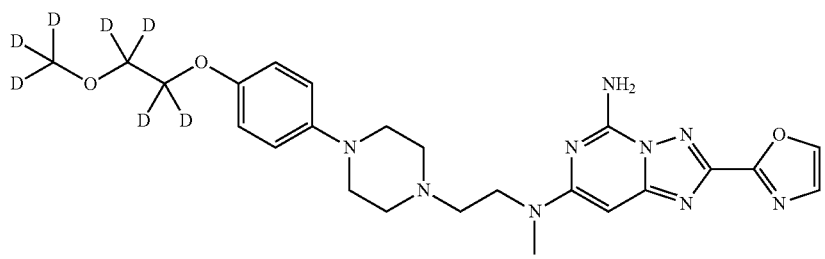 [SMILES: [2H]C([2H])([2H])OC([2H])([2H])C([2H])([2H])Oc1ccc(N2CCN(CCN(C)c3cc4nc(-c5ncco5)nn4c(N)n3)CC2)cc1]

A mixture of N-methyl-2-{4-[4-({2-[($^2$H$_3$)methyloxy]($^2$H$_4$)ethyl}oxy)phenyl]piperazin-1-yl}ethanamine (103 mg, 0.342 mmol), 7-chloro-2-(1,3-oxazol-2-yl)[1,2,4]triazolo[1,5-c]pyrimidin-5-amine (84.6 mg, 0.358 mmol) and cesium fluoride (161.6 mg, 1.064 mmol) in dimethyl sulfoxide (2 mL) was stirred at 120° C. for 21.5 hours. The mixture was cooled to room temperature. Aqueous sodium bicarbonate solution was added. The mixture was extracted with ethyl acetate (3×50 mL). The organic solution was filtrated to remove the semi-solid, washed with brine, dried over anhydrous sodium sulfate and concentrated in vacuo. The residue was purified by silica gel column chromatography, eluting with 1-5% methanol/dichloromethane to afford N$^7$-methyl-N$^7$-(2-{4-[4-({2-[($^2$H$_3$)methyloxy]($^2$H$_4$)ethyl}oxy)phenyl]piperazin-1-yl}ethyl)-2-(1,3-oxazol-2-yl)[1,2,4]triazolo[1,5-c]pyrimidine-5,7-diamine (12) (88.9 mg, 52% yield). $^1$H NMR (500 MHz, Chloroform-d) δ 7.81 (d, J=1.0 Hz, 1H), 7.34 (d, J=1.0 Hz, 1H), 6.87-6.83 (m, 4H), 5.91 (s, 1H), 5.69 (br, 2H), 3.71 (t, J=7.0 Hz, 2H), 3.08 (t, J=5.0 Hz, 4H), 3.05 (s, 3H), 2.66 (t, J=5.0 Hz, 4H), 2.59 (t, J=7.0 Hz, 2H). MS (EI) for C$_{24}$H$_{24}$D$_7$N$_9$O$_3$: 501 (MH$^+$).

78.3 mg were converted into the hydrochloric acid salt using acetonitrile and 1 M hydrochloric acid (86.7 mg).

Example 21

Synthesis of N$^7$-($^2$H$_3$)methyl-N$^7$-[2-{4-[4-({2-[($^2$H$_3$)methyloxy]($^2$H$_4$)ethyl}oxy)phenyl]piperazin-1-yl}($^2$H$_4$)ethyl]-2-(1,3-oxazol-2-yl)[1,2,4]triazolo[1,5-c]pyrimidine-5,7-diamine (Compound 16), Hydrochloride Salt

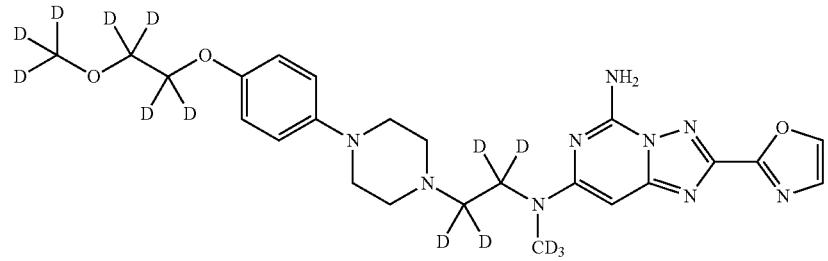

Compound 16

N$^7$-($^2$H$_3$)Methyl-N$^7$-[2-{4-[4-({2-[($^2$H$_3$)methyloxy]($^2$H$_4$)ethyl}oxy)phenyl]piperazin-1-yl}($^2$H$_4$)ethyl]-2-(1,3-oxazol-2-yl)[1,2,4]triazolo[1,5-c]pyrimidine-5,7-diamine was synthesized according to the following reaction scheme.

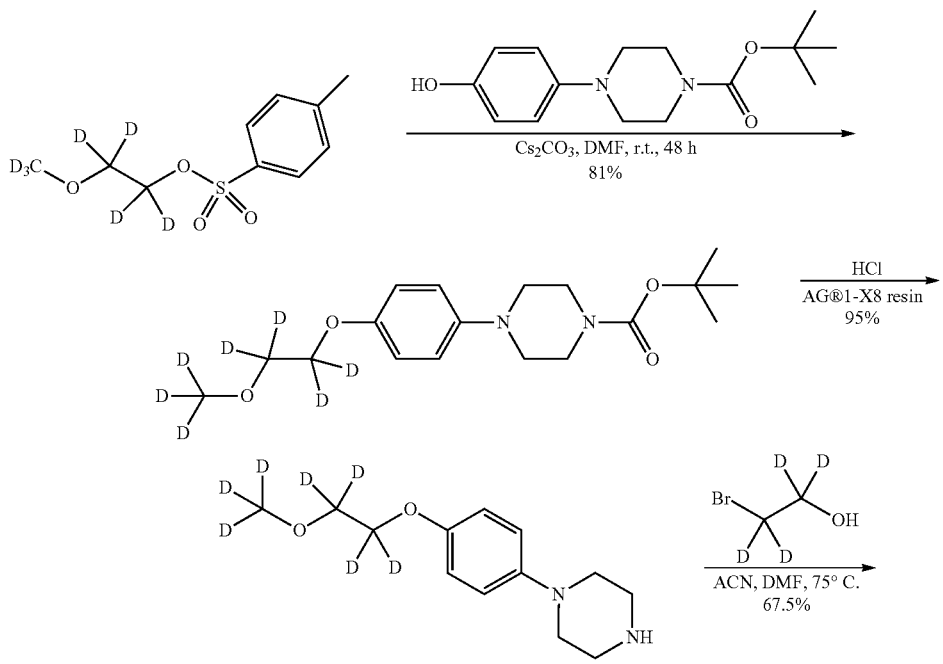

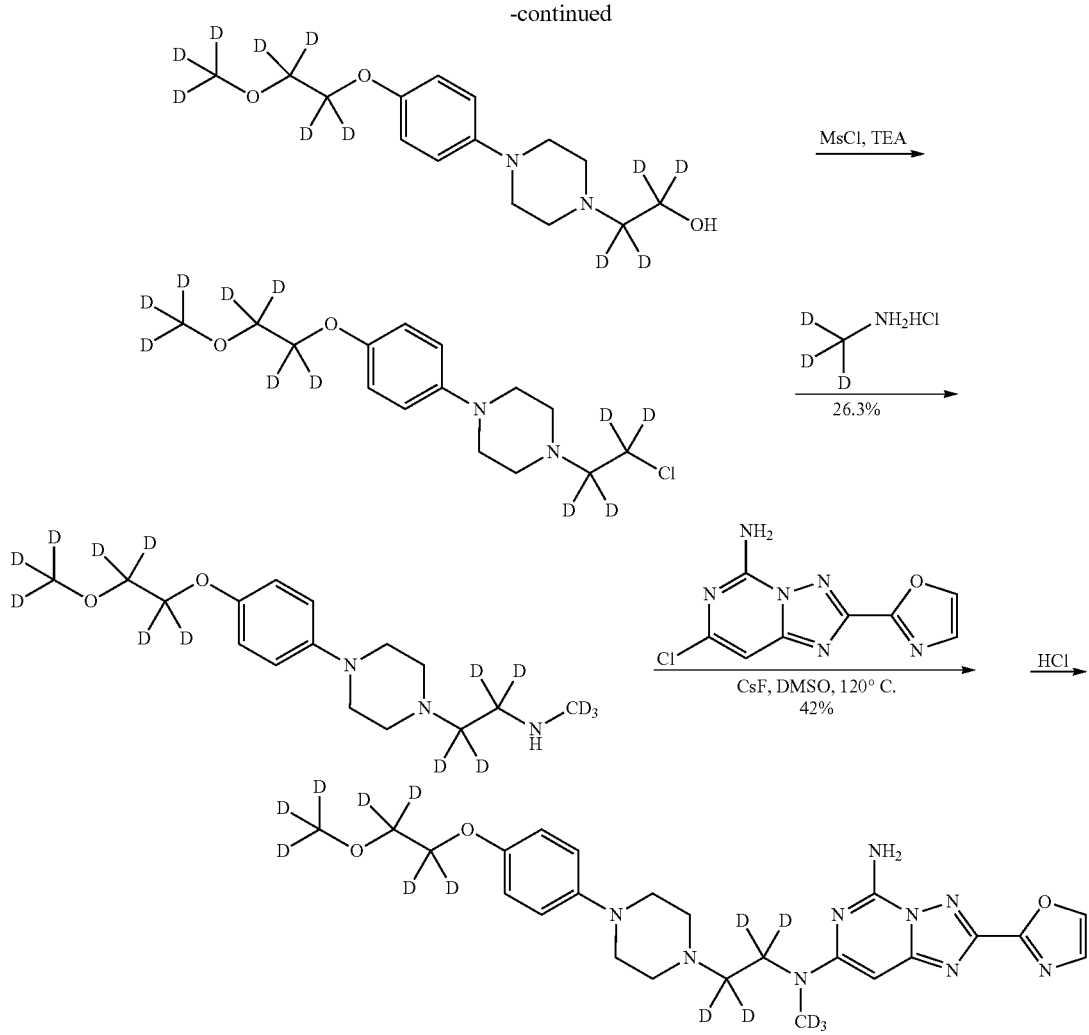

Step 1: Preparation of tert-butyl 4-[4-({2-[($^2$H$_3$)methyloxy]($^2$H$_4$)ethyl}oxy)phenyl]piperazine-1-carboxylate

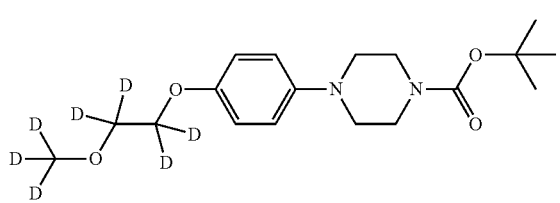 [SMILES: [2H]C([2H])([2H])OC([2H])([2H])C([2H])([2H])Oc1ccc(N2CCN(C(=O)OC(C)(C)C)CC2)cc1]

A mixture of tert-butyl 4-(4-hydroxyphenyl)piperazine-1-carboxylate (572.4 mg, 1.995 mmol) and 2-[($^2$H$_3$)methyloxy]($^2$H$_4$)ethyl 4-methylbenzenesulfonate (490 mg, 2.064 mmol) in dimethylformamide (20 mL) and in the presence of cesium carbonate (1.9607 g, 5.921 mmol) was stirred at room temperature for 48 hours. Water was added to quench the reaction. The reaction was extracted with ethyl acetate (3×35 mL). The combined organic solution was dried over anhydrous sodium sulfate and concentrated in vacuo to remove all the solvents. The residue was purified by silica gel column chromatography, eluting with 30-100% ethyl acetate in hexanes to afford tert-butyl 4-[4-({2-[($^2$H$_3$)methyloxy]($^2$H$_4$)ethyl}oxy)phenyl]piperazine-1-carboxylate as a white solid (552.6 mg, 81% yield). $^1$H NMR (500 MHz, Chloroform-d) δ 6.88-6.82 (m, 4H), 3.55 (t, J=5.0 Hz, 4H), 2.98 (t, J=5.0 Hz, 4H), 1.46 (s, 9H). MS (EI) for C$_{18}$H$_{21}$D$_7$N$_2$O$_4$: 344 (MH$^+$).

Step 2: Preparation of 1-[4-({2-[($^2$H$_3$)methyloxy]($^2$H$_4$)ethyl}oxy)phenyl]piperazine

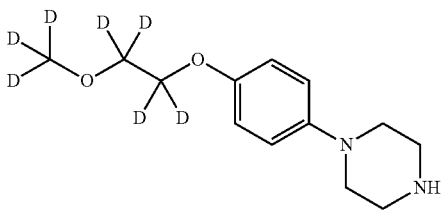 [SMILES: [2H]C([2H])([2H])OC([2H])([2H])C([2H])([2H])Oc1ccc(N2CCNCC2)cc1]

tert-Butyl 4-[4-({2-[($^2$H$_3$)methyloxy]($^2$H$_4$)ethyl}oxy)phenyl]piperazine-1-carboxylate (552 mg, 1.607 mmol) was dissolved in dichloromethane (6 mL), and then 4 N hydrochloric acid in dioxane (4 ml) was added. The mixture was stirred at room temperature for 40 min. More 1.25 N hydrochloric acid in methanol (4 mL) was added to afford a clear solution. The mixture was stirred at room temperature for 1 hour. The solution was concentrated in vacuo to remove all the solvents. The residue was dissolved in methanol, stirred with AG®1-X8 resin (20-50 mesh, hydroxide form), filtrated and washed with methanol. The solution was collected and concentrated in vacuo to afford 1-[4-({2-[($^2$H$_3$)methyloxy]($^2$H$_4$)ethyl}oxy)phenyl]piperazine as a white solid (371 mg, 95% yield). $^1$H NMR (500 MHz, Chloroform-d) δ 6.87-6.83 (m, 4H), 3.03 (s, 8H), 1.97 (br, 1H). MS (EI) for $C_{13}H_{13}D_7N_2O_2$: 244 (MH$^+$).

Step 3: Preparation of 2-{4-[4-({2-[($^2$H$_3$)methyloxy]($^2$H$_4$)ethyl}oxy)phenyl]piperazin-1-yl}($^2$H$_4$)ethanol

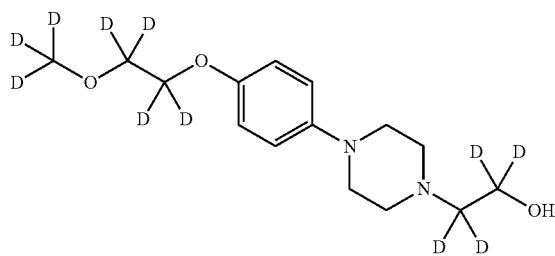 [SMILES: [2H]C([2H])([2H])OC([2H])([2H])C([2H])([2H])Oc1ccc(N2CCN(C([2H])([2H])C([2H])([2H])O)CC2)cc1]

A mixture of 1-[4-({2-[($^2$H$_3$)methyloxy]($^2$H$_4$)ethyl}oxy)phenyl]piperazine (190 mg, 0.780 mmol) and 2-bromo($^2$H$_4$)ethanol (121 mg, 0.891 mmol) in acetonitrile (8 mL) and in the presence of potassium carbonate (335.1 mg, 2.424 mmol) was stirred at 75° C. for 17 hours. More 2-bromo($^2$H$_4$)ethanol (129.8 mg) was added and the mixture was stirred at 75° C. for 5 hours. Additional 2-bromo($^2$H$_4$)ethanol (142.3 mg) was added and the mixture was stirred at 75° C. for 18.5 hours. The mixture was cooled to room temperature and concentrated in vacuo to remove the solvent. The residue was dissolved in a small amount of water, brine was added and the aqueous phase was extracted with ethyl acetate. The organic solution was dried over anhydrous sodium sulfate and concentrated in vacuo. The residue was purified by silica gel column chromatography, eluting with 1-10% methanol/dichloromethane to afford 2-{4-[4-({2-[($^2$H$_3$)methyloxy]($^2$H$_4$)ethyl}oxy)phenyl]piperazin-1-yl}($^2$H$_4$)ethanol as a white solid (153.6 mg, 67.5% yield). $^1$H NMR (500 MHz, Chloroform-d) δ 6.88-6.83 (m, 4H), 3.08 (t, J=5.0 Hz, 4H), 2.66 (t, J=5.0 Hz, 4H). MS (EI) for $C_{15}H_{13}D_{11}N_2O_3$: 292 (MH$^+$).

Step 4: Preparation of 1-[2-chloro($^2$H$_4$)ethyl]-4-[4-({2-[($^2$H$_3$)methyloxy]($^2$H$_4$)ethyl}oxy)phenyl]piperazine

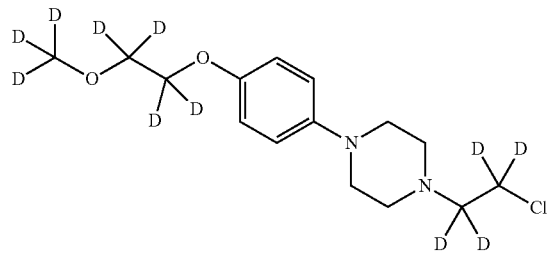 [SMILES: [2H]C([2H])([2H])OC([2H])([2H])C([2H])([2H])Oc1ccc(N2CCN(C([2H])([2H])C([2H])([2H])Cl)CC2)cc1]

2-{4-[4-({2-[($^2$H$_3$)Methyloxy]($^2$H$_4$)ethyl}oxy)phenyl]piperazin-1-yl}($^2$H$_4$)ethanol (103.7 mg, 0.361 mmol) was dissolved in dichloromethane (10 mL). Triethylamine (0.4 mL, 2.870 mmol) was added, followed by methane sulfonyl chloride (0.05 mL, 0.646 mmol). The resulting mixture was stirred at room temperature for 4 hours. Aqueous sodium bicarbonate solution was added to quench the reaction. The organic solution was separated and the aqueous solution was extracted with dichloromethane. The combined organic layers were washed with brine and concentrated in vacuo to afford crude 1-[2-chloro($^2$H$_4$)ethyl]-4-[4-({2-[($^2$H$_3$)methyloxy]($^2$H$_4$)ethyl}oxy)phenyl]piperazine, which was carried forward to the next step without further purification. MS (EI) for $C_{15}H_{12}D_{11}ClN_2O_2$: 310 (MH$^+$).

Step 5: Preparation of N-($^2$H$_3$)methyl-2-{4-[4-({2-[($^2$H$_3$)methyloxy]($^2$H$_4$)ethyl}oxy)phenyl]piperazin-1-yl}($^2$H$_4$)ethanamine

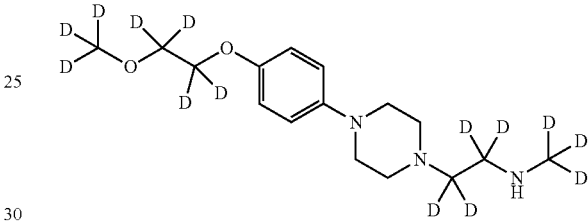

A mixture of 1-[2-chloro($^2$H$_4$)ethyl]-4-[4-({2-[($^2$H$_3$)methyloxy]($^2$H$_4$)ethyl}oxy)phenyl]piperazine (101 mg, 0.326 mmol), ($^2$H$_3$)methylamine hydrochloride (446 mg, 6.324 mmol) and diisopropylethylamine (0.19 mL, 1.091 mmol) in ethanol (2 mL) was stirred at 70° C. for 4 hours. The mixture was concentrated in vacuo to remove the solvent. The residue was taken in aqueous sodium bicarbonate solution and saturated sodium chloride and extracted with dichloromethane (4 times). The organic solution was dried over anhydrous sodium sulfate and concentrated in vacuo. The residue was purified by NH-silica gel column chromatography, eluting with 1-10% methanol/dichloromethane to afford N-($^2$H$_3$)methyl-2-{4-[4-({2-[($^2$H$_3$)methyloxy]($^2$H$_4$)ethyl}oxy)phenyl]piperazin-1-yl}($^2$H$_4$)ethanamine (26.4 mg, 26% yield) as an off-white solid. $^1$H NMR (500 MHz, Chloroform-d) δ 6.86-6.82 (m, 4H), 3.06 (t, J=5.0 Hz, 4H), 2.58 (t, J=5.0 Hz, 4H). MS (EI) for $C_{16}H_{13}D_{14}N_3O_2$: 308 (MH$^+$).

Step 6: Preparation of N$^7$-($^2$H$_3$)methyl-N$^7$-[2-{4-[4-({2-[($^2$H$_3$)methyloxy]($^2$H$_4$)ethyl}oxy)phenyl]piperazin-1-yl}($^2$H$_4$)ethyl]-2-(1,3-oxazol-2-yl)[1,2,4]triazolo[1,5-c]pyrimidine-5,7-diamine

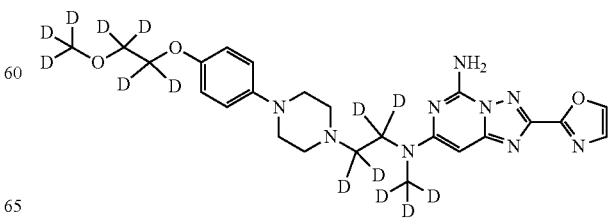

A mixture of N-(²H₃)methyl-2-{4-[4-({2-[(²H₃)methyloxy](²H₄)ethyl}oxy)phenyl]piperazin-1-yl}(²H₄)ethanamine (25.3 mg, 0.082 mmol), 7-chloro-2-oxazol-2-yl-[1,2,4]triazolo[1,5-c]pyrimidin-5-amine (24.3 mg, 0.103 mmol) and cesium fluoride (39 mg, 0.257 mmol) in dimethyl sulfoxide (1 mL) was stirred at 120° C. for 22.5 hours. The mixture was cooled to room temperature. Aqueous sodium bicarbonate solution was added and the mixture was extracted with ethyl acetate (3×50 mL). The organic solution was filtrated to remove the semi-solid, washed with brine, dried over anhydrous sodium sulfate and concentrated in vacuo. The residue was purified by silica gel column chromatography, eluting with methanol/dichloromethane to afford N⁷-(²H₃)methyl-N⁷-[2-{4-[4-({2-[(²H₃)methyloxy](²H₄)ethyl}oxy)phenyl]piperazin-1-yl}(²H₄)ethyl]-2-(1,3-oxazol-2-yl)[1,2,4]triazolo[1,5-c]pyrimidine-5,7-diamine (16) (28.1 mg, 67% yield) as a white solid. ¹H NMR (500 MHz, Chloroform-d) δ 7.77 (s, 1H), 7.32 (s, 1H), 6.85-6.81 (m, 4H), 6.11 (br, 2H), 5.88 (s, 1H), 3.07 (t, J=5.0 Hz, 4H), 2.64 (t, J=5.0 Hz, 4H). MS (EI) for C₂₄H₁₇D₁₄N₉O₃: 508 (MH⁺).

The free base was converted into the hydrochloric acid salt using acetonitrile and 1 N hydrochloric acid (31.4 mg).

Example 22

Synthesis of N⁷-(²H₃)methyl-N⁷-(2-{4-[4-({2-[(²H₃)methyloxy](²H₄)ethyl}oxy)phenyl]piperazin-1-yl}ethyl)-2-(1,3-oxazol-2-yl)[1,2,4]triazolo[1,5-c]pyrimidine-5,7-diamine (Compound 18), Hydrochloride Salt Compound 18

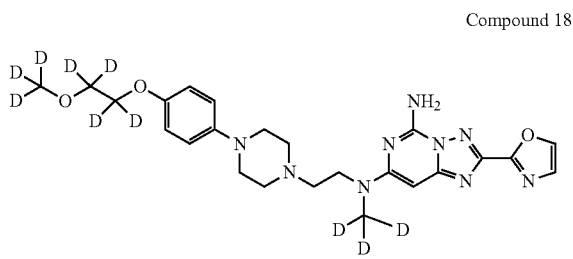 [SMILES: [2H]C([2H])([2H])OC([2H])([2H])C([2H])([2H])Oc1ccc(N2CCN(CCN(c3cc4nc(-c5ncco5)nn4c(N)n3)C([2H])([2H])[2H])CC2)cc1]

N⁷-(²H₃)Methyl-N⁷-(2-{4-[4-({2-[(²H₃)methyloxy](²H₄)ethyl}oxy)phenyl]piperazin-1-yl}ethyl)-2-(1,3-oxazol-2-yl)[1,2,4]triazolo[1,5-c]pyrimidine-5,7-diamine was synthesized according to the following reaction scheme.

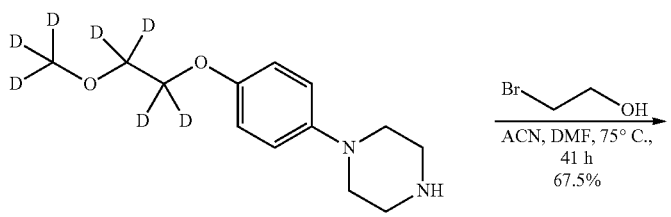

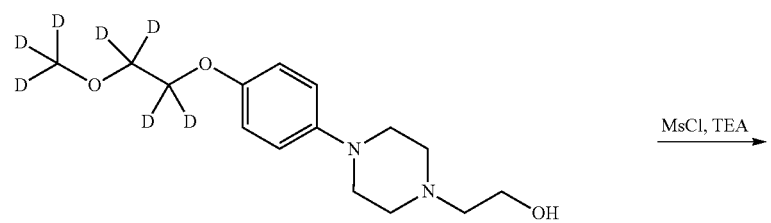

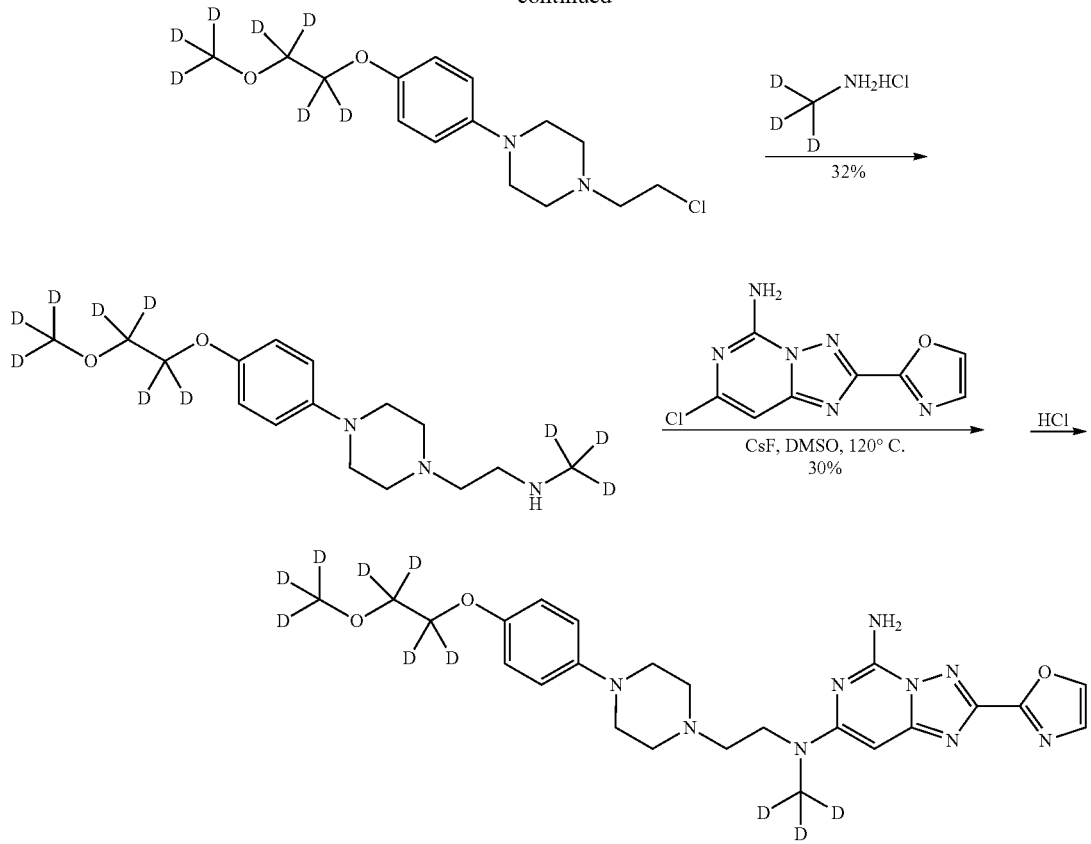

Step 1: Preparation of 2-{4-[4-({2-[($^2$H$_3$)methyloxy]($^2$H$_4$)ethyl}oxy)phenyl]piperazin-1-yl}ethanol

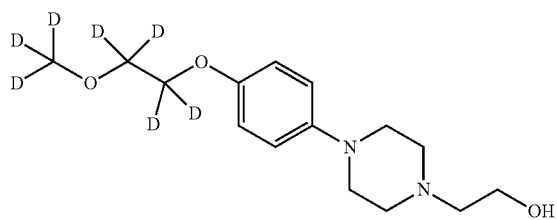 [SMILES: [2H]C([2H])([2H])OC([2H])([2H])C([2H])([2H])Oc1ccc(N2CCN(CCO)CC2)cc1]

A mixture of 1-[4-({2-[($^2$H$_3$)methyloxy]($^2$H$_4$)ethyl}oxy)phenyl]piperazine (172.8 mg, 0.710 mmol) and 2-bromoethanol (110 mg, 0.836 mmol) in acetonitrile (5 mL) in the presence of potassium carbonate (319.5 mg, 2.311 mmol) was stirred at 75° C. for 17 hours. More 2-bromethanol (123.4 mg) was added and the mixture was stirred at 75° C. for 4.5 hours. Additional 2-bromethanol (159.1 mg) was added and the mixture was stirred at 75° C. for 19 hours. The mixture was cooled to room temperature and concentrated in vacuo to remove the solvent. The residue was dissolved in aqueous sodium chloride solution and extracted with ethyl acetate. The organic solution was dried over anhydrous sodium sulfate and concentrated in vacuo. The residue was purified by silica gel column chromatography, eluting with 1-10% methanol/dichloromethane to afford 2-{4-[4-({2-[($^2$H$_3$)methyloxy]($^2$H$_4$)ethyl}oxy)phenyl]piperazin-1-yl}ethanol as a white solid (136.3 mg, 67% yield). $^1$H NMR (500 MHz, Chloroform-d) δ 6.88-6.82 (m, 4H), 3.63 (t, J=5.5 Hz, 2H), 3.09 (t, J=5.0 Hz, 4H), 2.66 (t, J=5.0 Hz, 4H), 2.59 (t, J=5.5 Hz, 2H). MS (EI) for $C_{15}H_{17}D_7N_2O_3$: 288 (MH$^+$).

Step 2: Preparation of 1-(2-chloroethyl)-4-[4-({2-[($^2$H$_3$)methyloxy]($^2$H$_4$)ethyl}oxy)phenyl]piperazine

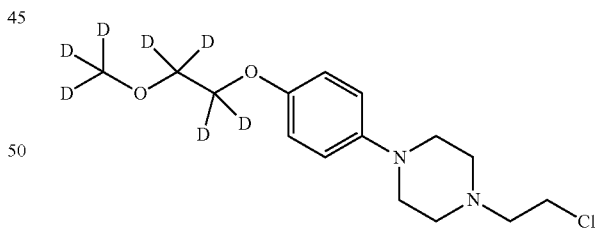

2-{4-[4-({2-[($^2$H$_3$)Methyloxy]($^2$H$_4$)ethyl}oxy)phenyl]piperazin-1-yl}ethanol (103.7 mg, 0.361 mmol) was dissolved in dichloromethane (10 mL). Triethylamine (0.4 mL, 2.870 mmol) was added, followed by methane sulfonyl chloride (0.05 mL, 0.646 mmol). The resulting mixture was stirred at room temperature for 4 hours. Aqueous sodium bicarbonate solution was added. The organic solution was separated and the aqueous solution was extracted with dichloromethane. The combined organic solution was washed with brine and concentrated in vacuo to afford 1-(2-chloroethyl)-4-[4-({2-[($^2$H$_3$)methyloxy]($^2$H$_4$) ethyl}oxy)phenyl]piperazine that was used without further purification. MS (EI) for $C_{15}H_{16}D_7ClN_2O_2$: 306 (MH$^+$).

Step 3: Preparation of N-(²H₃)methyl-2-{4-[4-({2-[(²H₃)methyloxy](²H₄)ethyl}oxy)phenyl]piperazin-1-yl}ethanamine

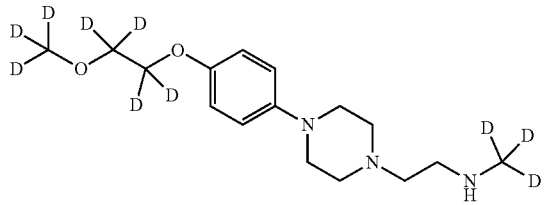 [SMILES: [2H]C([2H])([2H])NCCN1CCN(c2ccc(OC([2H])([2H])C([2H])([2H])OC([2H])([2H])[2H])cc2)CC1]

A mixture of 1-(2-chloroethyl)-4-[4-({2-[(²H₃)methyloxy](²H₄)ethyl}oxy)phenyl]piperazine (85.8 mg, 0.281 mmol), (²H₃)methylamine hydrochloride (360.7 mg, 5.114 mmol) and diisopropylethylamine (0.17 mL, 0.976 mmol) in ethanol (2 mL) was stirred at 70° C. for 1.5 hours. The mixture was concentrated in vacuo to remove the solvent. Aqueous sodium bicarbonate solution was added and the mixture was extracted with dichloromethane. The aqueous solution was saturated with sodium chloride and extracted with dichloromethane (2×35 mL). The combined organic layers were dried over anhydrous sodium sulfate and concentrated in vacuo. The residue was purified by NH-silica gel column chromatography, eluting with 1-10% methanol/dichloromethane to afford N-(²H₃)methyl-2-{4-[4-({2-[(²H₃)methyloxy](²H₄)ethyl}oxy)phenyl]piperazin-1-yl}ethanamine (36.3 mg, 43% yield). ¹H NMR (500 MHz, Chloroform-d) δ 6.87-6.82 (m, 4H), 3.06 (t, J=5.0 Hz, 4H), 2.68 (t, J=6.0 Hz, 2H), 2.58 (t, J=5.0 Hz, 4H), 2.52 (t, J=6.0 Hz, 2H). MS (EI) for C₁₆H₁₇D₁₀N₃O₂: 304 (MH⁺).

Step 4: Preparation of N⁷-(²H₃)methyl-N⁷-(2-{4-[4-({2-[(²H₃)methyloxy](²H₄)ethyl}oxy)phenyl]piperazin-1-yl}ethyl)-2-(1,3-oxazol-2-yl)[1,2,4]triazolo[1,5-c]pyrimidine-5,7-diamine

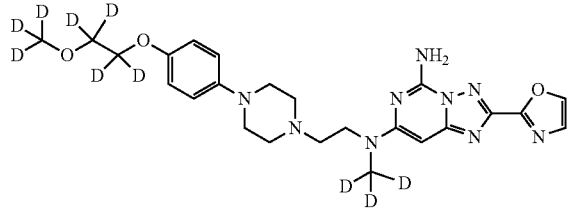 [SMILES: [2H]C([2H])([2H])OC([2H])([2H])C([2H])([2H])Oc1ccc(N2CCN(CCN(c3cc4nc(-c5ncco5)nn4c(N)n3)C([2H])([2H])[2H])CC2)cc1]

A mixture of N-(²H₃)methyl-2-{4-[4-({2-[(²H₃)methyloxy](²H₄)ethyl}oxy)phenyl]piperazin-1-yl}ethanamine (32 mg, 0.105 mmol), 7-chloro-2-oxazol-2-yl-[1,2,4]triazolo[1,5-c]pyrimidin-5-amine (38 mg, 0.161 mmol) and cesium fluoride (51.1 mg, 0.336 mmol) in dimethyl sulfoxide (0.5 mL) was stirred at 120° C. for 21.5 hours. The mixture was cooled to room temperature. Saturated aqueous sodium bicarbonate solution was added and the mixture was extracted with ethyl acetate (4×25 mL). The organic solution was filtrated to remove the semi-solid, washed with brine, dried over anhydrous sodium sulfate and concentrated in vacuo. The residue was purified by silica gel column chromatography, eluting with methanol/dichloromethane to afford the crude product. The crude product was further purified by reverse column chromatography, eluting with 5-50% acetonitrile/0.01 M hydrochloric acid/water. After the organic solvent was removed, about 1 mL of 1 M hydrochloric acid was added, and then the aqueous solution was lyophilized to afford N⁷-(²H₃)methyl-N⁷-(2-{4-[4-({2-[(²H₃)methyloxy](²H₄)ethyl}oxy)phenyl]piperazin-1-yl}ethyl)-2-(1,3-oxazol-2-yl)[1,2,4]triazolo[1,5-c]pyrimidine-5,7-diamine as the hydrochloric acid salt (18) (15.9 mg, 30% yield). ¹H NMR (500 MHz, Dimethyl sulfoxide-d₆) of the hydrochloric acid salt δ 9.93 (br, 1H), 8.35 (s, 1H), 7.89 (br, 2H), 7.50 (s, 1H), 6.90 (dd, J=9.0 Hz, 4H), 6.00 (s, 1H), 4.28 (br, 2H), 3.95 (t, J=6.5 Hz, 2H), 3.78 (m, 2H), 3.65 (m, 2H), 3.40 (m, J=2H), 3.22 (m, 2H), 3.00 (m, 2H). MS (EI) for C₁₆H₁₇D₁₀N₃O₂: 504 (MH⁺).

Example 23

Synthesis of N⁷-(²H₃)methyl-N⁷-[2-{4-[4-({2-[(²H₃)methyloxy](²H₄)ethyl}oxy)phenyl](²H₈)piperazin-1-yl}(²H₄)ethyl]-2-(1,3-oxazol-2-yl)[1,2,4]triazolo[1,5-c]pyrimidine-5,7-diamine (Compound 20), Hydrochloride Salt Compound 20

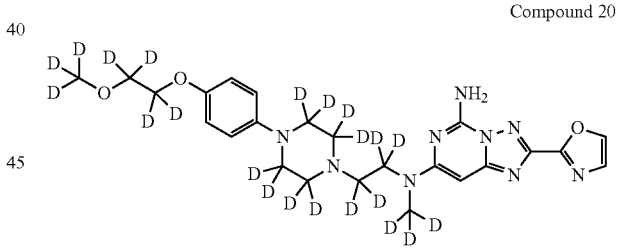

N⁷-(²H₃)Methyl-N⁷-[2-{4-[4-({2-[(²H₃)methyloxy](²H₄)ethyl}oxy)phenyl](²H₈)piperazin-1-yl}(²H₄)ethyl]-2-(1,3-oxazol-2-yl)[1,2,4]triazolo[1,5-c]pyrimidine-5,7-diamine was synthesized according to the following reaction scheme.

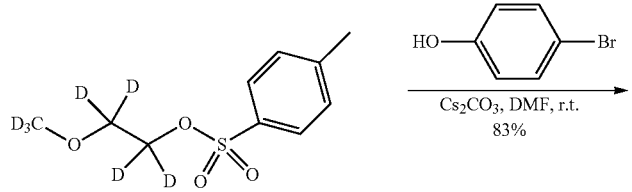

-continued
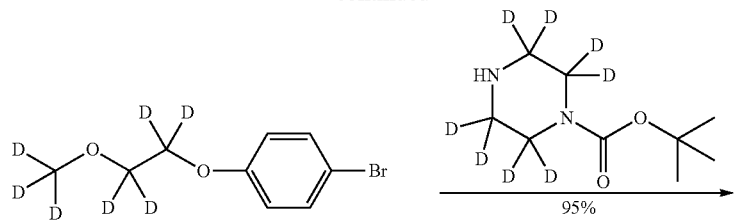
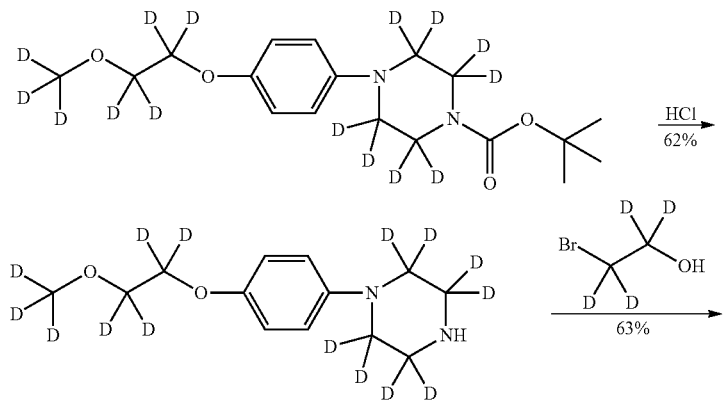
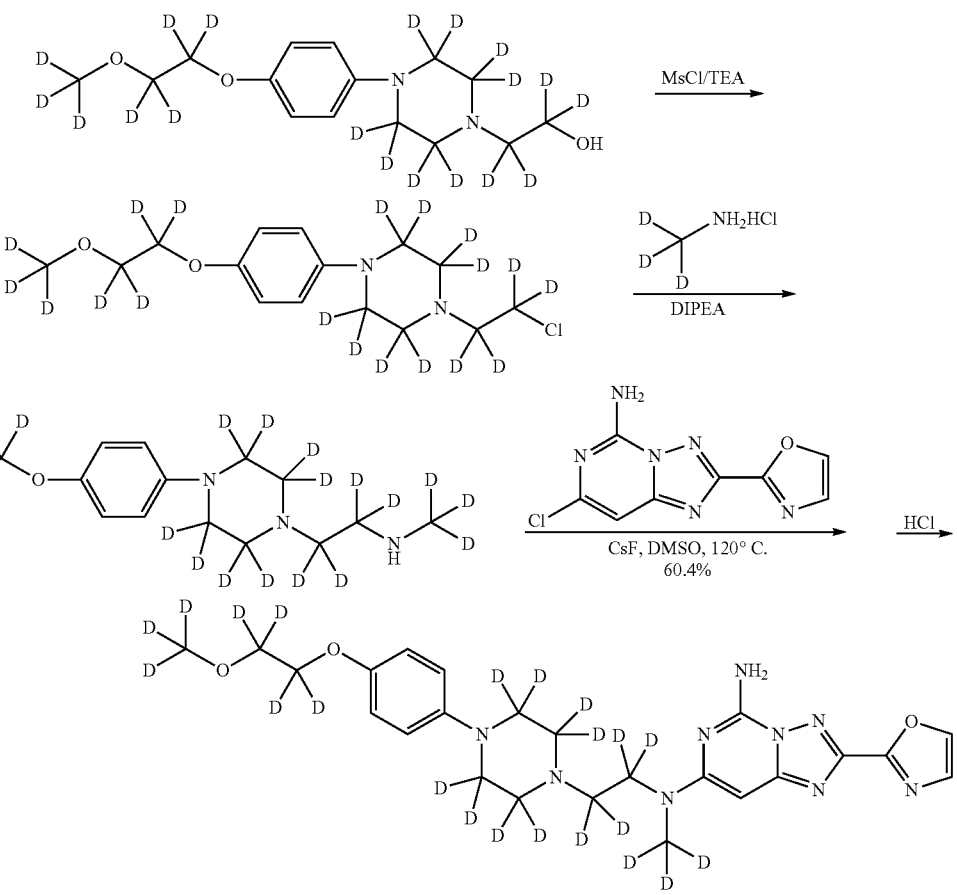

Step 1: Preparation of 1-bromo-4-({2-[($^2$H$_3$)methyloxy]($^2$H$_4$)ethyl}oxy)benzene

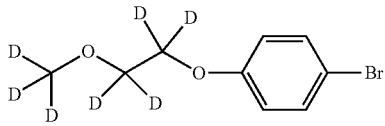 [SMILES: [2H]C([2H])([2H])OC([2H])([2H])C([2H])([2H])Oc1ccc(Br)cc1]

4-Bromophenol (1.0017 g, 5.7898 mmol) was dissolved in dimethylformamide (16 mL). Cesium carbonate (2.1804 g, 12.624 mmol) and 2-[($^2$H$_3$)methyloxy]($^2$H$_4$)ethyl 4-methylbenzenesulfonate (1.4102 g, 5.9422 mmol) were added. The resulting mixture was stirred at room temperature for 18 hours. Water was added and the mixture was extracted twice with ethyl acetate. The combined organic layers were washed twice with brine, dried over anhydrous sodium sulfate and concentrated in vacuo to remove solvents. The residue was purified by silica gel column chromatography, eluting with 10% ethyl acetate/hexanes to afford 1-bromo-4-({2-[($^2$H$_3$)methyloxy]($^2$H$_4$)ethyl}oxy)benzene (1.1441 g, 83% yield). $^1$H NMR (500 MHz, Chloroform-d) δ 7.36-7.33 (m, 2H), 6.80-6.77 (m, 2H).

Step 2: Preparation of tert-butyl 4-[4-({2-[($^2$H$_3$)methyloxy]($^2$H$_4$)ethyl}oxy)phenyl]($^2$H$_8$)piperazine-1-carboxylate

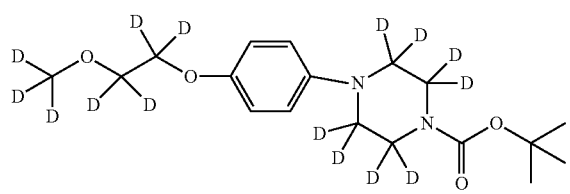 [SMILES: [2H]C([2H])([2H])OC([2H])([2H])C([2H])([2H])Oc1ccc(N2C([2H])([2H])C([2H])([2H])N(C(=O)OC(C)(C)C)C([2H])([2H])C2([2H])[2H])cc1]

A mixture of tert-butyl (2,2,3,3,5,5,6,6-$^2$H$_8$)piperazine-1-carboxylate (0.5394 g, 2.776 mmol), 1-bromo-4-({2-[($^2$H$_3$)methyloxy]($^2$H$_4$)ethyl}oxy)benzene (0.6639 g, 2.788 mmol), JohnPhos (194.4 mg, 0.632 mmol), sodium tert-butoxide (0.653 g, 6.591 mmol) and tris(dibenzylideneacetone)palladium (144.7 mg, 0.160 mmol) in dioxane (15 mL) was degassed and stirred at 50° C. under nitrogen for 5 hours. The reaction mixture was cooled to room temperature and then concentrated in vacuo to remove the solvents. The residue was mixed with aqueous ammonium chloride solution and extracted with dichloromethane twice. The organic solution was washed with brine, dried over anhydrous sodium sulfate and concentrated in vacuo. The residue was purified by silica gel column chromatography, eluting with 30% ethyl acetate in hexanes to afford tert-butyl 4-[4-({2-[($^2$H$_3$)methyloxy]($^2$H$_4$)ethyl}oxy)phenyl]($^2$H$_8$)piperazine-1-carboxylate (924.1 mg, 95% yield). $^1$H NMR (500 MHz, Chloroform-d) δ 6.85 (s, 4H), 1.45 (s, 9H). MS (EI) for C$_{18}$H$_{13}$D$_{15}$N$_2$O$_4$: 352 (MH$^+$).

Step 3: Preparation of 1-[4-({2-[($^2$H$_3$)methyloxy]($^2$H$_4$)ethyl}oxy)phenyl](2,2,3,3,5,5,6,6-$^2$H$_8$)piperazine

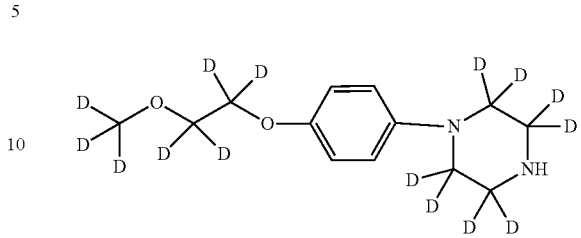

tert-Butyl 4-[4-({2-[($^2$H$_3$)methyloxy]($^2$H$_4$)ethyl}oxy)phenyl]($^2$H$_8$)piperazine-1-carboxylate (924 mg, 2.629 mmol) was dissolved in dichloromethane (6 mL), and then 4 N hydrochloric acid in dioxane (5 ml) was added. The mixture was stirred at room temperature for about 10 min and more 1.25 N hydrochloric acid in methanol (4 mL) was added to afford a clear solution. The mixture was stirred at room temperature for 4.5 hours. The solution was concentrated in vacuo to remove the solvents. The residue was dissolved in methanol and stirred with AG®1-X8 resin (20-50 mesh, hydroxide form), filtrated and washed with methanol. The solution was collected and concentrated in vacuo to afford 1-[4-({2-[($^2$H$_3$)methyloxy]($^2$H$_4$)ethyl}oxy)phenyl](2,2,3,3,5,5,6,6-$^2$H$_8$)piperazine as a white solid (660 mg, 99% yield). $^1$H NMR (500 MHz, Chloroform-d) δ 6.85 (m, 4H). MS (EI) for C$_{13}$H$_3$D$_{15}$N$_2$O$_2$: 252 (MH$^+$).

Step 4: Preparation of 2-{4-[4-({2-[($^2$H$_3$)methyloxy]($^2$H$_4$)ethyl}oxy)phenyl]($^2$H$_8$)piperazin-1-yl}($^2$H$_4$)ethanol

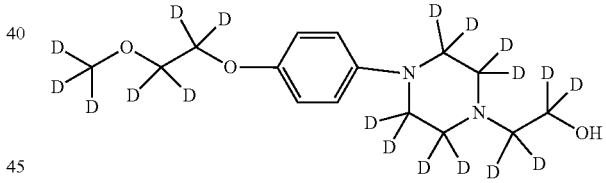

A mixture of 1-[4-({2-[($^2$H$_3$)methyloxy]($^2$H$_4$)ethyl}oxy)phenyl](2,2,3,3,5,5,6,6-$^2$H$_8$)piperazine (660 mg, 2.625 mmol) and 2-bromo($^2$H$_4$)ethanol (600.8 mg, 4.425 mmol) in acetonitrile (28 mL) and in the presence of potassium carbonate (1.5012 g, 10.862 mmol) was stirred at 75° C. for 2 hours. More 2-bromo($^2$H$_4$)ethanol (400 mg, 3.100 mmol) was added and the mixture was stirred at 75° C. for 2 hours. Additional 2-bromo($^2$H$_4$)ethanol (251 mg, 1.946 mmol) was added and the mixture was stirred at 75° C. for 1 h 20 min. Finally, more 2-bromo($^2$H$_4$)ethanol (277 mg, 2.147 mmol) was added and the mixture was stirred at 75° C. for 1 hour. The mixture was cooled to room temperature and concentrated in vacuo to remove the solvent. The residue was dissolved in aqueous sodium chloride solution and extracted with ethyl acetate. The organic solution was dried over anhydrous sodium sulfate and concentrated in vacuo. The residue was purified by silica gel column chromatography, eluting with 1-10% methanol/dichloromethane to afford 2-{4-[4-({2-[($^2$H$_3$)methyloxy]($^2$H$_4$)ethyl}oxy)phenyl]($^2$H$_8$)piperazin-1-yl}($^2$H$_4$)ethanol as a white solid (494.8 mg, 63% yield). $^1$H NMR (500 MHz, Chloroform-d) δ 6.87-6.83 (m, 4H). MS (EI) for $C_{15}H_5D_{19}N_2O_3$: 300 (MH$^+$).

Step 5: Preparation of 1-[2-chloro($^2$H$_4$)ethyl]-4-[4-({2-[($^2$H$_3$)methyloxy]($^2$H$_4$)ethyl}oxy)phenyl]($^2$H$_8$)piperazine

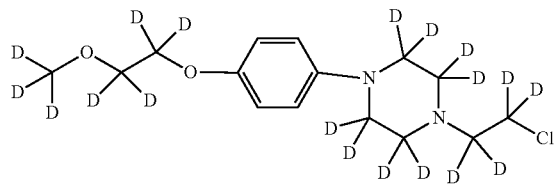 [SMILES: [2H]C([2H])([2H])OC([2H])([2H])C([2H])([2H])Oc1ccc(N2C([2H])([2H])C([2H])([2H])N(C([2H])([2H])C([2H])([2H])Cl)C([2H])([2H])C2([2H])[2H])cc1]

2-{4-[4-({2-[($^2$H$_3$)Methyloxy]($^2$H$_4$)ethyl}oxy)phenyl]($^2$H$_8$)piperazin-1-yl}($^2$H$_4$)ethanol (494.8 mg, 1.652 mmol) was dissolved in dichloromethane (20 mL), cooled to 0° C. and methane sulfonyl chloride (0.3 mL, 3.876 mmol) was added, followed by the addition of triethylamine (1.0 mL, 7.175 mmol). The resulting mixture was stirred at room temperature for 4 hours. Aqueous sodium bicarbonate solution was added. The organic solution was separated and the aqueous solution was extracted with dichloromethane. The combined organic layers were washed with brine twice and concentrated in vacuo to afford 1-[2-chloro($^2$H$_4$)ethyl]-4-[4-({2-[($^2$H$_3$)methyloxy]($^2$H$_4$)ethyl}oxy)phenyl]($^2$H$_8$)piperazine. $^1$H NMR (500 MHz, Chloroform-d) δ 6.84-6.82 (m, 4H). MS (EI) for $C_{15}H_4D_{19}ClN_2O_2$: 318 (MH$^+$).

Step 6: Preparation of N-($^2$H$_3$)methyl-2-{4-[4-({2-[($^2$H$_3$)methyloxy]($^2$H$_4$)ethyl}oxy)phenyl]($^2$H$_8$)piperazin-1-yl}($^2$H$_4$)ethanamine

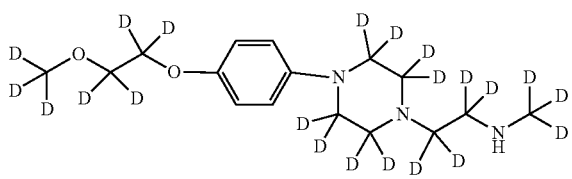 [SMILES: [2H]C([2H])([2H])NC([2H])([2H])C([2H])([2H])N1C([2H])([2H])C([2H])([2H])N(c2ccc(OC([2H])([2H])C([2H])([2H])OC([2H])([2H])[2H])cc2)C([2H])([2H])C1([2H])[2H]]

A mixture of 1-[2-chloro($^2$H$_4$)ethyl]-4-[4-({2-[($^2$H$_3$)methyloxy]($^2$H$_4$)ethyl}oxy)phenyl]($^2$H$_8$)piperazine (149.4 mg, 0.470 mmol), ($^2$H$_3$)methylamine hydrochloride (625.6 mg, 8.870 mmol) and diisopropylethylamine (0.1 mL, 0.574 mmol) in ethanol (2.0 mL) was stirred at 70° C. for 5 hours. The mixture was concentrated in vacuo to remove the solvent. The residue was mixed with aqueous sodium bicarbonate solution and extracted with dichloromethane (7 times). The organic solution was dried over anhydrous sodium sulfate and concentrated in vacuo. The residue was purified by NH-silica gel column chromatography, eluting with 1-10% methanol/dichloromethane to afford N-($^2$H$_3$)methyl-2-{4-[4-({2-[($^2$H$_3$)methyloxy]($^2$H$_4$)ethyl}oxy)phenyl]($^2$H$_8$)piperazin-1-yl}($^2$H$_4$)ethanamine as an off-white solid (12.6 mg, 8.5% yield). $^1$H NMR (500 MHz, Chloroform-d) δ 6.86-6.82 (m, 4H). MS (EI) for $C_{16}H_5D_{22}N_3O_2$: 316 (MH$^+$).

Step 7: Preparation of N$^7$-($^2$H$_3$)methyl-N$^7$-[2-{4-[4-({2-[($^2$H$_3$)methyloxy]($^2$H$_4$)ethyl}oxy)phenyl]($^2$H$_8$)piperazin-1-yl}($^2$H$_4$)ethyl]-2-(1,3-oxazol-2-yl)[1,2,4]triazolo[1,5-c]pyrimidine-5,7-diamine

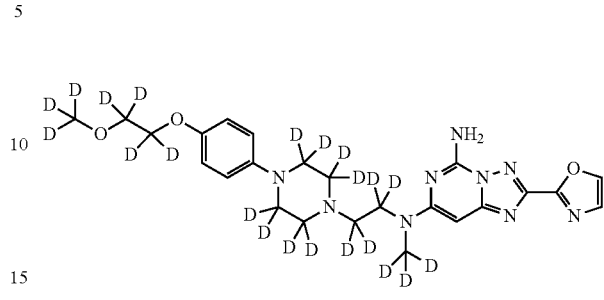

A mixture of N-($^2$H$_3$)methyl-2-{4-[4-({2-[($^2$H$_3$)methyloxy]($^2$H$_4$)ethyl}oxy)phenyl]($^2$H$_8$)piperazin-1-yl}($^2$H$_4$)ethanamine (12 mg, 0.038 mmol), 7-chloro-2-oxazol-2-yl-[1,2,4]triazolo[1,5-c]pyrimidin-5-amine (15.3 mg, 0.065 mmol) and cesium fluoride (22 mg, 0.145 mmol) in dimethyl sulfoxide (0.5 mL) was stirred at 120° C. for 5.5 hours. The mixture was cooled to room temperature. Saturated aqueous sodium bicarbonate solution was added and the mixture was extracted with ethyl acetate (4×50 mL). The organic solution was washed with brine, dried over anhydrous sodium sulfate and concentrated in vacuo. The residue was purified by NH-silica gel column chromatography, eluting with 1-10% methanol/dichloromethane to provide the crude product. The crude product was further purified by reverse column chromatography, eluting with 5-35% acetonitrile/0.01 M hydrochloric acid/water to afford N$^7$-($^2$H$_3$)methyl-N$^7$-[2-{4-[4-({2-[($^2$H$_3$)methyloxy]($^2$H$_4$)ethyl}oxy)phenyl]($^2$H$_8$)piperazin-1-yl}($^2$H$_4$)ethyl]-2-(1,3-oxazol-2-yl)[1,2,4]triazolo[1,5-c]pyrimidine-5,7-diamine dihydrochloride (20) as an off-yellow solid (13.5 mg, 60.4% yield). $^1$H NMR (500 MHz, Methanol-d$_4$) of hydrochloric acid salt δ 8.32 (s, 1H), 7.60 (s, 1H), 7.10 (m, 2H), 6.95-6.92 (m, 2H). MS (EI) for $C_{24}H_9D_{22}N_9O_3$: 516 (MH$^+$).

Example 24

Synthesis of N$^7$-(2-{4-[3-fluoro-5-({2-[($^2$H$_3$)methyloxy]($^2$H$_4$)ethyl}oxy)pyridin-2-yl]piperazin-1-yl}ethyl)-N$^7$-methyl-2-(1,3-oxazol-2-yl)[1,2,4]triazolo[1,5-c]pyrimidine-5,7-diamine (Compound 13), Hydrochloride Salt Compound 13

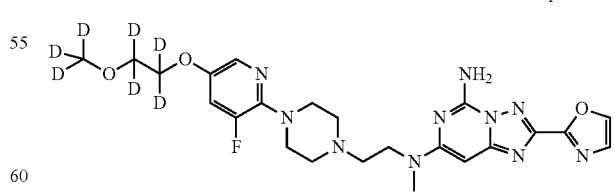

N$^7$-(2-{4-[3-Fluoro-5-({2-[($^2$H$_3$)methyloxy]($^2$H$_4$)ethyl}oxy)pyridin-2-yl]piperazin-1-yl}ethyl)-N$^7$-methyl-2-(1,3-oxazol-2-yl)[1,2,4]triazolo[1,5-c]pyrimidine-5,7-diamine was synthesized according to the following reaction scheme.

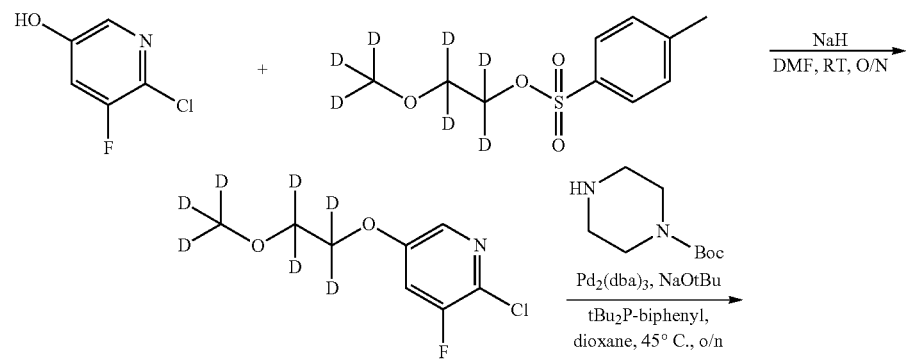
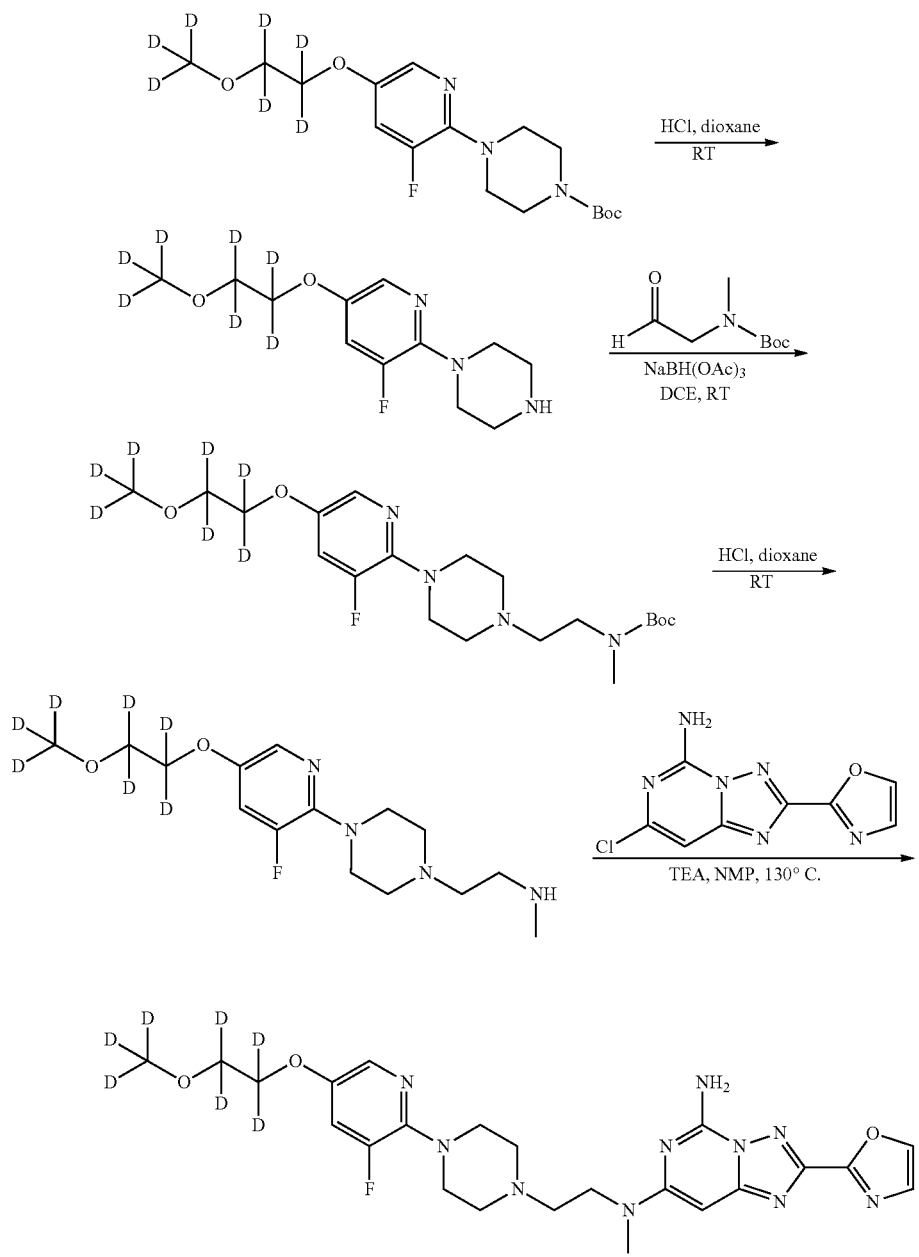

Step 1: Preparation of 2-chloro-3-fluoro-5-({2-[(²H₃)methyloxy](²H₄)ethyl}oxy)pyridine

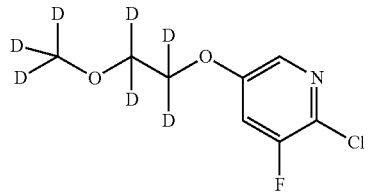 [SMILES: [2H]C([2H])([2H])OC([2H])([2H])C([2H])([2H])Oc1cnc(Cl)c(F)c1]

A 50 mL flask was charged with 6-chloro-5-fluoropyridin-3-ol (250 mg, 1.69 mmol), sodium hydride (61.0 mg, 2.54 mmol) and dry dimethylformamide (5 mL) and stirred at room temperature. After 2 minutes, neat 2-[(²H₃)methyloxy](²H₄)ethyl 4-methylbenzenesulfonate (402.2 mg, 1.69 mmol) was added in one portion, and the mixture was stirred overnight at room temperature. The mixture was partitioned between ethyl acetate (35 mL) and brine (25 mL). The aqueous layer was back-extracted with ethyl acetate (15 mL) and the combined organic layers were washed with brine (4×10 mL), dried (sodium sulfate), filtered and concentrated to afford crude 2-chloro-3-fluoro-5-({2-[(²H₃)methyloxy](²H₄)ethyl}oxy)pyridine (370 mg) as a brown oil, which was carried forward to the next step without further purification. MS (EI) for $C_8H_2D_7ClFNO_2$: 213 (MH⁺).

Step 2: Preparation of tert-butyl 4-[3-fluoro-5-({2-[(²H₃)methyloxy](²H₄)ethyl}oxy)pyridin-2-yl]piperazine-1-carboxylate

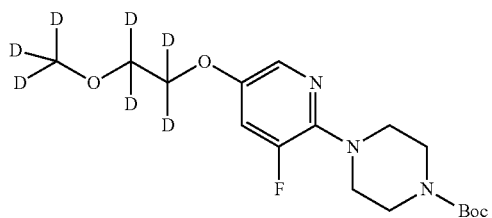 [SMILES: [2H]C([2H])([2H])OC([2H])([2H])C([2H])([2H])Oc1cnc(N2CCN(C(=O)OC(C)(C)C)CC2)c(F)c1]

A 50 mL flask was charged with tert-butyl piperazine-1-carboxylate (421.27 mg, 2.26 mmol), tris[(1E,4E)-1,5-diphenylpenta-1,4-dien-3-one]dipalladium (40 mg, 0.04 mmol), di-tert-butyl-(2-phenylphenyl)phosphine (57.11 mg, 0.19 mmol), sodium tert-butoxide (170 mg, 1.74 mmol) and purged with nitrogen, and dry nitrogen sparged dioxane (5 mL) was added. A solution of 2-chloro-3-fluoro-5-({2-[(²H₃)methyloxy](²H₄)ethyl}oxy)pyridine (370.0 g, 1.74 mmol) in dry nitrogen sparged dioxane (5 mL) was added, and the mixture stirred at room temperature for 10 min, then placed in an oil bath heated at 45° C. for 17 hours. The reaction was quenched with saturated ammonium chloride (2 mL), concentrated to remove most of the dioxane, then diluted with ethyl acetate (25 mL) and water (15 mL). The mixture was filtered through Celite®, diluted with brine (10 mL) and the organic layer washed with 1 M sodium dihydrogen phosphate (2×5 mL), dried (sodium sulfate), filtered and concentrated. The residue was subjected to flash chromatography (methanol:dichloromethane 1% to 6% yield) to afford tert-butyl 4-[3-fluoro-5-({2-[(²H₃)methyloxy](²H₄)ethyl}oxy)pyridin-2-yl]piperazine-1-carboxylate (230 mg, 0.63 mmol) as a brown-orange oil (two steps yield 36.5% yield). ¹H NMR (500 MHz, Chloroform-d) δ 7.80 (d, J=2.0 Hz, 1H), 7.02 (dd, J=13.0, 2.0 Hz, 1H), 3.57 (t, J=5.0 Hz, 4H), 3.27 (t, J=5.0 Hz, 4H), 1.50 (s, 3H). MS (EI) for $C_{17}H_{19}D_7FN_3O_4$: 363 (MH⁺).

Step 3: Preparation of 1-[3-fluoro-5-({2-[(²H₃)methyloxy](²H₄)ethyl}oxy)pyridin-2-yl]piperazine

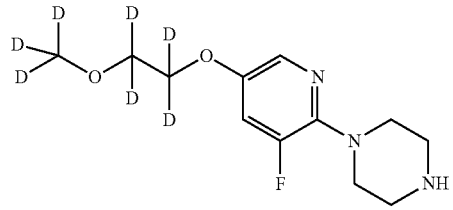 [SMILES: [2H]C([2H])([2H])OC([2H])([2H])C([2H])([2H])Oc1cnc(N2CCNCC2)c(F)c1]

4 M hydrogen chloride in dioxane (2 mL, 8 mmol) was added slowly over 2 minutes to a solution of tert-butyl 4-[3-fluoro-5-({2-[(²H₃)methyloxy](²H₄)ethyl}oxy)pyridin-2-yl]piperazine-1-carboxylate (230 mg, 0.63 mmol) in 1,4-dioxane (5 mL). After 5 minutes, the mixture began to effervesce. After 1 day, the solution was decanted, and the precipitate partitioned between ethyl acetate (20 mL) and 2 M sodium carbonate solution (25 mL). The organic layer was extracted with 0.5 M disodium hydrogen phosphate (5 mL), and 1 M sodium dihydrogen phosphate (2×5 mL). The aqueous phases were combined and acidified to pH 5 with neat 85% phosphoric acid, then washed with ethyl acetate (20 mL), basified to pH>12 with 12 M sodium hydroxide, and extracted with dichloromethane (10 mL). The dichloromethane layers were combined, dried (sodium sulfate), filtered and concentrated to afford 1-[3-fluoro-5-({2-[(²H₃)methyloxy](²H₄)ethyl}oxy)pyridin-2-yl]piperazine (130 mg, 78% yield) as a pale brown oil. ¹H NMR (500 MHz, Chloroform-d) δ 7.79 (d, J=2.0 Hz, 1H), 7.02 (dd, J=13.5, 2.0 Hz, 1H), 3.29 (m, 4H), 3.03 (t, J=5.0 Hz, 4H). MS (EI) for $C_{12}H_{11}D_7FN_3O_2$: 263 (MH⁺).

Step 4: Preparation of tert-butyl (2-{4-[3-fluoro-5-({2-[(²H₃)methyloxy](²H₄)ethyl}oxy)pyridin-2-yl]piperazin-1-yl}ethyl)methylcarbamate

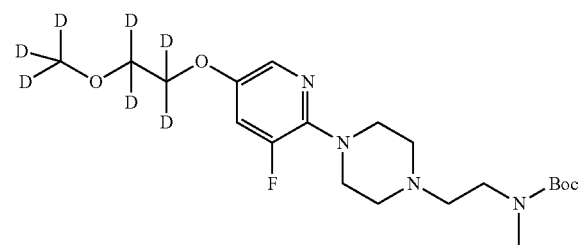 [SMILES: [2H]C([2H])([2H])OC([2H])([2H])C([2H])([2H])Oc1cnc(N2CCN(CCN(C)C(=O)OC(C)(C)C)CC2)c(F)c1]

Neat tert-butyl N-methyl-N-(2-oxoethyl)carbamate (0.11 mL, 0.64 mmol) was added to a stirred solution of 1-[3-fluoro-5-({2-[(²H₃)methyloxy](²H₄)ethyl}oxy)pyridin-2-yl]piperazine (130 mg, 0.50 mmol) in 1,2-dichloroethane (5 mL). Sodium triacetoxyborohydride (210 mg, 0.99 mmol) was then added in one portion, and the mixture stirred at room temperature. After 0.5 h, 2 M sodium carbonate solution was added (5 mL) and the mixture was diluted with ethyl acetate (30 mL), washed with 0.7 M disodium hydrogen phosphate (2×10 mL), 1 M sodium bicarbonate solution (10 mL), dried (sodium sulfate), filtered and concentrated to a yellow oil. Chromatography on silica (methanol/dichloromethane 1%~7% yield) afforded tert-butyl (2-{4-[3-fluoro-5-({2-[($^2$H$_3$)methyloxy]($^2$H$_4$)ethyl}oxy)pyridin-2-yl]piperazin-1-yl}ethyl)methylcarbamate (200 mg, 96% yield) as a pale yellow oil. $^1$H NMR (500 MHz, Chloroform-d) δ 7.80 (d, J=2.4 Hz, 1H), 7.00 (dd, J=13.3, 2.4 Hz, 1H), 3.45 (s, 3H), 3.43-3.29 (m, 6H), 2.91 (d, J=6.3 Hz, 3H), 2.65 (t, J=4.8 Hz, 4H), 2.55 (t, J=6.8 Hz, 2H), 1.45 (s, 9H). MS (EI) for $C_{20}H_{26}D_7FN_4O_4$: 420 (MH$^+$).

Step 5: Preparation of 2-{4-[3-fluoro-5-({2-[($^2$H$_3$)methyloxy]($^2$H$_4$)ethyl}oxy)pyridin-2-yl]piperazin-1-yl}-N-methylethanamine

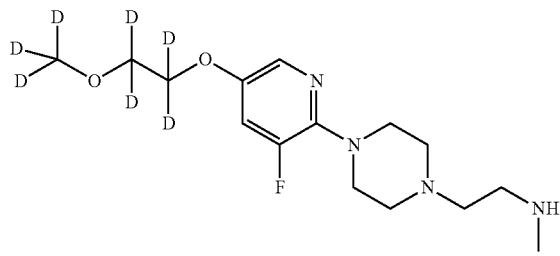 [SMILES: [2H]C([2H])([2H])OC([2H])([2H])C([2H])([2H])Oc1cnc(N2CCN(CCNC)CC2)c(F)c1]

A solution of tert-butyl (2-{4-[3-fluoro-5-({2-[($^2$H$_3$)methyloxy]($^2$H$_4$)ethyl}oxy)pyridin-2-yl]piperazin-1-yl}ethyl)methylcarbamate (230 mg, 0.63 mmol) in 1,4-dioxane (5 mL) was treated with hydrogen chloride, 4 M in dioxane (2 mL, 8 mmol) and the mixture stirred at room temperature. After 24 h, the suspension was concentrated to remove dioxane, and the residue partitioned between dichloromethane (15 mL) and 2 M sodium carbonate solution (15 mL). The aqueous layer was extracted with dichloromethane (2×15 mL), and the combined organic layers were dried (sodium sulfate), filtered and concentrated to afford 2-{4-[3-fluoro-5-({2-[($^2$H$_3$)methyloxy]($^2$H$_4$)ethyl}oxy)pyridin-2-yl]piperazin-1-yl}-N-methylethanamine (130 mg, 0.50 mmol) as a pale brown semi-solid. $^1$H NMR (500 MHz, Chloroform-d) δ 7.78 (d, J=2.5, 1.0 Hz, 1H), 7.01 (dd, J=13.5, 2.5 Hz, 1H), 3.35 (t, J=4.9 Hz, 4H), 2.74 (t, J=6.1 Hz, 2H), 2.62 (t, J=4.9 Hz, 4H), 2.57 (t, J=6.1 Hz, 2H), 2.47 (s, 3H). MS (EI) for $C_{15}H_{18}D_7FN_4O_2$: 320 (MH$^+$).

Step 6: Preparation of N$^7$-(2-{4-[3-fluoro-5-({2-[($^2$H$_3$)methyloxy]($^2$H$_4$)ethyl}oxy)pyridin-2-yl]piperazin-1-yl}ethyl)-N$^7$-methyl-2-(1,3-oxazol-2-yl)[1,2,4]triazolo[1,5-c]pyrimidine-5,7-diamine

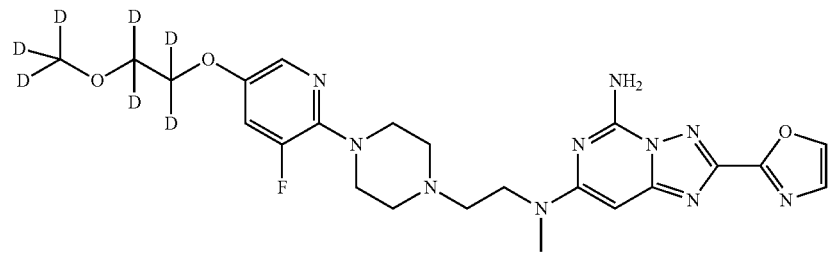 [SMILES: [2H]C([2H])([2H])OC([2H])([2H])C([2H])([2H])Oc1cnc(N2CCN(CCN(C)c3cc4nc(-c5ncco5)nn4c(N)n3)CC2)c(F)c1]

A 20 mL vial was charged with 2-{4-[3-fluoro-5-({2-[($^2$H$_3$)methyloxy]($^2$H$_4$)ethyl}oxy)pyridin-2-yl]piperazin-1-yl}-N-methylethanamine (115 mg, 0.36 mmol), 7-chloro-2-(1,3-oxazol-2-yl)[1,2,4]triazolo[1,5-c]pyrimidin-5-amine (76.7 mg, 0.32 mmol), triethylamine (0.1 mL, 0.72 mmol) and dry N-methyl-2-pyrrolidinone (5 mL). The mixture was heated at 120-130° C. for 3 days. The mixture was extracted with ethyl acetate (50 mL×3) and water (50 mL). The organic phase was combined and dried over anhydrous sodium sulfate. After removal of the solvents at reduced pressure, the residue was subjected to flash chromatography (methanol/dichloromethane 1% to 10% yield) to obtain N$^7$-(2-{4-[3-fluoro-5-({2-[($^2$H$_3$)methyloxy]($^2$H$_4$)ethyl}oxy)pyridin-2-yl]piperazin-1-yl}ethyl)-N$^7$-methyl-2-(1,3-oxazol-2-yl)[1,2,4]triazolo[1,5-c]pyrimidine-5,7-diamine (13) (18.3 mg, 9.8% yield) as a light yellow-brown glass. $^1$H NMR (500 MHz, Chloroform-d) δ 7.84 (d, J=1.5 Hz, 1H), 7.79 (d, J=1.5 Hz, 1H), 7.37 (t, J=1.0 Hz, 1H), 7.01 (dd, J=13.2, 2.5 Hz, 1H), 5.94 (s, 1H), 5.91 (s, 2H), 3.76 (t, J=6.5 Hz, 2H), 3.38-3.36 (m, 4H), 3.08 (s, 3H), 2.70-2.62 (m, 6H). MS (EI) for C$_{23}$H$_{22}$D$_7$FN$_{10}$O$_3$: 520 (MH$^+$).

The entire sample (18 mg, 35 µmol) was dissolved in acetonitrile (5 mL) and converted to the hydrochloride salt by treatment with 2 M hydrochloric acid in dioxane (35 µL, 0.070 µmol, 2 eq) and concentrated to dryness twice from acetonitrile. The residue was dissolved in water (2 mL), and the contents frozen (−78° C.) and lyophilized to afford the di-hydrochloride salt as a cream solid (21.0 mg).

Example 25

Synthesis of N$^7$-(2-{4-[4-(2-methoxyethoxy)phenyl]piperazin-1-yl}ethyl)-2-(1,3-oxazol-2-yl)[1,2,4]triazolo[1,5-c]pyrimidine-5,7-diamine (Compound 24), Hydrochloride Salt

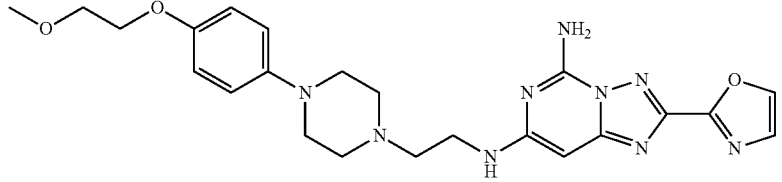

Compound 24

N$^7$-(2-{4-[4-(2-Methoxyethoxy)phenyl]piperazin-1-yl}ethyl)-2-(1,3-oxazol-2-yl)[1,2,4]triazolo[1,5-c]pyrimidine-5,7-diamine was synthesized according to the following reaction scheme.

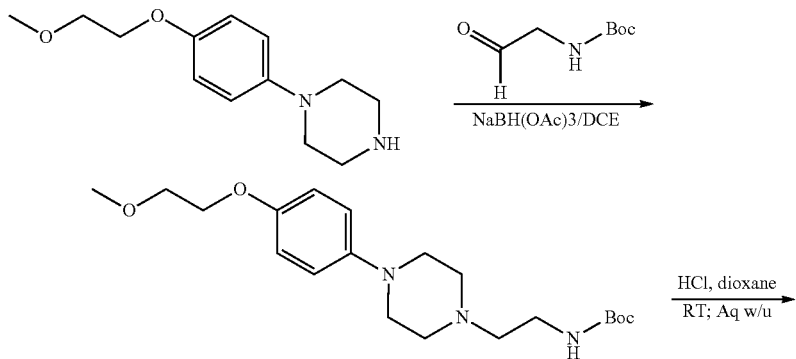

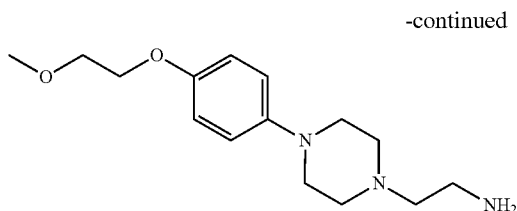
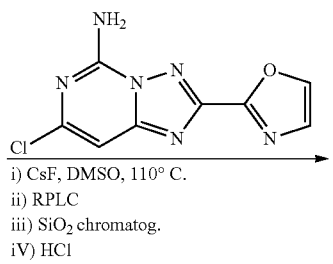

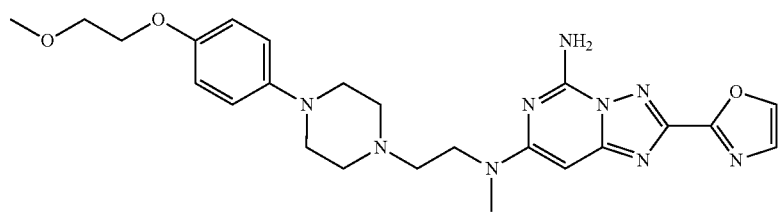

Step 1: Preparation of tert-butyl (2-{4-[4-(2-methoxyethoxy)phenyl]piperazin-1-yl}ethyl)carbamate

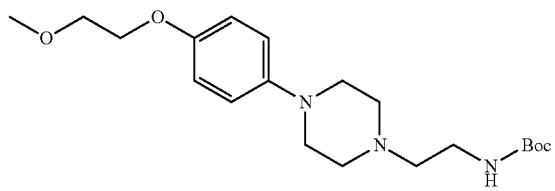 [SMILES: COCCOc1ccc(N2CCN(CCNC(=O)OC(C)(C)C)CC2)cc1]

The title compound was prepared using the method described in Step 1 of Compound 1. 1-[4-(2-methoxyethoxy)phenyl]piperazine (1.00 g, 4.24 mmol) yielded tert-butyl (2-{4-[4-(2-methoxyethoxy)phenyl]piperazin-1-yl}ethyl)carbamate (371 mg, 23% yield) as a very pale yellow oil, which solidified upon standing. $^1$H NMR (500 MHz, Chloroform-d) δ 6.89 (d, J=1.4 Hz, 4H), 5.03 (s, 1H), 4.09 (ddd, J=4.7, 3.8, 1.0 Hz, 2H), 3.75 (tt, J=5.5, 1.6 Hz, 2H), 3.29 (q, J=5.7 Hz, 2H), 3.11 (t, J=5.0 Hz, 4H), 2.63 (t, J=4.9 Hz, 4H), 2.54 (t, J=6.1 Hz, 2H), 1.48 (s, 9H). MS (EI) for $C_{15}H_{25}N_3O_4$: 380 (MH$^+$).

Step 2: Preparation of 2-{4-[4-(2-methoxyethoxy)phenyl]piperazin-1-yl}ethanamine

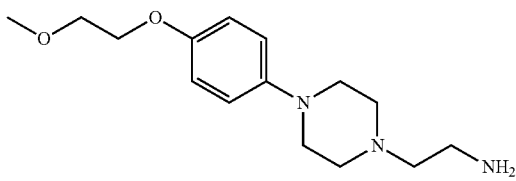 [SMILES: COCCOc1ccc(N2CCN(CCN)CC2)cc1]

The title compound was prepared using the method described in Step 2 of Compound 1. tert-Butyl (2-{4-[4-(2-methoxyethoxy)phenyl]piperazin-1-yl}ethyl)carbamate (371 mg, 0.98 mmol) and 4 M hydrochloric acid in dioxane (2.5 mL, 10 mmol) were used to give 2-{4-[4-(2-methoxyethoxy)phenyl]piperazin-1-yl}ethanamine (209 mg, 76% yield) as a light pink solid. MS (EI) for $C_{16}H_{27}N_3O_2$: 280 (MH$^+$).

Step 3: Preparation of N$^7$-(2-{4-[4-(2-methoxyethoxy)phenyl]piperazin-1-yl}ethyl)-2-(1,3-oxazol-2-yl)[1,2,4]triazolo[1,5-c]pyrimidine-5,7-diamine

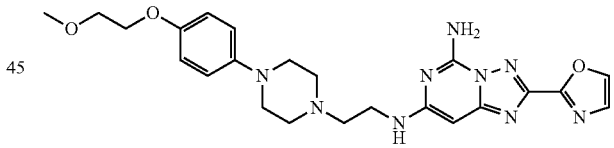

Using the approach described in Step 4 of compound 7, 2-{4-[4-(2-methoxyethoxy)phenyl]piperazin-1-yl}ethanamine (100 mg, 0.36 mmol), 7-chloro-2-(furan-2-yl)-[1,2,4]triazolo[1,5-c]pyrimidin-5-amine (77 mg, 0.33 mmol) and cesium fluoride (117 mg, 0.88 mmol) reacted in dry dimethyl sulfoxide (1.0 mL) to give N$^7$-(2-{4-[4-(2-methoxyethoxy)phenyl]piperazin-1-yl}ethyl)-2-(1,3-oxazol-2-yl)[1,2,4]triazolo[1,5-c]pyrimidine-5,7-diamine (A) (16.0 mg, 12.1% yield) as a white solid. $^1$H NMR (500 MHz, Chloroform-d) δ 7.86 (s, 1H), 7.39 (s, 1H), 6.90 (d, J=2.3 Hz, 4H), 5.90 (s, 2H), 5.41 (d, J=5.4 Hz, 1H), 4.10 (dd, J=5.7, 3.8 Hz, 2H), 3.82-3.68 (m, 2H), 3.47 (s, 3H), 3.32 (q, J=5.5 Hz, 2H), 3.24-3.07 (m, 4H), 2.70 (dt, J=20.4, 5.4 Hz, 6H). MS (EI) for $C_{23}H_{29}N_9O_3$: 480 (MH$^+$).

The compound was dissolved in acetonitrile and water and treated with 1 N hydrochloric acid. Solvents were removed in the lyophilizer to generate the hydrochloride salt of the title compound as an off-white solid.

Example 26

Synthesis of 2-(4-(4-(2-((5-amino-2-(oxazol-2-yl)-[1,2,4]triazolo[1,5-c]pyrimidin-7-yl)(methyl)amino)ethyl)piperazin-1-yl)phenoxy)ethan-1-ol (Compound 25)

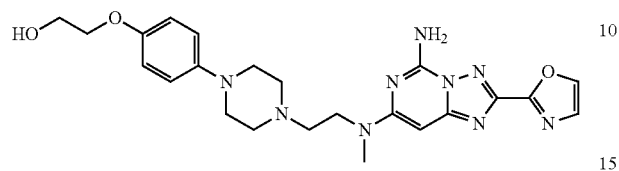

Compound 25 was synthesized according to the following:

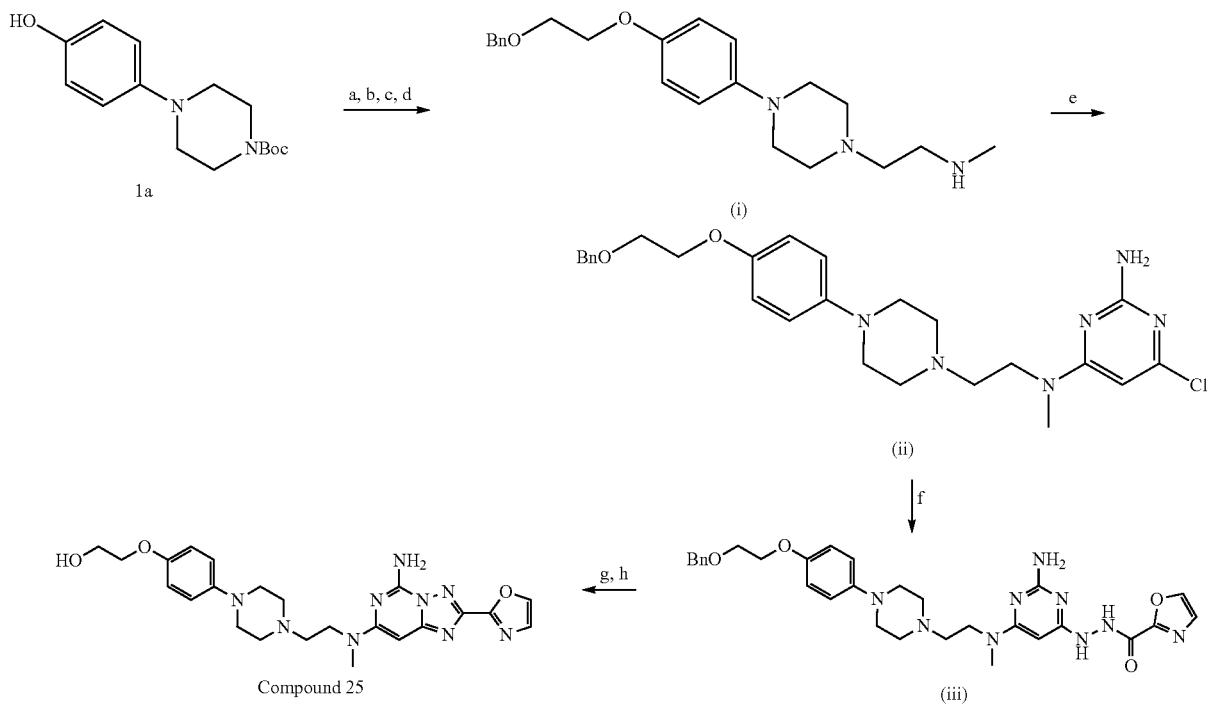

Reagents and typical conditions: a) Benzyl 2-bromoethyl ether; $Cs_2CO_3$, rt; b) 4 M HCl in dioxane; c) 2-chloroacetaldehyde 50% in water, $Na(CH_3COO)_3BH$, AcOH, MeOH; d) methylamine in EtOH 70° C.; e) 4,6-dichloropyrimidin-2-amine, ACN, 50-80° C.; f) oxazole-2-carbohydrazide, HCl, EtOH, 120° C., µW; g) N,O-bis(trimethylsilyl)acetamide, 120° C.; h) $H_2$ Pd/C, MeOH.

Step a: The synthesis of tert-butyl 4-(4-(2-(benzyloxy)ethoxy)phenyl)piperazine-1-carboxylate

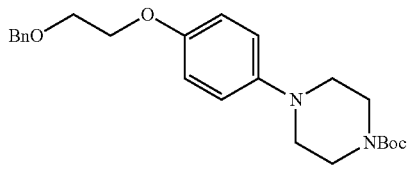 [SMILES: CC(C)(C)OC(=O)N1CCN(c2ccc(OCCOCc3ccccc3)cc2)CC1]

To a stirred solution of tert-butyl 4-(4-hydroxyphenyl)piperazine-1-carboxylate (1a) (6.72 g, 24.2 mmol), in dry N,N-dimethylformamide (30 mL), was added cesium carbonate (8.10 g, 24.88 mmol). The mixture was stirred at room temperature for 10 minutes before neat ((2-bromoethoxy)methyl)benzene (5.19 g, 24.2 mmol) was added in one portion. The mixture was stirred at 70° C. for 2 hours. The mixture was then partitioned between ethyl acetate (100 mL) and water (50 mL). The aqueous layer was extracted with ethyl acetate (3×50 mL), and the combined organic layers were washed with brine (2×50 mL), dried (sodium sulfate), filtered and concentrated in vacuo to afford tert-butyl 4-(4-(2-(benzyloxy)ethoxy)phenyl)piperazine-1-carboxylate (8.85 g, 89% yield) as a brown oil which was carried forward to the next step without further purification. MS (EI) for $C_{24}H_{32}N_2O_4$: 413 (MH$^+$).

Step b: The synthesis of 1-(4-(2-(benzyloxy)ethoxy)phenyl)piperazine

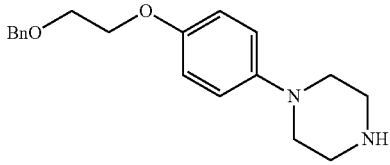 [SMILES: c1ccc(COCCOc2ccc(N3CCNCC3)cc2)cc1]

tert-butyl 4-(4-(2-(benzyloxy)ethoxy)phenyl)piperazine-1-carboxylate (9.00 g, 21.8 mmol) was treated with 4 N hydrochloric acid in dioxane (20 mL) and the immediate suspension was stirred at room temperature for 2 hours. The solvent was removed under reduced pressure and partitioned between EtOAc and 1 M $Na_2CO_3$. The organic layer was dried and concentrated to give 1-(4-(2-(benzyloxy)ethoxy)phenyl)piperazine as a beige solid that was used without further purification (7.60 g, 100% yield). MS (EI) for $C_{19}H_{24}N_2O_2$: 313 (MH$^+$).

Step c: The synthesis of 1-(4-(2-(benzyloxy)ethoxy)phenyl)-4-(2-chloroethyl)piperazine

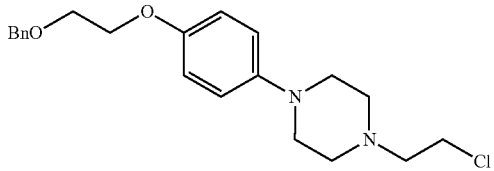 [SMILES: ClCCN1CCN(c2ccc(OCCOCc3ccccc3)cc2)CC1]

2-chloroacetaldehyde 50% in water (0.61 g, 7.68 mmol) was added to a suspension of 1-(4-(2-(benzyloxy)ethoxy)phenyl)piperazine (2.00 g, 6.40 mmol) in MeOH (25 mL) and AcOH (0.73 mL). The resulting solution was treated with sodium triacetoxyborohydride (2.71 g, 12.8 mmol) and stirred at room temperature for 2 hours. Water was added and the solvent was removed under reduced pressure. The residue was partitioned between DCM and 1 M $NaHCO_3$. The organic layer was dried and concentrated. The residue was purified by flash chromatography (0-10% MeOH in DCM) to afford 1-(4-(2-(benzyloxy)ethoxy)phenyl)-4-(2-chloroethyl)piperazine as a clear oil (440 mg, 18% yield). MS (EI) for $C_{21}H_{27}ClN_2O_2$: 375 (MH$^+$).

Step d: The synthesis of 2-(4-(4-(2-(benzyloxy)ethoxy)phenyl)piperazin-1-yl)-N-methylethan-1-amine (i)

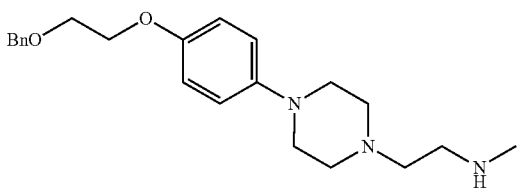 [SMILES: CNCCN1CCN(c2ccc(OCCOCc3ccccc3)cc2)CC1]

A stirred solution of 1-(4-(2-(benzyloxy)ethoxy)phenyl)-4-(2-chloroethyl)piperazine (0.44 g, 1.17 mmol) in 4 mL of 33% methylamine in EtOH was heated to 70° C. in sealed tube for 4 hours. The solution was cooled to room temperature and concentrated in vacuo to afford 2-(4-(4-(2-(benzyloxy)ethoxy)phenyl)piperazin-1-yl)-N-methylethan-1-amine as a beige solid (0.45 g, 95% yield). MS (EI) for $C_{22}H_{31}N_3O_2$: 370 (MH$^+$).

Step e: The synthesis of $N^4$-(2-(4-(4-(2-(benzyloxy)ethoxy)phenyl)piperazin-1-yl)ethyl)-6-chloro-$N^4$-methylpyrimidine-2,4-diamine

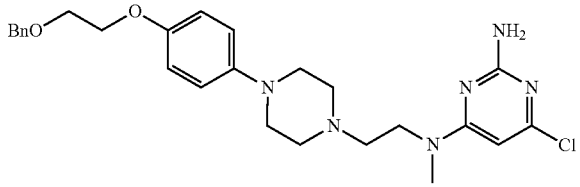 [SMILES: CN(CCN1CCN(c2ccc(OCCOCc3ccccc3)cc2)CC1)c1cc(Cl)nc(N)n1]

A suspension of compound (i) (0.35 g, 0.85 mmol) and 4,6-dichloropyrimidin-2-amine (0.14 g, 0.85 mmol) and 0.38 mL of triethylamine in 5 mL acetonitrile was heated at 60° C. for 3 hours. The solvent was removed under reduced pressure and the residue was dissolved in dichloromethane and washed with phosphate buffer (pH=6~ 6.5). The organic layer was dried over anhydrous magnesium sulfate, was filtered and the solvent was removed under reduced pressure to afford $N^4$-(2-(4-(4-(2-(benzyloxy)ethoxy)phenyl)piperazin-1-yl)ethyl)-6-chloro-$N^4$-methylpyrimidine-2,4-diamine (ii) as a yellow solid (0.39 g, 92% yield). MS (EI) for $C_{26}H_{33}ClN_6O_2$: 497 (MH$^+$).

Step f: The synthesis of N'-(2-amino-6-((2-(4-(4-(2-(benzyloxy)ethoxy)phenyl)piperazin-1-yl)ethyl)(methyl)amino)pyrimidin-4-yl)oxazole-2-carbohydrazide

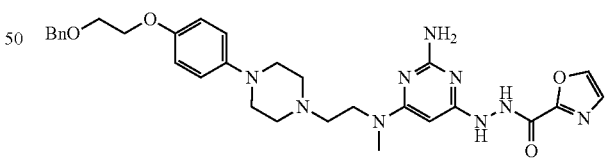

A suspension of compound (ii) (0.39 mg, 0.79 mmol) and oxazole-2-carbohydrazide (0.9~1.2 equiv.) in 3 mL of ethanol and 0.1 mL of concentrated hydrochloric acid was heated in a microwave oven at 120° C. for 20 minutes. The solvent was removed under reduced pressure, and the residue was purified by reverse phase chromatography (5-100% water/acetonitrile in 10 mM ammonium hydroxide/water) to yield N'-(2-amino-6-((2-(4-(4-(2-(benzyloxy)ethoxy)phenyl)piperazin-1-yl)ethyl)(methyl)amino)pyrimidin-4-yl)oxazole-2-carbohydrazide (iii) as a pink solid (0.12 g, 26% yield). MS (EI) for $C_{30}H_{37}N_9O_4$: 588 (MH$^+$).

Step g: The synthesis of N7-(2-(4-(4-(2-(benzyloxy)ethoxy)phenyl)piperazin-1-yl)ethyl)-N⁷-methyl-2-(oxazol-2-yl)-[1,2,4]triazolo[1,5-c]pyrimidine-5,7-diamine

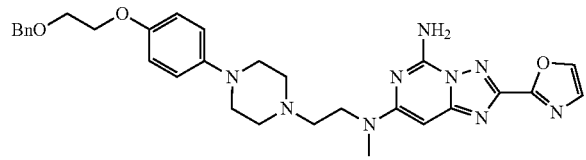 [SMILES: CN(CCN1CCN(c2ccc(OCCOCc3ccccc3)cc2)CC1)c1cc2nc(-c3ncco3)nn2c(N)n1]

A suspension of compound (iii) (0.12 g, 0.21 mmol) in 1.5 mL N,O-bis(trimethylsilyl)acetamide (3-6 equiv.) was heated at 100-150° C. for 2~8 hours. The crude product was cooled at 0° C. and treated with water and 1 N hydrochloric acid (5-10 equiv.). The resulting two layers were separated, and the aqueous phase was directly purified by reverse phase chromatography (5-100% water/acetonitrile in 10 mM ammonium hydroxide/water) to yield 165 mg of N7-(2-(4-(4-(2-(benzyloxy)ethoxy)phenyl)piperazin-1-yl)ethyl)-N⁷-methyl-2-(oxazol-2-yl)-[1,2,4]triazolo[1,5-c]pyrimidine-5,7-diamine as a beige solid that was taken immediately onto the next step. MS (EI) for $C_{30}H_{35}N_9O_3$: 570 (MH⁺).

Step h: The synthesis of Compound 25

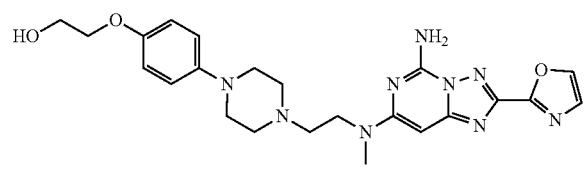 [SMILES: CN(CCN1CCN(c2ccc(OCCO)cc2)CC1)c1cc2nc(-c3ncco3)nn2c(N)n1]

To a stirred solution of an intermediate of compound N⁷-(2-(4-(4-(2-(benzyloxy)ethoxy)phenyl)piperazin-1-yl)ethyl)-N⁷-methyl-2-(oxazol-2-yl)-[1,2,4]triazolo[1,5-c]pyrimidine-5,7-diamine (100 mg, 0.16 mmol) in 1.1 ml of MeOH was added 5% Pd/C (20 mg, 0.16 mmol). The suspension was stirred at room temperature under $H_2$ balloon for 18 hours before the solution was filtered and concentrated. The residue was purified by reverse phase chromatography (5-100% water/acetonitrile in 10 mM ammonium hydroxide/water) to yield compound 25 as an off-white solid (18 mg, 25% yield over 2 steps). MS (EI) for $C_{23}H_{29}N_9O_3$: 480 (MH⁺). ¹H NMR (500 MHz, DMSO-$d_6$) δ 8.34 (s, 1H), 7.71 (s, 2H), 7.49 (s, 1H), 6.93-6.72 (m, 4H), 5.85 (s, 1H), 4.82 (t, J=5.6 Hz, 1H), 3.89 (t, J=5.1 Hz, 2H), 3.76-3.62 (m, 4H), 3.10-2.93 (m, 7H), 2.65-2.58 (m, 4H), 2.56-2.52 (m, 2H).

Example 27

Evaluation of Plasma Pharmacokinetic Parameters Following Intravenous (IV) or Oral (PO) Administration of Adenosine $A_{2A}$-Selective Receptor Antagonists Adult male Sprague-Dawley rats (230-250 g) (Charles River Labs, Hollister, CA) were utilized for the study. There were 2 rats/group. All animals were food fasted overnight with water provided ad libitum at all times. Compounds 1, 4, 14 and 19 were synthesized as described in Examples 2, 17, 7, and 12, respectively, and formulated in injectable water.

The morning of each dosing, individual doses were calculated based on current body weights on the day of dosing. The jugular vein cannula (JVC) and the carotid artery cannula (CAC) were externalized, flushed with HEP/saline (10 IU/mL HEP/mL saline), plugged, and labeled to identify the jugular vein and the carotid artery. The IV group animals were dosed at 0.5 mg/kg of Compound 1, 4, 14 or 19, respectively, intravenously via the jugular vein, while the PO dose was administered 2.5 mg/kg of Compound 1, 4, 14 or 19, respectively, orally via gavage. For the IV group, immediately following the dose of test article, the dead volume of the catheter was flushed with 0.9% saline to ensure the animals received the full dose.

Approximately 0.2 mL of blood was collected per time point from JVC. Blood samples were collected at 2 (IV group only), 5, 15, 30, 60, 120, 240, 360, 420 (Compound 19 only), 480, 720 (Compound 19 only), and 1440 minutes via the CAC and transferred immediately into $K_2$EDTA coated tubes pre-loaded 2 μl with quenching cocktail and placed on wet ice. The samples were centrifuged within 30 min after collection at 10,000 RPM for 5 minutes and the resulting plasma was separated. Plasma was transferred into microfuge tubes and placed on dry ice immediately. The plasma samples were stored at approximately −70° C. until bioanalysis.

Bioanalytical Analysis

Plasma samples were extracted by protein precipitation with acetonitrile containing 0.1% formic acid and doxepin for Compound 1 (available from Sigma-Aldrich) or SCH58261 for Compounds 4, 14 and 19 (available from Sigma-Aldrich) as an internal standard. Following vortex and centrifugation, supernatant was diluted 3-fold with water containing 0.1% formic acid and analyzed by LC-MS/MS.

Pharmacokinetic Analysis

Pharmacokinetic parameters (PK) were determined by non-compartmental analysis (NCA) using Phoenix 64 WinNonlin (version 8) and Dotmatics (version 5.0). Nominal doses and time points were used for the analysis. Concentrations below the limit of quantitation (BLQ) were treated as missing for NCA.

The following PK parameters were estimated using plasma concentration-time profile of each animal with the results presented in Table 3:

$AUC_{inf}$ Area under the concentration-time from zero to time infinity $AUC_{last}$ Area under the concentration-time from zero to time of last concentration value F Bioavailability CL Total body clearance $C_{max}$ Maximum (peak) concentration $MRT_{last}$ Mean residence time to last observable concentration $T_{max}$ Time to reach maximum or peak concentration following administration $V_{ss}$ Volume of distribution at steady state

TABLE 3

Plasma Pharmacokinetic Parameters of Compounds 1, 4, 14, and 19

| Compound Batch | Route | Formulation | $AUC_{inf}$ (hr * ng/mL) | $AUC_{last}$ (hr * ng/mL) | F (%) | CL (mL/min/kg) | $C_{max}$ (ng/mL) | $MRT_{last}$ (hr) | $T_{max}$ (hr) | $V_{ss}$ obs (L/kg) |
|---|---|---|---|---|---|---|---|---|---|---|
| Compound 1 (#1) | IV | Injectable Water | 233 | 228 | NA | 36.1 | 207 | 1.41 | 0.0333 | 3.44 |
| Compound 1 (#1) | PO | Injectable Water | 777 | 718 | 66.8 | NA | 242 | NA | 0.75 | NA |
| Compound 1 (#2) | IV | Injectable Water | 340 | 335 | NA | 24.6 | 311 | 1.45 | 0.0333 | 2.17 |
| Compound 1 (#2) | PO | Injectable Water | 1280 | 1220 | 75.5 | NA | 367 | NA | 1 | NA |
| Compound 19 | IV | Injectable Water | 1228.55 | 1217.5 | | 6.85 | 1024.1 | 1.4825 | 0.033 | 0.635 |
| Compound 19 | PO | Injectable Water | 5047.15 | 4976.65 | 82.7 | 9.05 | 1301.4 | 2.653 | 1.25 | NA |
| Compound 4 (#1) | IV | Injectable Water | 251 | 249 | NA | 33.6 | NA | 0.89 | NA | 1.93 |
| Compound 4 (#1) | PO | Injectable Water | 978 | 898 | 77.8 | NA | 231 | NA | 0.75 | NA |
| Compound 4 (#2) | IV | Injectable Water | 312 | 310 | NA | 26.8 | NA | 0.914 | NA | 1.53 |
| Compound 4 (#2) | PO | Injectable Water | 707 | 662 | 45.4 | NA | 172 | 2.55 | 0.5 | NA |
| Compound 14 | IV | Injectable Water | 526 | 523 | NA | 16.6 | NA | 0.977 | NA | 1.02 |
| Compound 14 | PO | Injectable Water | 1480 | 1370 | 56.1 | NA | 373 | 2.43 | 1 | NA |

NA: Not applicable

Compound 1

Total clearance (CL) was moderate (40-60% liver blood flow) and between 24.6 and 36.1 mL/min/kg. Mean residence time (MRT) following IV administration was also moderate and between 1.45 and 1.41 hours. The volume of distribution at steady state ($V_{ss}$) was low and between 2.17 and 3.44 L/kg (see Table 3).

After PG dosing, plasma concentrations rapidly increased and reached maximum levels ($C_{max}$) between 242 and 367 ng/mL between 0.75 and 1 hr (FIG. 1, Table 3). The bioavailability was between 67 and 7600 (see Table 3).

Pharmacokinetic parameters were further estimated in vivo after IV or PO administration of Compound 1 in mice and dogs with the results provided in Table 4 below.

TABLE 4

Plasma Pharmacokinetic Parameters in mice and dogs

| PK Summary | IV | | | | PO | |
|---|---|---|---|---|---|---|
| | Dose | CL | | | | |
| | IV/PO (mg/kg) | (mL/min/kg) | $V_{ss}$ (L/kg) | $T_{1/2}$ (hr) | $AUC_{inf}$ (hr * ng/mL) | F (%) |
| mouse | —/30 | — | — | — | 5760 | |
| dog | 0.2/1&10 | 12 | 5.2 | 6.0 | 2020/17900 | >100 |

Further parameters were assayed for Compound 1 using methods known in the art with the results shown in Table 5 below.

TABLE 5

| Compound 1 parameters | |
|---|---|
| Assay | Results |
| Permeability Caco-2 Papp (cm/s) | $14.5 \times 10^{-6}$ |
| Efflux Ratio (ER) | 1.6 |
| Solubility | ~5 mM (pH ~3) |
| | 20-40 µM (pH ~7) |
| Hepatic clearance in vitro $CL_{int}$ (µL/min/mg protein) | |
| Mouse liver microsomes | 29 |
| Rat liver microsomes | 17 |
| Dog liver microsomes | <1 |
| Human liver microsomes | 43 |
| Plasma protein binding (PPB) ($f_u$) | |
| Mouse | 0.19 |
| Rat | 0.15 |
| Dog | 0.43 |
| Human | 0.39 |

Compound 4

Oral profiles indicate rapid absorption with $T_{max}$ between 0.5 hr and 0.75 hr followed by a mono-phasic decline that was slower than after IV dosing suggesting a prolonged absorption phase.

Mean total plasma clearance was moderate (45-56% liver blood flow) and between 26.8 and 33.6 mL/min/kg. A low $V_{ss}$ of 1.93 and 1.53 L/kg was observed. Bioavailability was moderate and between 45.4 and 77.8% (see Table 3).

Compound 14

Mean total plasma clearance (CL) was low (~28% of liver blood flow) and 16.6 mL/min/kg. The plasma concentration vs time profile following PO dosing displayed a similar bi-phasic profile after $C_{max}$ as the profile following IV dosing. The MRT was moderate and $V_{ss}$ was low, with values of 0.977 hr and 1.02 L/kg, respectively.

Compound 19

Compound 19 was characterized by low (~10% liver blood flow) CL of 6.85 mL/min/kg, low $V_{ss}$ (0.635 L/kg), and a moderate MRT of 1.48 hr. Mean bioavailability was 82.7% (see Table 3).

Example 28

Evaluation of Concentration-Time Profiles Following In Vivo Administration of Compound 1

Adult male Sprague-Dawley rats (230-250 g) (Charles River Labs, Hollister, CA) were utilized for the study. There were 2 rats/group. All animals were food fasted overnight with water provided ad libitum at all times. Compound 1 was synthesized as described in Example 2 and formulated in injectable water.

The morning of each dosing, individual doses were calculated based on current body weights on the day of dosing. The jugular vein cannula (JVC) and the carotid artery cannula (CAC) were externalized, flushed with HEP/saline (10 IU/mL HEP/mL saline), plugged, and labeled to identify the jugular vein and the carotid artery. The IV group animals were dosed at 0.5 mg/kg of Compound 1 intravenously via the jugular vein, while the PO dose was administered 2.5 mg/kg of Compound 1 orally via gavage. For the IV group, immediately following the dose of test article, the dead volume of the catheter was flushed with 0.9% saline to ensure the animals received the full dose.

Approximately 0.2 mL of blood was collected per time point from JVC. Blood samples were collected at 2 (IV group only), 5, 15, 30, 60, 120, 240, 360, 480, and 1440 minutes via the CAC and transferred immediately into K$_2$EDTA coated tubes pre-loaded 2 μl with quenching cocktail and placed on wet ice. The samples were centrifuged within 30 min after collection at 10,000 RPM for 5 minutes and the resulting plasma was separated. Plasma was transferred into microfuge tubes and placed on dry ice immediately. The plasma samples were stored at approximately −70° C. until bioanalysis.

Plasma samples were extracted by protein precipitation with acetonitrile containing 0.1% formic acid and doxepin (available from Sigma-Aldrich) as an internal standard. Following vortex and centrifugation, supernatant was diluted 3-fold with water containing 0.1% formic acid and analyzed by LC-MS/MS.

The plasma concentration vs time profile after IV (■ and □) and PO (● and ○) administration of Compound 1 is shown in FIG. 1. The figure illustrates similar profiles for the two batches of Compound 1 tested. The higher concentrations observed in the second batch (□ and ○) might be due to dosing differences between the batches. The curves follow a multi-phasic decline, with a short distribution phase and with slower terminal disposition. Concentrations post 8 hr were below the limit of quantitation (BLQ).

Example 29

Evaluation of Concentration-Time Profiles Following In Vivo Administration of Compound 4

Adult male Sprague-Dawley rats (230-250 g) (Charles River Labs, Hollister, CA) were utilized for the study. There were 2 rats/group. All animals were food fasted overnight with water provided ad libitum at all times. Compound 4 was synthesized as described in Example 17.

Animals were administered 0.5 mg/kg of Compound 4 intravenously via the jugular vein, or 2.5 mg/kg of the compound orally via gavage as described in Example 28.

Approximately 0.2 mL of blood was collected per time point from JVC. Blood samples were collected at 2 (IV group only), 5, 15, 30, 60, 120, 240, 360, 480, and 1440 minutes via the CAC and transferred immediately into K$_2$EDTA coated tubes pre-loaded 2 μl with quenching cocktail and placed on wet ice. The samples were centrifuged within 30 min after collection at 10,000 RPM for 5 minutes and the resulting plasma was separated. Plasma was transferred into microfuge tubes and placed on dry ice immediately. The plasma samples were stored at approximately −70° C. until bioanalysis.

Pharmacokinetic Analysis

Figure 3:
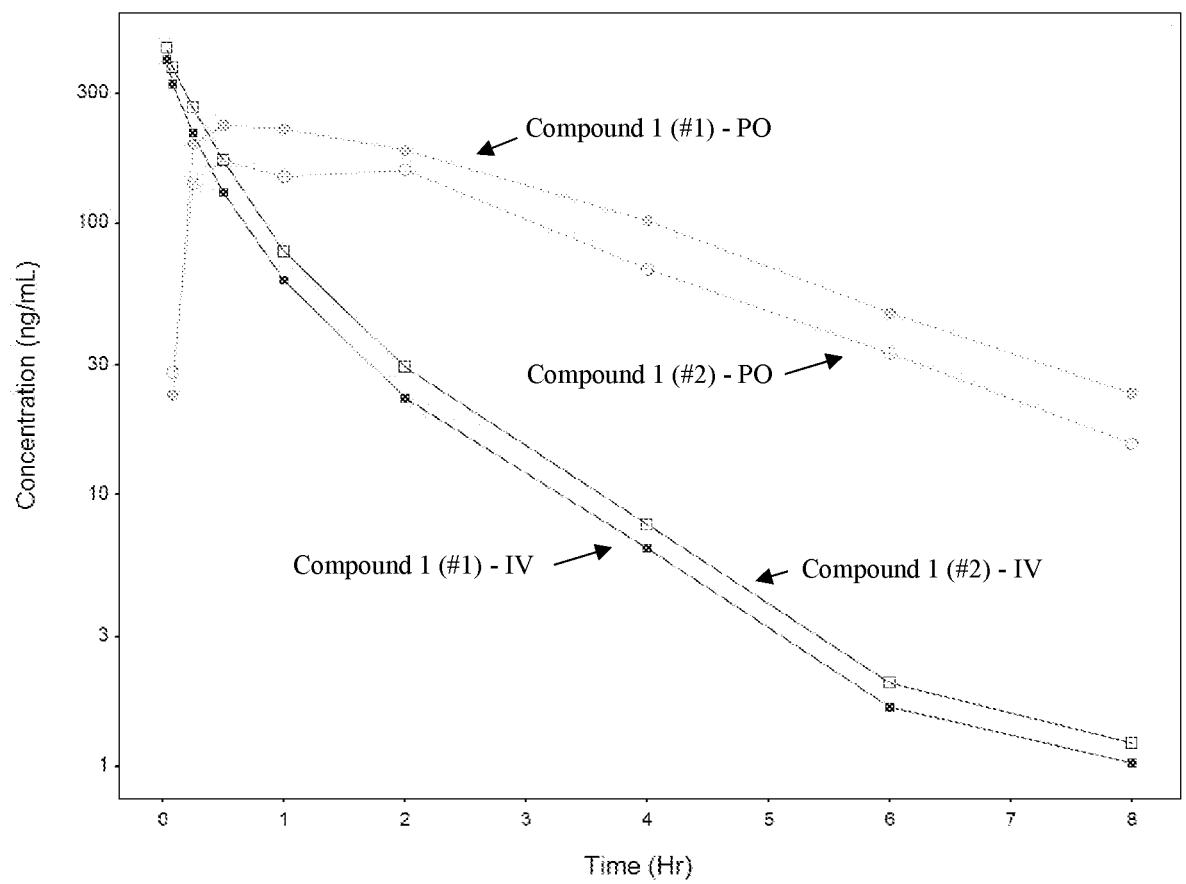
FIG. 3 is a plot of the plasma concentration (ng/mL) of $N^7$-(2-(4-(3-fluoro-5-(2-methoxyethoxy)pyridin-2-yl)piperazin-1-yl)ethyl)-$N^7$-methyl-2-(oxazol-2-yl)-[1,2,4]triazolo[1,5-c]pyrimidine-5,7-diamine (Compound 4) over time (Hr) following administration to mice of 0.5 mg/kg of Compound 4 intravenously (■ and □) or 2.5 mg/kg of Compound 4 orally via gavage (● and ○), as described in Example 29.

The plasma concentration vs time profile after IV (■ and □) and PO (● and ○) administration of Compound 4 is shown in FIG. 3. The figure illustrates similar profiles for the two batches of Compound 4 tested. The higher concentrations observed in the second batch (□ and ○) might be due to dosing differences between the batches. The IV curves follow a multi-phasic decline, with a short distribution phase and with slower terminal disposition. Concentrations post 8 hr were below the limit of quantitation (BLQ).

Example 30

Evaluation of Concentration-Time Profiles Following In Vivo Administration of Compound 14

Adult male Sprague-Dawley rats (230-250 g) (Charles River Labs, Hollister, CA) were utilized for the study. There were 2 rats/group. All animals were food fasted overnight with water provided ad libitum at all times. Compound 14 was synthesized as described in Example 7.

Animals were administered 0.5 mg/kg of Compound 14 intravenously via the jugular vein, or 2.5 mg/kg of the compound orally via gavage as described in Example 28.

Approximately 0.2 mL of blood was collected per time point from JVC. Blood samples were collected at 2 (IV group only), 5, 15, 30, 60, 120, 240, 360, 480, and 1440 minutes via the CAC and transferred immediately into K$_2$EDTA coated tubes pre-loaded 2 μl with quenching cocktail and placed on wet ice. The samples were centrifuged within 30 min after collection at 10,000 RPM for 5 minutes and the resulting plasma was separated. Plasma was transferred into microfuge tubes and placed on dry ice immediately. The plasma samples were stored at approximately −70° C. until bioanalysis.

Pharmacokinetic Analysis

Figure 4:
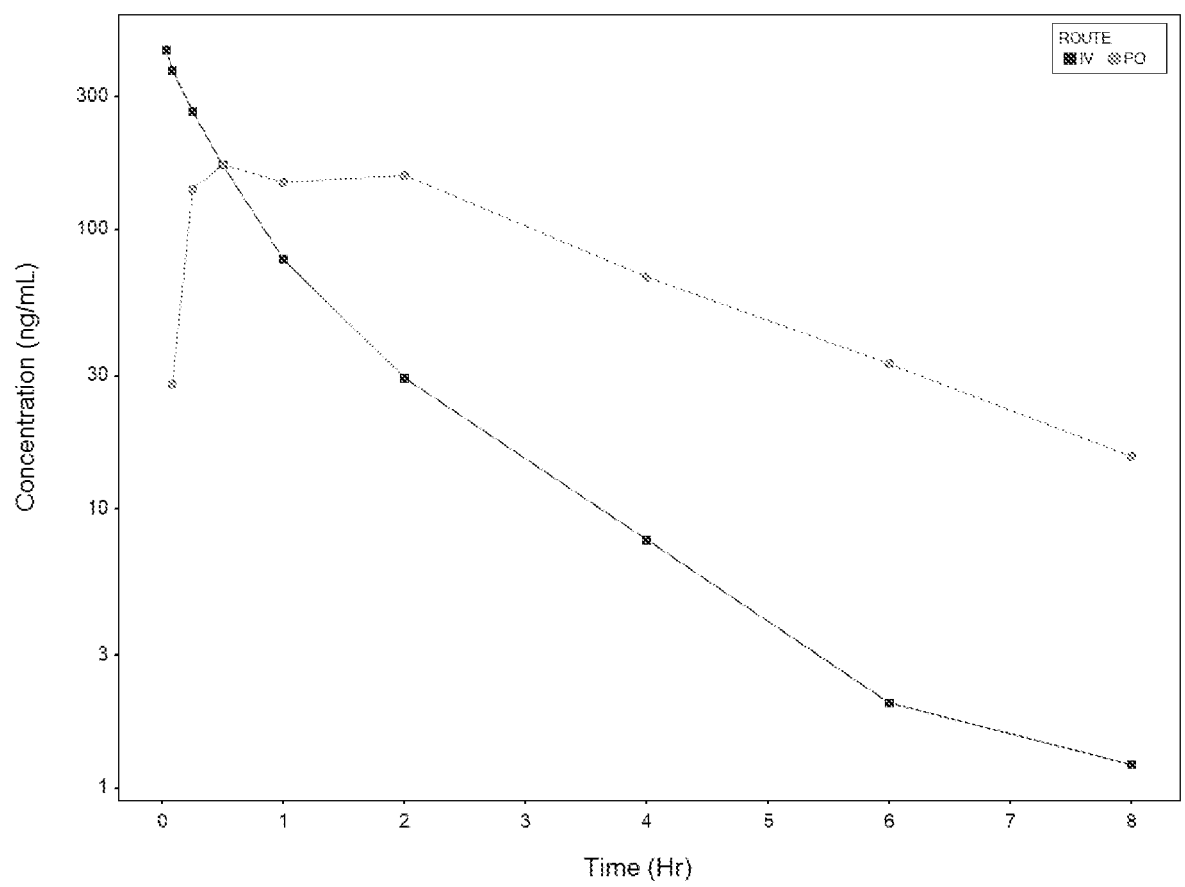
FIG. 4 is a plot of the plasma concentration (ng/mL) of N$^7$-(2-(4-(3-chloro-5-(2-methoxyethoxy)pyridin-2-yl)piperazin-1-yl)ethyl)-N$^7$-methyl-2-(oxazol-2-yl)-[1,2,4]triazolo[1,5-c]pyrimidine-5,7-diamine (Compound 14) over time (Hr) following administration to mice of 0.5 mg/kg of Compound 14 intravenously (■) or 2.5 mg/kg of Compound 14 orally via gavage (●), as described in Example 30.

The plasma concentration vs time profile after IV (■) and PO (●) administration of Compound 14 is shown in FIG. 4. This figure illustrates a bi-phasic decline after IV dosing and rapid absorption following PO administration with $T_{max}$ at 1 hr.

Example 31

Evaluation of Concentration-Time Profiles Following In Vivo Administration of Compound 19

Adult male Sprague-Dawley rats (230-250 g) (Charles River Labs, Hollister, CA) were utilized for the study. There were 2 rats/group. All animals were food fasted overnight with water provided ad libitum at all times. Compound 19 was synthesized as described in Example 12.

Animals were administered 0.5 mg/kg of Compound 19 intravenously via the jugular vein, or 2.5 mg/kg of the compound orally via gavage as described in Example 28.

Approximately 0.2 mL of blood was collected per time point from JVC. Blood samples were collected at 2 (IV group only), 5, 15, 30, 60, 120, 240, 360, 420, 480, 720, and 1440 minutes via the CAC and transferred immediately into $K_2$EDTA coated tubes pre-loaded 2 µl with quenching cocktail and placed on wet ice. The samples were centrifuged within 30 min after collection at 10,000 RPM for 5 minutes and the resulting plasma was separated. Plasma was transferred into microfuge tubes and placed on dry ice immediately. The plasma samples were stored at approximately −70° C. until bioanalysis.

Pharmacokinetic Analysis

Figure 2:
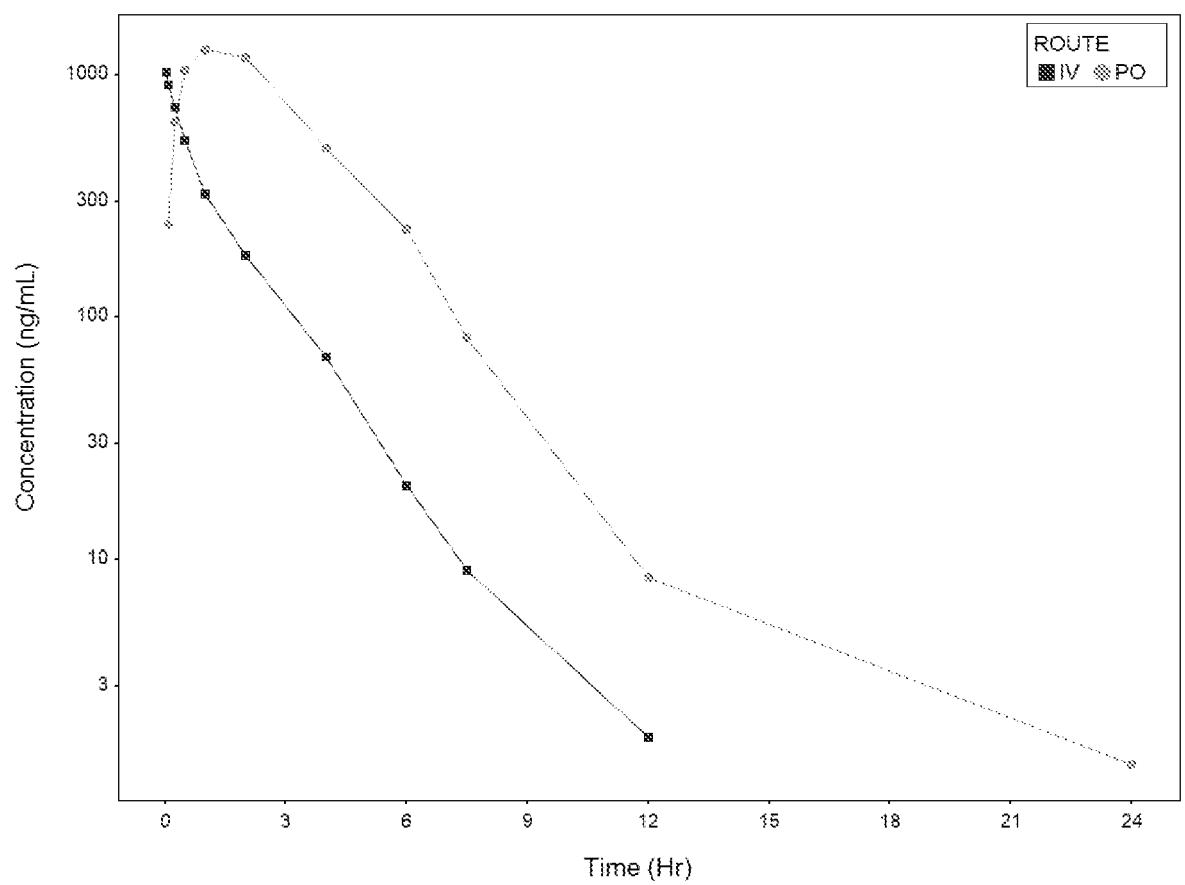
FIG. 2 is a plot of the plasma concentration (ng/mL) of $N^7$-(2-(4-(5-(2-methoxyethoxy)-3-(trifluoromethyl)pyridin-2-yl)piperazin-1-yl)ethyl)-$N^7$-methyl-2-(oxazol-2-yl)-[1,2,4]triazolo[1,5-c]pyrimidine-5,7-diamine (Compound 19) over time (Hr) following administration to mice of 0.5 mg/kg of Compound 19 intravenously (■) or 2.5 mg/kg of Compound 19 orally via gavage (●), as described in Example 31.

The plasma concentration vs time profile after IV (■) and PO (●) administration of Compound 19 is shown in FIG. 2. The plasma concentration vs time profile following PO dosing displayed a similar bi-phasic profile after $C_{max}$ as the profile following IV dosing.

Example 32

Plasma Pharmacokinetic Parameters Following Oral (PO) Administration of Adenosine $A_{2A}$-Selective Receptor Antagonists Plasma pharmacokinetic parameters were determined following oral (PO) administration of further compounds essentially as described in Example 28 with the results shown in Table 6.

TABLE 6

Plasma Pharmacokinetic Parameters

| Compound No. | AUC (ng * hr/mL) | CL (mL/min/kg) | % F | B/P (1 h) |
|---|---|---|---|---|
| 2 | 320 | 54 | 43 | 0.04 |
| 3 | 376 | 47 | 44 | 0.04 |
| 5 | 971 | 21 | 48 | 0.10 |
| 6 | 852 | 34 | 64 | 0.05 |
| 7 | 1024 | 24 | 60 | 0.07 |
| 8 | 1196 | 22 | 63 | 0.04 |
| 9 | 1167 | 23 | 65 | 0.04 |
| 10 | 819 | 30 | 57 | 0.09 |
| 11 | 708 | 30 | 63 | |
| 12 | 1002 | 23 | 56 | 0.03 |
| 13 | 709 | 33 | 57 | 0.06 |
| 15 | 1155 | 20 (t½ = 1.2 h) | 57 | 0.05 |
| 16 | 1195 | 20 | 58 | 0.06 |
| 17 | 406 | 44 | 43 | 0.03 |
| 18 | 900 | 33 | 71 | 0.09 |
| 20 | 1171 | 17 | 50 | 0.05 |
| 21 | 429 | 30 | 31 | 0.05 |
| 22 | 280 | 38 | 25 | 0.03 |
| 23 | 336 | 52 | 42 | 0.08 |
| 24 | 1067 | 28 | 70 | 0.11 |

ND is no data

Example 33

Receptor Binding of Adenosine $A_{2A}$-Selective Receptor Antagonists

Using conventional receptor binding assay techniques, Compounds 1-24 were assayed to determine binding activity at the $A_{2A}$, $A_1$, and $A_3$ receptors with the results shown in Table 7.

Receptor binding affinity of Compounds 1-24 was measured using radioligand binding assays using commercially obtained cell membranes prepared from cell lines overexpressing the $A_{2A}$, $A_1$, or $A_3$ receptors. Briefly, cell membrane preparations from cells expressing the specific receptor were mixed with the appropriate [$^3$H]-labeled tracer for the specific receptor and the test compound or a known inhibitor of receptor-ligand binding. Following 60 min incubation at room temperature to allow receptor-ligand complex formation, the complexes were collected by filtration, washed with 50 mM Tris HCl (pH 7.5) to remove radioligand that was not receptor-bound, and the remaining radioactivity determined by liquid scintillation counting. Specific radioligand binding was calculated for each test compound concentration and $IC_{50}$ values were determined by non-linear, regression analysis. Inhibition constants ($K_i$) were calculated using the equation of Cheng and Prusoff using the observed $IC_{50}$ of the tested compound, the concentration of radioligand employed in the assay and the experimentally determined values for the $K_d$ of the ligand. Table 7 shows the binding affinity (Ki, in nM) for Compounds 1-24 for the $A_{2A}$, $A_1$, and $A_3$ receptors.

As seen in Table 7, Compounds 1-24 have selective affinity for the $A_{2A}$ receptor over either of the $A_1$ or $A_3$ receptors. For most of the compounds, binding affinity at the $A_{2A}$ receptor is comparable to that of the reference compound.

TABLE 7

Receptor binding of adenosine $A_{2A}$-selective receptor antagonists

| | Potency Ki (nM) | | |
|---|---|---|---|
| Compound No. | $A_{2A}$ | $A_1$ | $A_3$ |
| 1 | 6 | 50000 | >10000 |
| 2 | 7 | 13000 | ND |
| 3 | 10 | 20090 | ND |
| 4 | 2 | 14000 | ND |
| 5 | 7 | >10000 | ND |
| 6 | 12 | >4000 | ND |
| 7 | 13 | >4000 | ND |
| 8 | 4 | >4000 | ND |
| 9 | 6 | >4000 | ND |
| 10 | 5.5 | >10000 | ND |
| 11 | 2.3 | 16926 | ND |
| 12 | 4 | >100000 | ND |
| 13 | 4 | 32400 | ND |
| 14 | 4 | 15000 | ND |
| 15 | 2.3 | 3942 | ND |
| 16 | 4 | >100000 | >10000 |
| 17 | 20 | 11750 | ND |
| 18 | 8 | >100000 | ND |
| 19 | 4 | 16000 | ND |
| 20 | 6 | >100000 | ND |
| 21 | 8 | 3077[1] | |
| 22 | 11 | 3198[1] | ND |
| 23 | 9 | 15500 | ND |
| 24 | 43 | >10000 | ND |
| Reference compound | 2.6 | 1272 | ND |

ND is no data;
[1] average of experiments

Example 34

Evaluation of Antitumor Activity in CT26-Induced Subcutaneous Lung Metastasis Tumor Model in Balb/C Mice Mice used were ~ 6-8 week-old female Balb/c mice subcutaneously inoculated with 2×10$^6$ mouse CT-26 cells.

Figure 5:
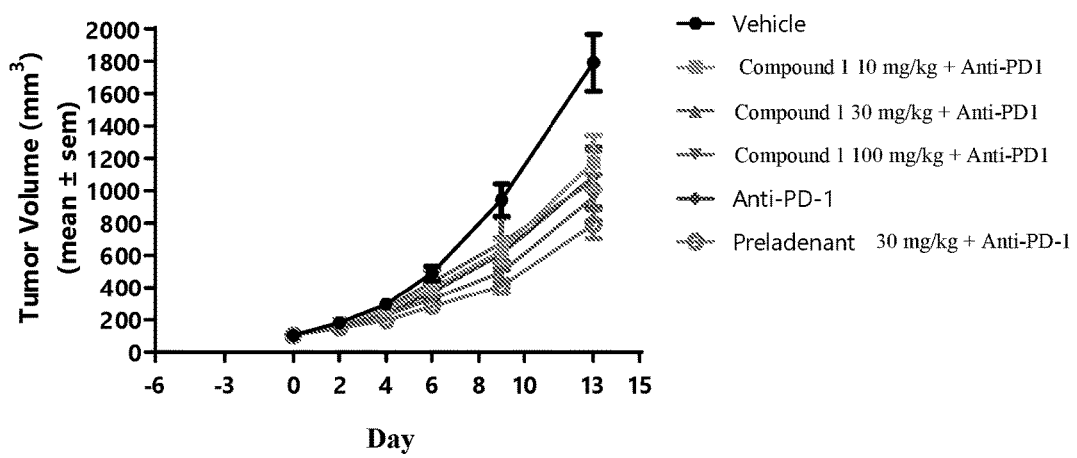
FIG. 5 is a graph of the mean tumor growth shown as tumor volume (mm$^3$) in a mouse CT-26 colon cancer model after treatment with one of the following: vehicle (qdx9) (●), N$^7$-(2-(4-(4-(2-methoxyethoxy)phenyl)piperazin-1-yl)ethyl)-N$^7$-methyl-2-(oxazol-2-yl)-[1,2,4]triazolo[1,5-c]pyrimidine-5,7-diamine (Compound 1) (10 mg/kg, qdx9)+anti-PD1 antibody (200 µg/mouse, q2dx4) (■); Compound 1 (30 mg/kg, qdx9)+anti-PD1 antibody (200 g/mouse, q2dx4) (▲), Compound 1 (100 mg/kg)+anti-PD1 antibody (200 µg/mouse, q2dx4) (▼), anti-PD1 antibody (200 µg/mouse, q2dx4) (♦), or preladenant (30 mg/kg, qdx9)+anti-PD1 antibody (200 µg/mouse, q2dx4) (○) as described in detail in Example 34.

Tumor cells were allowed to mature into tumors for 6 days prior to treatment, where tumors had an average volume of ~100 mm³. The mice were divided into six treatment groups as follows: vehicle (qdx9) PO+IP, Compound 1 (10 mg/kg, qdx9)+an exemplary anti-mouse PD1 (CD279) antibody (BioXCell) (200 µg/mouse, q2dx4); Compound 1 (30 mg/kg, qdx9)+anti-PD1 antibody (200 µg/mouse, q2dx4), Compound 1 (100 mg/kg)+anti-PD1 antibody (200 µg/mouse, q2dx4), anti-PD1 antibody (200 µg/mouse, q2dx4), or preladenant (30 mg/kg, qdx9)+anti-PD1 antibody (200 µg/mouse, q2dx4). Compound 1 and preladenant were administered orally. The anti-PD1 antibody was administered IP. Body weight was measured daily. Tumor growth of the CT26 cells was monitored three times per week by measuring the tumor volume size using a caliper with the results shown in FIG. 5.

Tumor growth inhibition (% TGI) as compared to the vehicle on day 13 is presented in Table 8 below.

TABLE 8

Tumor Growth Inhibition

| Treatment | % TGI |
|---|---|
| Compound 1 (10 mg/kg) + anti-PD1 antibody | 34 |
| Compound 1 (30 mg/kg) + anti-PD1 antibody | 41[1] |
| Compound 1 (100 mg/kg) + anti-PD1 antibody | 47[2] |
| Anti-PD1 antibody monotherapy | 39[1] |
| Preladenant 30 mg/kg + anti-PD1 antibody | 56[3] |

[1] ($p < 0.05$);
[2] ($p < 0.01$);
[3] ($p < 0.01$) (One-way ANOVA followed by Tukey's multiple comparison test)

The % TGI for Compound 1 combination therapy was comparable to preladenant combination therapy as well as anti-PD1 antibody monotherapy. Further, the 30 mg/kg and 100 mg/kg doses of Compound 1 had a higher % TGI as compared to anti-PD1 antibody monotherapy.

It is claimed:
1. A compound having a formula:

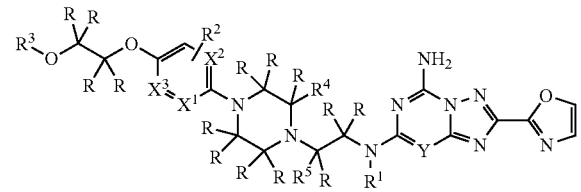

Formula I wherein R, in each instance, is independently selected from H and D;
$R^1$ is selected from —CH₃ and —CD₃;
$R^2$ is selected from the group consisting of H, F, Cl, —CF₃, —OCH₃, and —OCD₃;
$R^3$ is selected from hydrogen, —CH₃, —CD₃, and —CF₃;
$R^4$ and $R^5$ are each selected from H, D, or combine with the intervening atoms to form a 5-membered ring;
$X^1$, $X^2$ and $X^3$ are independently selected from —N— and —CH—; and
Y is selected from —CH— and —N—
wherein the compound is an adenosine $A_{2A}$ receptor ($A_{2A}R$) selective antagonist.

2. The compound of claim 1, having the formula selected from:

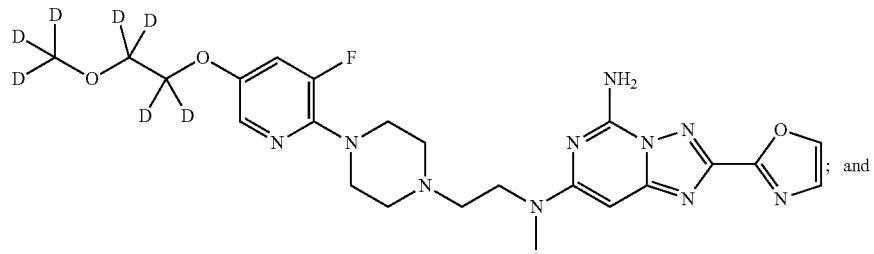

Compound 13

; and

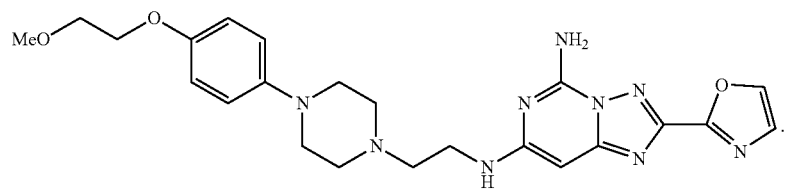

Compound 24

.

3. The compound of claim 1, having the following formula:
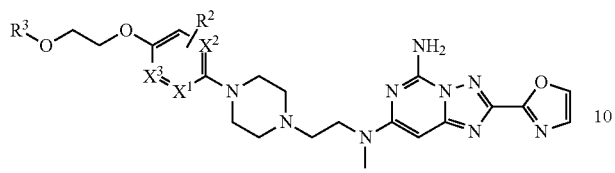
Formula Ia
wherein:
$X^1$, $X^2$ and $X^3$ are independently selected from —N— and —CH—;
$R^2$ is selected from the group consisting of H, F, Cl, —CF$_3$, —OCH$_3$, and —OCD$_3$; and
$R^3$ is selected from —CH$_3$, —CD$_3$, and —CF$_3$.
4. The compound of claim 3, having the formula selected from:
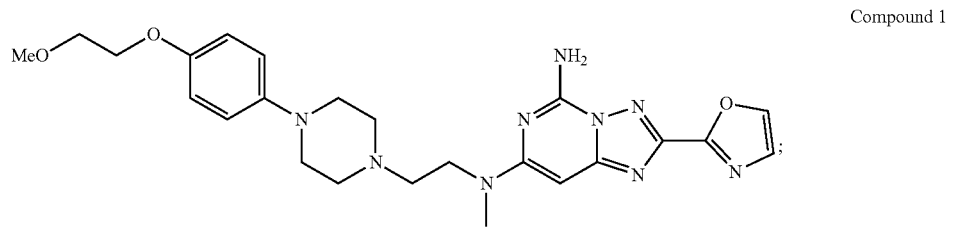
Compound 1
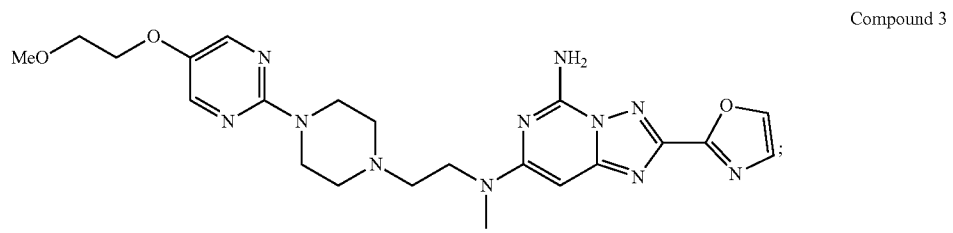
Compound 3
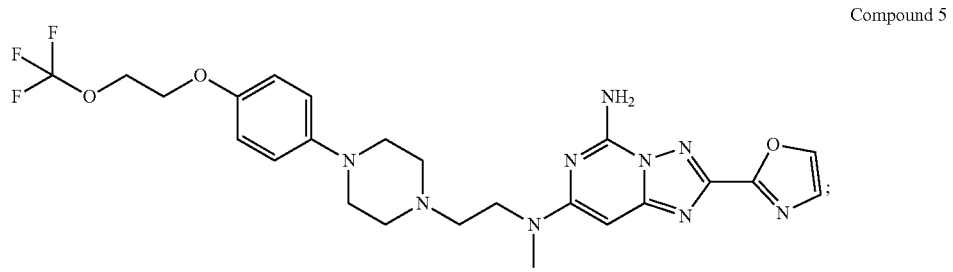
Compound 5
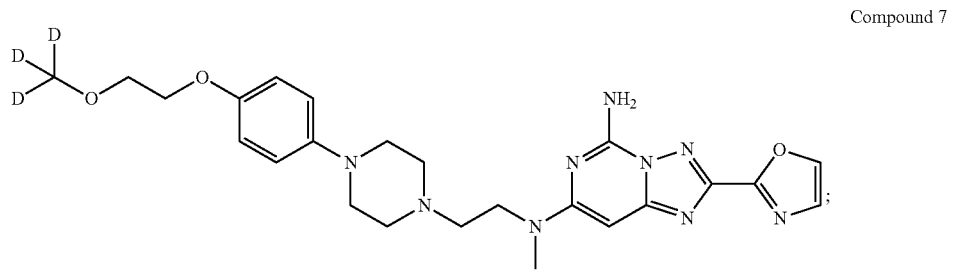
Compound 7

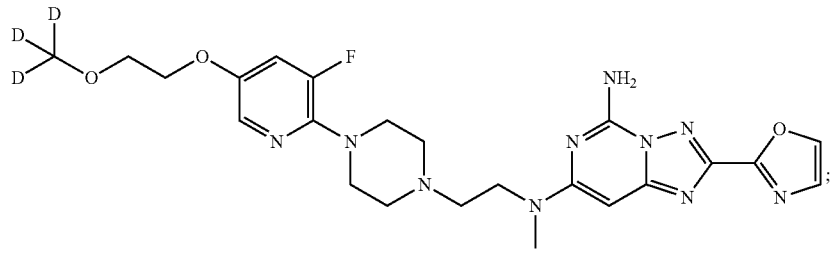
Compound 11
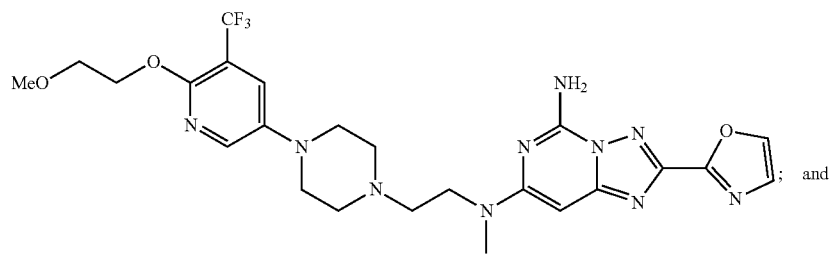
Compound 22; and
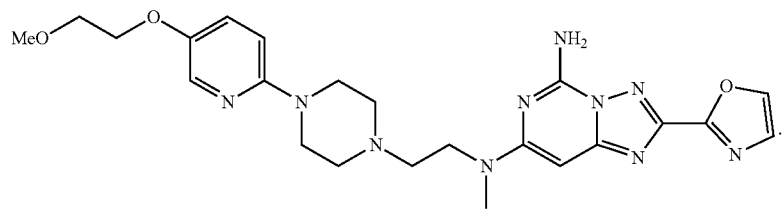
Compound 23.
5. The compound of claim 1, having the following formula:
Formula Ib
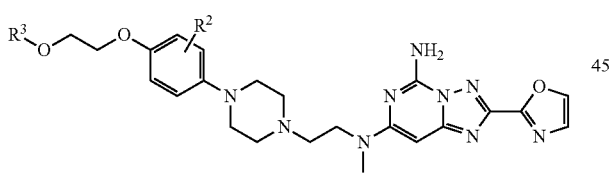
wherein:
R² is selected from the group consisting of F, Cl, —CF₃, —OCH₃, and —OCD₃; and
R³ is selected from —CH₃, —CD₃, and —CF₃.
6. The compound of claim 5, having the formula selected from:
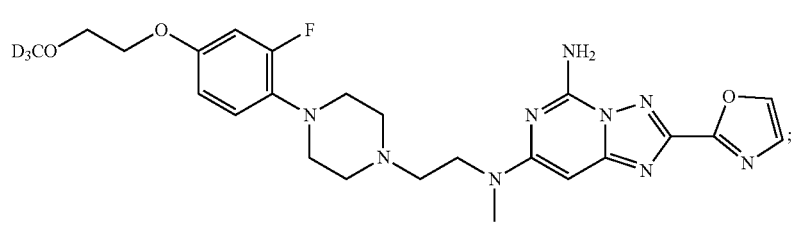
Compound 10

Compound 15
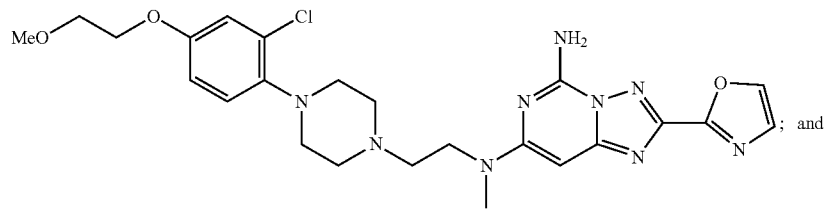
; and
Compound 17
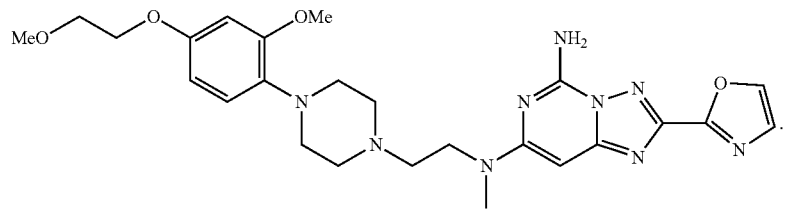
.
7. The compound of claim 1, having the following formula:
Formula Ic
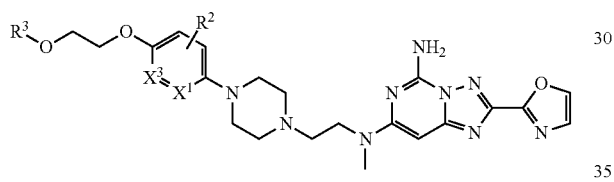
wherein:
one of $X^1$ or $X^2$ is —N— and the other of $X^1$ or $X^2$ is —CH—;
$R^2$ is selected from the group consisting of F, Cl, and —CF$_3$; and
$R^3$ is selected from —CH$_3$, —CD$_3$, and —CF$_3$.
8. The compound of claim 7, having the formula selected from:
Compound 4
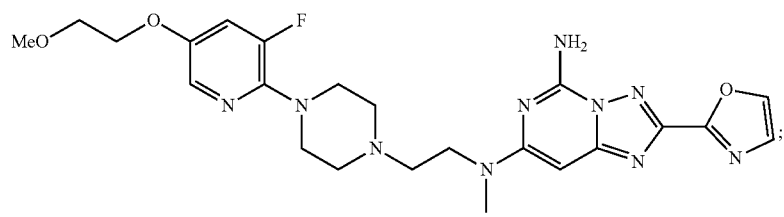
;
Compound 11
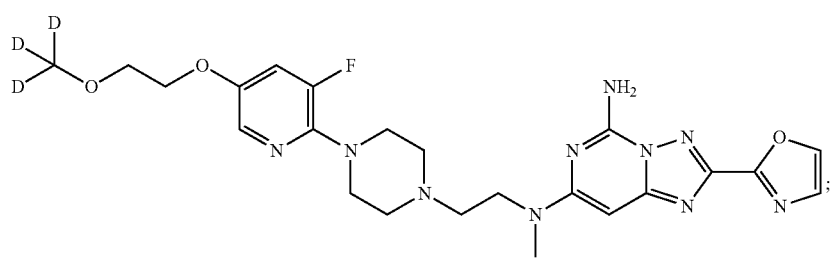
;

Compound 14

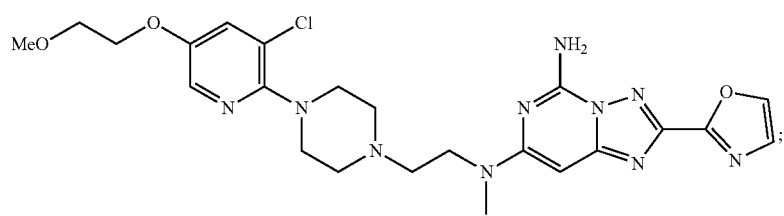

Compound 19

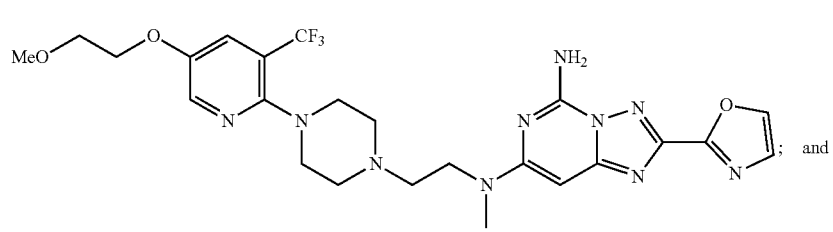
; and

Compound 22

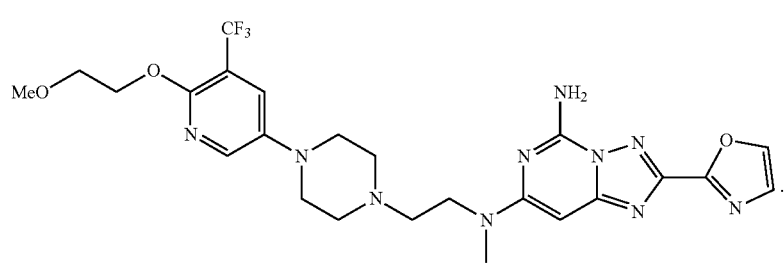
.

9. The compound of claim 1, having the following formula:

Formula Id

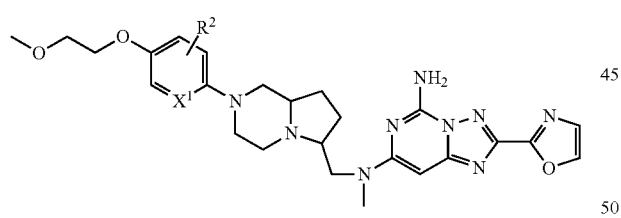

wherein:
$X^1$ is selected from —N— and —CH—;
$R^2$ is selected from the group consisting of H, F, Cl, —CF$_3$, —OCH$_3$, and —OCD$_3$.

10. The compound of claim 9, having the formula:

Compound 21

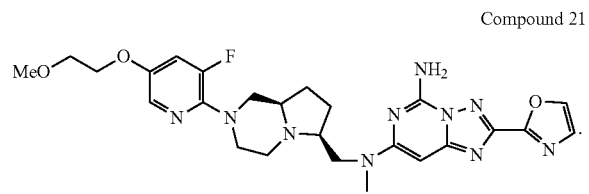 [SMILES: COCCOc1cnc(N2CCN3[C@H](CC[C@H]3CN(C)c3cc4nc(-c5ncco5)nn4c(N)n3)C2)c(F)c1]

11. The compound of claim 1, having the following formula:

Formula Ie

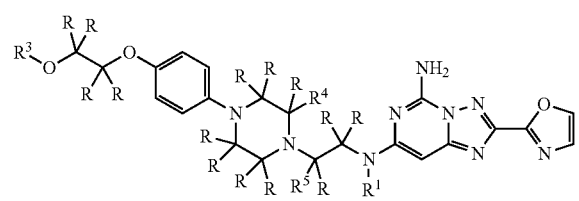

wherein:
R, in each instance, is independently selected from H and D;
$R^1$ is selected from —CH$_3$ and —CD$_3$;
$R^3$ is selected from —CH$_3$ and —CD$_3$; and
$R^4$ and $R^5$ are each selected from H and D.

12. The compound of claim 11, having the formula selected from:
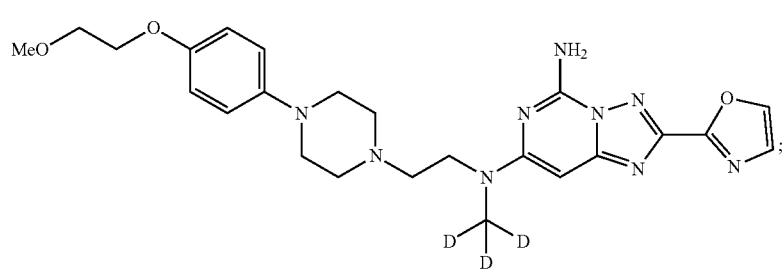
Compound 6
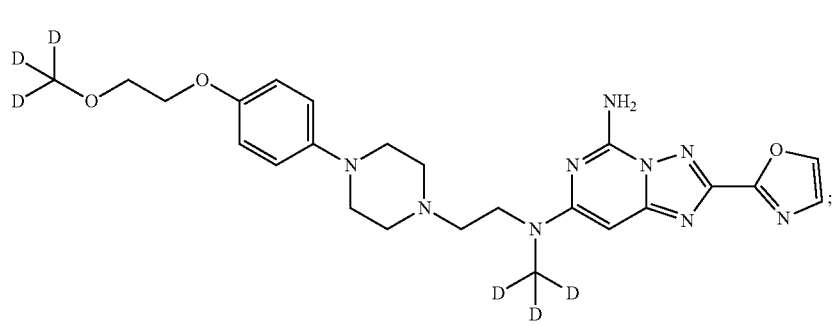
Compound 8
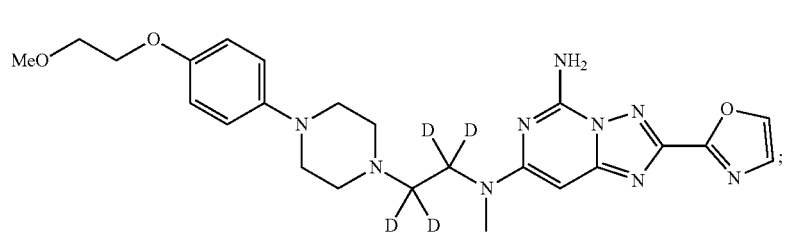
Compound 9
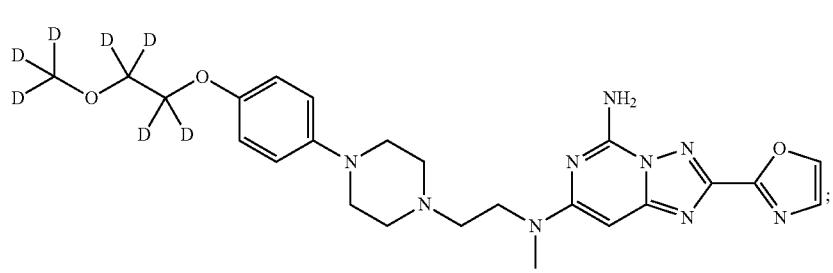
Compound 12
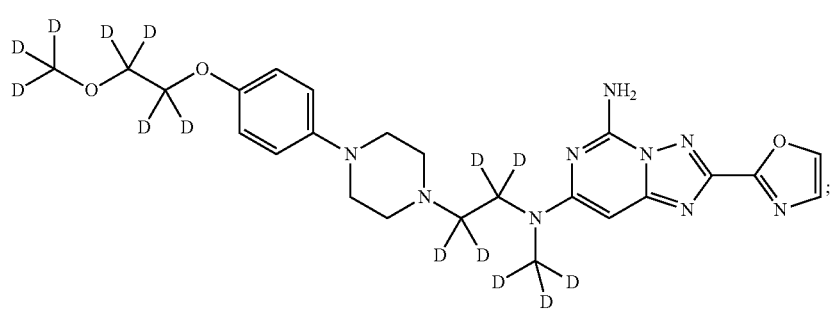
Compound 16

Compound 18

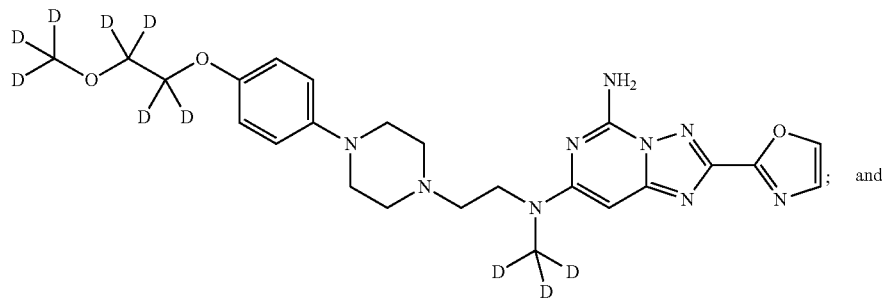

Compound 20

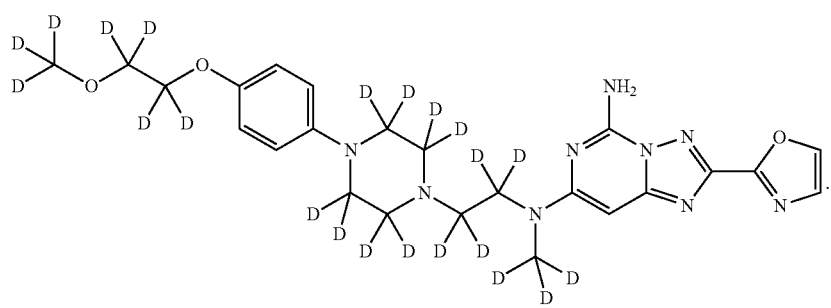

13. The compound of claim 1, wherein the compound is a pharmaceutically acceptable salt.

14. A metabolite of the compound of claim 1.

15. A composition comprising:
a compound having a formula:

Formula I

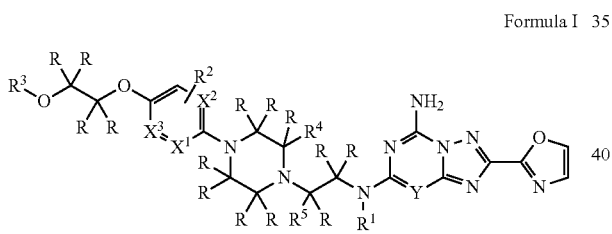

wherein R, in each instance, is independently selected from H and D;
$R^1$ is selected from —$CH_3$ and —$CD_3$;
$R^2$ is selected from the group consisting of H, F, Cl, —$CF_3$, —$OCH_3$, and —$OCD_3$;
$R^3$ is selected from hydrogen, —$CH_3$, —$CD_3$, and —$CF_3$;
$R^4$ and $R^5$ are each selected from H, D, or combine with the intervening atoms to form a 5-membered ring;
$X^1$, $X^2$ and $X^3$ are independently selected from —N— and —CH—; and
Y is selected from —CH— and —N—;
wherein the compound is an adenosine $A_{2A}$ receptor ($A_{2A}$R) selective antagonist and
a pharmaceutically acceptable excipient.

16. A dosage form comprising the composition of claim 15.

17. A method of treating a subject suffering from cancer, comprising:
administering to the subject a therapeutically effective amount of a compound having a formula:

Formula I

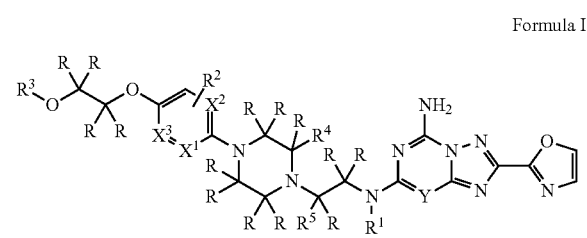

wherein R, in each instance, is independently selected from H and D;
$R^1$ is selected from —$CH_3$ and —$CD_3$;
$R^2$ is selected from the group consisting of H, F, Cl, —$CF_3$, —$OCH_3$, and —$OCD_3$;
$R^3$ is selected from hydrogen, —$CH_3$, —$CD_3$, and —$CF_3$;
$R^4$ and $R^5$ are each selected from H, D, or combine with the intervening atoms to form a 5-membered ring;
$X^1$, $X^2$ and $X^3$ are independently selected from —N— and —CH—; and
Y is selected from —CH— and —N—
wherein the compound is an adenosine $A_{2A}$ receptor ($A_{2A}$R) selective antagonist.

* * * * *